US012623070B2

(12) United States Patent
Gad et al.

(10) Patent No.: US 12,623,070 B2
(45) Date of Patent: May 12, 2026

(54) TRANSCUTANEOUS ELECTRICAL SPINAL CORD NEUROMODULATOR AND USES THEREOF

(71) Applicants: The Regents of the University of California, Oakland, CA (US); Scuola Internazionale Superiore di Studi Avanzati (SISSA), Trieste (IT); University of Southern California, Los Angeles, CA (US)

(72) Inventors: Parag Gad, Woodland Hills, CA (US); Victor Reggie Edgerton, Los Angeles, CA (US); Giuliano Taccola, Udine (IT); Evgeniy I. Kreydin, Los Angeles, CA (US)

(73) Assignees: The Regents of the University of California, Oakland, CA (US); Scoula Internazionale Superiore di Studi Avanzati—Sissa, Trieste (IT); University of Southern California, Los Angeles, CA (US)

( * ) Notice: Subject to any disclaimer, the term of this patent is extended or adjusted under 35 U.S.C. 154(b) by 650 days.

(21) Appl. No.: 17/611,534

(22) PCT Filed: May 20, 2020

(86) PCT No.: PCT/US2020/033830
§ 371 (c)(1),
(2) Date: Nov. 15, 2021

(87) PCT Pub. No.: WO2020/236946
PCT Pub. Date: Nov. 26, 2020

(65) Prior Publication Data
US 2022/0233848 A1     Jul. 28, 2022

Related U.S. Application Data

(60) Provisional application No. 62/876,583, filed on Jul. 19, 2019, provisional application No. 62/851,572, filed on May 22, 2019.

(51) Int. Cl.
*A61N 1/05* (2006.01)
*A61B 5/308* (2021.01)
(Continued)

(52) U.S. Cl.
CPC ............ *A61N 1/0553* (2013.01); *A61B 5/308* (2021.01); *A61B 5/313* (2021.01); *A61B 5/395* (2021.01);
(Continued)

(58) Field of Classification Search
CPC .... A61N 1/0553; A61N 1/025; A61N 1/0456; A61N 1/0492; A61N 1/06;
(Continued)

(56) References Cited

U.S. PATENT DOCUMENTS

| 2,868,343 A | 1/1959 | Sproul |
| 3,543,761 A | 12/1970 | Bradley et al. |
(Continued)

FOREIGN PATENT DOCUMENTS

| AU | 2012204526 A1 | 7/2013 |
| CA | 2649663 A1 | 11/2007 |
(Continued)

OTHER PUBLICATIONS

International Search Report and Written Opinion dated Jun. 28, 2022, in PCT Application No. PCT/US2022/024673.
(Continued)

*Primary Examiner* — Benjamin J Klein
*Assistant Examiner* — Daniel Tehrani
(74) *Attorney, Agent, or Firm* — Quarles & Brady LLP

(57) ABSTRACT

In various embodiments electrical stimulators are provided for transcutaneous and/or epidural stimulation. In certain embodiments the stimulator provides one or more channels configured to provide one or more of the following stimulation patterns: i) monophasic electrical stimulation with a
(Continued)

DC offset; ii) monophasic electrical stimulation with charge balance; iii) delayed biphasic electrical stimulation with a DC offset; iv) delayed biphasic electrical stimulation with charge balance; v) amplitude modulated dynamic stimulation; and/or vi) frequency modulated dynamic stimulation.

14 Claims, 104 Drawing Sheets

(51) Int. Cl.

| | |
|---|---|
| A61B 5/313 | (2021.01) |
| A61B 5/395 | (2021.01) |
| A61N 1/02 | (2006.01) |
| A61N 1/04 | (2006.01) |
| A61N 1/06 | (2006.01) |
| A61N 1/36 | (2006.01) |
| A61N 1/372 | (2006.01) |

(52) U.S. Cl.
CPC ........... *A61N 1/025* (2013.01); *A61N 1/0456* (2013.01); *A61N 1/0492* (2013.01); *A61N 1/06* (2013.01); *A61N 1/36003* (2013.01); *A61N 1/36007* (2013.01); *A61N 1/36031* (2017.08); *A61N 1/37247* (2013.01)

(58) Field of Classification Search
CPC ............ A61N 1/36003; A61N 1/36007; A61N 1/36031; A61N 1/37247; A61N 1/36157; A61N 1/36171; A61N 1/36175; A61N 1/36178; A61N 1/0452; A61N 1/36021; A61N 1/36034; A61N 1/36062; A61N 1/36192; A61N 1/36196; A61N 1/0551; A61N 1/36071; A61N 1/36025; A61N 1/36017; A61N 1/36014; A61N 1/36067; A61N 1/36103; A61B 5/308; A61B 5/313; A61B 5/395; A61B 5/30
See application file for complete search history.

(56) References Cited

U.S. PATENT DOCUMENTS

| | | | |
|---|---|---|---|
| 3,650,277 A | 3/1972 | Sjostrand et al. |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |

| | | | |
|---|---|---|---|
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,340,298 B1 | 3/2008 | Barbut |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |

(56) References Cited

U.S. PATENT DOCUMENTS

| | | |
|---|---|---|
| 7,725,193 B1 | 5/2010 | Chu |
| 7,729,781 B2 | 6/2010 | Swoyer et al. |
| 7,734,340 B2 | 6/2010 | De Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,840,270 B2 | 11/2010 | Ignagni et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 11,266,850 B2 | 3/2022 | Prouza et al. |
| 11,298,533 B2 | 4/2022 | Edgerton et al. |
| 11,400,284 B2 | 8/2022 | Gerasimenko et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0093131 A1 | 5/2003 | Loeb et al. |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |

(56) References Cited

U.S. PATENT DOCUMENTS

| | | |
|---|---|---|
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0150034 A1 | 6/2007 | Rooney et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0279896 A1 | 11/2008 | Heinen et al. |
| 2008/0294211 A1 | 11/2008 | Moffitt |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0229166 A1 | 9/2009 | Sawrie |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |

(56)  References Cited

U.S. PATENT DOCUMENTS

| | | |
|---|---|---|
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2011/0301662 A1 | 12/2011 | Bar-Yoseph et al. |
| 2012/0006793 A1 | 1/2012 | Swanson |
| 2012/0011222 A1 | 1/2012 | Yasukawa et al. |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | Macdonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0053645 A1 | 3/2012 | Ayanoor-Vitikkate et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0066411 A1 | 3/2013 | Thacker et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-Ezra et al. |
| 2014/0058292 A1 | 2/2014 | Alford et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0142652 A1 | 5/2014 | Francois et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0243924 A1* | 8/2014 | Zhu ................... A61N 1/36146 607/46 |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1* | 2/2016 | Gerasimenko ....... A61N 1/0456 607/48 |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1* | 5/2016 | Edgerton ................. A61N 1/06 607/45 |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0175586 A1 | 6/2016 | Edgerton et al. |
| 2016/0220813 A1 | 8/2016 | Edgerton et al. |

(56)                    References Cited

U.S. PATENT DOCUMENTS

| | | |
|---|---|---|
| 2016/0235977 A1 | 8/2016 | Lu et al. |
| 2016/0263376 A1 | 9/2016 | Yoo et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2016/0339239 A1 | 11/2016 | Yoo et al. |
| 2017/0007831 A1 | 1/2017 | Edgerton et al. |
| 2017/0128729 A1 | 5/2017 | Netoff et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1 | 12/2017 | Yoo et al. |
| 2018/0008826 A1 | 1/2018 | Dimarco |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0117334 A1 | 5/2018 | Jung |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0333574 A1* | 11/2018 | Pal ...................... A61N 1/0476 |
| 2018/0353755 A1 | 12/2018 | Edgerton et al. |
| 2018/0361146 A1 | 12/2018 | Gerasimenko et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192852 A1 | 6/2019 | De Ridder |
| 2019/0192864 A1 | 6/2019 | Koop et al. |
| 2019/0247650 A1 | 8/2019 | Tran |
| 2019/0269917 A1 | 9/2019 | Courtine et al. |
| 2019/0381313 A1 | 12/2019 | Lu |
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0187278 A1 | 6/2021 | Lu |
| 2021/0236837 A1 | 8/2021 | Lu |
| 2021/0378991 A1 | 12/2021 | Lu et al. |
| 2022/0161042 A1 | 5/2022 | Lu |
| 2022/0313993 A1 | 10/2022 | Gerasimenko et al. |

FOREIGN PATENT DOCUMENTS

| | | |
|---|---|---|
| CA | 2823592 A1 | 7/2012 |
| CA | 2856202 A1 | 5/2013 |
| CA | 2864473 A1 | 5/2013 |
| CN | 101227940 A | 7/2008 |
| CN | 103263727 A | 8/2013 |
| CN | 104307098 A | 1/2015 |
| EP | 0630987 A1 | 12/1994 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2688642 A2 | 1/2014 |
| EP | 2810689 A1 | 12/2014 |
| EP | 2810690 A1 | 12/2014 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3323468 A1 | 5/2018 |
| EP | 3328481 A1 | 6/2018 |
| EP | 3527258 A1 | 8/2019 |
| JP | H0326620 A | 2/1991 |
| JP | 3184145 B2 | 7/2001 |
| JP | 2002517283 A | 6/2002 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2011502586 A | 1/2011 |
| JP | 2012515060 A | 7/2012 |
| JP | 2013508119 A | 3/2013 |
| JP | 2014514043 A | 6/2014 |
| JP | 2016506255 A | 3/2016 |
| JP | 6132856 B2 | 5/2017 |
| JP | 2017104685 A | 6/2017 |
| JP | 2017525509 A | 9/2017 |
| JP | 2018524113 A | 8/2018 |
| KR | 20070120478 A | 12/2007 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 A | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | WO-9747357 A1 | 12/1997 |
| WO | 0007658 A1 | 2/2000 |
| WO | WO-0234331 A2 | 5/2002 |
| WO | WO-02092165 A1 | 11/2002 |
| WO | WO-03005887 A2 | 1/2003 |
| WO | WO-03026735 A2 | 4/2003 |
| WO | WO-03092795 A1 | 11/2003 |
| WO | WO-2004087116 A2 | 10/2004 |
| WO | WO-2005002663 A2 | 1/2005 |
| WO | WO-2005051306 A2 | 6/2005 |
| WO | WO-2005065768 A1 | 7/2005 |
| WO | WO-2005087307 A2 | 9/2005 |
| WO | WO-2006135751 A2 | 12/2006 |
| WO | WO-2006138069 A1 | 12/2006 |
| WO | WO-2007007058 A1 | 1/2007 |
| WO | WO-2007012114 A1 | 2/2007 |
| WO | WO-2007047852 A2 | 4/2007 |
| WO | WO-2007081764 A2 | 7/2007 |
| WO | WO-2007107831 A2 | 9/2007 |
| WO | WO-2008075294 A1 | 6/2008 |
| WO | WO-2008070807 A3 | 9/2008 |
| WO | WO-2008109862 A2 | 9/2008 |
| WO | WO-2008121891 A1 | 10/2008 |

(56) References Cited

FOREIGN PATENT DOCUMENTS

| WO | WO-2009042217 A1 | 4/2009 |
|---|---|---|
| WO | WO-2009111142 A2 | 9/2009 |
| WO | WO-2010021977 A1 | 2/2010 |
| WO | WO-2010055421 A1 | 5/2010 |
| WO | WO-2010083308 A1 | 7/2010 |
| WO | WO-2010114998 A1 | 10/2010 |
| WO | WO-2010124128 A1 | 10/2010 |
| WO | WO-2011005607 A1 | 1/2011 |
| WO | WO-2011136875 A1 | 11/2011 |
| WO | WO-2012050200 A1 | 4/2012 |
| WO | WO-2012075195 A1 | 6/2012 |
| WO | WO-2012080964 A1 | 6/2012 |
| WO | WO-2012094346 A2 | 7/2012 |
| WO | WO-2012100260 A2 | 7/2012 |
| WO | WO-2012129574 A2 | 9/2012 |
| WO | WO-2013071307 A1 | 5/2013 |
| WO | WO-2013071309 A1 | 5/2013 |
| WO | WO-2013152124 A1 | 10/2013 |
| WO | WO-2013188965 A1 | 12/2013 |
| WO | WO-2014005075 A1 | 1/2014 |
| WO | WO-2014031142 A1 | 2/2014 |
| WO | WO-2014089299 A2 | 6/2014 |
| WO | WO-2014144785 A1 | 9/2014 |
| WO | WO-2014149895 A1 | 9/2014 |
| WO | WO-2014205356 A2 | 12/2014 |
| WO | WO-2014209877 A1 | 12/2014 |
| WO | WO-2015000800 A1 | 1/2015 |
| WO | WO-2015048563 A2 | 4/2015 |
| WO | WO-2015063127 A1 | 5/2015 |
| WO | WO-2015106286 A1 | 7/2015 |
| WO | 2015179571 A1 | 11/2015 |
| WO | WO-2016029159 A2 | 2/2016 |
| WO | WO-2016033369 A1 | 3/2016 |
| WO | WO-2016033372 A1 | 3/2016 |
| WO | WO-2016064761 A1 | 4/2016 |
| WO | WO-2016110804 A1 | 7/2016 |
| WO | WO-2016112398 A1 | 7/2016 |
| WO | WO-2016172239 A1 | 10/2016 |
| WO | WO-2017011410 A1 | 1/2017 |
| WO | WO-2017024276 A1 | 2/2017 |
| WO | WO-2017035512 A1 | 3/2017 |
| WO | WO-2017044904 A1 | 3/2017 |
| WO | WO-2017058913 A1 | 4/2017 |
| WO | WO-2017062508 A1 | 4/2017 |
| WO | WO-2017117450 A1 | 7/2017 |
| WO | WO-2017146659 A1 | 8/2017 |
| WO | 2018/0035521 A1 | 2/2018 |
| WO | WO-2018039296 A2 | 3/2018 |
| WO | WO-2018106843 A1 | 6/2018 |
| WO | WO-2018140531 A1 | 8/2018 |
| WO | 2018/0187241 A1 | 10/2018 |
| WO | 2018217791 A1 | 11/2018 |
| WO | WO-2019211314 A1 | 11/2019 |
| WO | WO-2020041502 A1 | 2/2020 |
| WO | WO-2020041633 A1 | 2/2020 |
| WO | WO-2020236946 A1 | 11/2020 |

OTHER PUBLICATIONS

JP Office Action dated Aug. 21, 2023 in Application No. JP2021-510130 with English Translation.
U.S. Non-Final Office Action dated Aug. 16, 2023, in U.S. Appl. No. 17/269,970.
Andersson, et al., (2003) "CNS Involvement in Overactive Bladder." Drugs, 63(23): 2595-2611.
Angeli et al. (2014) "Altering spinal cord excitability enables voluntary movements after chronic complete paralysis in humans" Brain 137: 1394-1409.
Australian Examination report No. 1 dated Dec. 21, 2020 issued in AU 2020200152.
Australian Examination report No. 1 dated Jan. 11, 2019 issued in AU 2014324660.
Australian Examination report No. 2 dated Nov. 7, 2019 issued in AU 2014324660.

Australian Examination report No. 3 dated Jan. 6, 2020 issued in AU 2014324660.
Australian Patent Examination Report No. 1 dated Jan. 6, 2020 issued in AU 2019206059.
Australian Patent Examination Report No. 1 dated Jul. 11, 2016 issued in AU 2012334926.
Australian Patent Examination Report No. 1 dated Jul. 18, 2019 issued in AU 2015308779.
Australian Patent Examination Report No. 1 dated Jun. 14, 2019 issued in AU 2015305237.
Australian Patent Examination Report No. 1 dated May 11, 2018 issued in AU 2014228794.
Australian Patent Examination Report No. 2 dated Apr. 17, 2020 issued in AU 2015305237.
Australian Patent Examination Report No. 2 dated May 20, 2020 issued in AU 2015308779.
CA Office Action dated Oct. 21, 2021 in CA Application No. CA2958924.
CA Office Action dated Sep. 28, 2021, in application No. CA2925754.
Canadian 2nd Office Action dated Apr. 9, 2021 issued in CA 2,906,779.
Canadian Office Action dated Aug. 14, 2020 issued in CA 2,864,473.
Canadian Office Action dated Aug. 31, 2018 issued in CA 2,864,473.
Canadian Office Action dated Jul. 30, 2019 issued in CA 2,864,473.
Canadian Office Action dated May 7, 2020 issued in CA 2,906,779.
Canadian Office Action dated Nov. 27, 2020 issued in CA 2,925,754.
Chinese First Office Action dated Jan. 6, 2021 issued in CN 201680058067.8.
Courtine, Grégoire et al. (2007) "Modulation of multisegmental monosynaptic responses in a variety of leg muscles during walking and running in humans," J Physiol. 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" Europe PMC Funders Author Manuscripts, Artif Organs 35(3):257-262, 12 pp.
Desantana et al. (Dec. 2008) "Effectiveness of Transcutaneous Electrical Nerve Stimulation for Treatment of Hyperalgesia and Pain," Curr Rheumatol Rep. 10(6):492-499, 12 pp.
Dimitrijevic et al. (1998) "Evidence for a spinal central pattern generator in humans." Ann N Y Acad Sci. 860:360-76.
Drummond, et al. (1996) "Thoracic impedance used for measuring chest wall movement in postoperative patients," British Journal of Anaesthesia, 77: 327-332.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) Neurology, 74:173-176.
Edgerton and Harkema (2011) "Epidural stimulation of the spinal cord in spinal cord injury: current status and future challenges" Expert Rev Neurother. 11(10): 1351-1353. doi:10.1586/ern.11.129 [NIH Public Access—Author Manuscript—5 pages].
European Communication pursuant to Rule 114(2) EPC regarding observations by a third party dated Mar. 27, 2015 issued in EP 12 847 885.6.
European Extended Search Report dated Apr. 21, 2020 issued in EP 19201998.2.
European Extended Search Report dated Apr. 4, 2018 issued in EP 15834593.4.
European Extended Search Report dated Aug. 17, 2021 issued in EP 21166801.7.
European Extended Search Report dated Dec. 13, 2018 issued in EP 16833973.7.
European Extended Search Report dated Feb. 19, 2019 issued in EP 16825005.8.
European Extended Search Report dated Jan. 22, 2021 issued in EP 20175385.2.
European Extended Search Report dated Mar. 1, 2018 issued in EP 15836927.2.
European Extended Search Report dated May 10, 2017 issued in EP 14849355.4.

(56)                References Cited

OTHER PUBLICATIONS

European Extended Search Report dated May 6, 2015 issued in EP 12 847 885.6.
European Extended Search Report dated Nov. 8, 2016 issued in EP 14765477.6.
European Extended Search Report dated Sep. 7, 2020 issued in EP 18744685.1.
European Office Action dated Apr. 15, 2016 issued in EP 12 847 885.6.
European Office Action dated Jul. 17, 2019 issued in EP 15834593.4.
European Office Action dated Jul. 20, 2018 issued in EP 14849355.4.
European Office Action dated Jul. 30, 2020 issued in EP 15834593.4.
European Office Action dated Nov. 14, 2018 issued in EP 14765477.6.
European Office Action dated Sep. 27, 2019 issued in EP 14765477.6.
European Office Action [Decision to Refuse] dated Oct. 28, 2021 issued in EP 15834593.4.
European Reply to Communication of Apr. 15, 2016 dated Oct. 24, 2016 in EP 12 847 885.6.
European Search Report dated Apr. 19, 2022, in Application No. EP20190851613.
European Search Report dated Apr. 19, 2022, in Application No. EP20190852797.
European Second Office Action dated Feb. 16, 2017 issued in EP 12 847 885.6.
Fong et al. (2009) "Recovery of control of posture and locomotion after a spinal cord injury: solutions staring us in the face," Progress in Brain Research, Elsevier Amsterdam, NL, 175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," Top. Spinal Cord Inj. Rehabil;11(2):50-63.
Gerasimenko et al. (2015) "Initiation and modulation of locomotor circuitry output with multisite transcutaneous electrical stimulation of the spinal cord in noninjured humans." J Neurophysiol. 113:834-42.
Gerasimenko et al. (2015) "Transcutaneous electrical spinal-cord stimulation in humans." Ann Phys Rehabil Med. 58(4):225-231. doi:10.1016/j.rehab.2015.05.003.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," J Neurosci. 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," J Neurophysiol. 98:2525-2536.
Harkema et al. (2011) "Effect of Epidural stimulation of the lumbosacral spinal cord on voluntary movement, standing, and assisted stepping after motor complete paraplegia: a case study" Lancet 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," Spinal Cord. 40:65-68.
Hofstoetter, U.S. et al. (Aug. 2008) "Modification of Reflex Responses to Lumbar Posterior Root Stimulation by Motor Tasks in Healthy Subjects," Artif Organs, 32(8):644-648.
Hovey, et al. (2006) "The Guide to Magnetic Stimulation," The Magstim Company Ltd, 45 pages.
Ichiyama et al. (2005) "Hindlimb stepping movements in complete spinal rats induced by epidural spinal cord stimulation" Neuroscience Letters, 383:339-344.
Japanese 2nd Office Action dated Mar. 22, 2021 issued in JP 2018-501208.

Japanese Office Action dated Jul. 13, 2020 issued in JP 2018-501208.
JP Office Action dated Nov. 29, 2021, in Application No. JP2019-539960 with English translation.
Kapetanakis, et al. (2017) "Cauda Equina Syndrome Due to Lumbar Disc Herniation: a Review of Literature," Folia Medica, 59(4): 377-86.
Kitano K., Koceja D.M. (2009) "Spinal reflex in human lower leg muscles evoked by transcutaneous spinal cord stimulation," J Neurosci Methods. 180:111-115.
Kondo, et al. (1997) "Laser monitoring of chest wall displacement," Eur Respir J., 10: 1865-1869.
Krenn et al. (2013) "Selectivity of transcutaneous stimulation of lumbar posterior roots at different spinal levels in humans." Biomed Tech (Berl) 58 (Suppl. 1) DOI 10.1515/bmt-2013-4010, 2 pages.
Ladenbauer et al. (2010) "Stimulation of the human lumbar spinal cord with implanted and surface electrodes: a computer simulation study." IEEE Trans Neural Syst Rehabil Eng. 18:637-45.
Minasian et al. (2010) "Transcutaneous stimulation of the human lumbar spinal cord: Facilitating locomotor output in spinal cord injury," Conf. Proceedings Soc. for Neurosci., Abstract No. 286.19, 1 page.
Minassian et al. (Aug. 2011) "Transcutaneous spinal cord stimulation," International Society for Restorative Neurology, http://restorativeneurology.org/resource-center/assessments/transcutaneous-lumbar-spinal-cord-stimulation/; http://restorativeneurology.org/wp-content/uploads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," Muscle & Nerve 35:327-336.
Nandra et al., (2014) "Microelectrode Implants for Spinal Cord Stimulation in Rats," Thesis, California Institute of Technology, Pasadena, California, Defended on Sep. 24, 2014, 104 pages.
Nandra et al., (Jan. 23, 2011) "A Parylene-Based Microelectrode Arrary Implant for Spinal Cord Stimulation in Rats," Conf. Proc. IEEE Eng. Med. Biol. Soc., pp. 1007-1010.
Niu et al., (2018) "A Proof-of-Concept Study of Transcutaneous Magnetic Spinal Cord Stimulation for Neurogenic Bladder," Scientific Reports, 8: 12549 (12 pages).
PCT Declaration of Non-Establishment of International Search Report and Written Opinion dated Dec. 1, 2015 issued in PCT/US2015/046378.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
PCT International Preliminary Report on Patentability and Written Opinion dated Dec. 2, 2021 issued in PCT/US2020/033830.
PCT International Preliminary Report on Patentability and Written Opinion dated Feb. 15, 2018 issued in PCT/US2016/045898.
PCT International Preliminary Report on Patentability and Written Opinion dated Feb. 21, 2017 issued in PCT/US2015/046378.
PCT International Preliminary Report on Patentability and Written Opinion dated Feb. 23, 2021 issued in PCT/US2019/047551.
PCT International Preliminary Report on Patentability and Written Opinion dated Feb. 23, 2021 issued in PCT/US2019/047777.
PCT International Preliminary Report on Patentability and Written Opinion dated Feb. 28, 2017 issued in PCT/US2015/047268.
PCT International Preliminary Report on Patentability and Written Opinion dated Feb. 28, 2017 issued in PCT/US2015/047272.
PCT International Preliminary Report on Patentability and Written Opinion dated Jan. 25, 2018 issued in PCT/US2016/041802.
PCT International Preliminary Report on Patentability and Written Opinion dated Jul. 10, 2013 issued in PCT/US2012/020112.
PCT International Preliminary Report on Patentability and Written Opinion dated Jul. 30, 2019 issued in PCT/US2018/015098.
PCT International Preliminary Report on Patentability and Written Opinion dated Mar. 8, 2018 issued in PCT/US2016/049129.
PCT International Preliminary Report on Patentability and Written Opinion dated Nov. 26, 2019 issued in PCT/US2018/033942.

(56) References Cited

OTHER PUBLICATIONS

PCT International Preliminary Report on Patentability dated May 22, 2014 issued in PCT/US2012/064878.
PCT International Preliminary Report on Patentability dated Sep. 24, 2015 issued in PCT/US2014/029340.
PCT International Search Report and Written Opinion dated Aug. 31, 2018 issued in PCT/US2018/033942.
PCT International Search Report and Written Opinion dated Aug. 6, 2014 issued in PCT/US2014/029340.
PCT International Search Report and Written Opinion dated Dec. 3, 2015 issued in PCT/US2015/047272.
PCT International Search Report and Written Opinion dated Dec. 5, 2016 issued in PCT/US2016/045898.
PCT International Search Report and Written Opinion dated Dec. 5, 2016 issued in PCT/US2016/049129.
PCT International Search Report and Written Opinion dated Dec. 8, 2015 issued in PCT/US2015/047268.
PCT International Search Report and Written Opinion dated Mar. 12, 2018 issued in PCT/US2018/015098.
PCT International Search Report and Written Opinion dated Mar. 19, 2013 issued in PCT/US2012/064878.
PCT International Search Report and Written Opinion dated Nov. 14, 2019 issued in PCT/US2019/047777.
PCT International Search Report and Written Opinion dated Nov. 21, 2019 issued in PCT/US2019/047551.
PCT International Search Report and Written Opinion dated Oct. 14, 2020 issued in PCT/US2020/033830.
PCT International Search Report and Written Opinion dated Sep. 12, 2016 issued in PCT/US2016/041802.
PCT International Search Report dated Jul. 30, 2012 issued in PCT/US2012/020112.
PCT International Search Report dated Mar. 19, 2013 issued in PCT/US2012/064874.
PCT International Search Report dated Oct. 31, 2012 issued in PCT/US2012/030624.
PCT International Search Report dated Sep. 3, 2012 issued in PCT/US2012/022257.
Rodger et al., (2007) "High Density Flexible Parylene-Based Multielectrode Arrays for Retinal and Spinal Cord Stimulation," Transducers & Eurosensors, Proc. Of the 14th International Conference on Solid-State Sensors, Actuators and Microsystems, Lyon, France, Jun. 10-14, 2007, IEEE, pp. 1385-1388.
Roy et al. (2012) "Effect of percutaneous stimulation at different spinal levels on the activation of sensory and motor roots." Exp Brain Res. 223:281-9.
Sayenko et al. (2014) "Neuromodulation of evoked muscle potentials induced by epidural spinal-cord stimulation in paralyzed individuals." J Neurophysiol. 111:1088-99.
Sayenko et al. (2015) "Spinal segment-specific transcutaneous stimulation differentially shapes activation pattern among motor pools in humans." J Appl Physiol. 118:1364-74.
Seifert et al. (Nov. 1, 2002) "Restoration of Movement Using Functional Electrical Stimulation and Bayes' Theorem," The Journal of Neuroscience, 22(1):9465-9474.
Shafik, A (1996) "Extrapelvic cavernous nerve stimulation in erectile dysfunction. Human study" Andrologia 28(3):151-6. doi: 10.1111/j.1439-0272.1996.tb02774.x [Abstract—2 pages].
Shafik, et al. (2000) "Magnetic stimulation of the cavernous nerve for the treatment of erectile dysfunction in humans" International Journal of Impotence Research 12: 137-141.
Szava et al., (Jan. 2011) "Transcutaneous electrical spinal cord stimulation: Biophysics of a new rehabilitation method after spinal cord injury", ISBN: 978-3-639-34154-6 [95 pages].
Tanabe et al. (2008) "Effects of transcutaneous electrical stimulation combined with locomotion-like movement in the treatment of post-stroke gait disorder: a single-case study," 30(5):411-416 abstract, 1 page.
Temel, et al. (2004) "Deep brain stimulation of the thalamus can influence penile erection" International Journal of Impotence Research 16: 91-94.

Troni et al. (2011) "A methodological reappraisal of non invasive high voltage electrical stimulation of lumbosacral nerve roots." Clin Neurophysiol. 122:2071-80.
US 2nd Notice of Allowance dated Jun. 4, 2020 issued in U.S. Appl. No. 15/505,053.
US Final Office Action dated Apr. 19, 2019 issued in U.S. Appl. No. 15/208,529.
US Final Office Action dated Apr. 25, 2017 issued in U.S. Appl. No. 14/775,618.
US Final Office Action dated Aug. 6, 2020 issued in U.S. Appl. No. 15/750,499.
US Final Office Action dated Dec. 30, 2019 issued in U.S. Appl. No. 15/344,381.
US Final Office Action dated Dec. 6, 2021 issued in U.S. Appl. No. 16/615,765.
US Final Office Action dated Jul. 13, 2017 issued in U.S. Appl. No. 15/208,529.
US Final Office Action dated Jul. 16, 2021 issued in U.S. Appl. No. 15/753,963.
US Final Office Action dated Jul. 20, 2021 issued in U.S. Appl. No. 15/975,678.
US Final Office Action dated Jul. 29, 2020 issued in U.S. Appl. No. 15/975,678.
US Final Office Action dated Nov. 20, 2020 issued in U.S. Appl. No. 15/740,323.
US Final Office Action dated Nov. 26, 2021 issued in U.S. Appl. No. 15/740,323.
US Final Office Action dated Sep. 21, 2015 issued in U.S. Appl. No. 14/355,812.
U.S. Non-Final office Action dated May 11, 2022, in U.S. Appl. No. 15/740,323.
US Notice of Allowance dated Apr. 13, 2016 issued in U.S. Appl. No. 14/355,812.
US Notice of Allowance dated Apr. 27, 2021 issued in U.S. Appl. No. 15/344,381.
US Notice of Allowance dated Aug. 1, 2018 issued in U.S. Appl. No. 15/025,201.
US Notice of Allowance dated Dec. 13, 2021 issued in U.S. Appl. No. 15/753,963.
US Notice of Allowance dated Feb. 13, 2020 issued in U.S. Appl. No. 15/505,053.
US Notice of Allowance dated Jan. 18, 2018 issued in U.S. Appl. No. 14/775,618.
US Notice of Allowance dated Jun. 17, 2020 issued in U.S. Appl. No. 15/208,529.
US Notice of Allowance dated Mar. 4, 2022 issued in U.S. Appl. No. 15/975,678.
US Notice of Allowance dated May 19, 2021 issued in U.S. Appl. No. 16/200,467.
US Notice of Allowance dated May 4, 2020 issued in U.S. Appl. No. 15/506,696.
US Office Action dated Apr. 10, 2020 issued in U.S. Appl. No. 16/200,467.
US Office Action dated Apr. 17, 2019 issued in U.S. Appl. No. 15/344,381.
US Office Action dated Apr. 7, 2020 issued in U.S. Appl. No. 15/740,323.
US Office Action dated Apr. 8, 2015 issued in U.S. Appl. No. 14/355,812.
US Office Action dated Aug. 4, 2020 issued in U.S. Appl. No. 15/344,381.
US Office Action dated Aug. 6, 2021 issued in U.S. Appl. No. 15/750,499.
US Office Action dated Feb. 10, 2021 issued in U.S. Appl. No. 15/975,678.
US Office Action dated Jan. 5, 2022 issued in U.S. Appl. No. 17/269,970.
US Office Action dated Jan. 8, 2020 issued in U.S. Appl. No. 15/975,678.
US Office Action dated Jul. 13, 2016 issued in U.S. Appl. No. 14/775,618.
US Office Action dated Jul. 22, 2019 issued in U.S. Appl. No. 15/506,696.

(56)        References Cited

OTHER PUBLICATIONS

US Office Action dated Jul. 27, 2018 issued in U.S. Appl. No. 15/208,529.
US Office Action dated Jun. 4, 2019 issued in U.S. Appl. No. 15/505,053.
US Office Action dated Mar. 29, 2021 issued in U.S. Appl. No. 15/740,323.
US Office Action dated May 12, 2021 issued in U.S. Appl. No. 16/615,765.
US Office Action dated Nov. 13, 2020 issued in U.S. Appl. No. 15/753,963.
US Office Action dated Nov. 24, 2020 issued in U.S. Appl. No. 16/200,467.
US Office Action dated Oct. 18, 2016 issued in U.S. Appl. No. 15/208,529.
US Office Action dated Oct. 28, 2019 issued in U.S. Appl. No. 15/208,529.
US Office Action dated Oct. 3, 2017 issued in U.S. Appl. No. 15/025,201.
US Office Action dated Oct. 31, 2019 issued in U.S. Appl. No. 15/750,499.
U.S. Restriction Requirement dated Apr. 19, 2022 in U.S. Appl. No. 16/479,201.
Vital Signs—Cleveland Clinic [retrieved on Nov. 22, 2021] Retrieved from the Internet: URL: https://my.clevelandclinic.org/health/articles/10881-vital-signs [7 pages].
Wang, et al. (2017) "Incidence of C5 nerve root palsy after cervical surgery," Medicine, 96(45), 14 pages.
Ward, Alex R. (Feb. 2009) "Electrical Stimulation Using Kilohertz-Frequency Alternating Current," (2009) Phys Ther.89(2):181-190 [published online Dec. 18, 2008].
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 21 pages.
Anderson, K., "Targeting Recovery: Priorities of the Spinal Cord-Injured Population," Journal of Neurotrauma, vol. 11, No. 10, Oct. 2004, 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Augustine GJ, Purves D, Fitzpatrick D, eds., "Autonomic Regulation of the Bladder." Neuroscience, 2nd edition, Sunderland (MA): Sinauer Associates; 2001, Available from: https://www.ncbi.nlm.nih.gov/books/NBK10886/ ; downloaded Dec. 4, 2022, 2 pp.
Azimi, J. et al., "Batch Active Learning via Coordinated Matching", In Proceedings of the 29th International Conference on Machine Learning, (2012), 8 pages.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.

Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
CA Office Action dated Jul. 14, 2022 in Application No. CA2958924.
CA Office Action dated Jun. 19, 2023, in Application No. CA3030615.
CA Office Action dated Sep. 6, 2022, in Application No. CA3030615.
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Capogrosso, M., et al., "A Computational Model for Epidural Electrical Stimulation of Spinal Sensorimotor Circuits", Journal of Neuroscience, Dec. 4, 2013, vol. 33, No. 49, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Danner, S. et al., "Human spinal locomotor control is based on flexibly organized burst generators," Brain, vol. 138, No. 3, Available Online Jan. 12, 2015, Mar. 2015, 12 pages.
Danner, S. M. et al., "Body Position Influences Which neural structures are recruited by lumbar transcutaneous spinal cord stimulation", PLoS ONE, vol. 11, No. 1, (2016), 13 pages.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 Page.
Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.

(56)        References Cited

OTHER PUBLICATIONS

Edgerton, V. et al., "Training Locomotor Networks," Brain Research Reviews, vol. 57, Published Online Sep. 16, 2007, (Jan. 2008), 25 pages.

Fleshman, J. et al., "Electronic Architecture of Type-Identified a-Motoneurons in the Cat Spinal Cord," Journal of Neurophysiology, vol. 60, No. 1, (Jul. 1, 1988), 26 pages.

Frey, M. et al., "A Novel Mechatronic Body Weight Support System," IEEE Transactions on Neural Systems and Rehabilitation Engineering, vol. 14, No. 3, (Sep. 18, 2006), 11 pages.

Fuentes, R. et al., "Spinal Cord Stimulation Restores Locomotion in Animal Models of Parkinson's Disease," Science, vol. 323, No. 5921, (Mar. 20, 2009), 14 pages.

Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.

Gerasimenko, Yu. P. et al., "Noninvasive Reactivation of Motor Descending Control after Paralysis", Journal of Neurotrauma, vol. 32, (2015), 13 pages.

Gilja, V. et al., "A high-performance neural prosthesis enabled by control algorithm design," Nature Neuroscience, vol. 15, No. 12, Published Online Nov. 18, 2012, (Dec. 2012), 56 pages.

Gittins, J. C., "Bandit Processes and Dynamic Allocation Indices", Journal of the Royal Statistical Society B, vol. 41, No. 2, (1979), pp. 148-164.

Giuliano, F. et al., "Neural control of erection", Physiology & Behavior, vol. 83, No. 2, Nov. 15, 2004, pp. 189-201.

Guyatt, G. H. et al., "The 6-minute walk: a new measure of exercise capacity in patients with chronic heart failure," Canadian Medical Association Journal, vol. 132, No. 8, (Apr. 15, 1985), 5 pages.

Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.

Harkema, S. et al., "Human Lumbosacral Spinal Cord Interprets Loading During Stepping," Journal of Neurophysiology, vol. 77, No. 2, (Feb. 1, 1997), 15 pages.

Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.

Hashtrudi-Zaad, K. et al., "On the Use of Local Force Feedback for Transparent Teleoperation," Proceedings of the 1999 IEEE International Conference on Robotics and Automation, (May 10, 1999), 7 pages.

Hennig, P. et al., "Entropy search for information-efficient global optimization" Journal of Machine Learning Research (JMLR), vol. 13, (Jun. 2012), pp. 1809-1837.

Hidler, J. et al., "ZeroG: Overground gait and balance training system," Journal of Rehabilitation Research & Development, vol. 48, No. 4, Available as Early as Jan. 1, 2011, (2011), 12 pages.

Hines, M. L. et al., "The Neuron Simulation Environment," Neural Computation, vol. 9, No. 6, (Aug. 15, 1997), 26 pages.

Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.

Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.

Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.

Ivanenko, Y. P. et al., "Temporal Components of the Motor Patterns Expressed by the Human Spinal Cord Reflect Foot Kinematics,"

Journal of Neurophysiology, vol. 90, No. 5, Nov. 2003, Published Online Jul. 9, 2003, (2003), 11 pages.

Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.

Jarosiewicz, B. et al., "Virtual typing by people with tetraplegia using a self-calibrating intracortical brain-computer interface," Science Translational Medicine, vol. 7, No. 313, (Nov. 11, 2015), 11 pages.

Jilge, B. et al., "Initiating extension of the lower limbs in subjects with complete spinal cord injury by epidural lumbar cord stimulation", Exp Brain Res., vol. 154, (2004), pp. 308-326.

Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 11 pages.

Jones, D. R. et al., "Efficient Global Optimization of Expensive Black-Box Functions", Journal of Global Optimization, vol. 13, (1998), pp. 455-492.

Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.

JP Office Action dated Nov. 21, 2022, in Application No. 2021-188658 with English translation.

JP Office Action dated Feb. 17, 2023 in Application No. JP2019-539960 with English translation.

JP Office Action dated Jul. 18, 2023 in Application No. JP2021-509772 with English translation.

JP Office Action dated Sep. 26, 2022, in Application No. JP2019-539960 with English translation.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Las Vegas, Nevada, (Sep. 9, 1998), 6 pages.

Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.

Kleinberg, R. et al., "Multi-armed bandits in metric spaces", In STOC, Computer and Automation Research Institute of the Hungarian Academy of Sciences, Budapest, Hungary, (2008), pp. 681-690.

Kocsis, L. et al. "Bandit Based Monte-Carlo Planning", European Conference on Machine Learning, Springer, Berlin, Heidelberg, (Sep. 2006), pp. 282-293.

Krassioukov, A. et al., "A Systematic Review of the Management of Autonomic Dysreflexia Following Spinal Cord Injury," Archives of Physical Medicine and Rehabilitation, vol. 90, No. 4, Apr. 2009, 27 pages.

Krassioukov, A. et al., "A Systematic Review of the Management of Orthostatic Hypotension Following Spinal Cord Injury," Archives of Physical Medicine and Rehabilitation, vol. 90, No. 5, May 2009, 22 pages.

Krause, A. et al. "Contextual Gaussian Process Bandit Optimization", In Advances in Neural Information Processing Systems (NIPS), (2011), 9 pages.

Krause, A. et al., "Near-optimal Nonmyopic Value of Information in Graphical Models", In UAI, (2005), 8 pages.

Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.

Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 11 pages.

(56) References Cited

OTHER PUBLICATIONS

Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.

Liu, J. et al., "Stimulation of the Parapyramidal Region of the Neonatal Rat Brain Stem Produces Locomotor-Like Activity Involving Spinal 5-HT7 and 5-HT2A Receptors", Journal of Neurophysiology, vol. 94, No. 2, Published Online May 4, 2005, (Aug. 1, 2005), 13 pages.

Lizotte, D. et al., "Automatic gait optimization with Gaussian process regression", In IJCAI, (2007), pp. 944-949.

Lovely, R. et al., "Effects of Training on the Recovery of Full-Weight-Bearing Stepping in the Adult Spinal Cat," Experimental Neurology, vol. 92, No. 2, (May 1986), 15 pages.

Lozano, A. et al., "Probing and Regulating Dysfunctional Circuits Using Deep Brain Stimulation," Neuron, vol. 77, No. 3, (Feb. 6, 2013), 19 pages.

Mcintyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.

Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.

Minassian, K. et al., "Human lumbar cord circuitries can be activated by extrinsic tonic input to generate locomotor-like activity", Human Movement Science, vol. 26, No. 2, (2007), pp. 275-295.

Minassian, K. et al., "Neuromodulation of lower limb motor control in restorative neurology", Clinical Neurology and Neurosurgery, vol. 114, (2012), pp. 489-497.

Minassian, K. et al., "Peripheral and Central Afferent Input to the Lumbar Cord", Biocybernetics and Biomedical Engineering, vol. 25, No. 3, (2005), pp. 11-29.

Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.

Minev, I. R. et al., "Electronic dura mater for long-term multimodal neural interfaces," Science Magazine, vol. 347, No. 6218, (Jan. 9, 2015), 64 pages.

Minoux, M., Accelerated greedy algorithms for maximizing submodular set functions. Optimization Techniques, LNCS, (1978), pp. 234-243.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.

Murg, M et al., "Epidural electric stimulation of posterior structures of the human lumbar spinal cord: 1. Muscle twitches—a functional method to define the site of stimulation", Spinal Cord, vol. 38, (2000), pp. 394-402.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.

Musienko, P. et al., "Controlling specific locomotor behaviors through multidimensional monoaminergic modulation of spinal circuitries," The Journal of Neuroscience, vol. 31, No. 25, (Jun. 22, 2011), 15 pages.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nandra, M. S. et al., "A wireless microelectrode implant for spinal cord stimulation and recording in rats", Presentation Abstract, 2013, 104 Pages.

National Health Service., "Lumbar Decompression Surgery: When it's used", NHS, Apr. 28, 2022, https://www.nhs.uk/conditions/lumbar-decompression-surgery/why-its-done/#:-:text=Cauda%20equina%20syndrome%20is%20a,is%20severe%20or%20getting%20worse.

Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.

Pearson, K. G., "Generating the walking gait: role of sensory feedback," Progress in Brain Research, vol. 143, Chapter 12, Published Online Nov. 28, 2003, (2004), 7 pages.

Phillips, A. et al., "Contemporary Cardiovascular Concerns after Spinal Cord Injury: Mechanisms, Maladaptations, and Management," Journal of Neurotrama, vol. 32, No. 24, Dec. 15, 2015, 17 pages.

Phillips, A. et al., "Perturbed and spontaneous regional cerebral blood flow responses to changes in blood pressure after high-level spinal cord injury: the effect of midodrine," Journal of Applied Physiology, vol. 116, No. 6, Mar. 15, 2014, Available Online Jan. 16, 2014, 9 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, May 2014, 8 pages.

Pratt, G. et al., "Stiffness Isn't Everything," Proceedings of the Fourth International Symposium on Experimental Robotics, (Jun. 30, 1995), 6 pages.

Pratt, J. et al., "Series elastic actuators for high fidelity force control," Industrial Robot: An International Journal, vol. 29, No. 3, Available as Early as Jan. 1, 2002, 13 pages.

Prochazka, A. et al., "Ensemble firing of muscle afferents recorded during normal locomotion in cats," The Journal of Physiology, vol. 507, No. 1, (Feb. 15, 1998), 12 pages.

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning (GPML) Toolbox", The Journal of Machine Learning Research, vol. 11, (2010), pp. 3011-3015.

Rasmussen, C. E. et al., "Gaussian Processes for Machine Learning", The MIT Press, Cambridge, Massachusetts, (2006), 266 pages.

Rasmussen, C. E. "Gaussian Processes in Machine Learning", L.N.A.I., vol. 3176, (2003) pp. 63-71.

Rattay, F. et al., "Epidural electrical stimulation of posterior structures of the human lumbosacral cord: 2. Quantitative analysis by computer modeling", Spinal Cord, vol. 38, (2000), pp. 473-489.

Reinkensmeyer, D. et al., "Tools for understanding and optimizing robotic gait training," Journal of Rehabilitation Research & Development, vol. 43, No. 5, (Aug. 2006), 14 pages.

Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.

Robbins, H., "Some Aspects of the Sequential Design of Experiments", Bull. Amer. Math. Soc., vol. 58, (1952), pp. 527-535.

Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.

Ryzhov, I. O. et al., "The knowledge gradient algorithm for a general class of online learning problems", Operations Research, vol. 60, No. 1, (2012), pp. 180-195.

Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.

(56) References Cited

OTHER PUBLICATIONS

Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.

Srinivas, N. et al., "Gaussian process optimization in the bandit setting: No regret and experimental design", In Proceedings of the 27th International Conference on Machine Learning, (2010), 17 pages.

Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.

Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.

Sun, F. et al., "Sustained axon regeneration induced by co-deletion of PTEN and SOCS3", Nature, vol. 480, No. 7377, Published Online Nov. 6, 2011, (Dec. 15, 2011), 12 pages.

Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.

Tenne, Y. et al., "Computational Intelligence in Expensive Optimization Problems", vol. 2 of Adaptation, Learning, and Optimization, Springer, Berlin Heidelberg, (2010), pp. 131-162.

Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.

U.S. Final Office Action dated Apr. 6, 2023 in U.S. Appl. No. 16/615,765.

U.S. Final Office Action dated Jun. 1, 2023 in U.S. Appl. No. 16/479,201.

U.S. Final Office Action dated Oct. 13, 2022, in U.S. Appl. No. 17/269,970.

U.S. Non Final Office Action dated Aug. 25, 2022 in U.S. Appl. No. 16/479,201.

U.S. Non-Final Office Action dated Apr. 28, 2023, in U.S. Appl. No. 17/270,402.

U.S. Non-Final Office Action dated Feb. 15, 2023 in U.S. Appl. No. 15/740,323.

U.S. Non-Final office Action dated Jun. 20, 2022 in U.S. Appl. No. 16/615,765.

U.S. Restriction Requirement dated Dec. 1, 2022 in U.S. Appl. No. 17/270,402.

Vallery, H. et al., "Compliant Actuation of Rehabilitation Robots," IEEE Robotics & Automation Magazine, vol. 15, No. 3, (Sep. 12, 2008), 10 pages.

Van Den Brand, R. et al., "Restoring Voluntary Control of Locomotion after Paralyzing Spinal Cord Injury," Science Magazine, vol. 336, No. 6085, (Jun. 1, 2012), 5 pages.

Wan, D. et al., "Life-threatening outcomes associated with autonomic dysreflexia: A clinical review," Journal of Spinal Cord Medicine, vol. 37, No. 1, (Jan. 2014), 9 pages.

Wenger, N. et al. "Closed-loop neuromodulation of spinal sensorimotor circuits controls refined locomotion after complete spinal cord injury" Sci Transl Med. Sep. 24, 2014, vol. 6, Issue 255, (10 pages).

Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.

Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.

Wernig, A. et al., "Laufband locomotion with body weight support improved walking in persons with severe spinal cord injuries", Paraplegia, vol. 30, No. 4, (Apr. 1992), 10 pages.

Wernig, A., "Ineffectiveness of Automated Locomotor Training," Archives of Physical Medicine and Rehabilitation, vol. 86, No. 12, (Dec. 2005), 2 pages.

Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.

Widmer, C. et al., Inferring latent task structure for multitask learning by multiple kernel learning, BMC Bioinformatics, vol. 11, (Suppl 8:S5), (2010), 8 pages.

Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.

Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.

Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.

Zhang, T. C. et al., "Mechanisms and models of spinal cord stimulation for the treatment of neuropathic pain," Brain Research, vol. 1569, Published Online May 4, 2014, (Jun. 20, 2014), 13 pages.

Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.

Examination Report in Australian Application No. 2024216471; received on Feb. 9, 2026.

* cited by examiner

A

Biphasic electrical stimulation signal – no delay

Delayed biphasic electrical stimulation signal

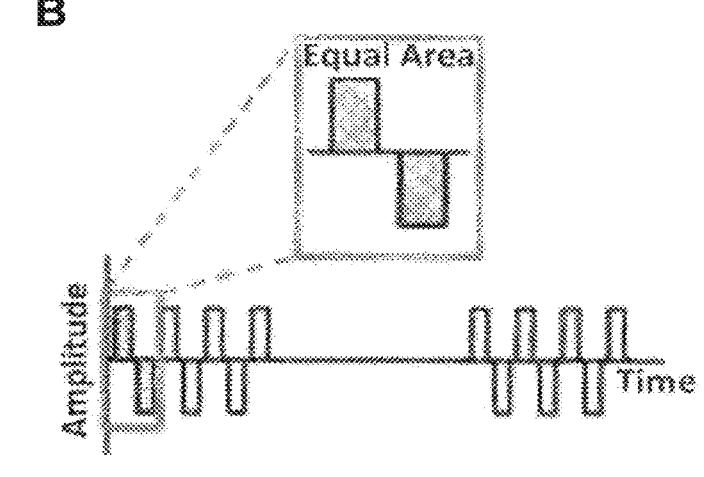
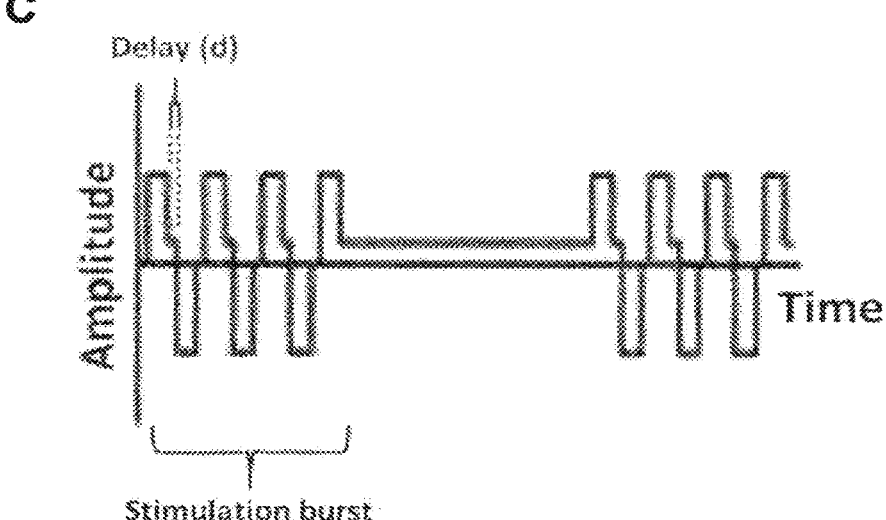
Fig. 2, cont'd.

A

B

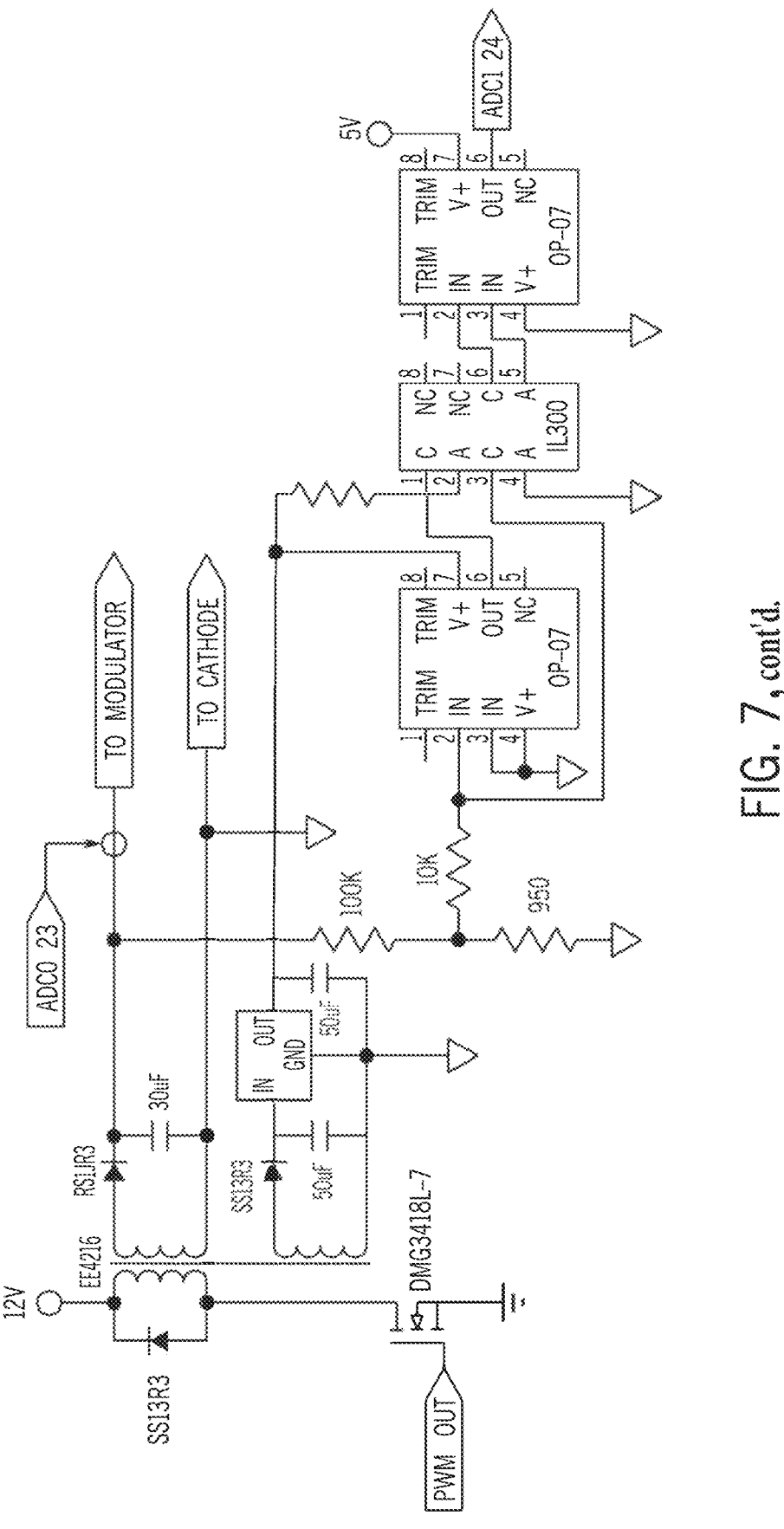
FIG. 7, cont'd.

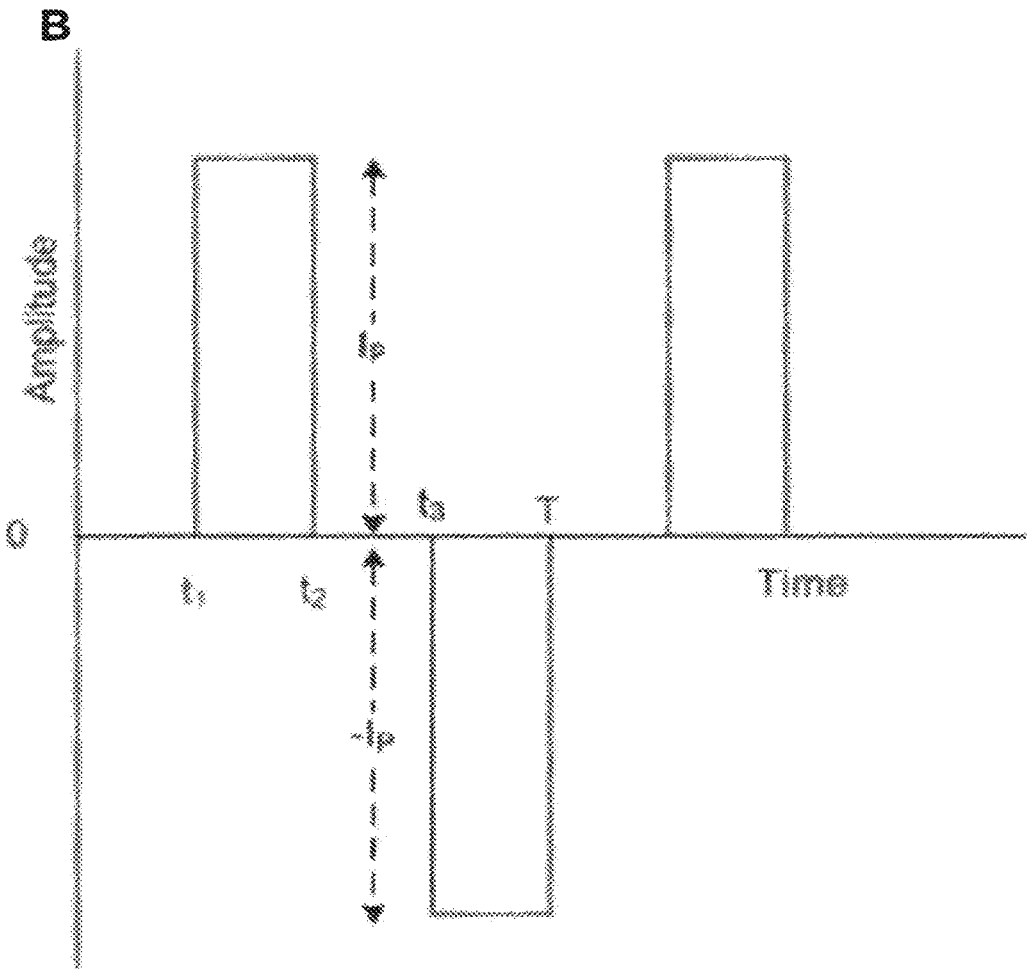
Fig. 8, cont'd.

A

B
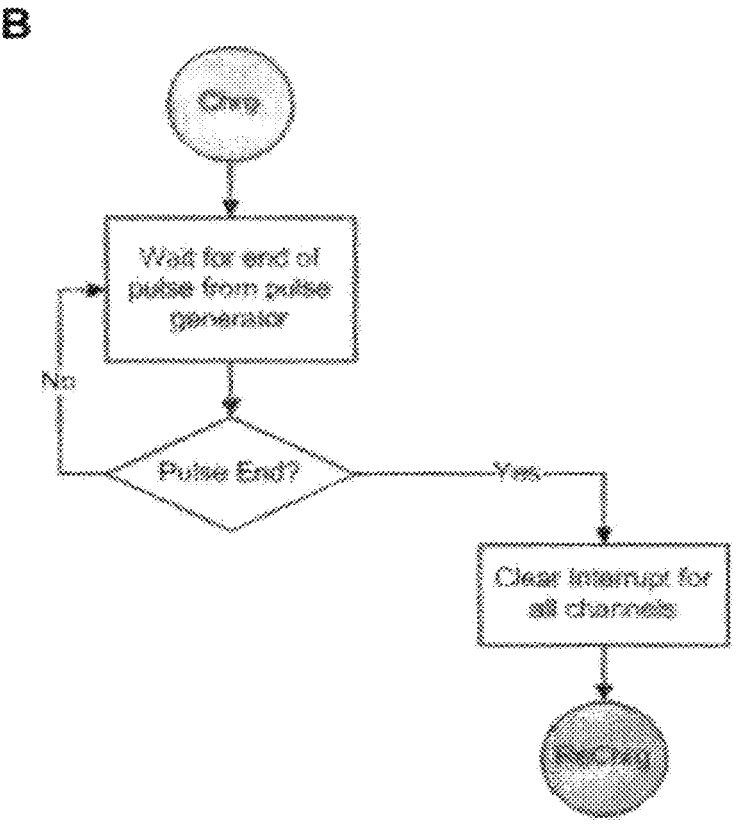
Fig. 12, cont'd.

A

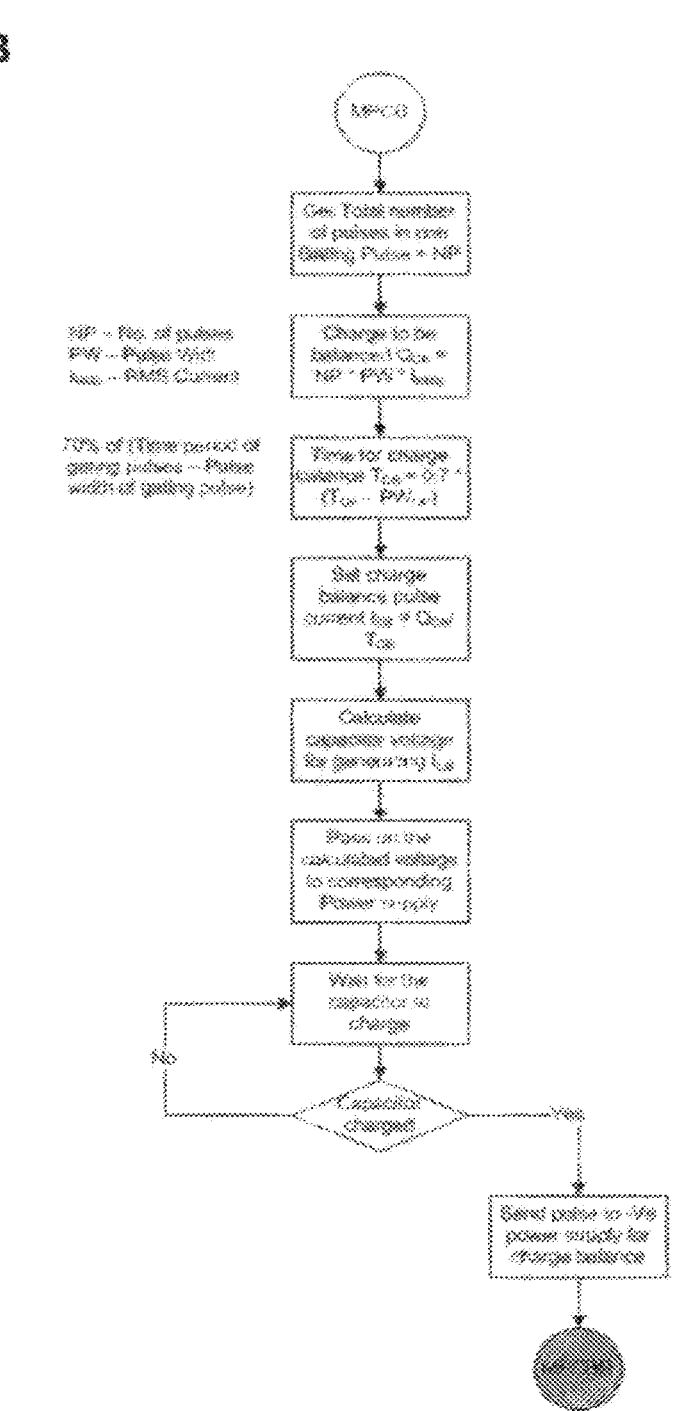
Fig. 15, cont'd.

C
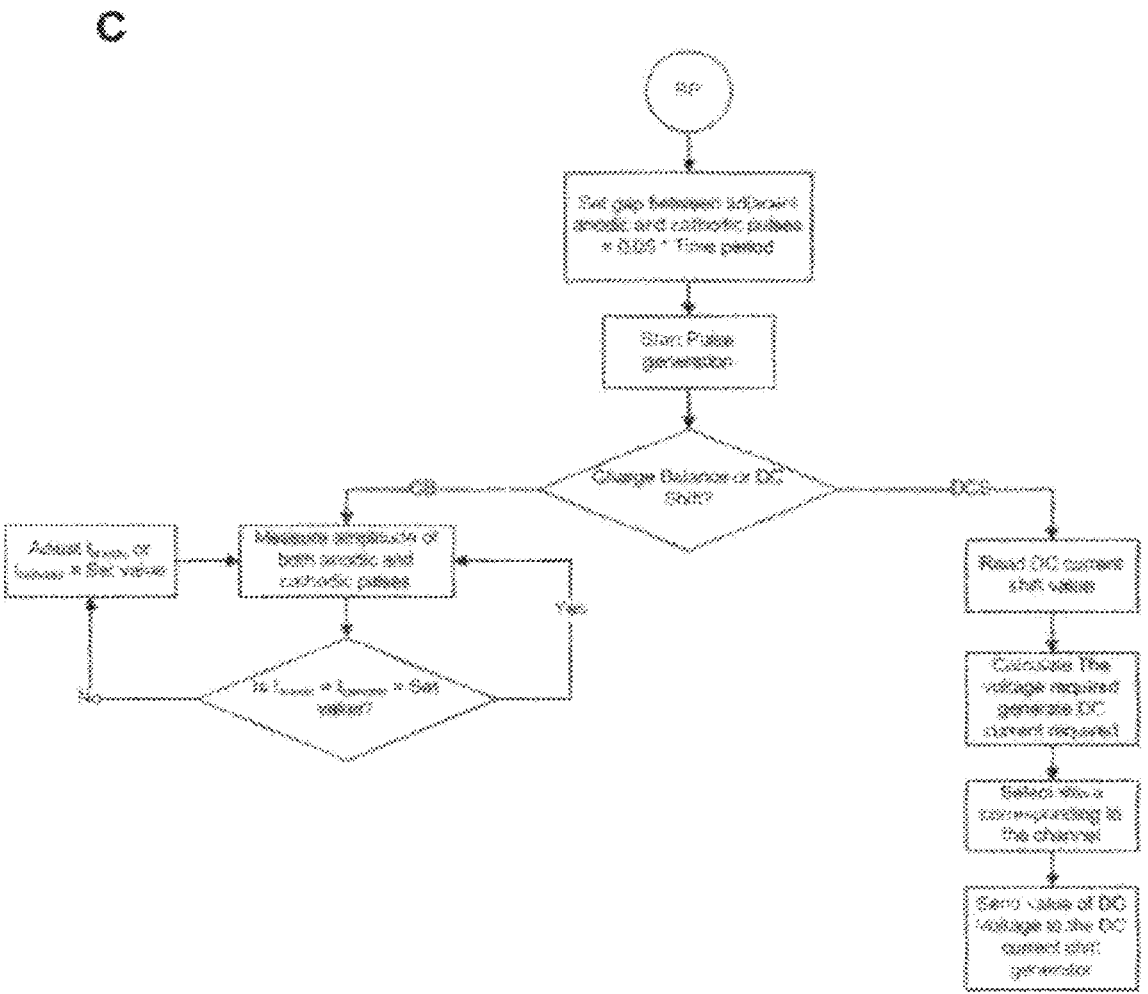
Fig. 15, cont'd.

A

B
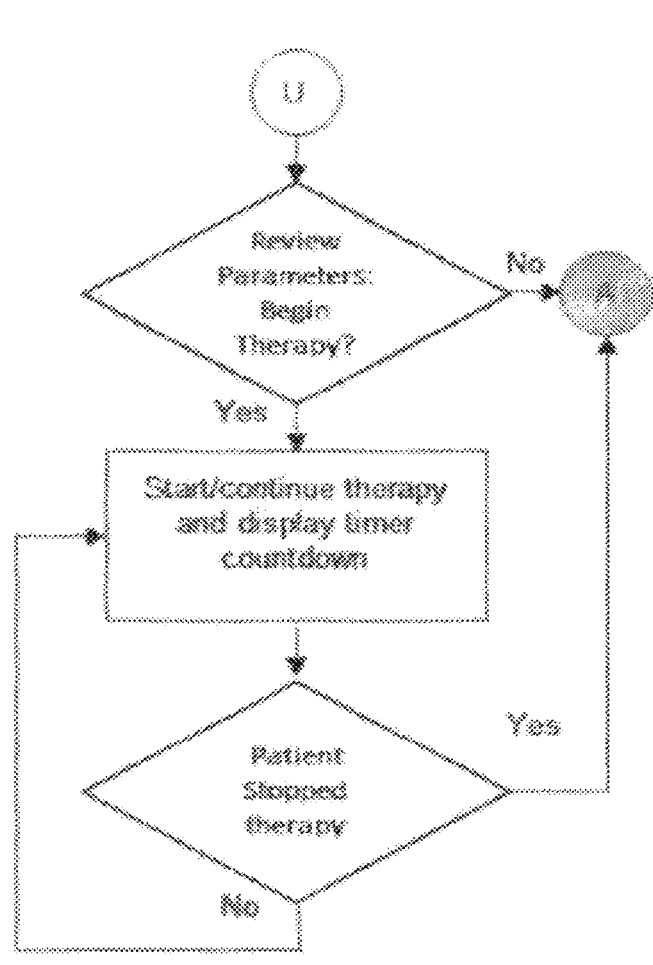
Fig. 19, con't.d

C
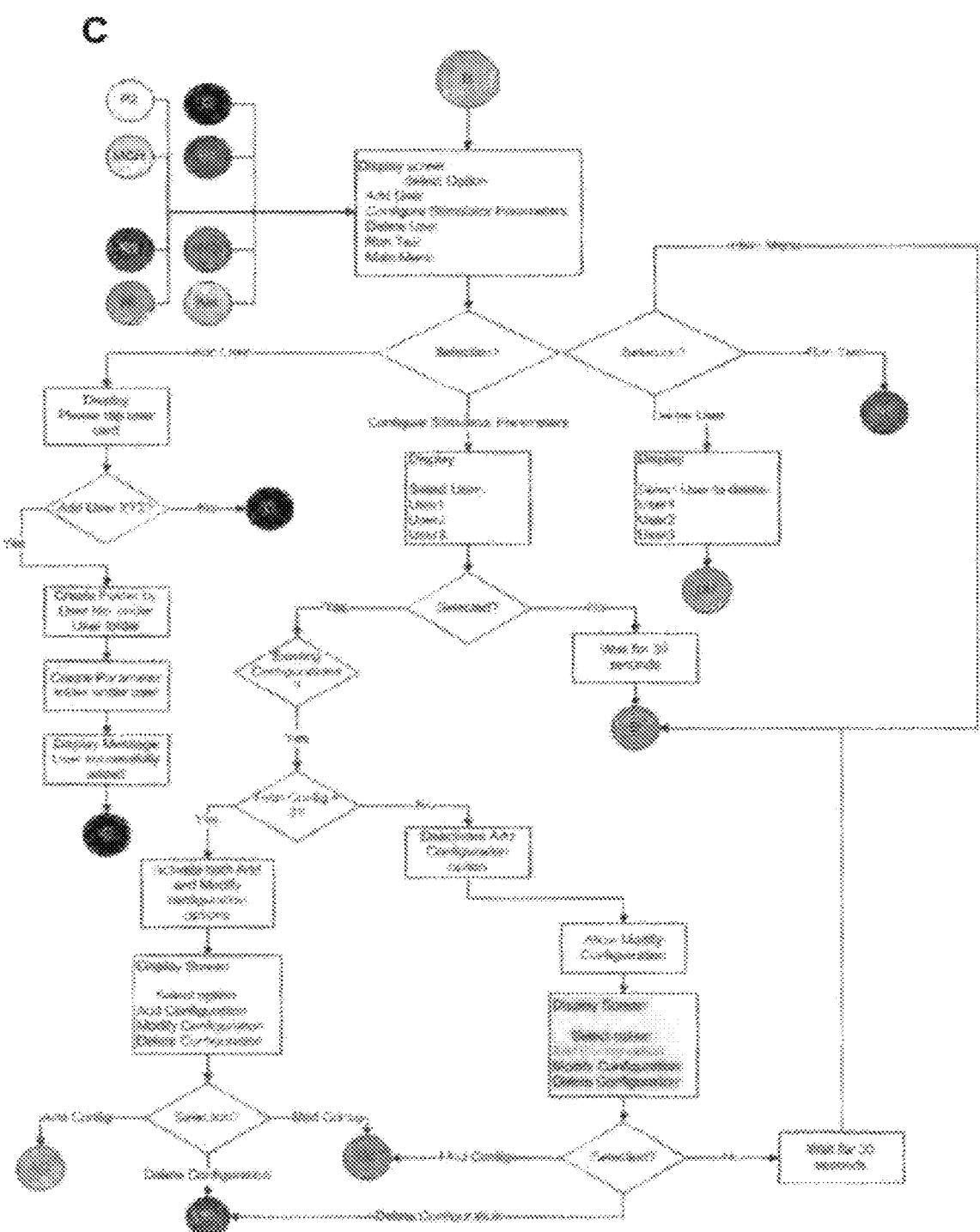
Fig. 19, con't.d

D
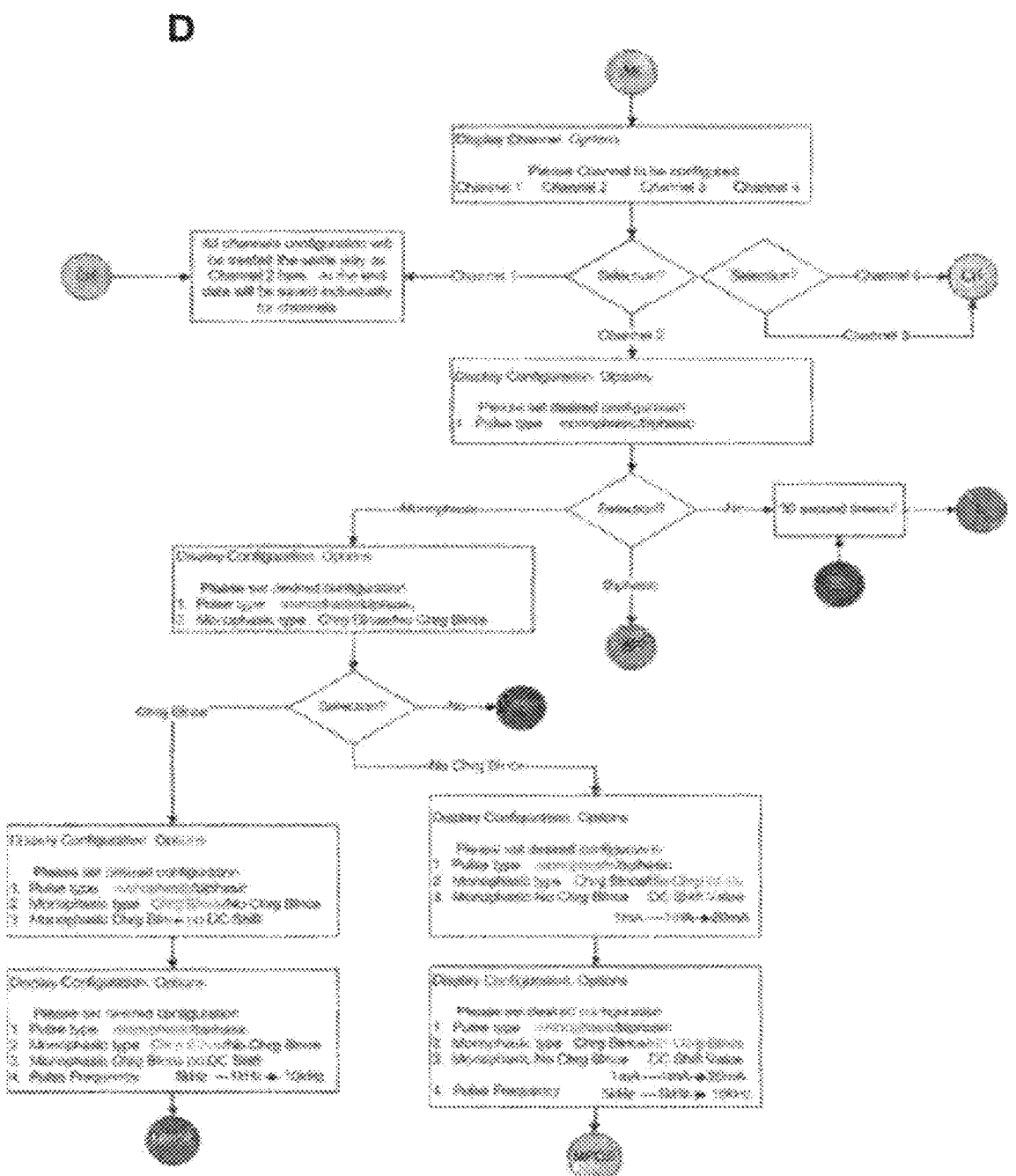
Fig. 19, con't.d

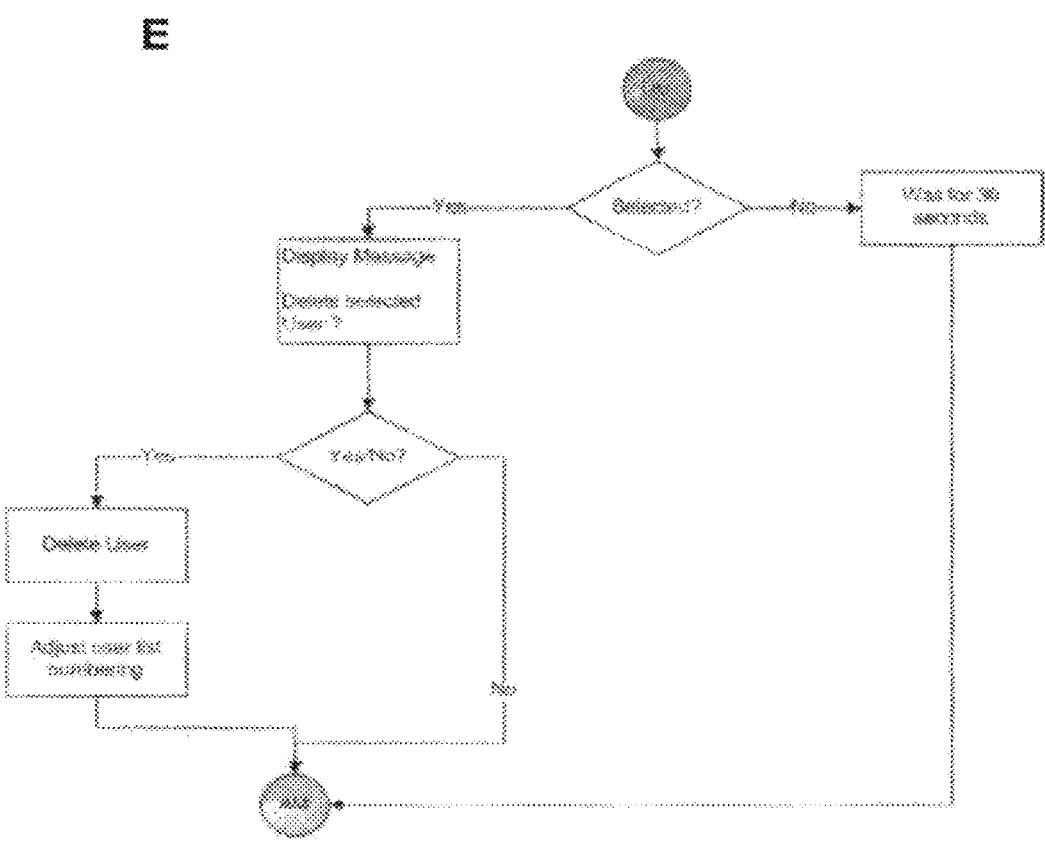
Fig. 19, con't.d

F
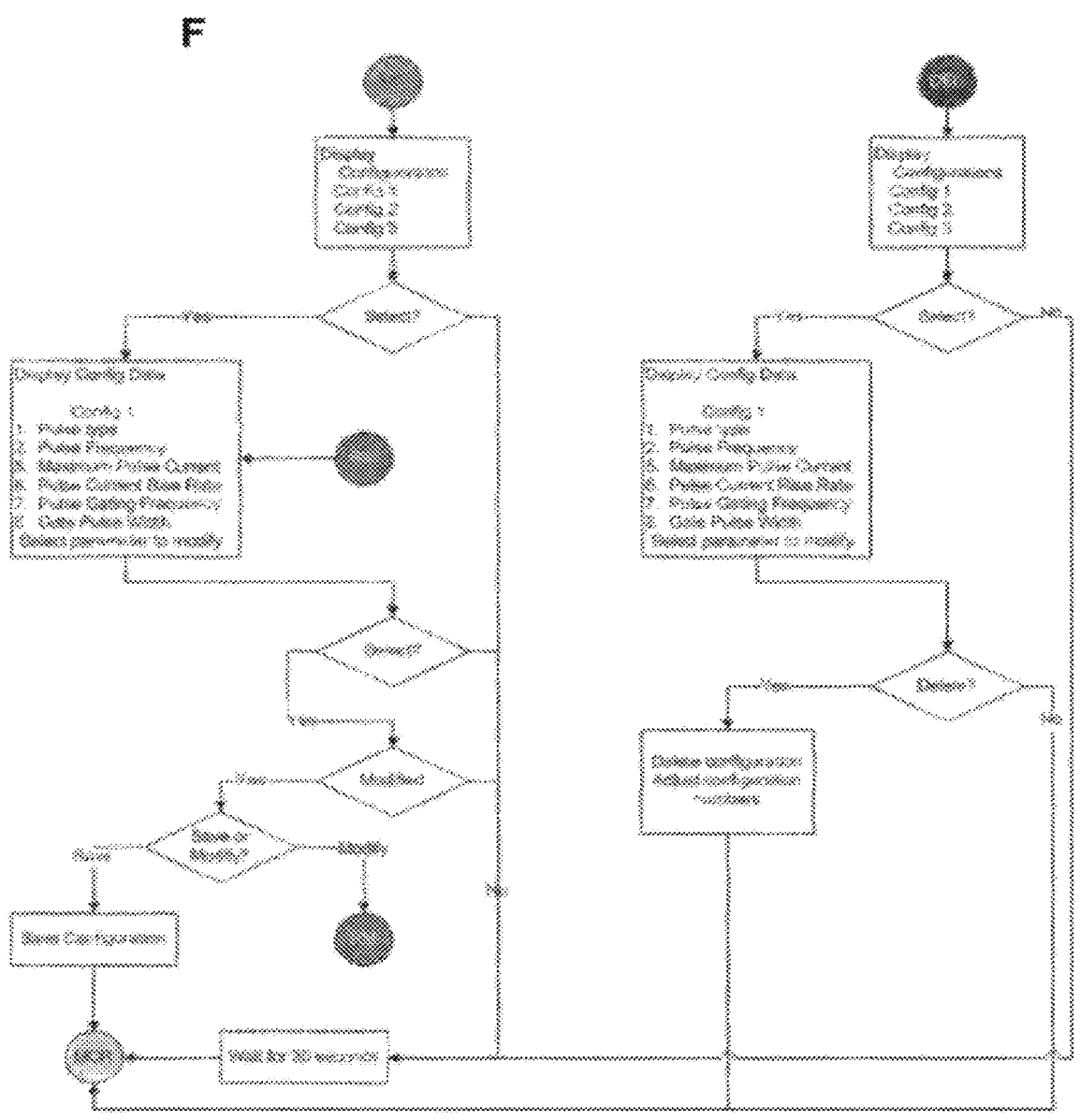
Fig. 19, con't.d

G
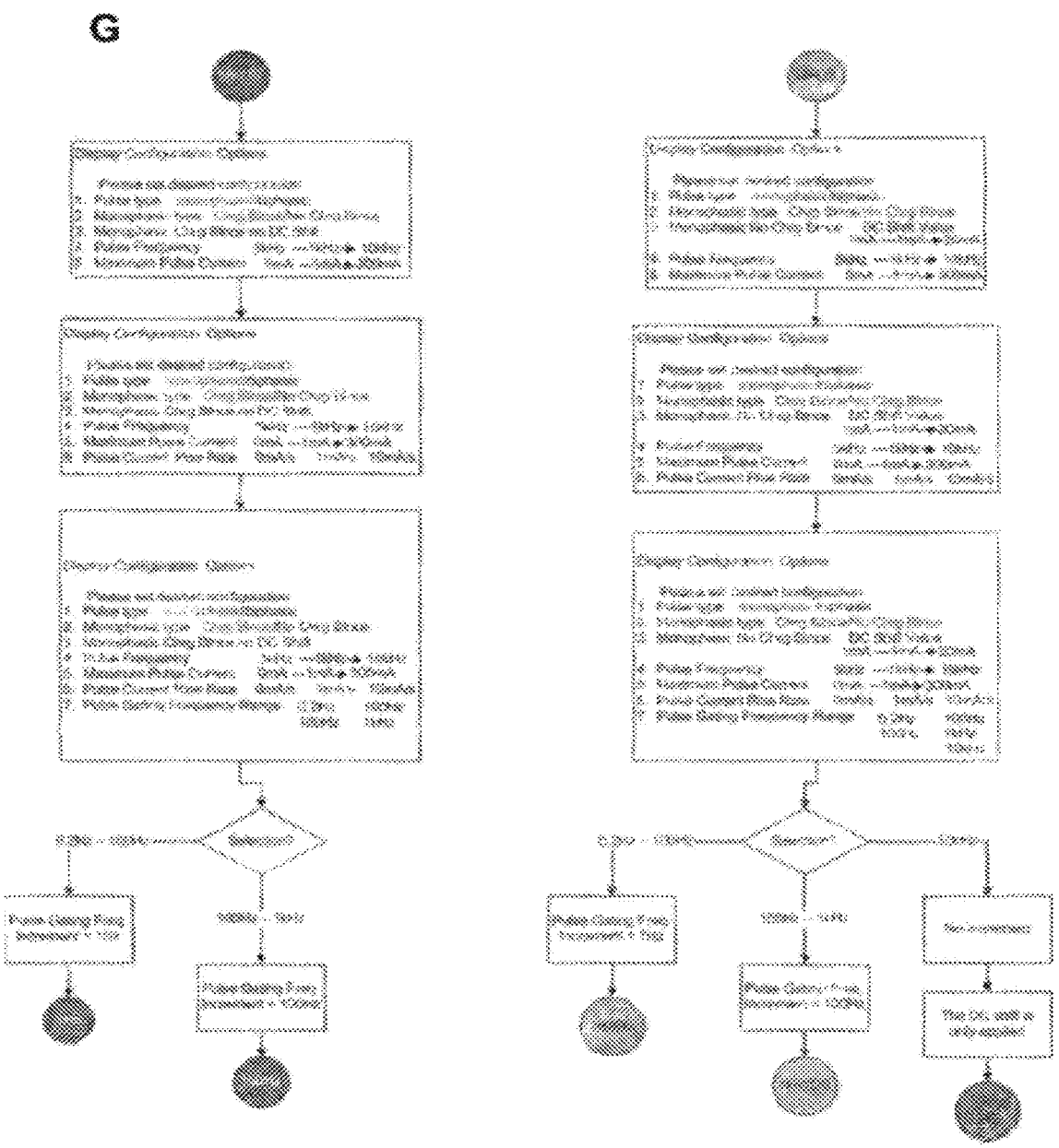
Fig. 19, con't.d

H
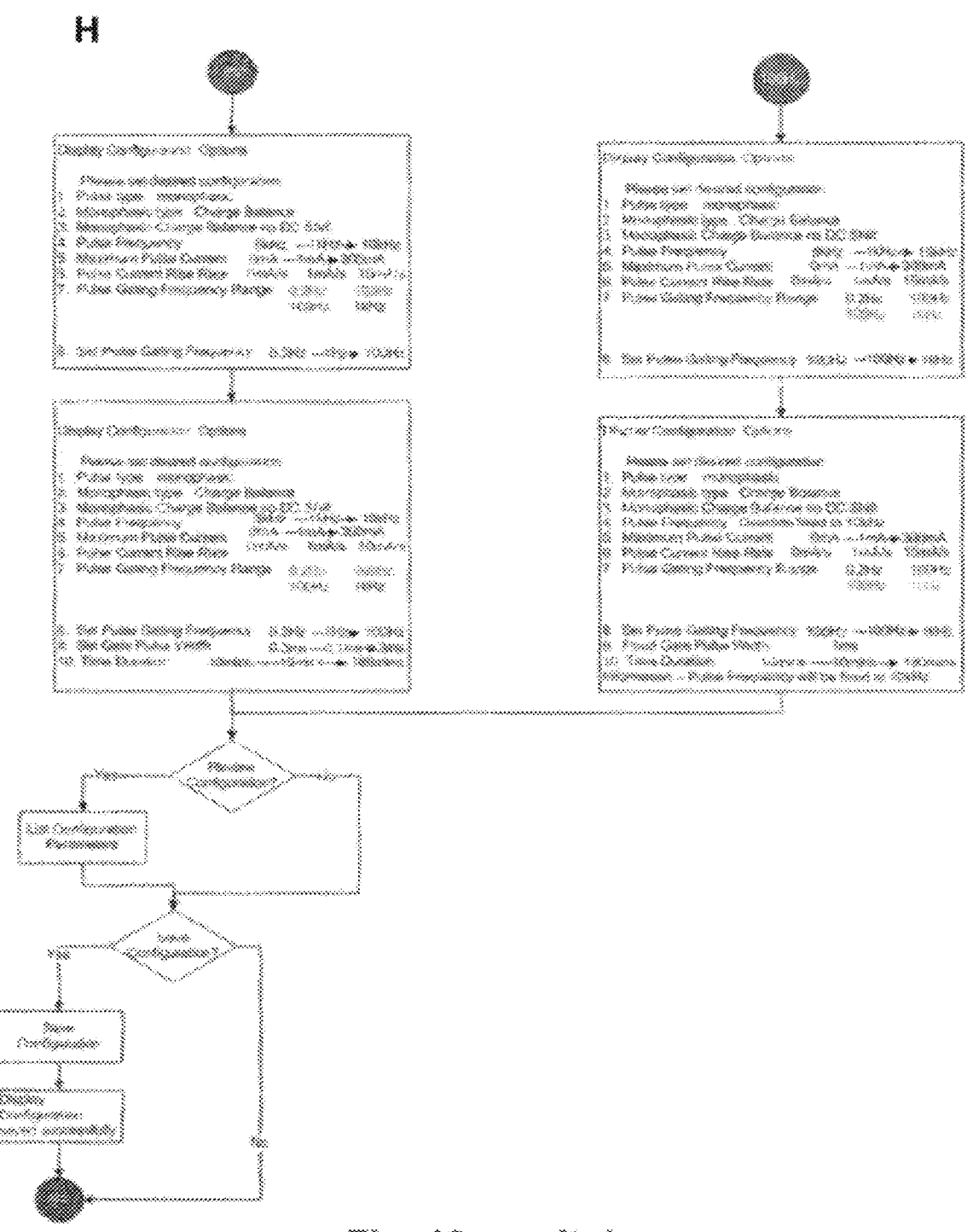
Fig. 19, con't.d

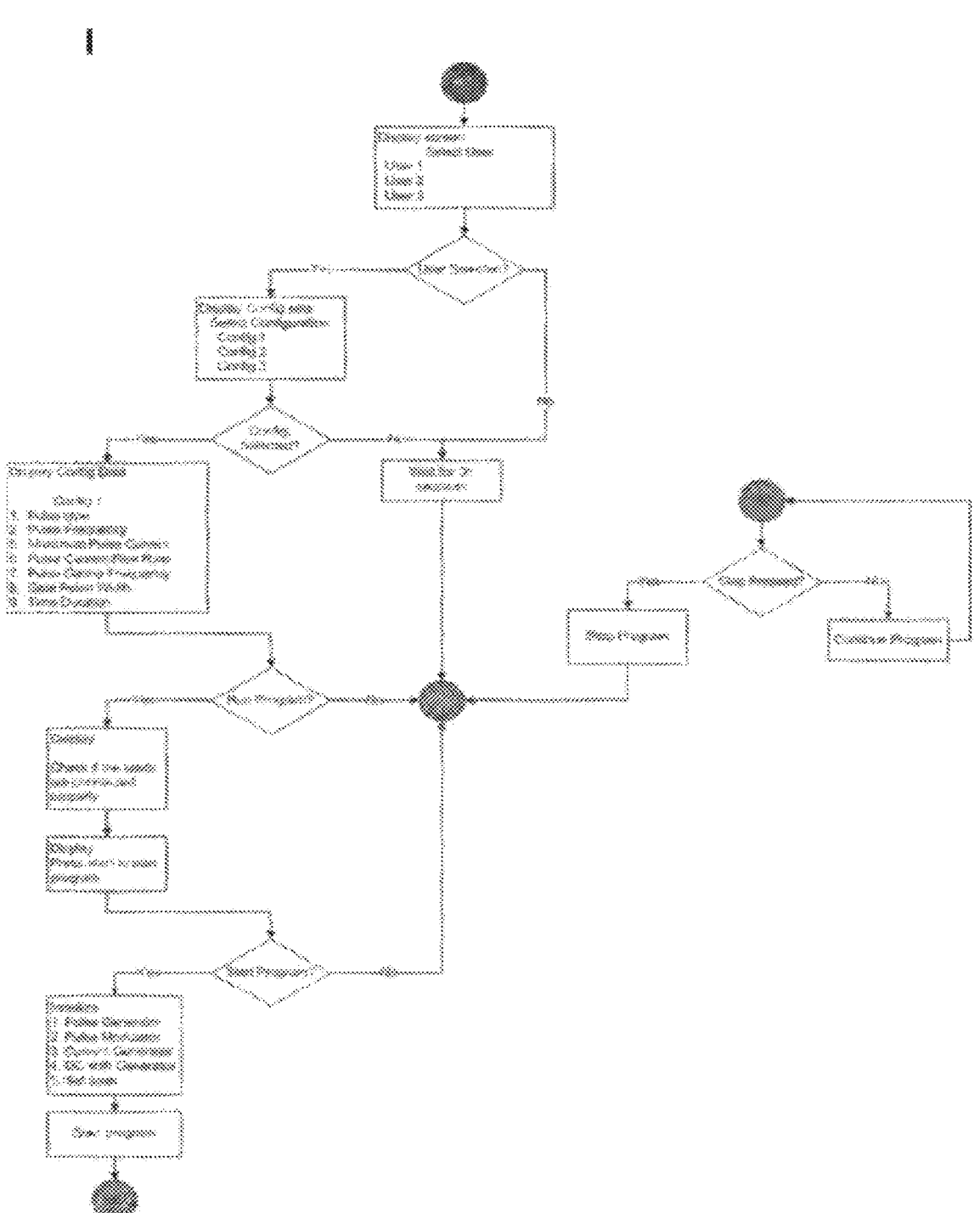
Fig. 19, con't.d

J
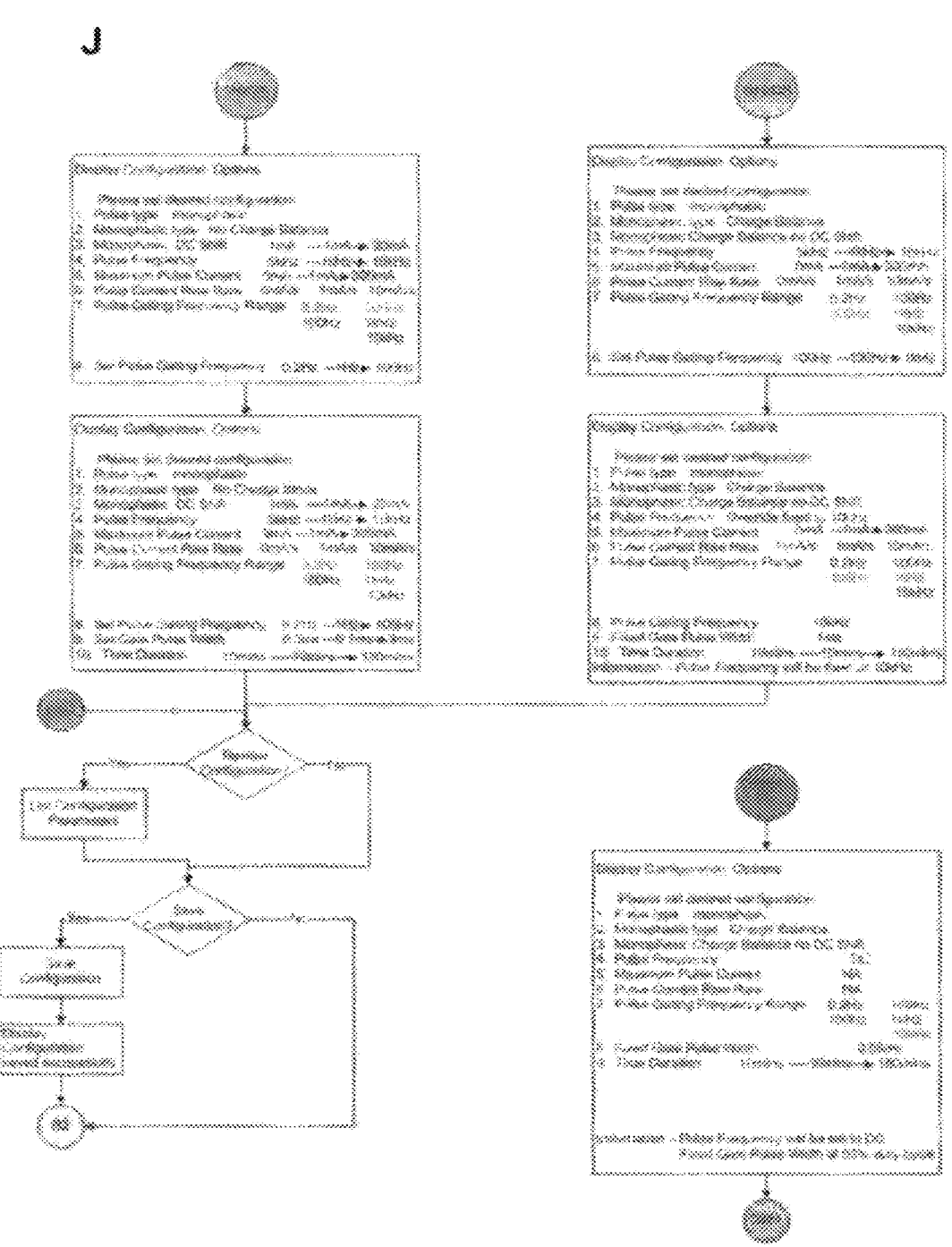
Fig. 19, con't.d

K
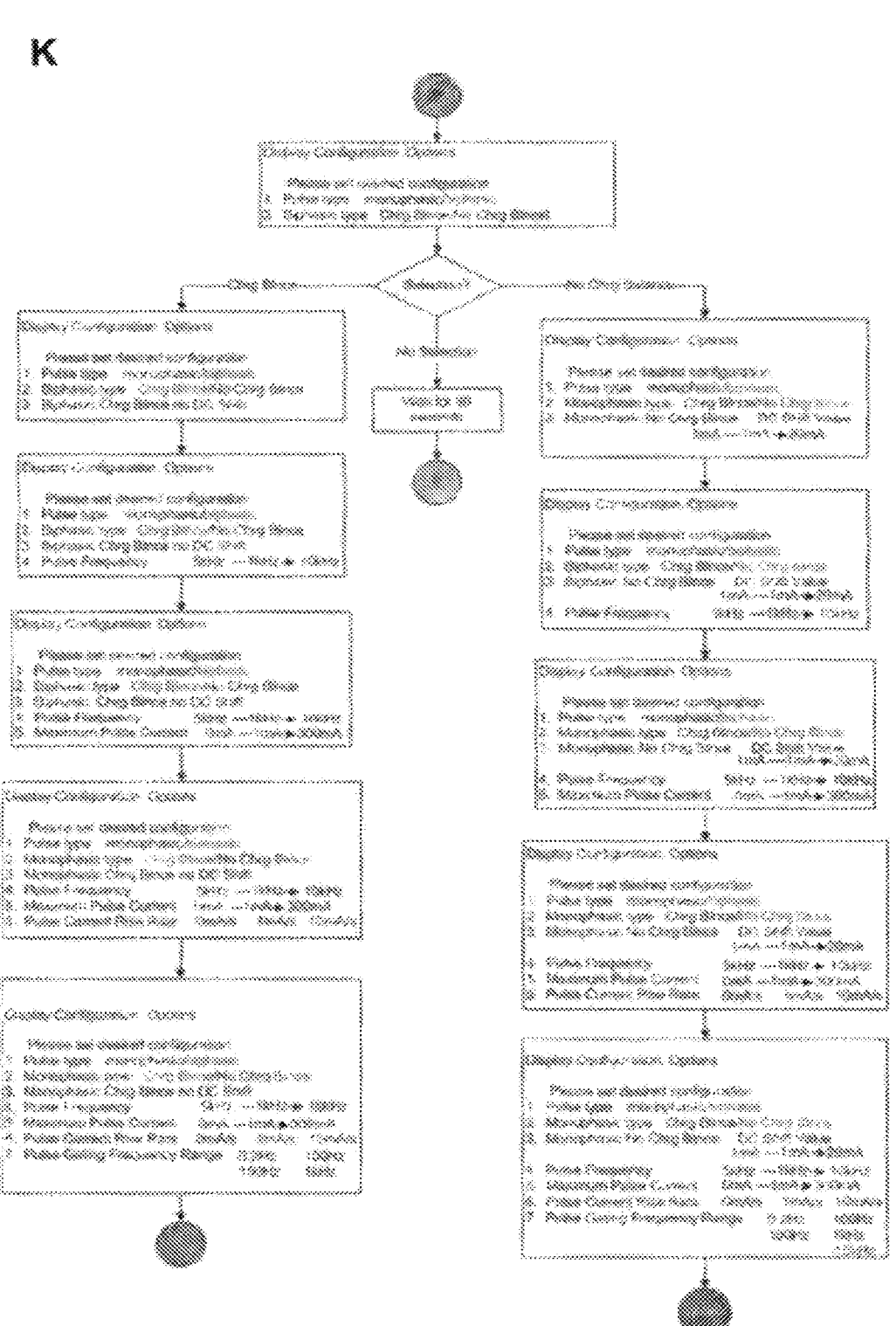
Fig. 19, con't.d

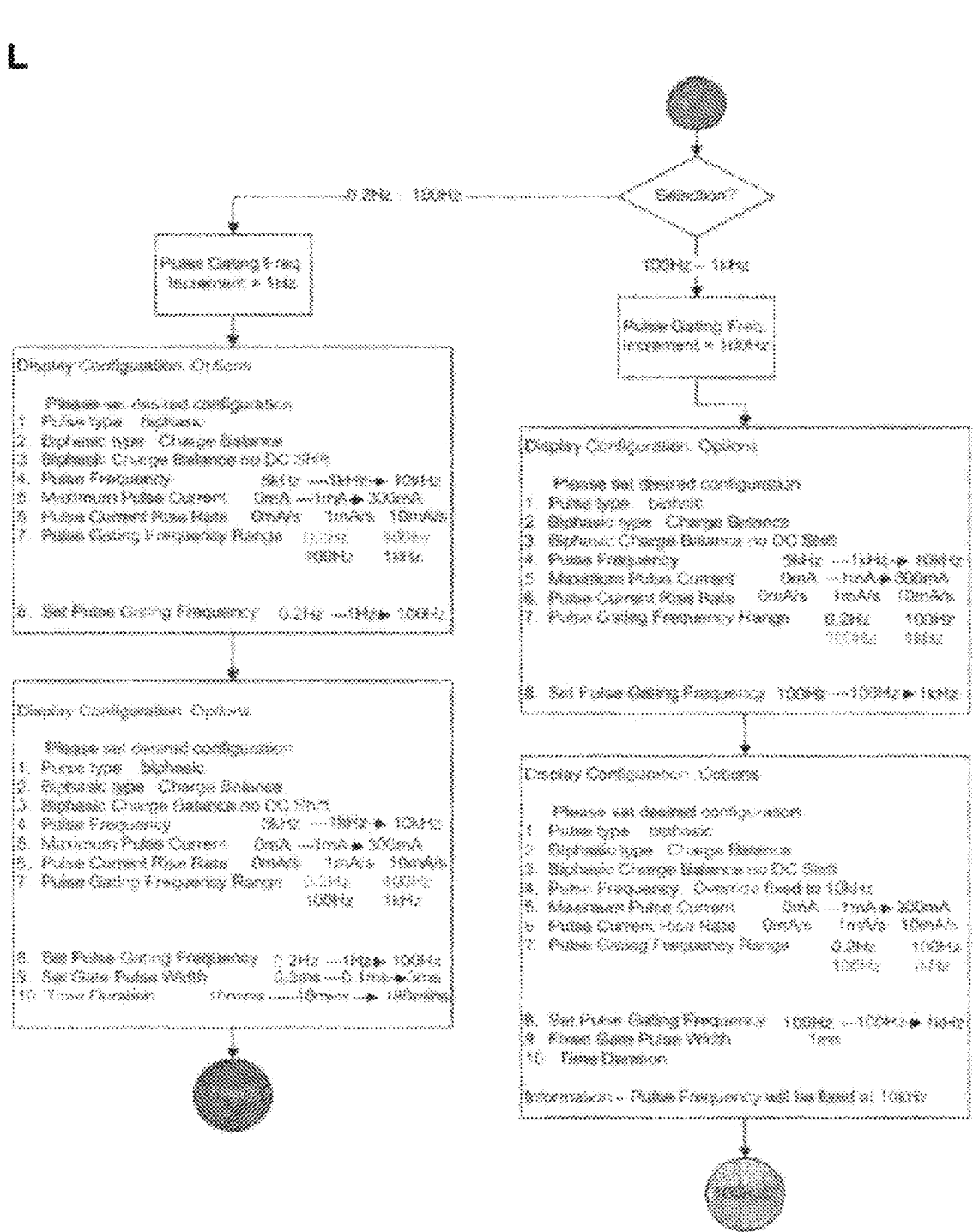
Fig. 19, con't.d

M
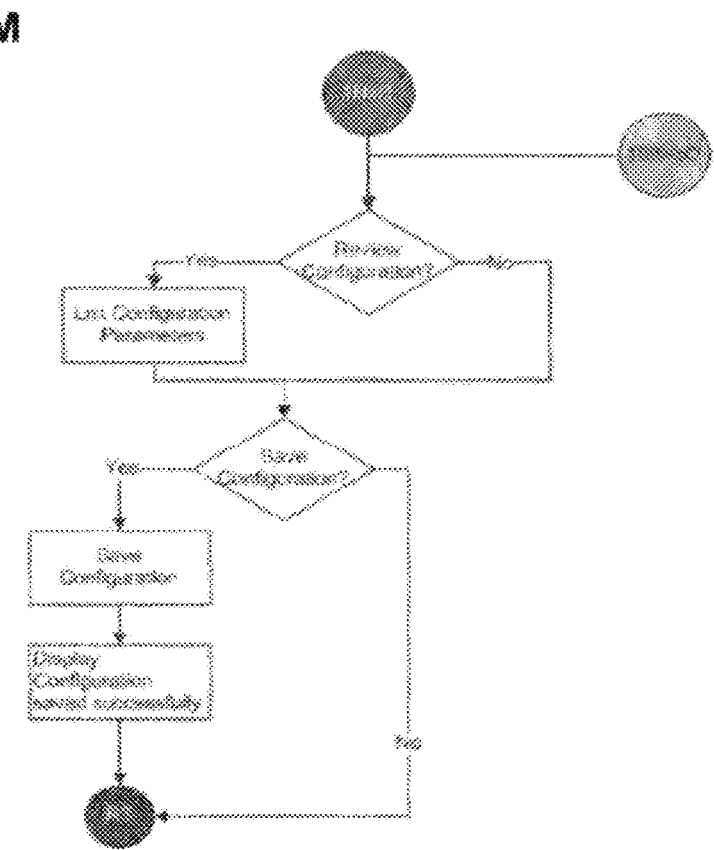
Fig. 19, con't.d

N
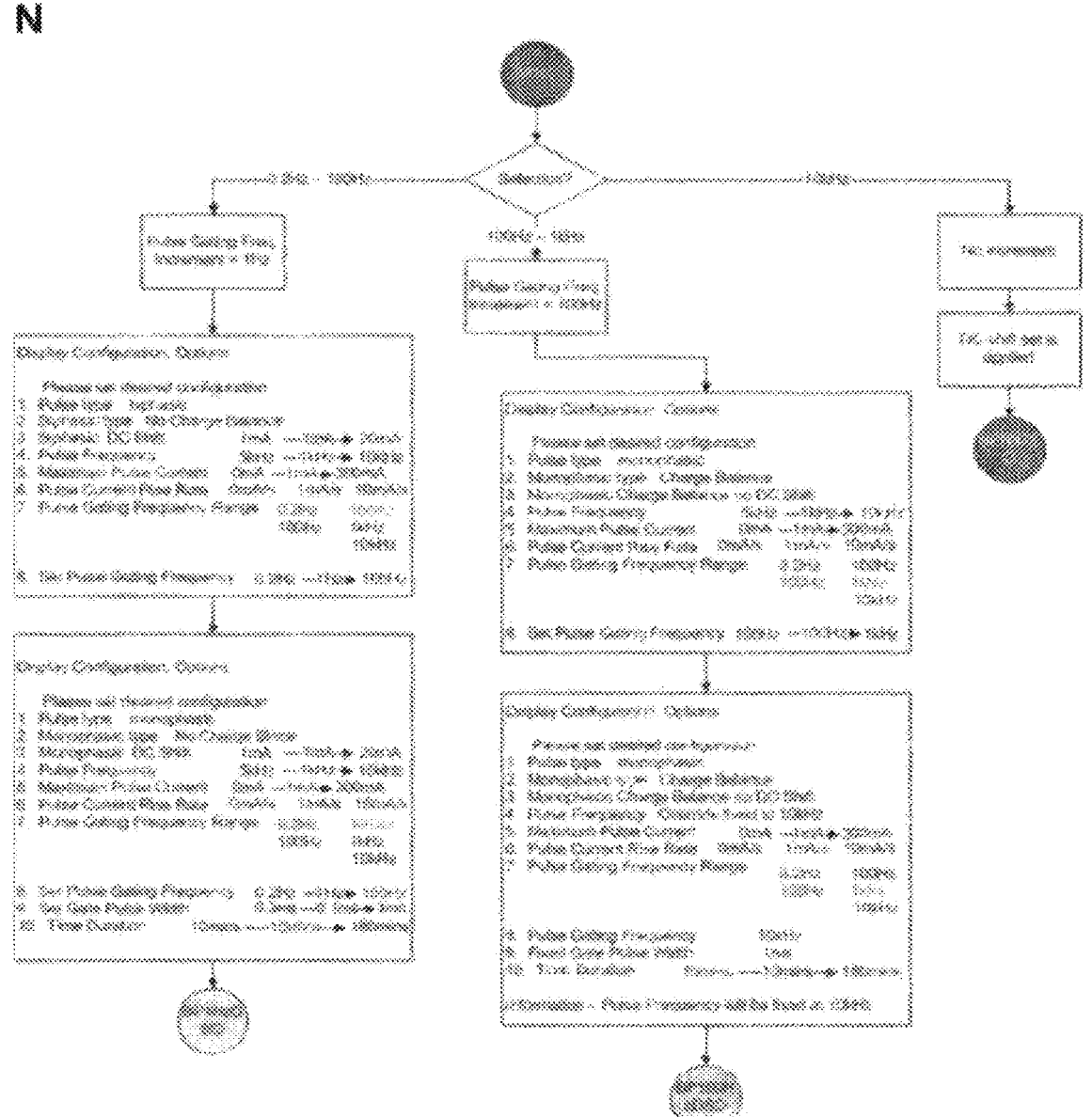
Fig. 19, con't.d

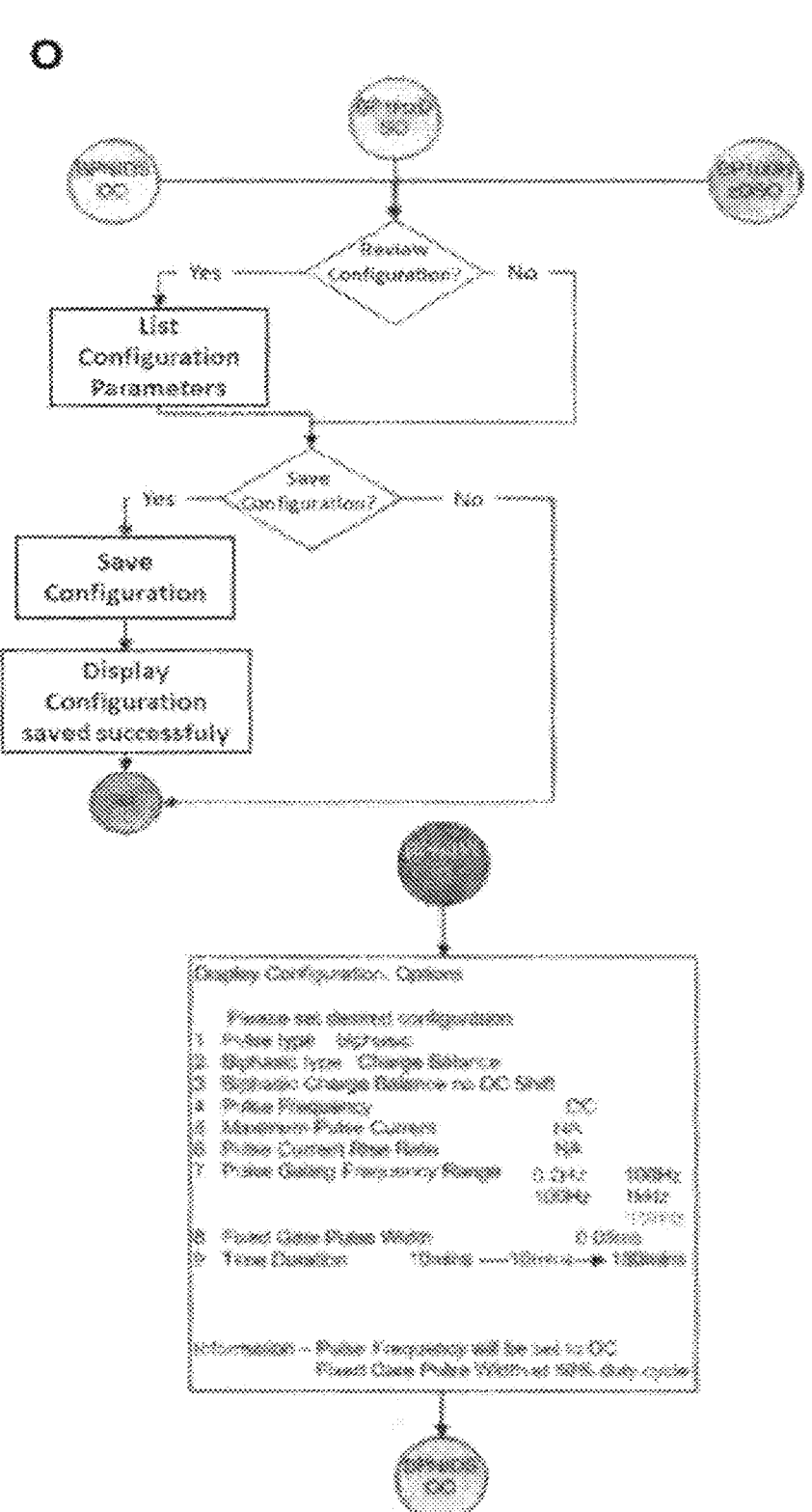
Fig. 19, con't.d

Ch 1: ⊥⊥⊥_____⊥⊥_____⊥⊥_____⊥⊥_____⊥⊥_____⊥⊥_____

Ch 2: ____⊥⊥⊥⊥⊥____⊥⊥⊥⊥⊥____⊥⊥⊥⊥⊥____⊥⊥⊥⊥⊥____⊥⊥⊥⊥⊥____⊥⊥⊥⊥⊥____⊥⊥⊥⊥⊥

Ch 3: _____⊥⊥⊥_⊥⊥⊥_⊥⊥⊥_⊥⊥⊥_⊥⊥⊥_⊥⊥⊥_⊥⊥⊥_⊥⊥⊥_⊥⊥⊥_⊥⊥⊥_⊥⊥⊥_⊥⊥⊥_⊥⊥⊥_⊥⊥⊥___

Ch 1:  2 sec on, 10 sec off
　　Ch 2:  5 sec on, 5 sec off
　　Ch 3:  3 sec on, 1 sec off, and so on

Fig. 20

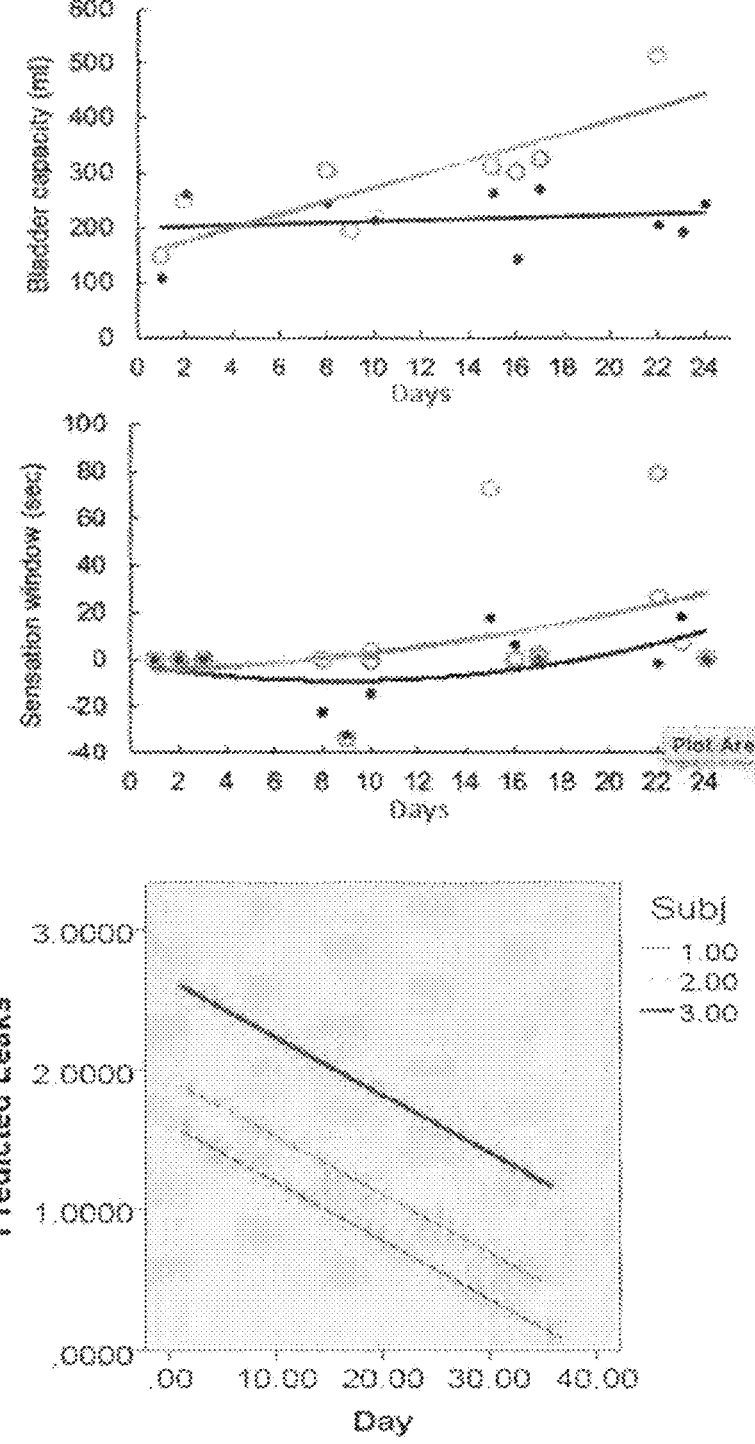
Fig. 27, cont'd.

A URETHANE ANESTHETIZED ADULT RAT

B DYNAMIC STIMULATION PROTOCOL

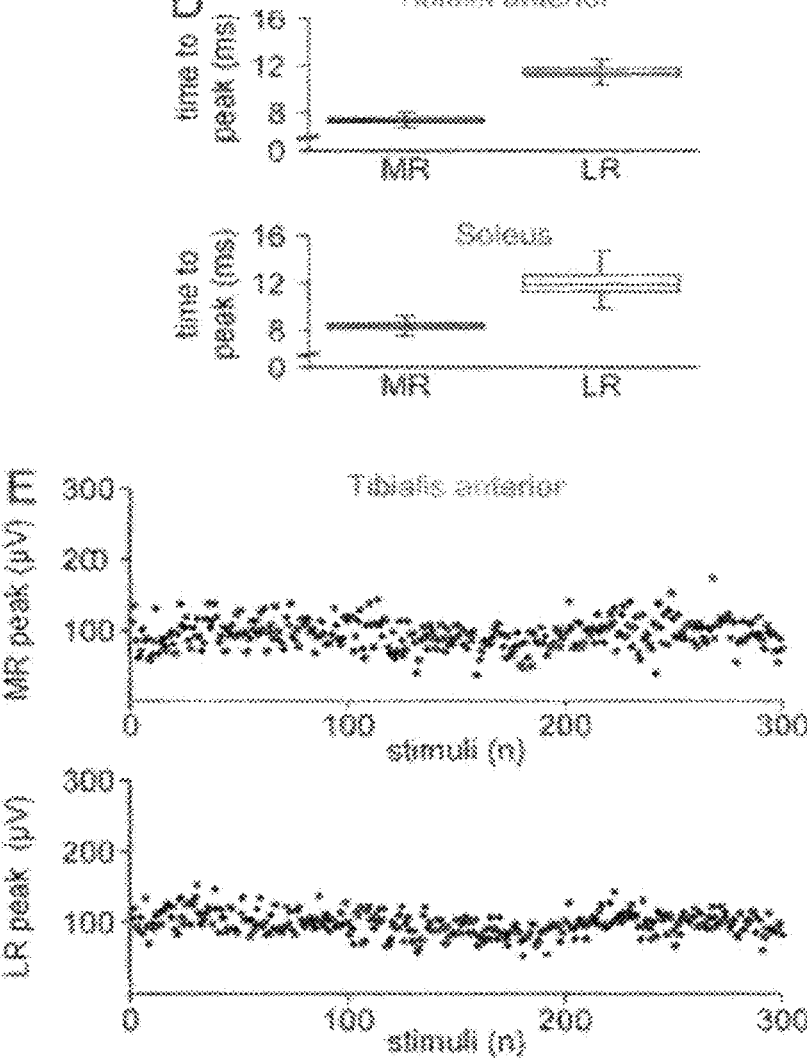
Fig. 29, cont'd.

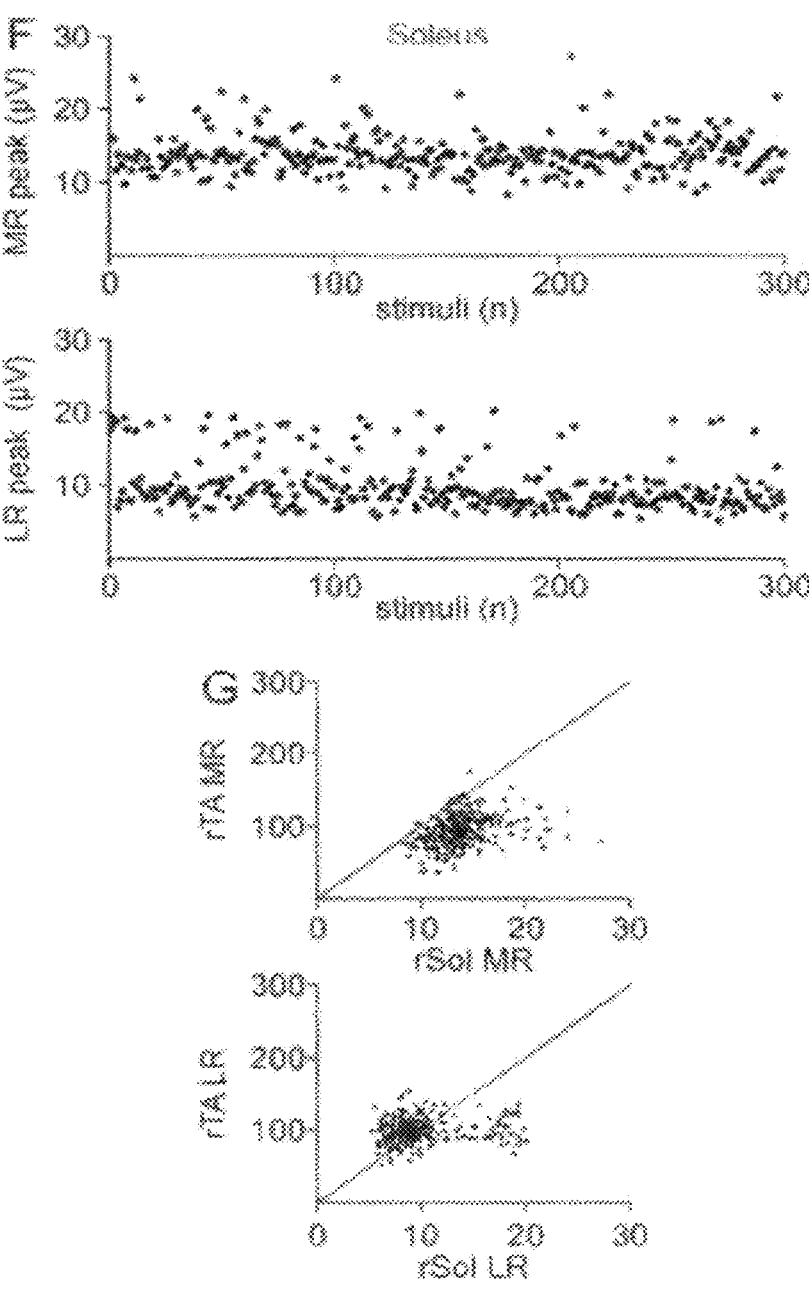
Fig. 29, cont'd.

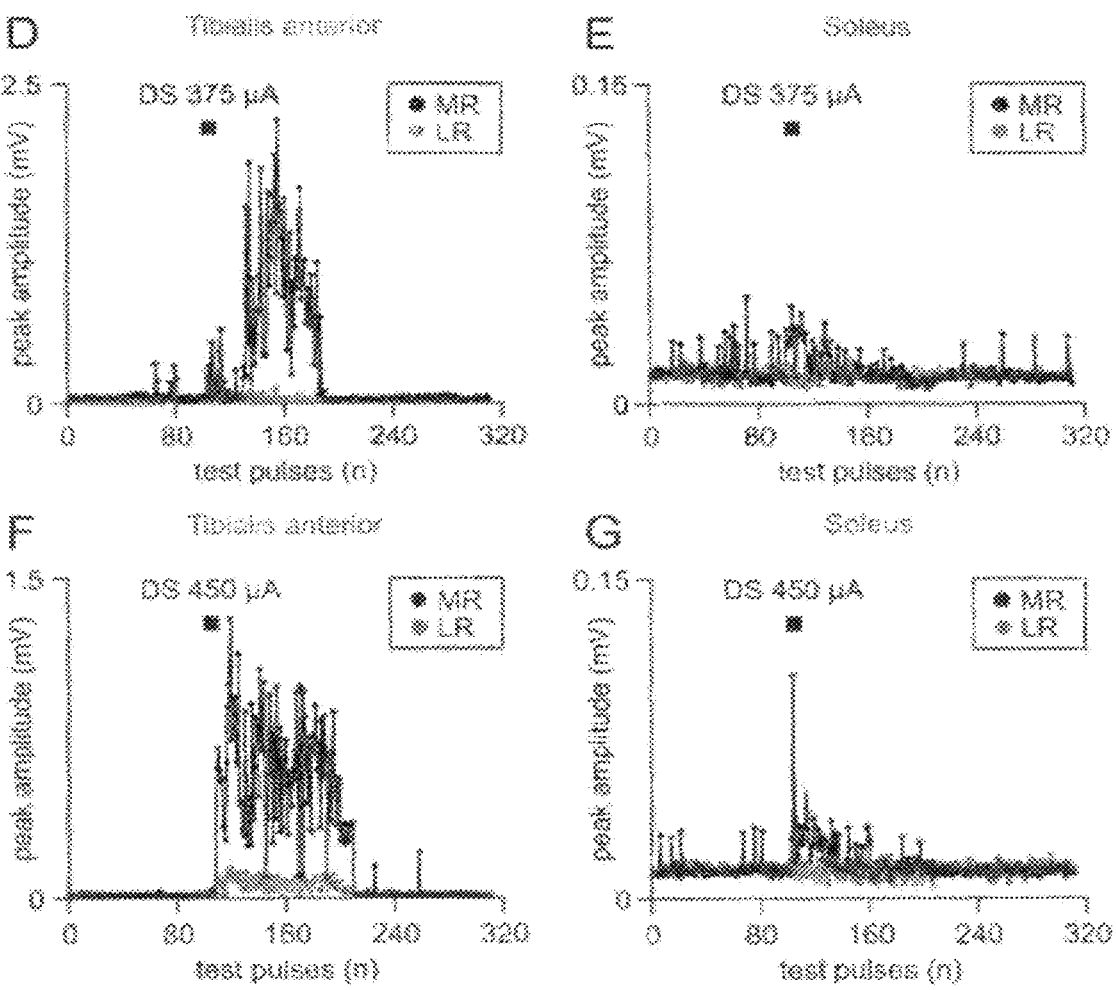
Fig. 30, cont'd.

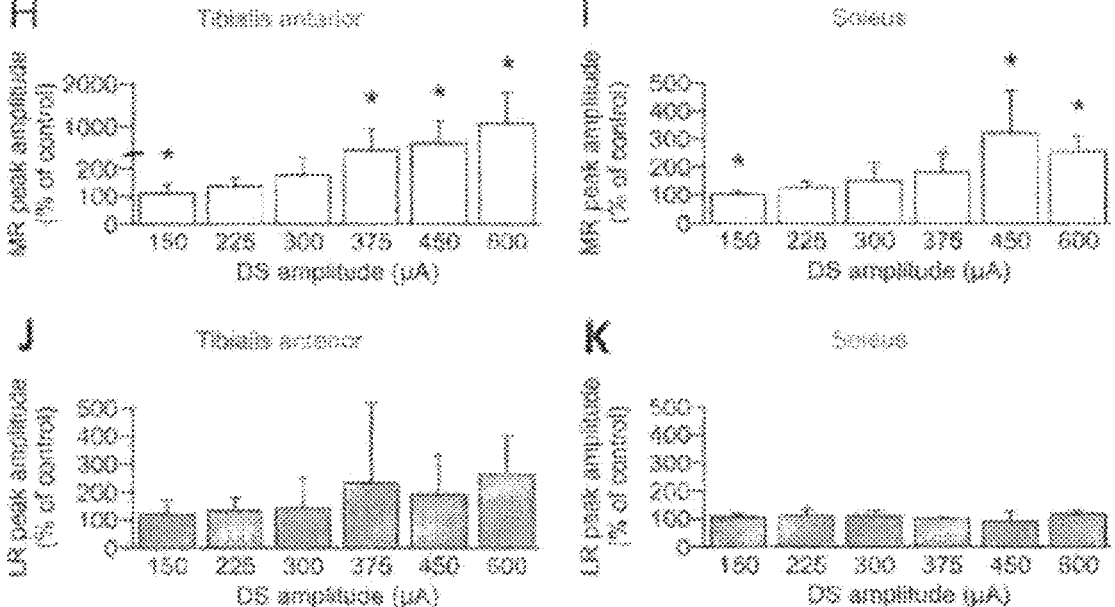
Fig. 30, cont'd.

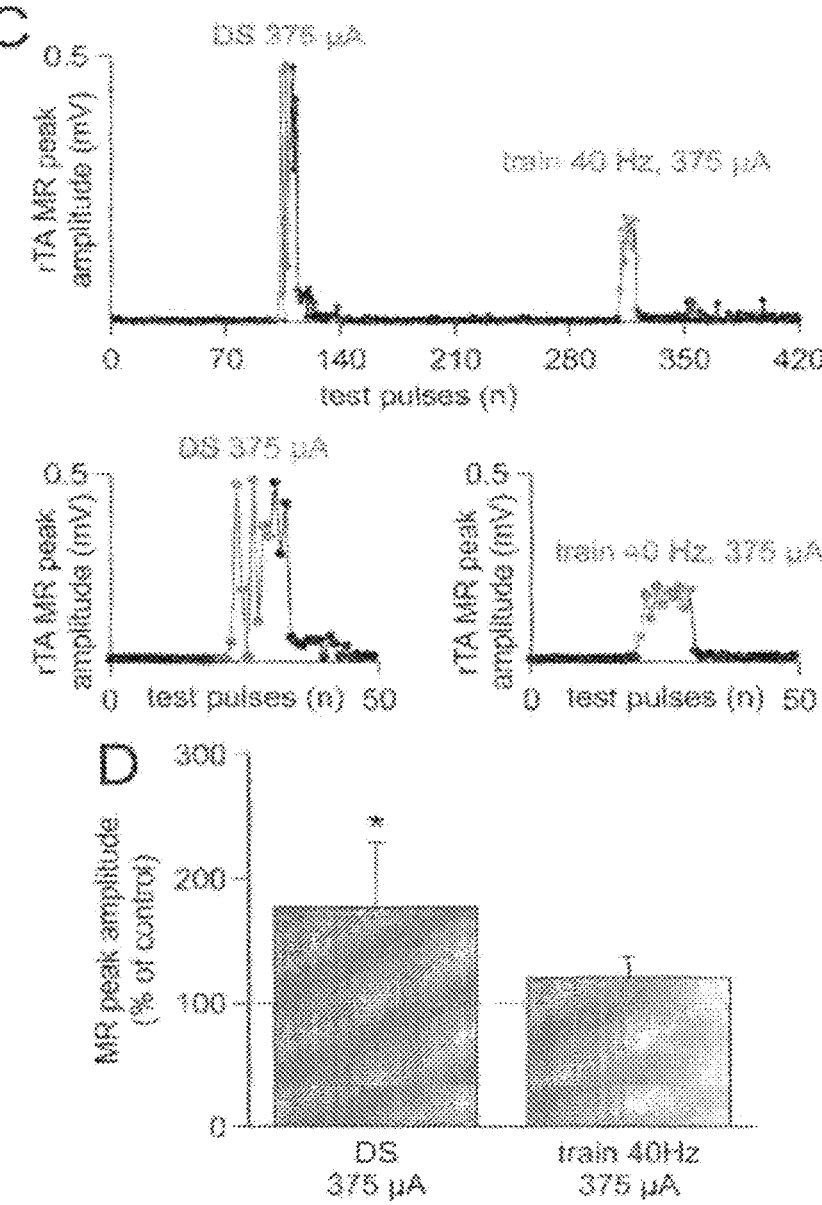
Fig. 31, cont'd.

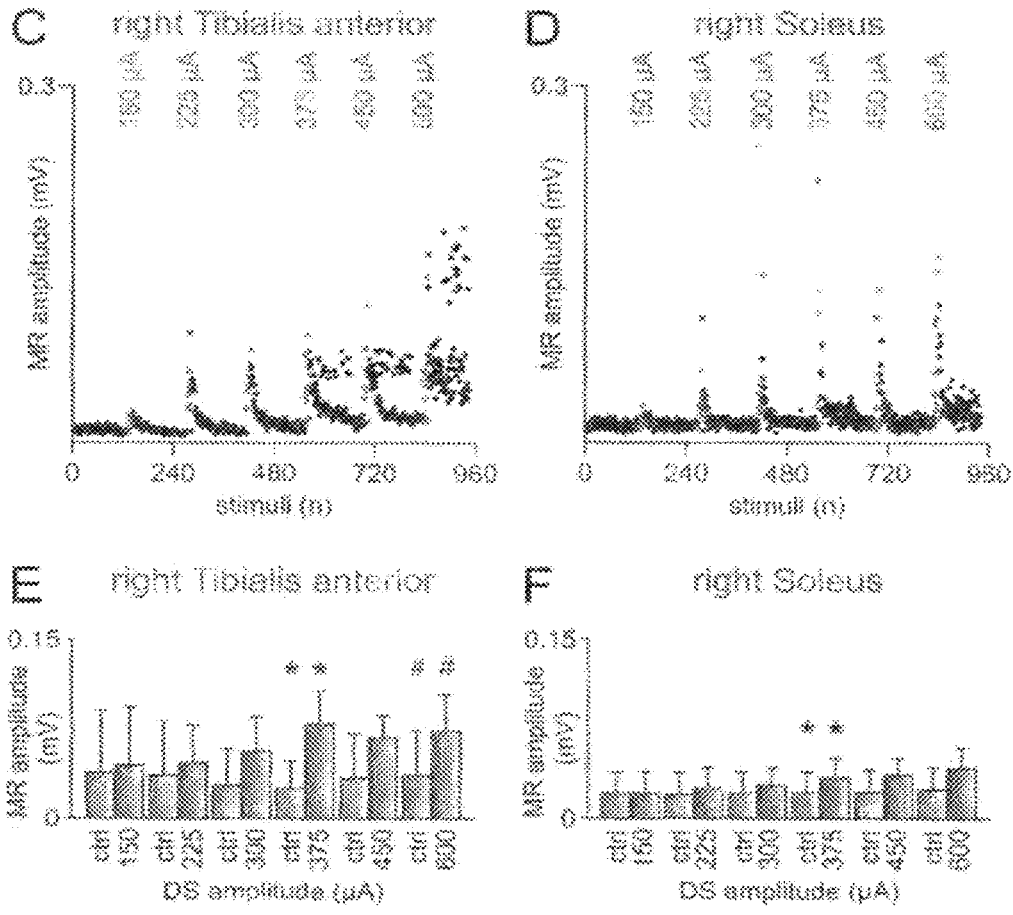
Fig. 32, cont'd.

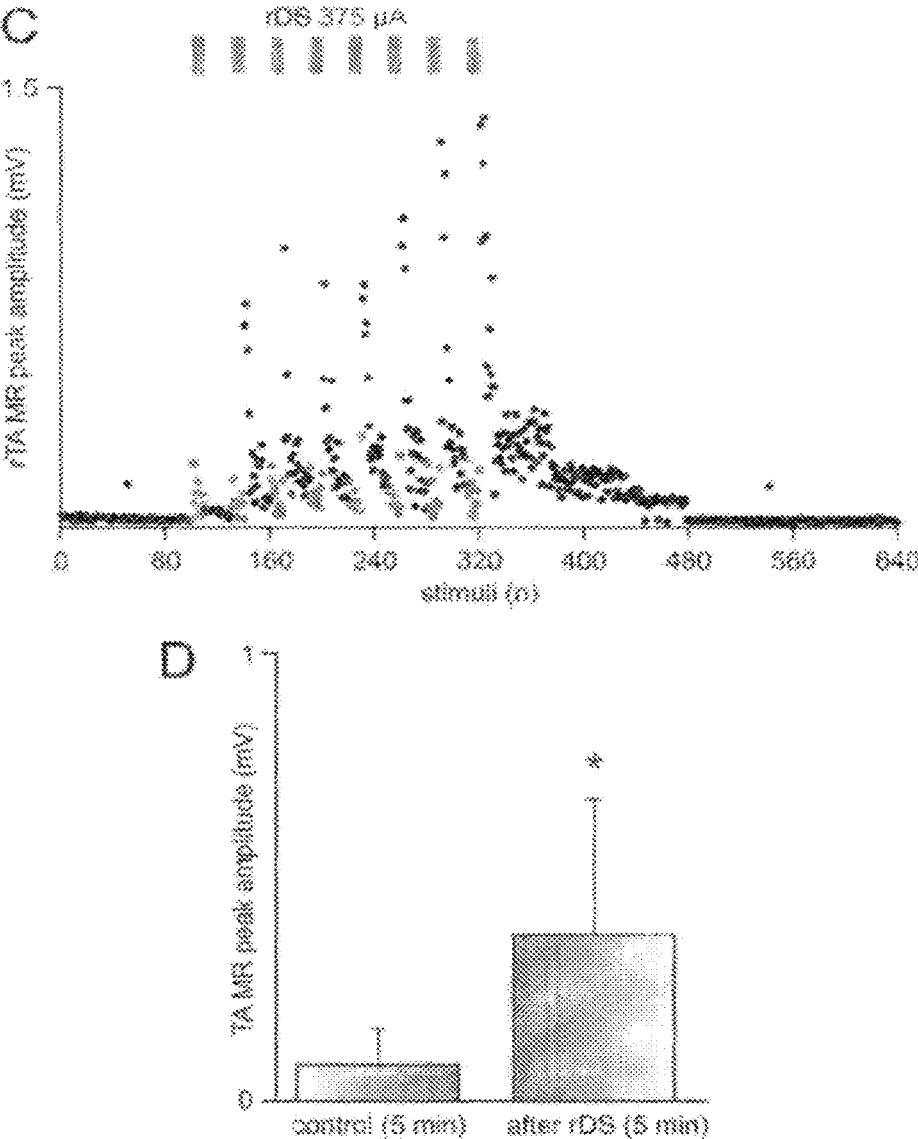
Fig. 33, cont'd.

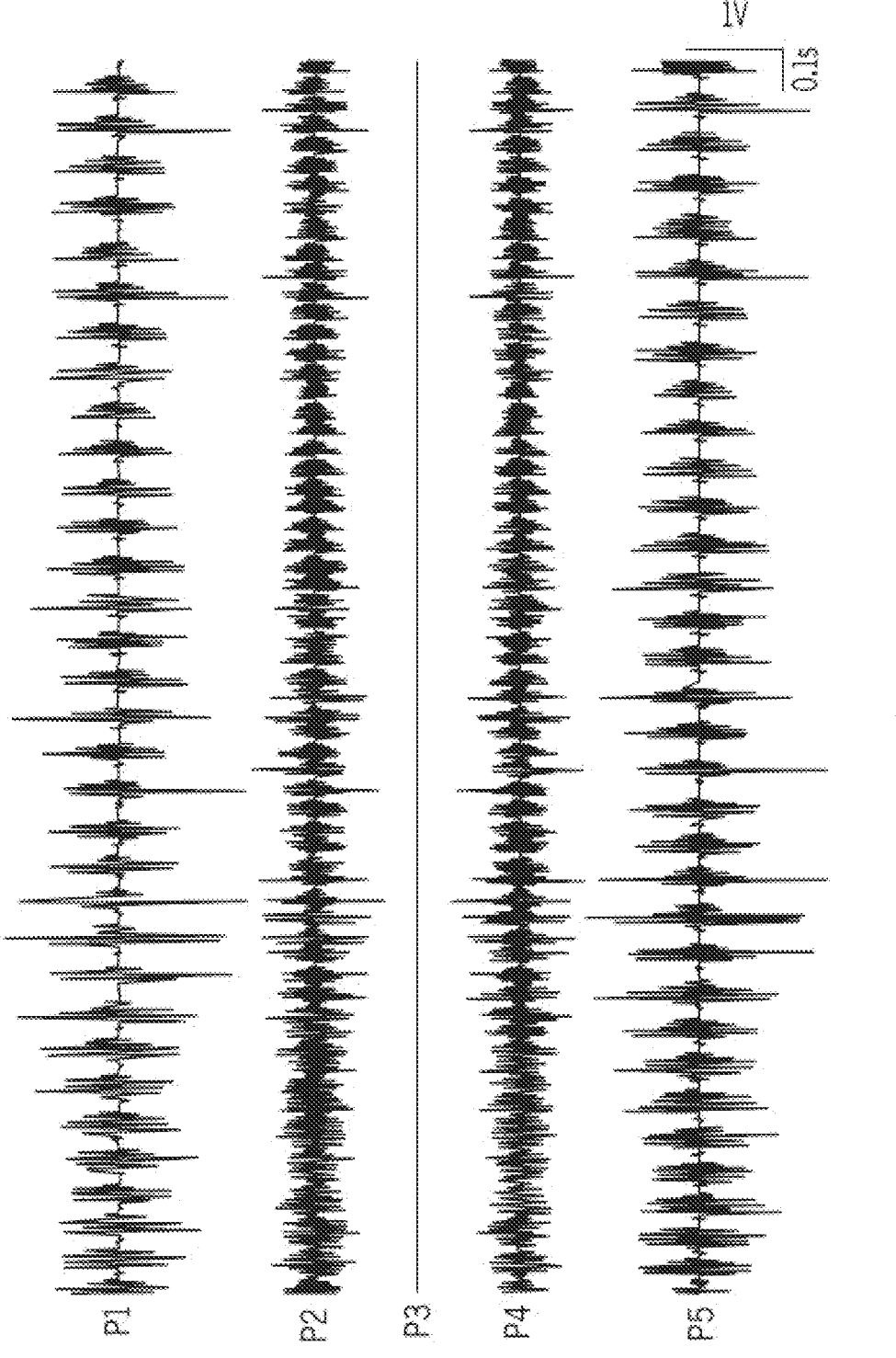
FIG. 36, CONT'D.

D
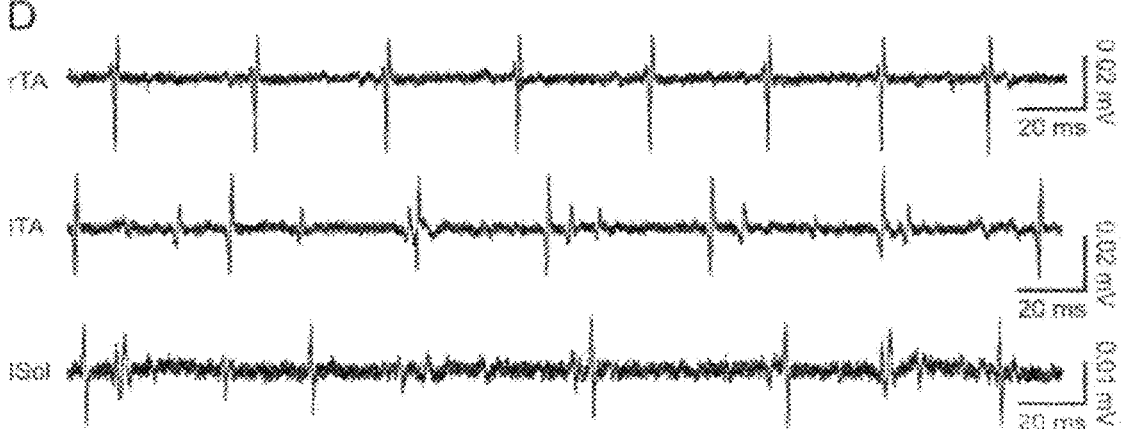
Fig. 37, cont'd.

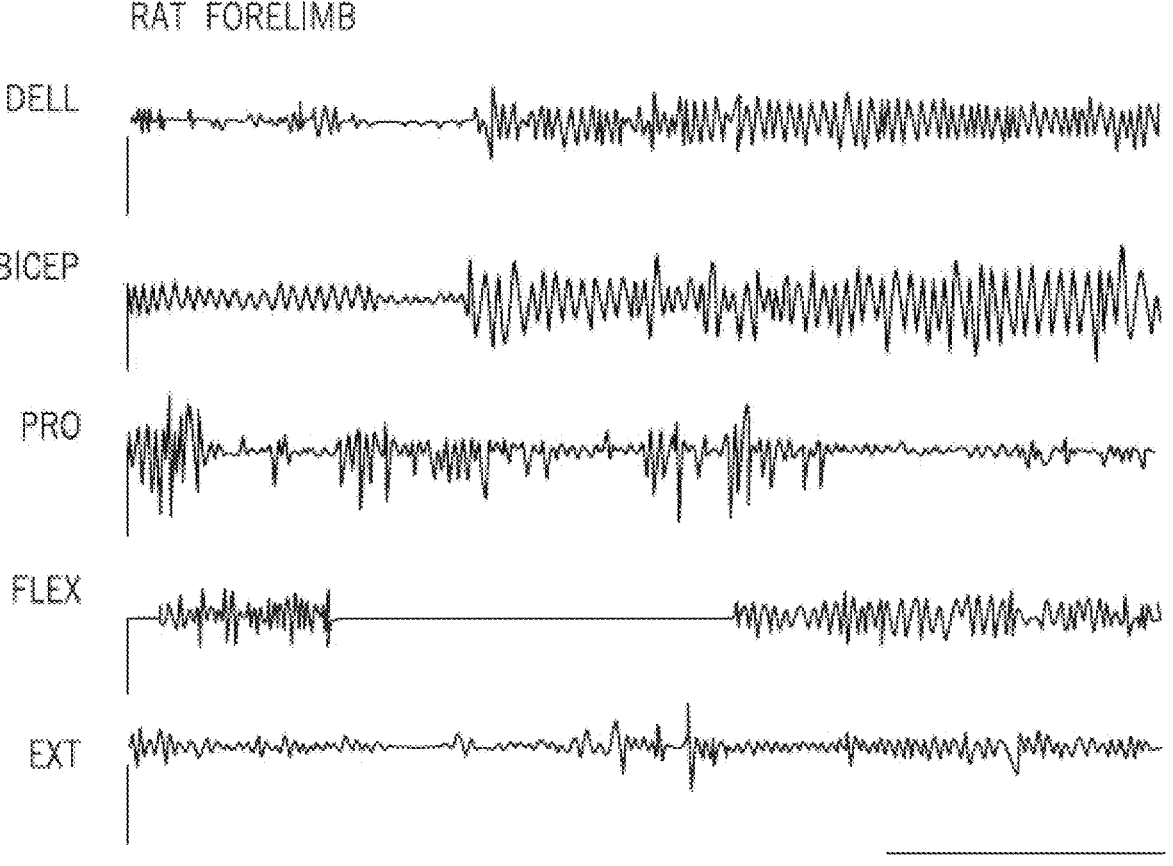
FIG. 38, CONT'D.

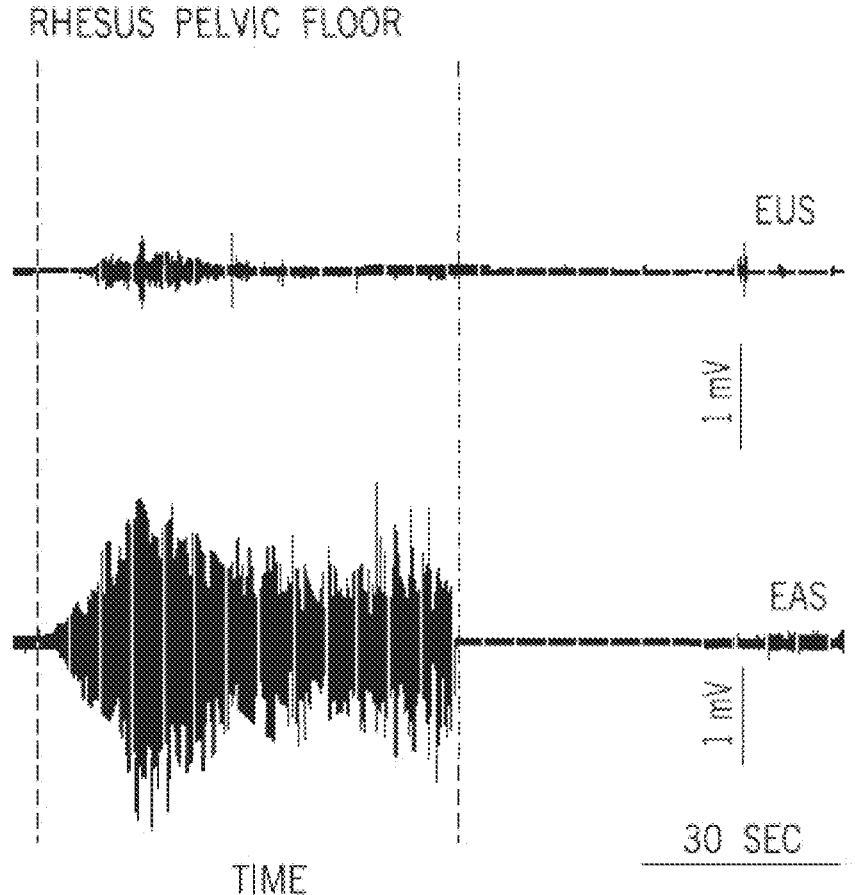
FIG. 38, CONT'D.

RHESUS PELVIC FLOOR
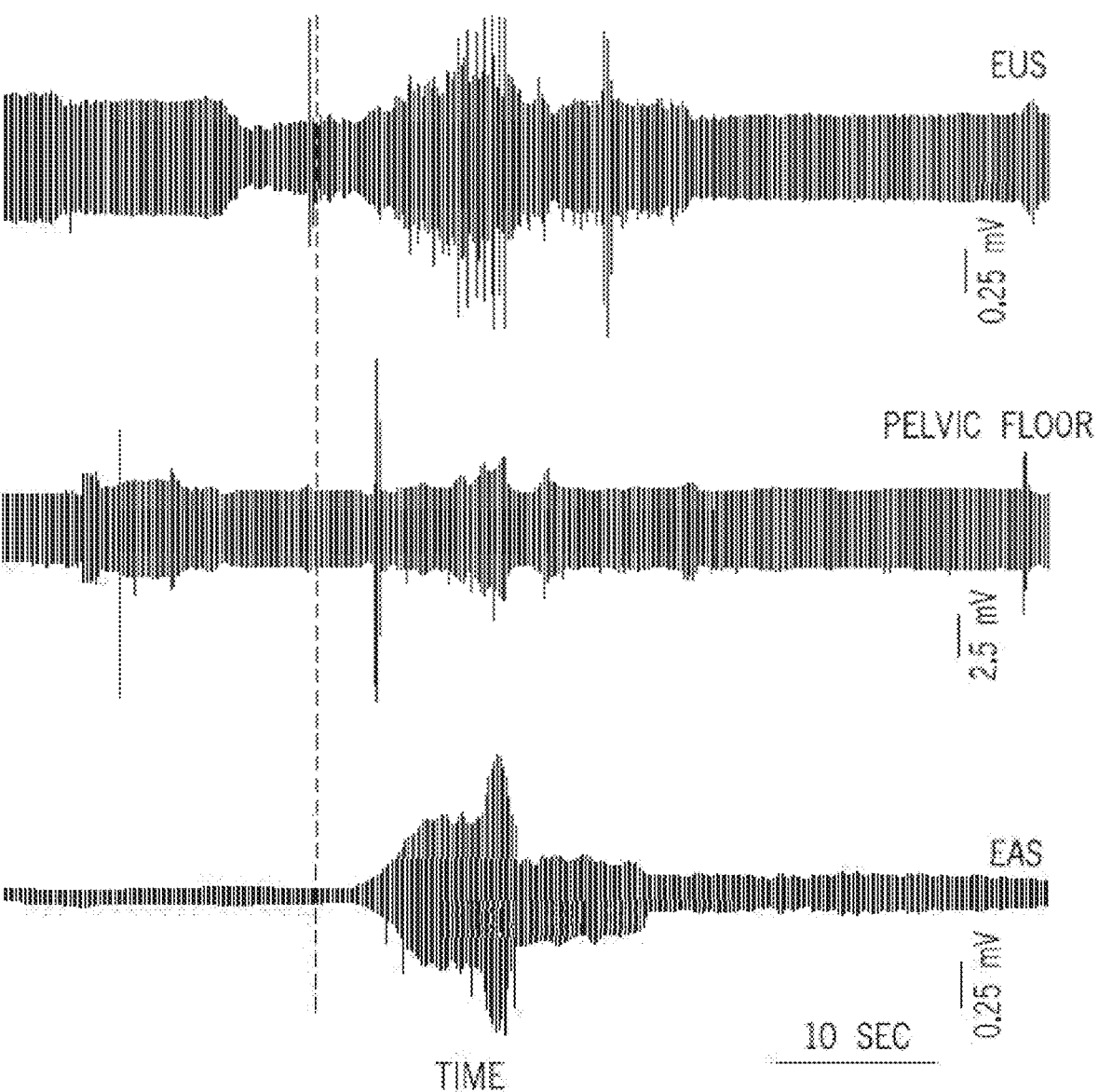
FIG. 38, CONT'D.

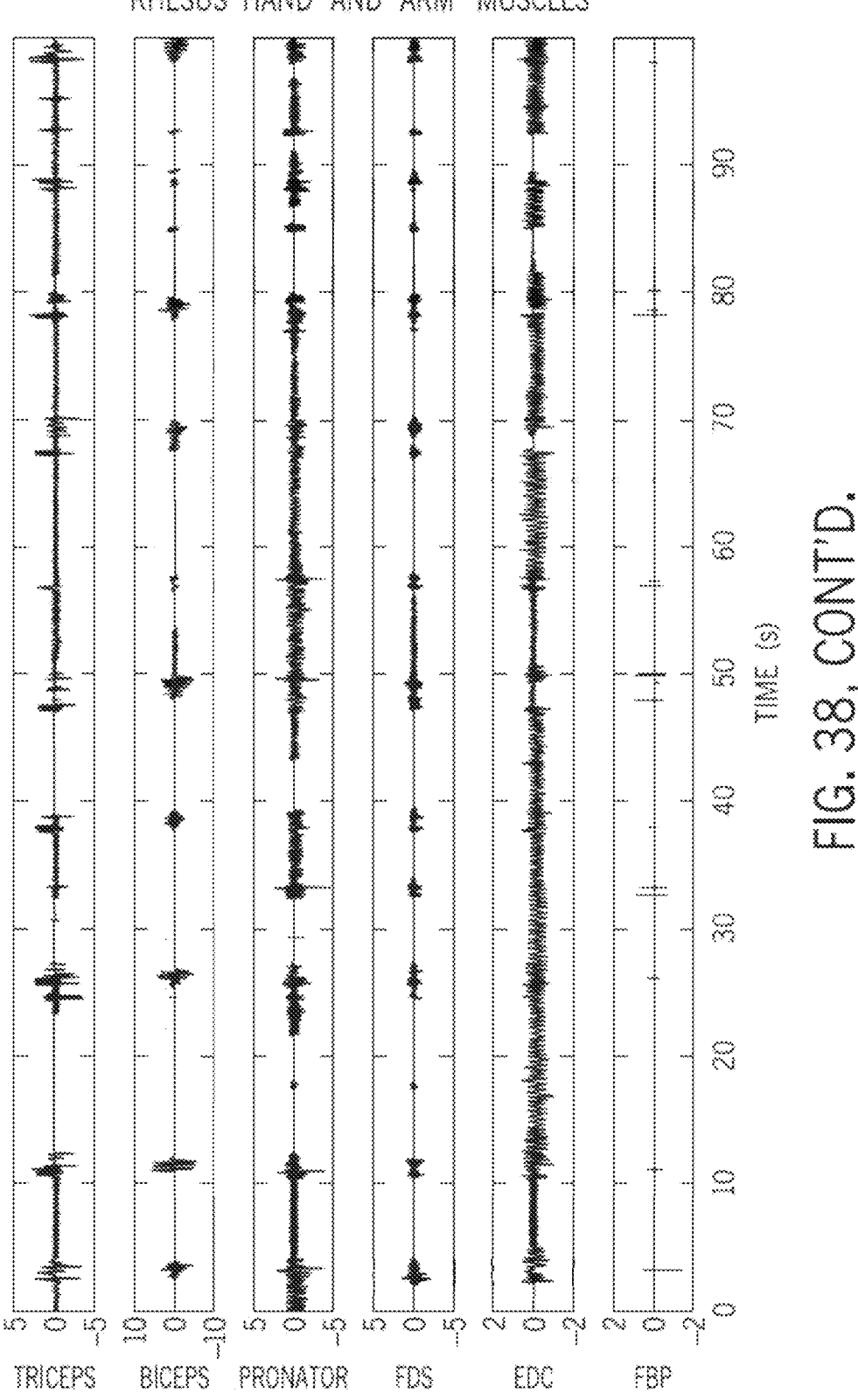
FIG. 38, CONT'D.

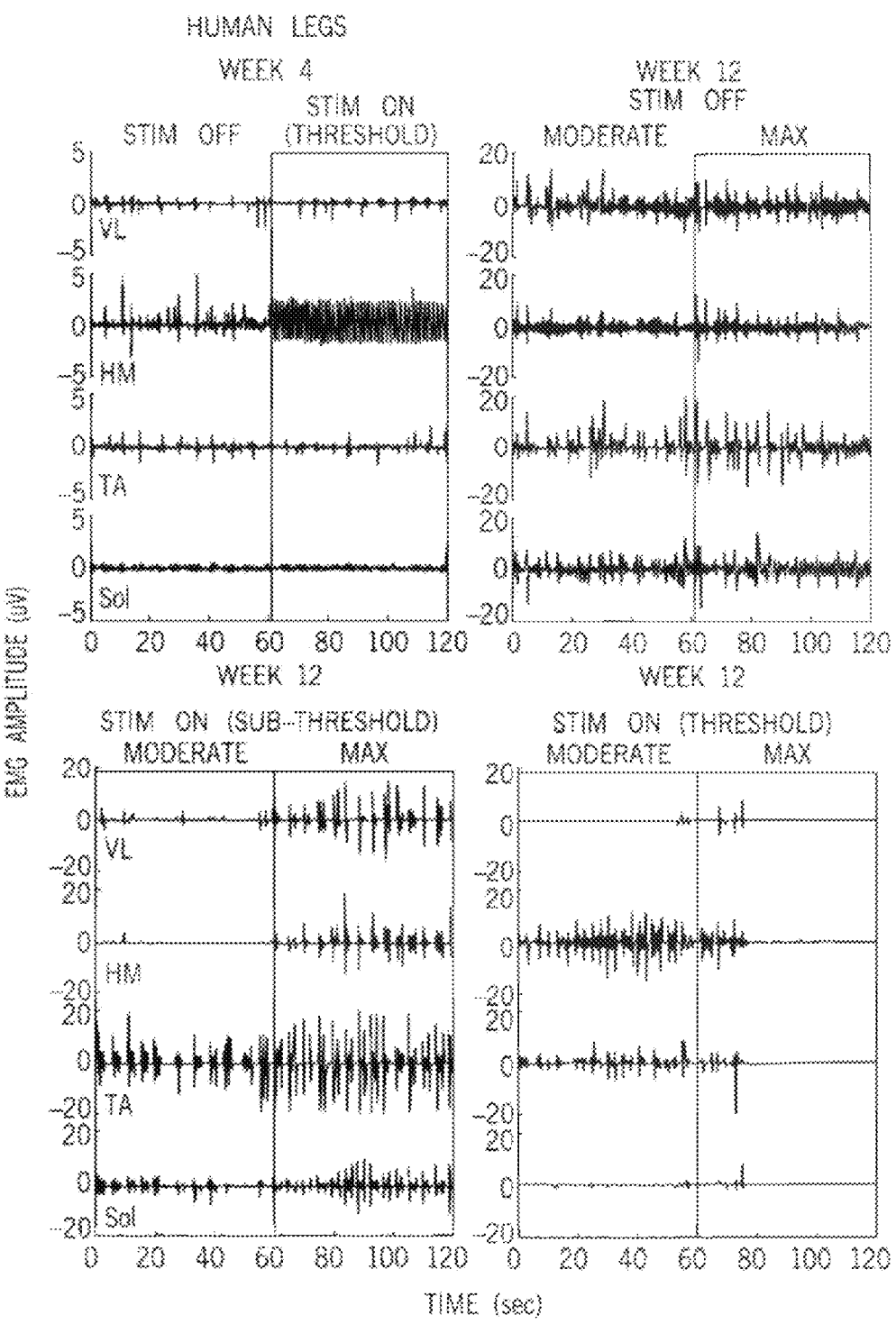
FIG. 38, CONT'D.

HUMANS HAND AND ARMS
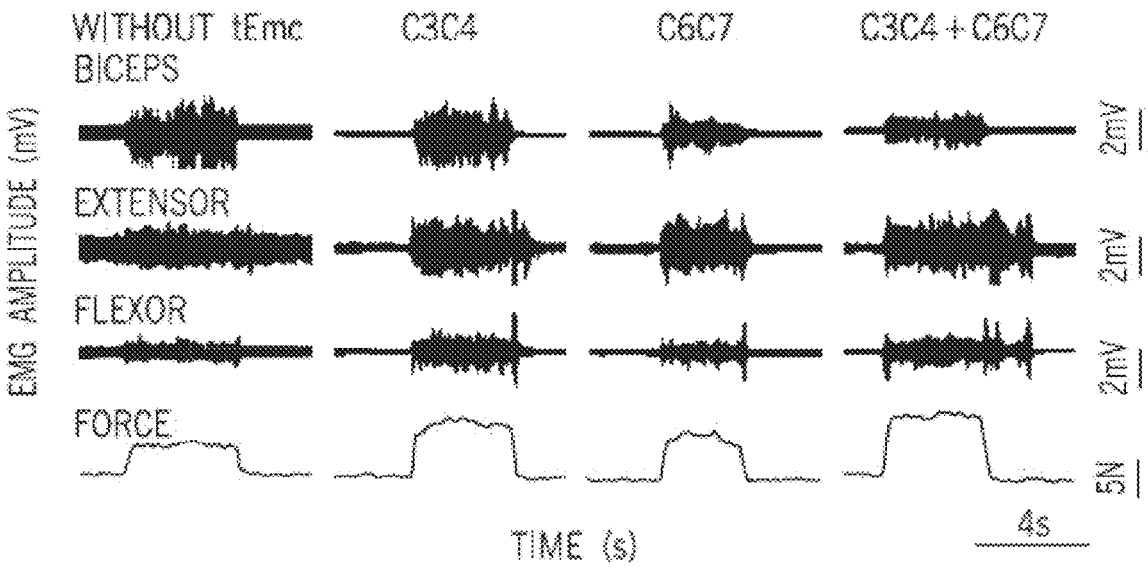
TIME (s)
HUMANS PELVIC FLOOR
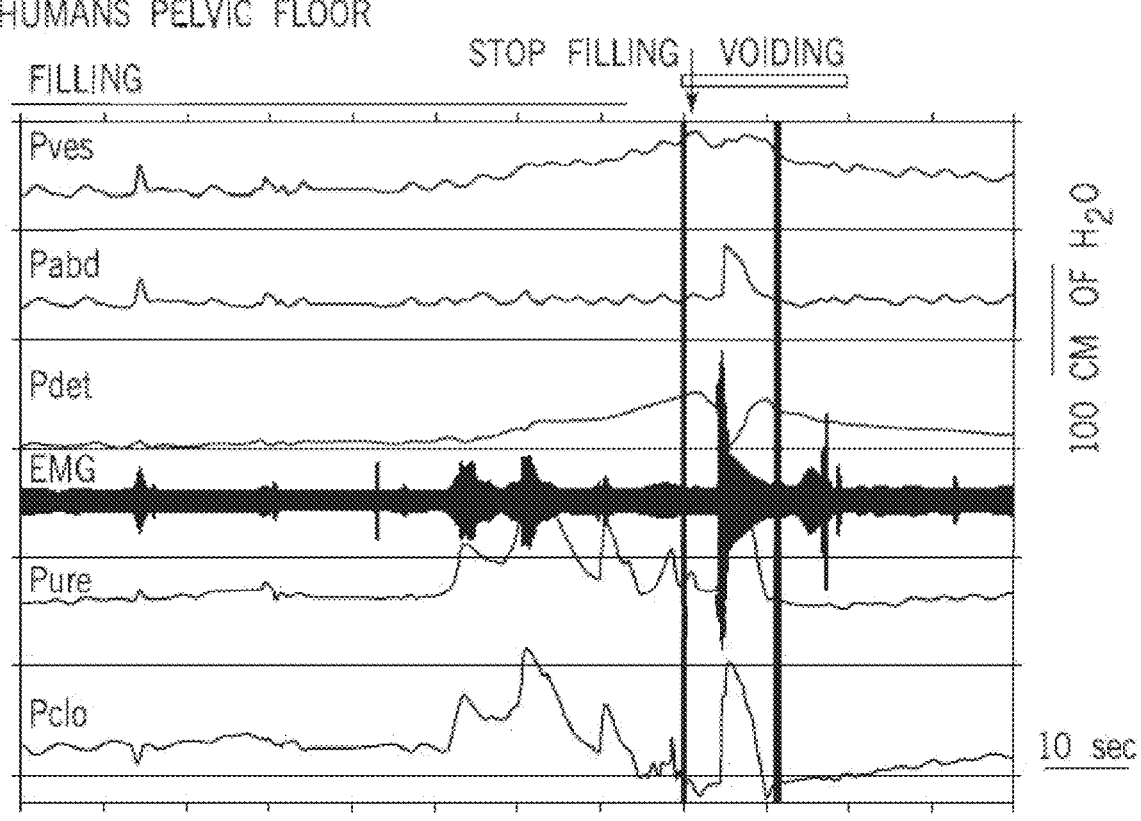
FIG. 38, CONT'D.

A

B

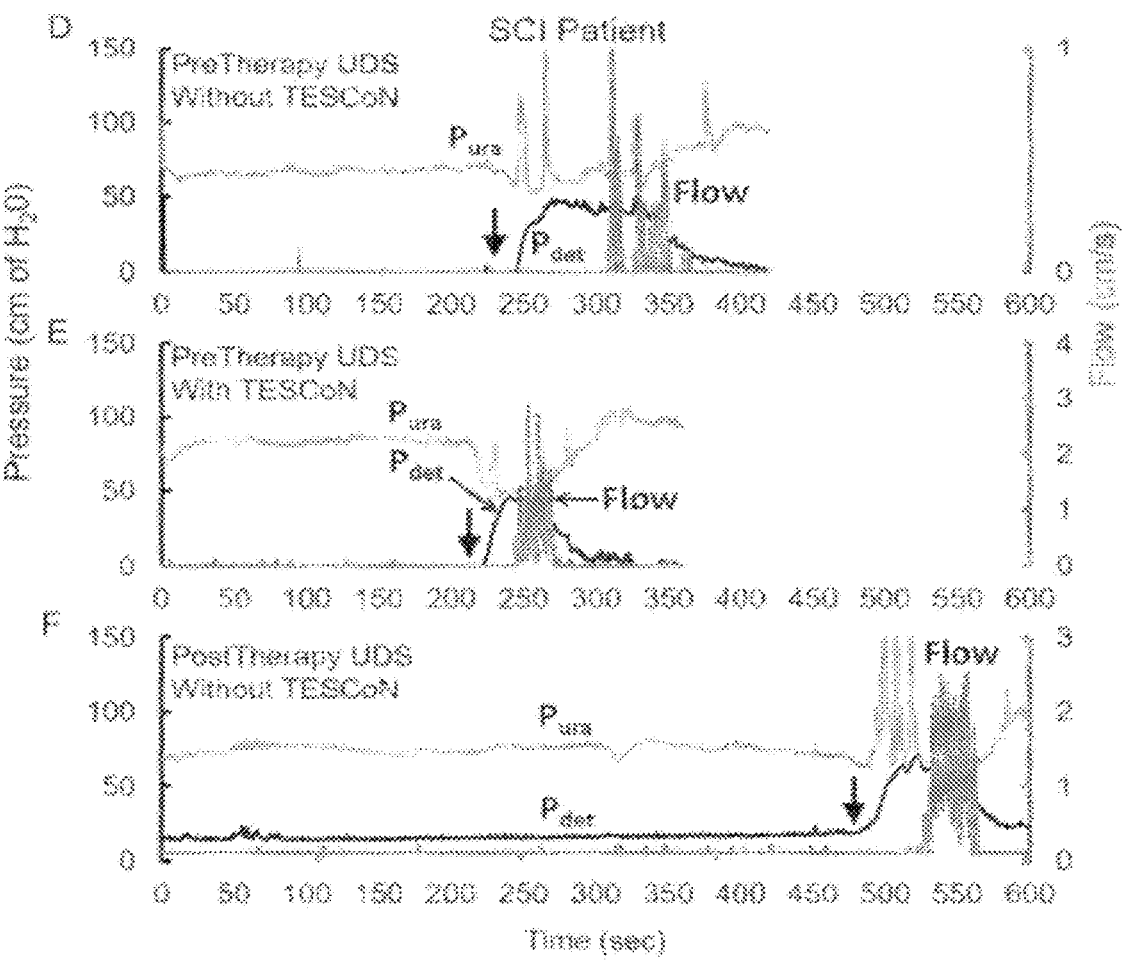
Fig. 47, cont'd.

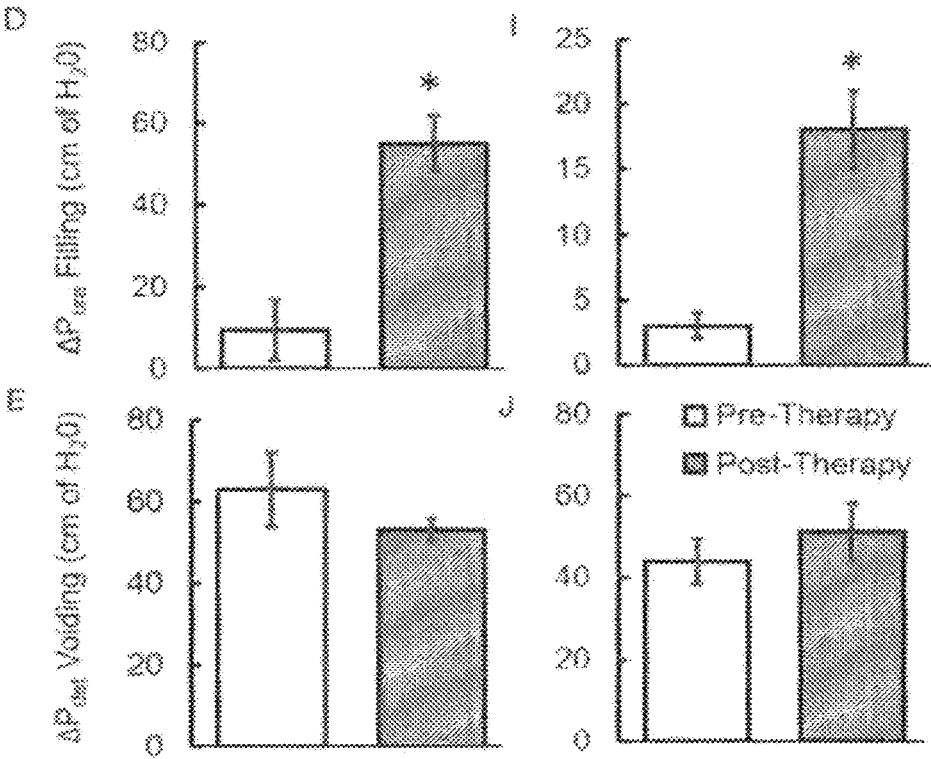
Fig. 50, cont'd.

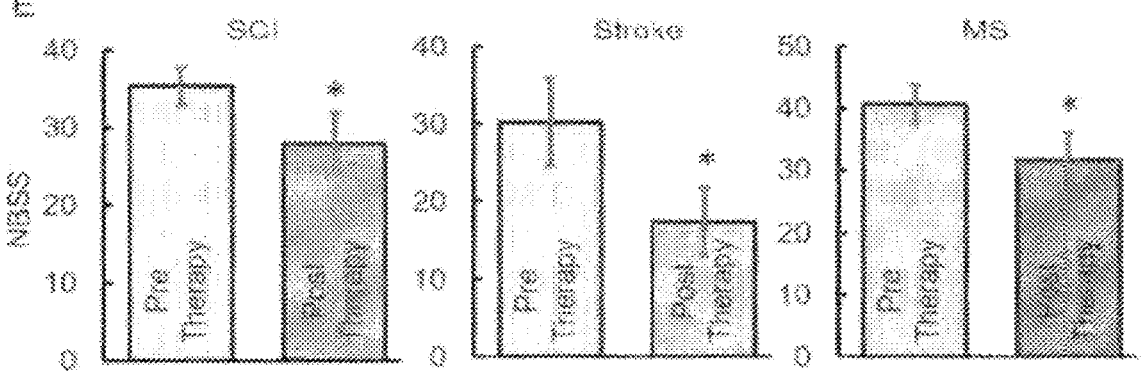
Fig. 51, cont'd.

TRANSCUTANEOUS ELECTRICAL SPINAL CORD NEUROMODULATOR AND USES THEREOF

CROSS-REFERENCE TO RELATED APPLICATIONS

This application is a U.S. 371 National Phase of PCT/US2020/033830, filed on May 20, 2020, which claims benefit of and priority to U.S. Ser. No. 62/876,583, filed on Jul. 19, 2019, and to U.S. Ser. No. 62/851,572, filed on May 22, 2019, all of which are incorporated herein by reference in their entirety for all purposes.

STATEMENT OF GOVERNMENTAL SUPPORT

This invention was made with government support under Grant Number EB007165, awarded by the National Institutes of Health. The government has certain rights in the invention.

BACKGROUND

Serious spinal cord injuries (SCI) affect approximately 1.3 million people in the United States, and roughly 12-15,000 new injuries occur each year. Of these injuries, approximately 50% are complete spinal cord injuries in which there is essentially total loss of sensory and/or motor function and autonomic function below the level of the spinal lesion. Additionally, numerous neurodegenerative conditions (e.g., stroke, Parkinson's disease, Huntington's disease, Alzheimer's disease, amyotrophic lateral sclerosis (ALS), primary lateral sclerosis (PLS), dystonia, cerebral palsy, and the like) and other traumas (e.g., hemispherictomy, dorsal and/or ventral root rhizotomy or avulsion, and the like) can result in partial or total loss of sensory and/or motor function and autonomic function. Further, Overactive Bladder (OAB) leading to urgency, increased frequency and urinary incontinence and is one of the most prevalent conditions in the US and affects approximately 37M Americans. This condition, although not life-threatening, is a huge burden and takes a significant toll on the quality of life for anyone living with this condition. and negatively affects people both physically, psychologically, economically and may lead people to alter their lives.

Neuronal networks formed by the interneurons of the spinal cord that are located in the brainstem, cervical, thoracic, and lumbar enlargements, such as the spinal networks (SNs), can play an important role in the control of posture, locomotion, movements of the upper limbs, trunk, breathing, speech, coughing, eating, vision and cardiovascular, bladder and/or bowel and sexual function. Most researchers believe that essentially all mammals, including humans, have spinal networks in the various regions of the spinal cord. Normally, the activity of spinal cord networks is regulated supraspinally and by peripheral sensory input. In the case of disorders of the connections between the brain and spinal cord, e.g., as a result of traumatic spinal cord lesions or various neurodegenerative conditions, motor tasks can be enabled by electrical stimulation of the lumbosacral and cervical segments as well as the brainstem. Such stimulation has been provided using epidural stimulation or transcutaneous electrical stimulation (see, e.g., PCT/US2014/057886, PCT/US2014/029340, PCT/US2016/045898, PCT/US2015/047268, PCT/US2015/046378, PCT/US2016/049129, and the like).

However, the use of systems to provide transcutaneous electrical stimulation has been hampered by the necessity to deliver relatively high voltage stimulation at the skin surface often resulting in discomfort and/or irritation and reduced subject compliance.

SUMMARY

In various embodiments electrical stimulators are provided for transcutaneous and/or epidural stimulation. In certain embodiments the stimulator provides one or more channels configured to provide one or more of the following stimulation patterns: i) monophasic electrical stimulation with a DC offset; ii) monophasic electrical stimulation with charge balance; iii) delayed biphasic electrical stimulation with a DC offset; iv) delayed biphasic electrical stimulation with charge balance; v) amplitude modulated dynamic stimulation; and/or vi) frequency modulated dynamic stimulation.

Various embodiments contemplated herein may include, but need not be limited to, one or more of the following:

Embodiment 1: A transcutaneous or epidural electrical spinal cord stimulator, said stimulator comprising one or more channels configured to provide one or more of the following stimulation patterns:

i) monophasic electrical stimulation with a DC offset;

ii) monophasic electrical stimulation with charge balance;

iii) delayed biphasic electrical stimulation with a DC offset;

iv) delayed biphasic electrical stimulation with charge balance;

v) amplitude modulated dynamic stimulation; and/or vi) frequency modulated dynamic stimulation.

Embodiment 2: The electrical stimulator of embodiment 1, wherein said stimulator comprises two or more independently configurable channels each capable of independently providing one or more of said stimulation patterns.

Embodiment 3: The electrical stimulator of embodiment 1, wherein said stimulator comprises four or more independently configurable channels each capable of independently providing one or more of said stimulation patterns.

Embodiment 4: The electrical stimulator of embodiments 2-3, wherein said two or more or said four or more channels provide said stimulation patterns with respect to a common neutral line.

Embodiment 5: The electrical stimulator of embodiments 2-3, wherein each of said two or more or each of said four or more channels provide said stimulation patterns with respect to neutral line for that channel.

Embodiment 6: The electrical stimulator according to any one of embodiments 1-5, wherein the monophasic or biphasic electrical stimulation comprises bursts of carrier high frequency pulses where the frequency end amplitude of said bursts provides a stimulation signal frequency and amplitude, and the frequency of said high frequency carrier pulses comprising said bursts is a pain suppression carrier frequency.

Embodiment 7: The electrical stimulator of embodiment 6, where the high frequency carrier comprises a pulse frequency sufficient to reduce or block pain or discomfort produced by the stimulation signal.

Embodiment 8: The electrical stimulator of embodiment 6, wherein said frequency provides pain relief to pelvic floor, lower extremity, back, upper extremity to patients suffering from eurological and idiopathic pain with TESCoN therapy.

Embodiment 9: The electrical stimulator according to any one of embodiments 6-8, where the high frequency pulses range in frequency from about 5 kHz up to about 100 KHz, or from about 10 kHz up to about 50 Khz, or from about 10 kHz up to about 30 kHz, or from about 10 kHz up to about 20 kHz.

Embodiment 10: The electrical stimulator according to any one of embodiments 6-9, where said stimulator provides control of the frequency of the high frequency carrier in steps of 1 kHz at a frequency ranging from 5 to 10 kHz, and in steps of 10 kHz at a frequency ranging from 10 kHz up to 100 kHz.

Embodiment 11: The electrical stimulator according to any one of embodiments 1-10, wherein one or more channels of said electrical stimulator is configured to provide monophasic electrical stimulation with a DC offset.

Embodiment 12: The electrical stimulator according to any one of embodiments 1-11, wherein one or more of channels of said electrical stimulator is configured to provide monophasic electrical stimulation with charge balance.

Embodiment 13: The electrical stimulator according to any one of embodiments 1-12, wherein one or more channels of said electrical stimulator is configured to provide delayed biphasic electrical stimulation with a DC offset.

Embodiment 14: The electrical stimulator according to any one of embodiments 1-13, wherein one or more channels of said electrical stimulator is configured to provide delayed biphasic electrical stimulation with charge balance.

Embodiment 15: The electrical stimulator according to any one of embodiments 13-14, wherein the delay in said biphasic electrical stimulation ranges from about 0.1 μsec up to about 2 μsec, or from about 0.1 μsec up to about 1 μsec.

Embodiment 16: The electrical stimulator according to any one of embodiments 1-15, wherein one or more channels of said electrical stimulator is configured to provide amplitude modulated dynamic stimulation.

Embodiment 17: The electrical stimulator according to any one of embodiments 1-16, wherein one or more channels of said electrical stimulator is configured to provide frequency modulated dynamic stimulation.

Embodiment 18: The electrical stimulator of embodiment 17, wherein one or more channels of said frequency modulated dynamic stimulation ranges in frequency from about 1 Hz to about 1000 Hz.

Embodiment 19: The electrical stimulator according to any one of embodiments 16-18, wherein said dynamic stimulation is sourced from a biosignal.

Embodiment 20: The electrical stimulator of embodiment 19, wherein said biosignal comprises a signal derived from an EMG, and EEG, or an EKG.

Embodiment 21: The electrical stimulator of embodiment 20, wherein said biosignal is recorded from a mammal.

Embodiment 22: The electrical stimulator of embodiment 21, wherein said biosignal is recorded from a human or from a non-human primate.

Embodiment 23: The electrical stimulator according to any one of embodiments 19-22, wherein said biosignal comprises a biosignal recorded from a mammal when the mammal is standing, stepping, moving the arms, storing/emptying the bladder, storing/emptying the bowel, breathing.

Embodiment 24: The electrical stimulator according to any one of embodiments 1-23, wherein said electrical stimulator is configured to provide a stimulation amplitude ranging from about 1 mA, or from about 3 mA, or from about 5 mA up to about 500 mA, or up to about 400 mA, or up to about 300 mA, or up to about 250 mA, or up to about 200 mA for each of said one or more channels.

Embodiment 25: The electrical stimulator of embodiment 24, wherein said electrical stimulator is configured to provide a stimulation amplitude ranging from about 5 mA up to about 200 mA for each of said one or more channels.

Embodiment 26: The electrical stimulator according to any one of embodiments 1-25, wherein said stimulator is configured to provide pulses that pass a current of 300 mA peak through an impedance of about 300 to about 2000 ohms, or from about 300 to about 900 ohms for each of said one or more channels.

Embodiment 27: The electrical stimulator according to any one of embodiments 1-11, 13, and 16-26, wherein said electrical stimulator is configured to provide a stimulation having a DC offset ranging from about 1 mA to about 30 mA, or from about 1 mA to about 20 mA.

Embodiment 28: The electrical stimulator according to any one of embodiments 1-27, wherein said stimulator is configured to provide a stimulation frequency (burst frequency) for one or more of said channels ranging in frequency from 0.2 Hz up to 10 kHz.

Embodiment 29: The electrical stimulator according to any one of embodiments 1-28, wherein said stimulator provides stimulation frequency control in steps of 1 Hz at a frequency ranging from 0.2 Hz to 100 Hz.

Embodiment 30: The electrical stimulator according to any one of embodiments 1-29, wherein said stimulator provides stimulation frequency control, in steps of 100 Hz at a frequency ranging from 100 Hz to 1 kHz.

Embodiment 31: The electrical stimulator according to any one of embodiments 1-30, wherein said stimulator provides stimulation frequency control in steps of 1 kHz at a frequency ranging from 1 kHz to 10 kHz.

Embodiment 32: The electrical stimulator according to any one of embodiments 1-31, wherein said stimulator is configured to provide a stimulation pulse (burst) width ranging from about 0.1 ms up to about 20 ms, or up to about 10 ms, or up to about 5 ms, or up to about 4 ms, or from about 0.2 ms up to about 3 ms.

Embodiment 33: The electrical stimulator according to any one of embodiments 1-32, wherein said stimulator is configured to provide a stimulation pulse (burst) width controllable in steps of 0.1 ms.

Embodiment 34: The electrical stimulator according to any one of embodiments 1-33, wherein said stimulator is configured to provide a pulse width fixed at 1 ms at stimulation frequencies over 10 kHz.

Embodiment 35: The electrical stimulator according to any one of embodiments 1-34, wherein said stimulator is configured to control the timing between stimulation signals delivered by different channels.

Embodiment 36: The electrical stimulator according to any one of embodiments 1-35, wherein said electrical stimulator comprises:

a microprocessor unit for receiving and/or programming and/or storing a stimulation pattern for one or more channels comprising said stimulator;

a pulse generating unit under control of said microprocessor;

a pulse modulator (gating) unit under control of said microprocessor;

and an input/output unit providing user control over said electrical stimulator.

Embodiment 37: The electrical stimulator of embodiment 36, wherein said electrical stimulator further comprises a DC shift (offset) generating unit under control of said microprocessor.

Embodiment 38: The electrical stimulator of embodiment 37, wherein said DC shift generating unit comprises a component of said pulse generating unit.

Embodiment 39: The electrical stimulator according to any one of embodiments 36-38, wherein said stimulator further comprises a charge balancing unit.

Embodiment 40: The electrical stimulator according to any one of embodiments 36-39, wherein said electrical stimulator comprise a current control unit.

Embodiment 41: The electrical stimulator according to any one of embodiments 36-40, wherein said stimulator further comprises a monitoring unit.

Embodiment 42: The electrical stimulator of embodiment 41, wherein said monitoring unit monitors lead impedance.

Embodiment 43: The electrical stimulator according to any one of embodiments 41-42, wherein said monitoring unit monitors output current.

Embodiment 44: The electrical stimulator according to any one of embodiments 36-43, wherein said input output unit is directly electrically connected to said stimulator.

Embodiment 45: The electrical stimulator according to any one of embodiments 36-43, wherein said input output unit is operably coupled to said stimulator through a wireless connection, a network connection, a wifi connection, or a Bluetooth connection.

Embodiment 46: The electrical stimulator according to any one of embodiments 36-45, wherein said electrical stimulator comprises a smart card reader and/or a biometric reader.

Embodiment 47: The electrical stimulator of embodiment 46, wherein said electrical stimulator comprises a smart card reader.

Embodiment 48: The electrical stimulator of embodiment 46, wherein said smart card reader is configured to input a patient identifier, and optionally, a treatment protocol associated with said patient identifier.

Embodiment 49: The electrical stimulator of embodiment 46, wherein said electrical stimulator comprises a biometric reader.

Embodiment 50: The electrical stimulator of embodiment 49, wherein said biometric reader recognizes a fingerprint, a face, and/or an iris.

Embodiment 51: The electrical stimulator according to any one of embodiments 49-50, wherein said biometric reader identifies a subject to be treated.

Embodiment 52: The electrical stimulator according to any one of embodiments 1-51, wherein said electrical stimulator is operably coupled to a database.

Embodiment 53: The electrical stimulator of embodiment 52, wherein said database provides treatment protocols.

Embodiment 54: The electrical stimulator of embodiment 52, wherein said database provides treatment protocols for a subject identified to said stimulator by said smart card reader and/or by said biometric reader.

Embodiment 55: The electrical stimulator according to any one of embodiments 1-54, wherein said stimulator is configured to provide two modes of operation: i) an administrator mode for clinicians and researchers; and ii) a patient mode.

Embodiment 56: The electrical stimulator of embodiment 55, wherein said administrator mode provides the ability to input and store one or more programs comprising stimulation parameters for one or more of said one or more channels.

Embodiment 57: The electrical stimulator of embodiment 56, wherein said administration mode provides the ability to store up to 5 stimulation programs, or up to 10 stimulation programs.

Embodiment 58: The electrical stimulator according to any one of embodiments 55-57, wherein said administrator mode provides the ability to input and store electrode placement locations for presentation in patient mode.

Embodiment 59: The electrical stimulator according to any one of embodiments 55-58, wherein said administrator mode provides the ability to measure impedance across each channel and display it to the administrator.

Embodiment 60: The electrical stimulator according to any one of embodiments 55-59, wherein said patient mode permits program selection using a patient identifier.

Embodiment 61: The electrical stimulator of embodiment 60, wherein said patient identifier is selected from the group consisting of a smart card, a patient biometric (eye, facial recognition, thumb or fingerprint recognition) reader, an alphanumeric patient ID, a medical bracelet, smartphone app/tap, smartwatch app/tap, smart ring tap.

Embodiment 62: The electrical stimulator according to any one of embodiments 55-61, wherein said patient mode identifies for the patient sites for transcutaneous stimulation electrodes to be placed.

Embodiment 63: The electrical stimulator according to any one of embodiments 55-62, wherein said patient mode turns on the therapy.

Embodiment 64: The electrical stimulator of embodiment 63, wherein said patient mode turns on therapy after detecting placement of the necessary electrodes.

Embodiment 65: The electrical stimulator according to any one of embodiments 55-64, wherein said patient mode permits the user to set ramp rate options.

Embodiment 66: The electrical stimulator of embodiment 65, wherein said patient mode permits the user to set up ramp rate options ranging from about 1 mA/sec to about 10 mA/sec.

Embodiment 67: The electrical stimulator according to any one of embodiments 1-66, wherein each active channel of said stimulator is electrically coupled to one or more electrodes for transcutaneous electrical stimulation.

Embodiment 68: The electrical stimulator of embodiment 67, wherein said electrodes comprise paddle electrodes.

Embodiment 69: The electrical stimulator of embodiment 67, wherein said electrodes comprise self-adhesive (e.g., round/square/rectangular, etc.) hydrogel electrodes.

Embodiment 70: The electrical stimulator of embodiment 68, wherein said paddle electrodes are disposed on the surface of the skin of a subject that is to be stimulated.

Embodiment 71: The electrical stimulator of embodiment 68, wherein said paddle electrodes are disposed in clothing.

Embodiment 72: The electrical stimulator of embodiment 68, wherein said paddle electrodes are disposed on a toilet seat.

Embodiment 73: The electrical stimulator of embodiment 68, wherein said paddle electrodes are disposed on a chair or couch.

Embodiment 74: The electrical stimulator of embodiment 67, wherein said electrodes comprise needle electrodes.

Embodiment 75: A method of applying transcutaneous electrical stimulation to a subject, said method comprising: providing a stimulator according to any one of embodiments 1-66, wherein said stimulator stores one or more stimulation programs and one or more channels of said stimulator are electrically coupled to one or more transcutaneous stimulation electrodes disposed on the surface of a subject's body;

and operating said stimulator according to one or more of said programs to provide transcutaneous electrical stimulation to said subject.

Embodiment 76: The method of embodiment 75, wherein said subject has a spinal cord injury, an ischemic brain injury, and/or a neurodegenerative condition.

Embodiment 77: The method of embodiment 76, wherein said subject has a spinal cord injury that is clinically classified as motor incomplete.

Embodiment 78: The method of embodiment 76, wherein said subject has a spinal cord injury that is clinically classified as motor complete.

Embodiment 79: The method of embodiment 76, wherein said subject has an ischemic brain injury.

Embodiment 80: The method of embodiment 79, wherein said ischemic brain injury is brain injury from stroke or acute trauma.

Embodiment 81: The method of embodiment 76, wherein said subject has a neurodegenerative pathology.

Embodiment 82: The method of embodiment 81, wherein said neurodegenerative pathology is associated with a condition selected from the group consisting of stroke, Parkinson's disease, Huntington's disease, Alzheimer's disease, amyotrophic lateral sclerosis (ALS), primary lateral sclerosis (PLS), dystonia, hemispherictomy, transverse myelitis, conus medularis injury (lower motor neuron injury) and cerebral palsy.

Embodiment 83: The method of embodiment 75, wherein said subject has an idiopathic condition of overactive bladder, and/or constipation.

Embodiment 84: The method of embodiment 75, wherein said subject has a muscle loss due to inactive lifestyle, and/or obesity, and/or aging.

Embodiment 85: The method of embodiment 75, wherein said subject has neuropathic pain in lower extremity and/or upper extremity and/or back and/or pelvic floor muscles and/or bladder and/or perineum vagina.

Embodiment 86: The method of embodiment 75, wherein said subject has chronic idiopathic pain in lower extremity and/or upper extremity and/or back and/or pelvic floor muscles and/or bladder and/or perineum vagina.

Embodiment 87: The method of embodiment 75, wherein said subject has pain due to fibromyalgia, and/or interstitial cystitis, and/or chronic prostatitis, and/or chronic pelvic pain syndrome and/or painful bladder syndrome.

Embodiment 88: The method according to any one of embodiments 75-87, wherein said stimulator provides one or more of the following stimulation patterns on one or more independently controlled channels:

i) monophasic electrical stimulation with a DC offset;

ii) monophasic electrical stimulation with charge balance;

iii) delayed biphasic electrical stimulation with a DC offset;

iv) delayed biphasic electrical stimulation with charge balance;

v) amplitude modulated dynamic stimulation;

and/or vi) frequency modulated dynamic stimulation.

Embodiment 89: The method of embodiment 88, wherein said stimulator provides the same stimulation modality and stimulation parameters on 2 or more different channels or on 3 or more different channels, or on 4 or more different channels.

Embodiment 90: The method of embodiment 88, wherein said stimulator provides a different stimulation modality and/or different stimulation parameters on 2 or more different channels or on 3 or more different channels, or on 4 or more different channels.

Embodiment 91: The method according to any one of embodiments 88-90, wherein the monophasic or biphasic electrical stimulation comprises bursts of carrier high frequency pulses where the frequency end amplitude of said bursts provides a stimulation signal frequency and amplitude, and the frequency of said high frequency carrier pulses comprising said bursts is a pain suppression carrier frequency.

Embodiment 92: The method of embodiment 91, where the high frequency carrier comprises a pulse frequency sufficient to reduce or block pain or discomfort produced by the stimulation signal.

Embodiment 93: The method according to any one of embodiments 91-92, where the high frequency pulses range in frequency from about 5 kHZ up to about 100 KHz, or from about 10 kHz up to about 50 Khz, or from about 10 khZ up to about 30 kHz, or from about 10 kHz up to about 20 kHz.

Embodiment 94: The method according to any one of embodiments 88-93, wherein one or more channels of said electrical stimulator provide monophasic electrical stimulation with a DC offset.

Embodiment 95: The method according to any one of embodiments 88-94, wherein one or more of channels of said electrical stimulator provide monophasic electrical stimulation with charge balance.

Embodiment 96: The method according to any one of embodiments 88-95, wherein one or more channels of said electrical stimulator provide biphasic electrical stimulation with a DC offset.

Embodiment 97: The method according to any one of embodiments 88-96, wherein one or more channels of said electrical stimulator provide biphasic electrical stimulation with charge balance.

Embodiment 98: The method according to any one of embodiments 88-97, wherein one or more channels of said electrical stimulator provide amplitude modulated dynamic stimulation.

Embodiment 99: The method according to any one of embodiments 88-98, wherein one or more channels of said electrical stimulator provide frequency modulated dynamic stimulation.

Embodiment 100: The method of embodiment 99, wherein one or more channels of said frequency modulated dynamic stimulation ranges in frequency from about 1 Hz to about 1000 Hz.

Embodiment 101: The method according to any one of embodiments 99-100, wherein said dynamic stimulation is sourced from a biosignal.

Embodiment 102: The method of embodiment 101, wherein said biosignal comprises a signal derived from an EMG, and EEG, or an EKG.

Embodiment 103: The method of embodiment 102, wherein said biosignal is recorded from a mammal.

Embodiment 104: The method of embodiment 103, wherein said biosignal is recorded from a human or from a non-human primate.

Embodiment 105: The method according to any one of embodiments 101-104, wherein said biosignal comprises a biosignal recorded from a mammal when the mammal is standing, stepping, moving the arms, storing/emptying the bladder, storing/emptying the bowel, breathing.

Embodiment 106: The method according to any one of embodiments 88-105, wherein said electrical stimulator provide a stimulation amplitude ranging from about 1 mA, or from about 3 mA, or from about 5 mA up to about 500 mA, or up to about 400 mA, or up to about 300 mA, or up to about 250 mA, or up to about 200 mA for each of said one or more channels.

Embodiment 107: The method of embodiment 106, wherein one or more channels of said electrical stimulator provide a stimulation amplitude ranging from about 5 mA up to about 200 mA for each of said one or more channels.

Embodiment 108: The method according to any one of embodiments 88-107, wherein said stimulator provides pulses that pass a current of 300 mA peak through an impedance of about 300 ohms to about 2000 ohms, or from about 300 ohms to about 900 ohms for each of said one or more channels.

Embodiment 109: The method according to any one of embodiments 88-94, 96, and 98-108, wherein said electrical stimulator provides a stimulation having a DC offset ranging from about 1 mA up to about 20 mA.

Embodiment 110: The method according to any one of embodiments 88-109, wherein said stimulator provides a stimulation frequency (burst frequency) for one or more of said channels ranging in frequency from 0.2 Hz up to 10 kHz.

Embodiment 111: The method according to any one of embodiments 88-110, wherein said stimulator provides a stimulation pulse (burst) width on said one or more channels ranging from about 0.1 ms up to about 20 ms, or up to about 10 ms, or up to about 5 ms, or up to about 4 ms, or from about 0.2 ms up to about 3 ms.

Embodiment 112: The method according to any one of embodiments 88-111, wherein said stimulator provides a pulse width fixed at 1 ms at stimulation frequencies over 10 kHz.

Embodiment 113: The method according to any one of embodiments 75-112, wherein said electrical stimulation provides transcutaneous electrical stimulation of the spinal cord.

Embodiment 114: The method according to any one of embodiments 75-113, wherein said electrical stimulation enhances/facilitates endogenous neural circuitry activity.

Embodiment 115: The method according to any one of embodiments 75-114, wherein said electrical stimulation does not substantially provide peripheral nerve stimulation.

Embodiment 116: The method according to any one of embodiments 75-115, wherein at least one channel of said transcutaneous electrical stimulation is applied over or more regions straddling or spanning a region selected from the group consisting of the brainstem, C0-C1, C0-C2, C0-C3, C0-C4, C0-C5, C0-C6, C0-C7, C0-T1, C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7- T1.

Embodiment 117: The method of embodiment 116, wherein at least one channel of said transcutaneous electrical stimulation is applied over a region comprising or consisting of C2-C3 or a region therein.

Embodiment 118: The method of embodiment 117, wherein at least one channel of said transcutaneous electrical stimulation is applied at C3.

Embodiment 119: The method according to any one of embodiments 75-118, wherein at least one channel of said transcutaneous electrical stimulation is applied over the thoracic spinal cord or a region thereof.

Embodiment 120: The method of embodiment 119, wherein at least one channel of said transcutaneous electrical stimulation is applied over or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3- T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5- T10, T5-T11, T5-T12, T6-T6, T6-T7, T6-T8, T6-T9, T6-T10, T6-T11, T6-T12, T7-T7, T7- T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, and T12-T12.

Embodiment 121: The method according to any one of embodiments 75-120, wherein at least one channel of said transcutaneous electrical stimulation is applied over the lumbar spinal cord or a region thereof.

Embodiment 122: The method of embodiment 121, wherein at least one channel of said transcutaneous electrical stimulation is applied over or more regions straddling or spanning a region selected from the group consisting of L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 123: The method of embodiment 121, wherein at least one channel of said transcutaneous electrical stimulation is applied over the coccyx.

Embodiment 124: The method according to any one of embodiments 75-123, wherein at least one channel of said transcutaneous electrical stimulation is applied over a region between T11 and L4.

Embodiment 125: The method of embodiment 124, wherein at least one channel of said transcutaneous electrical stimulation is applied over or more regions selected from the group consisting of T11-T12, L1-L2, and L2-L3.

Embodiment 126: The method of embodiment 124, wherein at least one channel of said transcutaneous electrical stimulation is applied over L1-L2 and/or over T11-T12.

Embodiment 127: The method according to any one of embodiments 75-126, wherein said transcutaneous electrical stimulation simultaneously facilitates locomotor function and/or hand and arm function and/or speech function and/or breathing function and/or eating and chewing function and/or cardiovascular function and/or vision and focus and/or bladder and bowel.

Embodiment 128: The method according to any one of embodiments 75-126, wherein said transcutaneous electrical stimulation provides chronic pain relief to pelvic floor, and/or lower extremity, and/or upper extremity, and/or back, and/or bladder and/or bowel and/or vaginal to patients suffering from neurological and idiopathic pain with TES-CoN therapy.

Embodiment 129: The method according to any one of embodiments 75-126, wherein said transcutaneous electrical stimulation provides a reduction or elimination of pain.

Embodiment 130: The method of embodiment 129, wherein said transcutaneous electrical stimulation provides pain relief to one or more of pelvic floor, lower extremity, back, upper extremity to patients suffering from neurological and idiopathic pain.

Embodiment 131: The method according to any one of embodiments 75-126, wherein said transcutaneous electrical stimulation facilities locomotor function (standing and/or stepping).

Embodiment 132: The method according to any one of embodiments 75-131, wherein said transcutaneous electrical stimulation facilitates arm and/or hand control.

Embodiment 133: The method according to any one of embodiments 75-132, wherein said transcutaneous electrical stimulation facilitates speech function.

Embodiment 134: The method according to any one of embodiments 75-132, wherein said transcutaneous electrical stimulation facilitates breathing function.

Embodiment 135: The method according to any one of embodiments 75-132, wherein said transcutaneous electrical stimulation facilitates eating and chewing function.

Embodiment 136: The method according to any one of embodiments 75-132, wherein said transcutaneous electrical stimulation facilitates coughing function.

Embodiment 137: The method according to any one of embodiments 75-132, wherein said transcutaneous electrical stimulation facilitates vision and focus.

Embodiment 138: The method according to any one of embodiments 75-132, wherein said transcutaneous electrical stimulation facilitates cardiovascular function.

Embodiment 139: The method according to any one of embodiments 75-132, wherein said transcutaneous electrical stimulation facilitates sexual function.

Embodiment 140: The method according to any one of embodiments 75-132, wherein said transcutaneous electrical stimulation facilitates bladder and/or bowel function.

Embodiment 141: The method of embodiment 140, wherein said transcutaneous electrical stimulation is applied over or more sites selected from T10-T11, T11-T12, T12-L1, L1-L2, L2-L3, and L3-L4.

Embodiment 142: The method according to any one of embodiments 140-141, wherein said transcutaneous electrical stimulation produces an improvement in bladder function.

Embodiment 143: The method of embodiment 142, wherein said improvement in bladder function is characterized by one or more metrics selected from the group consisting of improved urodynamic bladder capacity, improved urodynamic voiding efficiency, improved quality of life scores assessed via Neurogenic Bladder Symptom Score, a reduction in incontinence episodes assessed via 4-day voiding diary, and a reduced frequency of urinary tract infections.

Embodiment 144: The method according to any one of embodiments 142-143, wherein said improvement in bladder function is characterized by one or more metrics selected from the group consisting of a 50% or greater reduction in incontinence episodes, a 50% or more increase in bladder capacity (or increase to 300 ml, whichever is higher), and a reduction in Neurogenic Bladder Symptom Score.

Embodiment 145: The method according to any one of embodiments 140-141, wherein said transcutaneous electrical stimulation produces an improvement in bowel function.

Embodiment 146: The method of embodiment 145, wherein said improvement in bowel function is characterized by one or more metrics selected from the group consisting of an improvement in time to complete bowel program, a change in the number of complete spontaneous bowel movements per week, an improvement in motility index (pressure amplitude and number of contractions (via colonic manometry)), improved constipation and fecal incontinence scores (Cleveland Clinic Constipation Scoring System, Neurogenic Bowel Dysfunction Score), a change in anal sphincter resting, squeeze pressure, length of the high-pressure zone and pressure profile of the anal canal (via high-resolution anorectal manometry), and an improved quality of life (PAC-QOL score).

Embodiment 147: The method according to any one of embodiments 145-146, wherein said improvement in bowel function is characterized by one or more metrics selected from the group consisting of a 50% or greater reduction in time to complete bowel program, a 50% or greater reduction in digital stimulation/suppository use, and a reduction (e.g., a 3-point or greater reduction) in Neurogenic Bowel Dysfunction Score.

Embodiment 148: The method according to any one of the embodiments 138-147, wherein said transcutaneous electrical stimulation produces simultaneous improvement in bladder and bowel function or bladder and sexual function or bladder and bowel and sexual function or bladder and cardiovascular function.

Embodiment 149: The method according to any one of embodiments 140-148, wherein said transcutaneous electrical stimulation is applied at a frequency ranging from about 0.5 Hz up to about 100 Hz, or from about 1 Hz up to about 50 Hz, or from about 10 Hz up to about 30 Hz, or from about 0.5 Hz to about 1 Hz, or from about 1 Hz to about 2 Hz, or from about 2 Hz to about 5 Hz, or from about 5 Hz to about 10 Hz, or from about 10 Hz to about 30 Hz, or from about 30 Hz to about 100 Hz to induce bladder or bowel voiding.

Embodiment 150: The method according to any one of embodiments 140-148, wherein said transcutaneous electrical stimulation is applied at a frequency of about 10 Hz to about 30 Hz, about 30 Hz to about 50 Hz, about 50 Hz to about 100 Hz, about 100 Hz to about 1 Khz, or about 1 Khz to about 10 Khz to induce bladder or bowel retention.

Embodiment 151: The method according to any one of embodiments 75-150, wherein said subject is administered at least one monoaminergic agonist.

Embodiment 152: The method of embodiment 151, wherein said at least one monoaminergic agonist comprises an agent selected from the group consisting of a serotonergic drug, a dopaminergic drug, a noradrenergic drug, a GABAergic drug, and a glycinergic drug.

Embodiment 153: The method of embodiment 152, wherein said agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetra-hydro-3-benzazepin-8-ol (SCH-23390), Quinpirole, and Eticlopride.

Embodiment 154: The method of embodiment 152, wherein said monoaminergic agonist is buspirone.

Embodiment 155: The method according to any one of embodiments 75-154, wherein said subject is a non-human mammal.

Embodiment 156: The method according to any one of embodiments 75-154, wherein said subject is a human.

Embodiment 157: A method of applying dynamic electrical stimulation to a subject, said method comprising:

provide a stimulator according to any one of embodiments 1-66, wherein said stimulator stores one or more stimulation programs, and wherein one or more channels of said stimulator are electrically coupled to one or more transcutaneous stimulation electrodes disposed on the surface of a subjects body, and/or wherein one or more channels of said stimulator are electrically coupled to one or more epidural electrodes disposed on a region of the spinal cord; and operating said stimulator according to one or more of said programs to provide dynamic transcutaneous electrical stimulation to said subject and/or to provide dynamic epidural stimulation to said subject.

Embodiment 158: The method of embodiment 157, wherein said subject has a spinal cord injury, an ischemic brain injury, and/or a neurodegenerative condition.

Embodiment 159: The method of embodiment 158, wherein said subject has a spinal cord injury that is clinically classified as motor incomplete.

Embodiment 160: The method of embodiment 158, wherein said subject has a spinal cord injury that is clinically classified as motor complete.

Embodiment 161: The method of embodiment 158, wherein said subject has an ischemic brain injury.

Embodiment 162: The method of embodiment 161, wherein said ischemic brain injury is brain injury from stroke or acute trauma.

Embodiment 163: The method of embodiment 158, wherein said subject has a neurodegenerative pathology.

Embodiment 164: The method of embodiment 163, wherein said neurodegenerative pathology is associated with a condition selected from the group consisting of stroke, Parkinson's disease, Huntington's disease, Alzheimer's disease, amyotrophic lateral sclerosis (ALS), primary lateral sclerosis (PLS), dystonia, hemispherictomy, transverse myelitis, conus medularis injury (lower motor neuron injury) and cerebral palsy.

Embodiment 165: The method of embodiment 157, wherein said subject has an idiopathic condition of overactive bladder, and/or constipation.

Embodiment 166: The method of embodiment 157, wherein said subject has muscle loss due to inactive lifestyle.

Embodiment 167: The method of embodiment 157, wherein said subject is obese.

Embodiment 168: The method of embodiment 157, wherein said subject has muscle loss associated with aging.

Embodiment 169: The method of embodiment 157, wherein said subject has pain due to fibromyalgia, and/or interstitial cystitis, and/or chronic prostatitis, and/or chronic pelvic pain syndrome and/or painful bladder syndrome.

Embodiment 170: The method according to any one of embodiments 157-169, wherein said stimulator provides one or more of the following stimulation patterns on one or more independently controlled channels: amplitude modulated dynamic stimulation; and/or frequency modulated dynamic stimulation.

Embodiment 171: The method of embodiment 170, wherein said stimulator provides the same stimulation modality and stimulation parameters on 2 or more different channels or on 3 or more different channels, or on 4 or more different channels.

Embodiment 172: The method of embodiment 170, wherein said stimulator provides the a different stimulation modality and/or different stimulation parameters on 2 or more different channels or on 3 or more different channels, or on 4 or more different channels.

Embodiment 173: The method according to any one of embodiments 157-172, wherein at least one channel of said stimulator is coupled to an epidural electrode and provides dynamic epidural stimulation.

Embodiment 174: The method according to any one of embodiments 157-173, wherein at least one channel of said stimulator is coupled to a transcutaneous stimulation electrode and provides dynamic transcutaneous electrical stimulation.

Embodiment 175: The method of embodiment 174, wherein said transcutaneous electrical stimulation comprises frequency modulated stimulation.

Embodiment 176: The method according to any one of embodiments 157-175, wherein at least one channel of said stimulator is coupled to an epidural electrode and provides amplitude modulated dynamic epidural stimulation.

Embodiment 177: The method according to any one of embodiments 157-175, wherein at least one channel of said stimulator is coupled to a transcutaneous stimulation electrode and provides amplitude modulated dynamic transcutaneous electrical stimulation.

Embodiment 178: The method according to any one of embodiments 176-177, wherein said amplitude modulated dynamic epidural stimulation and/or said amplitude modulated dynamic transcutaneous electrical stimulation comprises a stimulation signal derived from an electromyograph recording.

Embodiment 179: The method of embodiment 178, wherein said electromyograph recording is derived from EMG from leg muscle during standing, and/or stepping, and/or in a Gravity Neutral device and/or from hand and/or arm, and/or breathing, and/or coughing, and/or eating, and/or after administration of a stimulant (e.g., coffee).

Embodiment 180: The method according to any one of embodiments 157-179, wherein said transcutaneous electrical stimulation and/or said epidural stimulation provides electrical stimulation of the spinal cord.

Embodiment 181: The method according to any one of embodiments 157-180, wherein said transcutaneous electrical stimulation and/or said epidural stimulation enhances/facilitates endogenous neural circuitry activity.

Embodiment 182: The method according to any one of embodiments 157-181, wherein said transcutaneous electrical stimulation and/or epidural stimulation does not substantially provide peripheral nerve stimulation.

Embodiment 183: The method according to any one of embodiments 157-182, wherein at least one channel of said transcutaneous electrical stimulation and/or epidural stimulation is applied at (epidural) or over (transcutaneous) one or more regions straddling or spanning a region selected from the group consisting of the brainstem, C0-C1, C0-C2, C0-C3, C0-C4, C0-C5, C0-C6, C0-C7, C0-T1, C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

Embodiment 184: The method of embodiment 183, wherein at least one channel of said transcutaneous electrical stimulation and/or epidural stimulation is applied at (epidural) or over (transcutaneous) a region comprising or consisting of C2-C3 or a region therein.

Embodiment 185: The method of embodiment 184, wherein at least one channel of said transcutaneous electrical stimulation and/or epidural stimulation is applied at (epidural) or over (transcutaneous) C3.

Embodiment 186: The method according to any one of embodiments 157-185, wherein at least one channel of said transcutaneous electrical stimulation and/or epidural stimulation is applied at (epidural) or over (transcutaneous) the thoracic spinal cord or a region thereof.

Embodiment 187: The method of embodiment 186, wherein at least one channel of said transcutaneous electrical stimulation and/or epidural stimulation is applied at (epidural) or over (transcutaneous) one or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, and T12-T12.

Embodiment 188: The method according to any one of embodiments 157-187, wherein at least one channel of said transcutaneous electrical stimulation and/or epidural stimulation is applied at (epidural) or over (transcutaneous) the lumbar spinal cord or a region thereof.

Embodiment 189: The method of embodiment 188, wherein at least one channel of said transcutaneous electrical stimulation and/or epidural stimulation is applied at (epidural) or over (transcutaneous) one or more regions straddling or spanning a region selected from the group consisting of L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 190: The method of embodiment 188, wherein at least one channel of said transcutaneous electrical stimulation and/or epidural stimulation is applied at (epidural) or over (transcutaneous) the coccyx.

Embodiment 191: The method according to any one of embodiments 157-190, wherein at least one channel of said transcutaneous electrical stimulation and/or epidural stimulation is applied at (epidural) or over (transcutaneous) a region between T11 and L4.

Embodiment 192: The method of embodiment 191, w wherein at least one channel of said transcutaneous electrical stimulation and/or epidural stimulation is applied at (epidural) or over (transcutaneous) one or more regions selected from the group consisting of T11-T12, L1-L2, and L2-L3.

Embodiment 193: The method of embodiment 191, wherein at least one channel of said transcutaneous electrical stimulation and/or epidural stimulation is applied at (epidural) or over (transcutaneous) L1-L2 and/or over T11-T12.

Embodiment 194: The method according to any one of embodiments 157-193, wherein said transcutaneous electrical stimulation facilities locomotor function (standing and/or stepping).

Embodiment 195: The method according to any one of embodiments 157-194, wherein said transcutaneous electrical stimulation wherein said stimulation facilitates arm and/or hand control.

Embodiment 196: The method according to any one of embodiments 157-195, wherein said transcutaneous electrical stimulation wherein said stimulation facilitates bladder and/or bowel function.

Embodiment 197: The method according to any one of embodiments 132-196, wherein said subject is administered at least one monoaminergic agonist.

Embodiment 198: The method of embodiment 197, wherein said at least one monoaminergic agonist comprises an agent selected from the group consisting of a serotonergic drug, a dopaminergic drug, a noradrenergic drug, a GABAergic drug, and a glycinergic drug.

Embodiment 199: The method of embodiment 198, wherein said agent comprises one or more drugs selected from the group consisting of 4-(benzodioxan-5-yl)1-(indan-2-yl)piperazine (S15535), 4-amino-(6-chloro-2-pyridyl)-1 piperidine hydrochloride (SR 57227A), 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), 8-hydroxy-2-(di-n-propylamino)tetralin (8-OH-DPAT), alnespirone (s-20,499), befiradol, binospirone (mdl-73,005), buspirone, clonidine, enilospirone (cerm-3,726), eptapirone (F-11,440), eticlopride., F-15,599, gepirone (ariza, variza), ipsapirone (tvx-q-7,821), ketanserin, methoxamine, N-{2-[4-(2-methoxy-phenyl)-1-piperazinyl]ethyl}-N-(2-pyridinyl)cyclo-hexanecarboxamide (WAY 100.635), ondanesetron, prazosin, quinpirole, quipazine, revospirone (bay-vq-7,813), tandospirone, tandospirone (sediel), yohimbine, and zalospirone (WY-47,846).

Embodiment 200: The method of embodiment 198, wherein said monoaminergic agonist is buspirone.

Embodiment 201: The method according to any one of embodiments 157-200, wherein said subject is a non-human mammal.

Embodiment 202: The method according to any one of embodiments 157-200, wherein said subject is a human.

Embodiment 203: A toilet seat comprising one or more transcutaneous stimulation electrodes where said transcutaneous electrodes are configured to contact a subject siting on said toilet seat at one or more locations where transcutaneous stimulation facilitates bladder and/or bowel voiding.

Embodiment 204: A garment or other wearable device comprising one or more transcutaneous stimulation electrodes where said transcutaneous electrodes are configured to contact a subject wearing said garment at one or more locations where said transcutaneous stimulation facilitates bladder and/or bowel retention.

Embodiment 205: The toilet seat of embodiment 203 or garment of embodiment 204, wherein said transcutaneous stimulation electrodes are located to contact a subject at one or more locations selected from the group consisting of C3-4 to C01 and/or over the Buttocks (S2-S3 foramen and roots).

Embodiment 206: A couch, chair, office chair, bed, or recliner comprising one or more transcutaneous stimulation electrodes where said transcutaneous electrodes are configured to contact a subject siting on said toilet seat at one or more locations where transcutaneous stimulation facilitates bladder and/or bowel retention.

Definitions

The terms "monophasic pulse pattern" or "monophasic stimulation" refers to stimulation pulses that are only negative or only positive with respect to a neutral lead (see, e.g., FIG. 1, panel A). Where a monophasic pulse pattern is charge balanced, however, a current may be applied between stimulation pulses (or stimulation pulse bursts) that is opposite in sign to the stimulation pulses (see, e.g., FIG. 1, panel B).

The term biphasic pulse pattern or biphasic stimulation refers to stimulation pulses that include pulses that are positive and pulses that are negative with respect to a neutral lead (see, e.g., FIG. 2, panel A). Where biphasic pulse patterns are charge balanced, the charge balance can be obtained by maintaining equal areas of anodic and cathodic pulses (see, e.g., FIG. 2, panel B). In a delayed biphasic pulse patter, there is a delay between the positive and negative pulse (see, e.g., FIG. 2, panel A, bottom).

The term "high frequency carrier" refers to a pulse pattern that is higher frequency than the "stimulation" pulse pattern. As illustrated in FIG. 1, panels A-C, the stimulation signal is produced by bursts of pulses. The pulses comprising each burst are the "high frequency carrier". The burst frequency is the stimulation frequency.

The term "module" or "unit" when used with respect to a pulse generation unit, a power conditioning unit, a pulse modulating (gating) unit, a shift generator unit, a charge balance unit, an DC current control unit, a monitoring unit, and the like refers to an electrical circuit configured to provide the stated functionality (e.g., pulse generation, gating pulse generation, etc.). The circuit may be independent from other circuits comprising the stimulator or may represent a subcomponent of a "larger" circuit.

The term "biosignal" refers to an electrical signal that has been recorded from a biological organism, or an electrical signal derived from such a signal, e.g., where the signal amplitude is normalized to a pre-selected current or voltage. In certain embodiments the biosignal is from a vertebrate. In certain embodiments the biosignal is from a mammal (e.g., a human, a non-human primate, etc.). In certain embodiments the biosignal is from an EEG, and EMG, or an EKG.

As used herein "electrical stimulation" or "stimulation" means application of an electrical signal that may be either excitatory or inhibitory to a muscle or neuron and/or to groups of neurons and/or interneurons. It will be understood that an electrical signal may be applied to one or more electrodes with one or more return electrodes.

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation. The term TESSLA (i.e., Transcutaneous Electrical Spinal Stimulation for Locomotor (or Lower Extremity, or Lower urinary tract) activation) can also be used.

The term "epidural electrical stimulation" or "epidural stimulation" refers to the application of an electrical current to the spinal cord via an implanted electrode or an implanted electrode array (e.g., implanted over the dura (the protective coating) of the spinal cord).

The term "motor complete" when used with respect to a spinal cord injury indicates that there is no motor function below the lesion, (e.g., no movement can be voluntarily induced in muscles innervated by spinal segments below the spinal lesion.

Monophasic pulse modulated signal with DC shift and no charge balance. Note amplitude refers to current.

Figure 2:
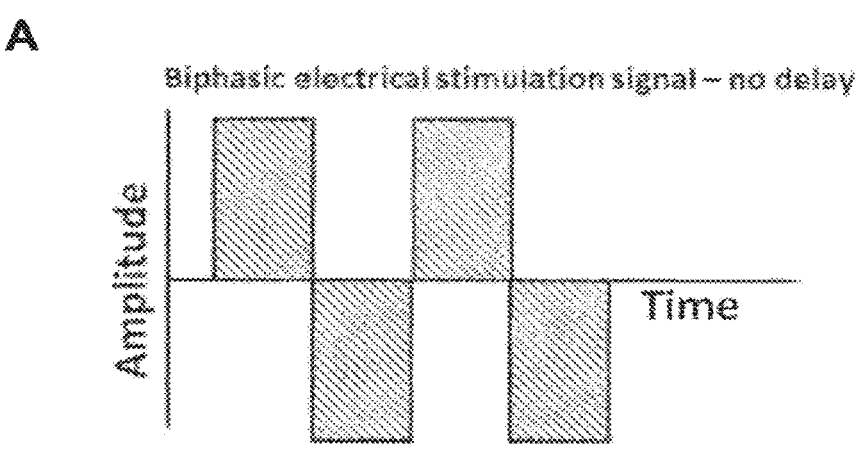
Figure 2:
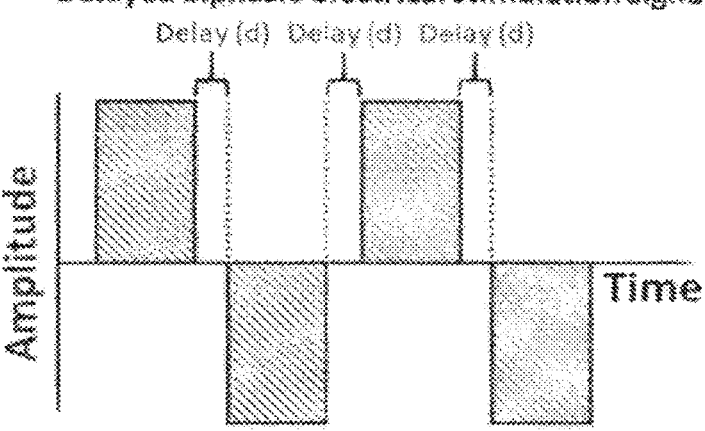

FIG. 2, panels A-C, illustrates various biphasic stimulation patterns. Panel A) Comparison of a biphasic stimulation signal (top) with a delayed biphasic stimulation signal (bottom) where the delay is given by time "d". Panel B) Delayed biphasic pulse modulated signal with charge balance. Charge balance is obtained by maintaining equal areas of anodic and cathodic pulses. Panel C) Delayed biphasic pulse modulated signal with DC shift (offset). Note amplitude refers to current.

Figure 3:
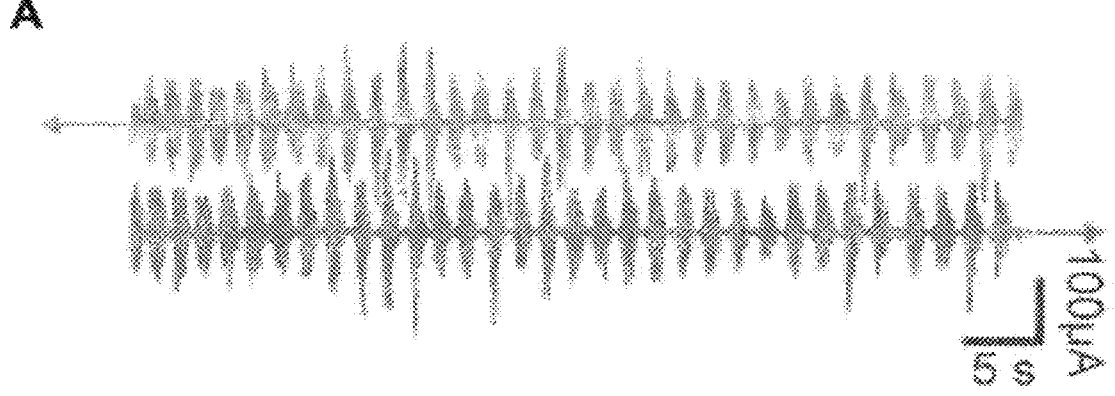
Figure 3:
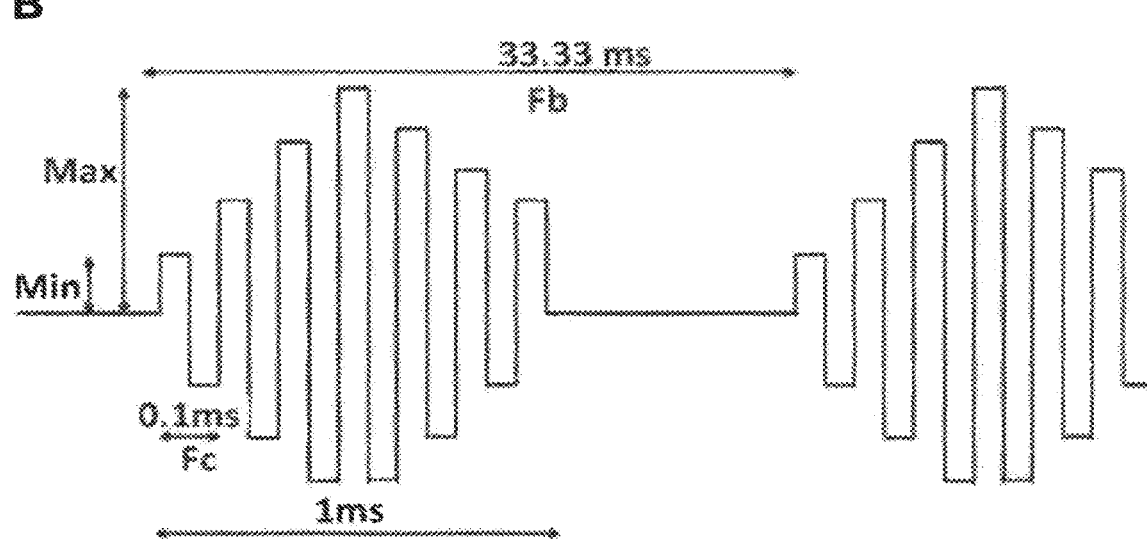

FIG. 3, panels A-B, illustrates dynamic stimulation. Panel A) Illustrative frequency modulated dynamic stimulation. Based on a data file (e.g., an ascii file) downloaded into the device a particular waveform can be generated. The only parameter that needs to be programmed is the maximum amplitude, and the other bursts are then scaled proportionally. Panel B) Illustrative amplitude modulated dynamic stimulation. This is similar to biphasic stimulation, but with the amplitude of each carrier frequency progressively modulated within a burst in a symmetric (or asymmetric) manner). Note amplitude refers to current.

Figure 4A:
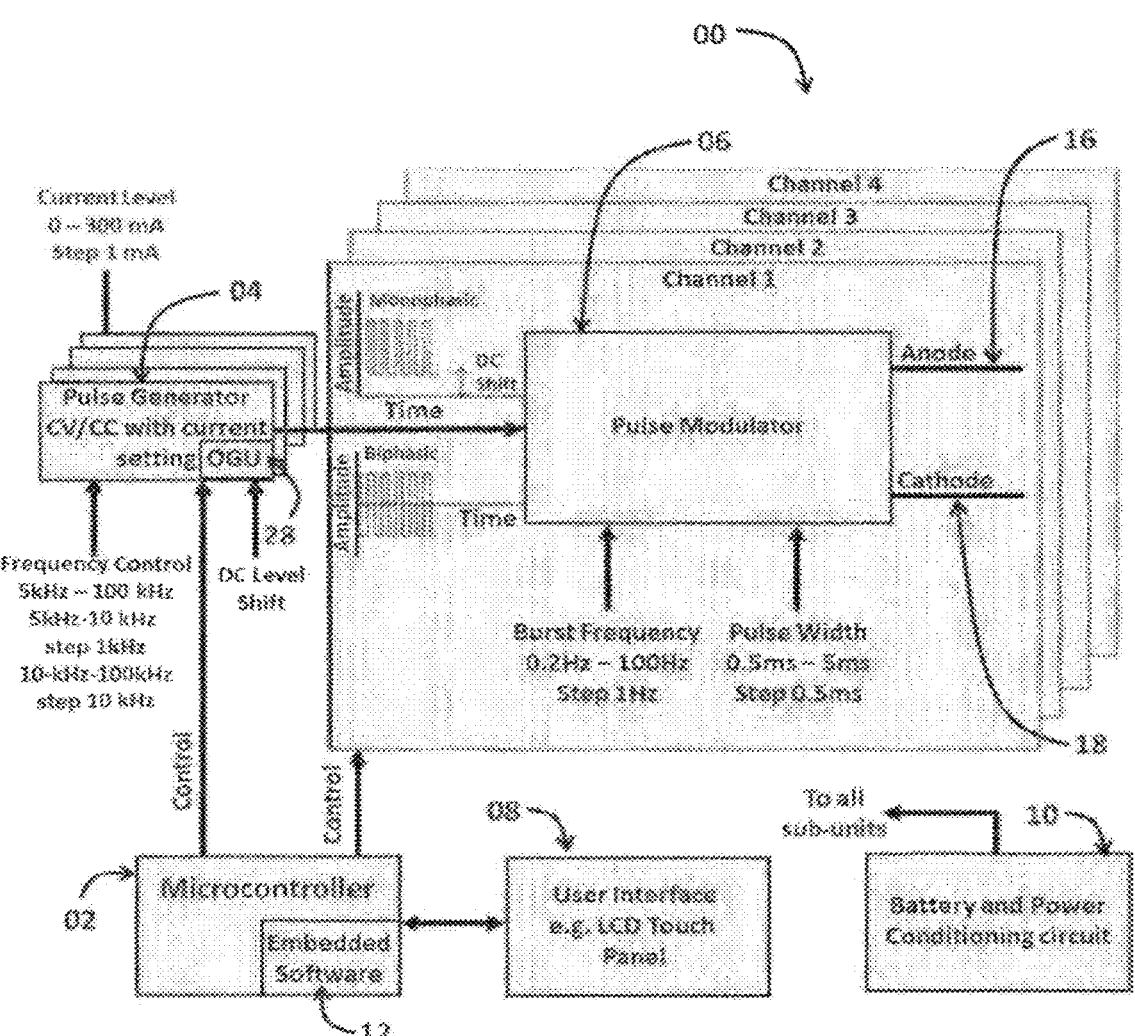
Figure 4B:
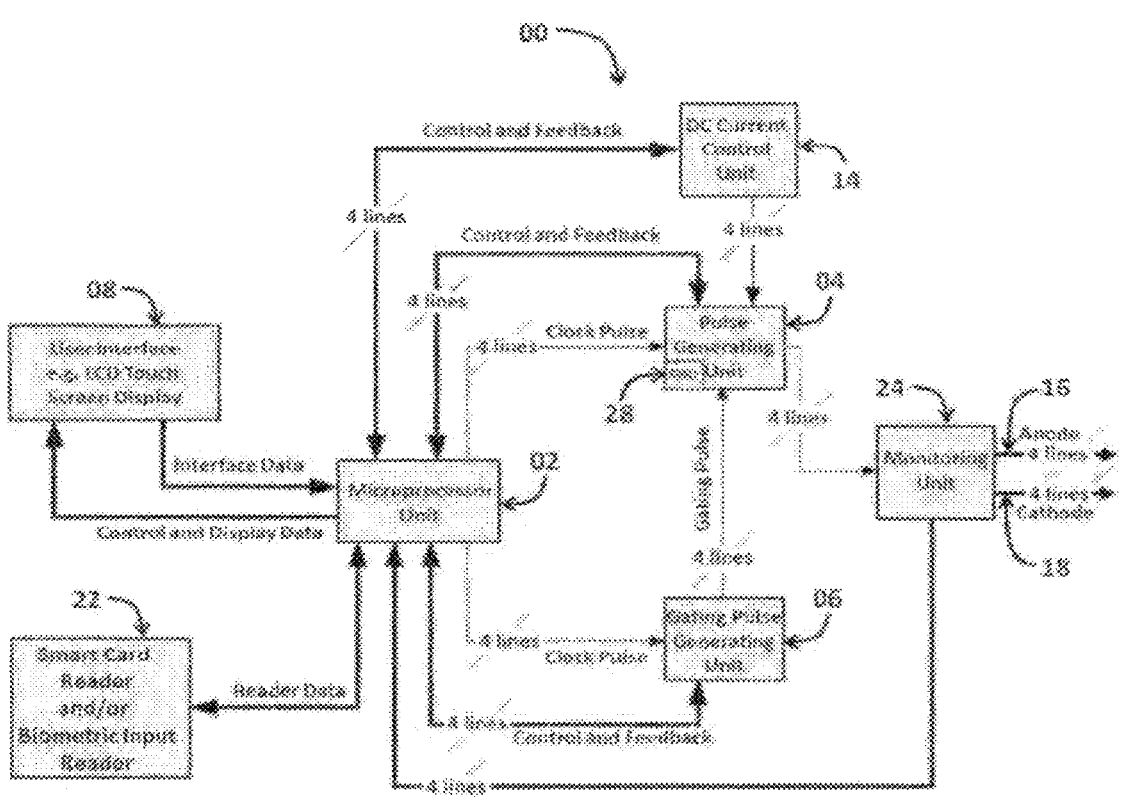
Figure 4C:
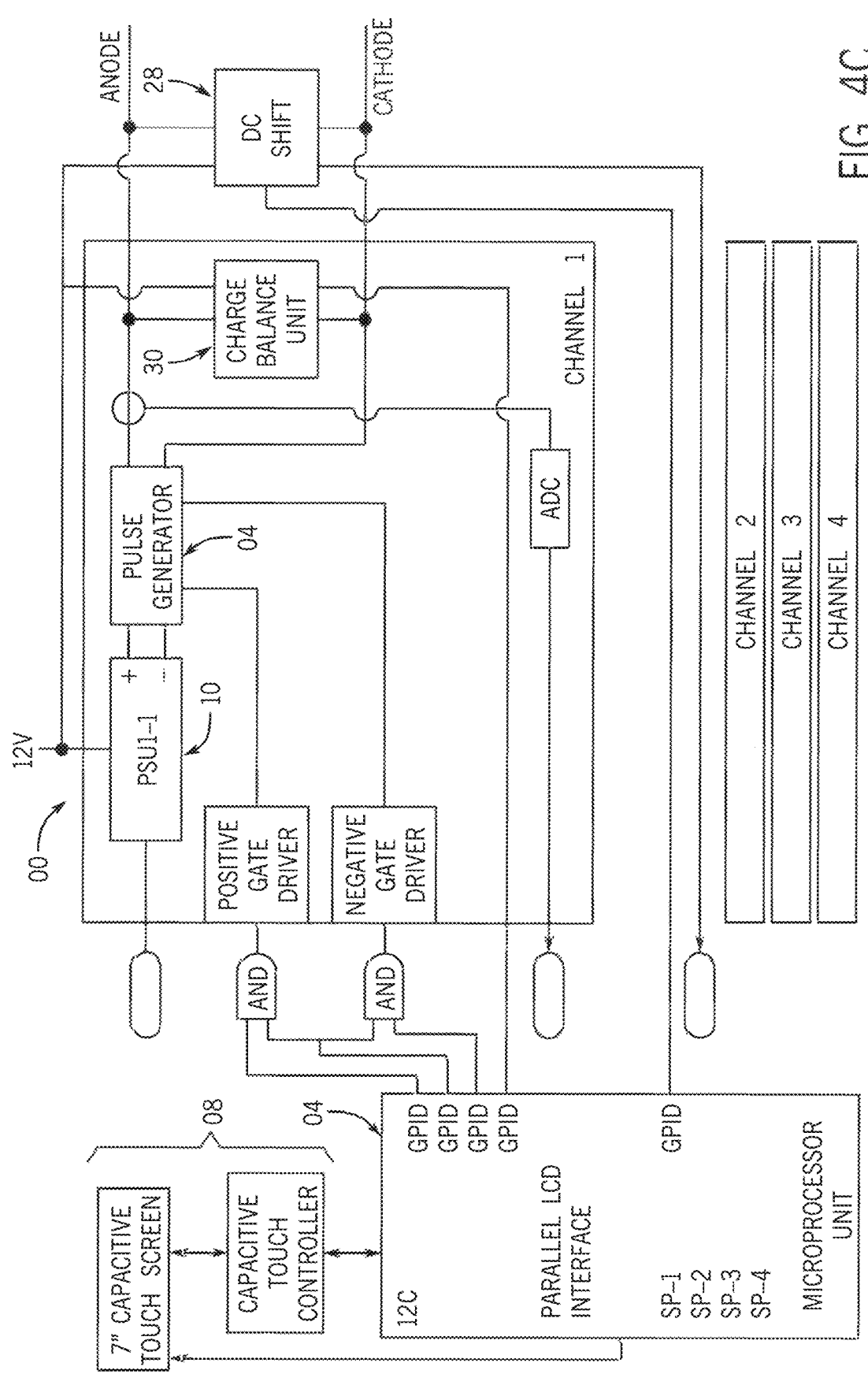

FIGS. 4A, 4B, and 4C, show block diagrams of illustrative embodiments of a four channel electrical stimulator.

Figure 5:
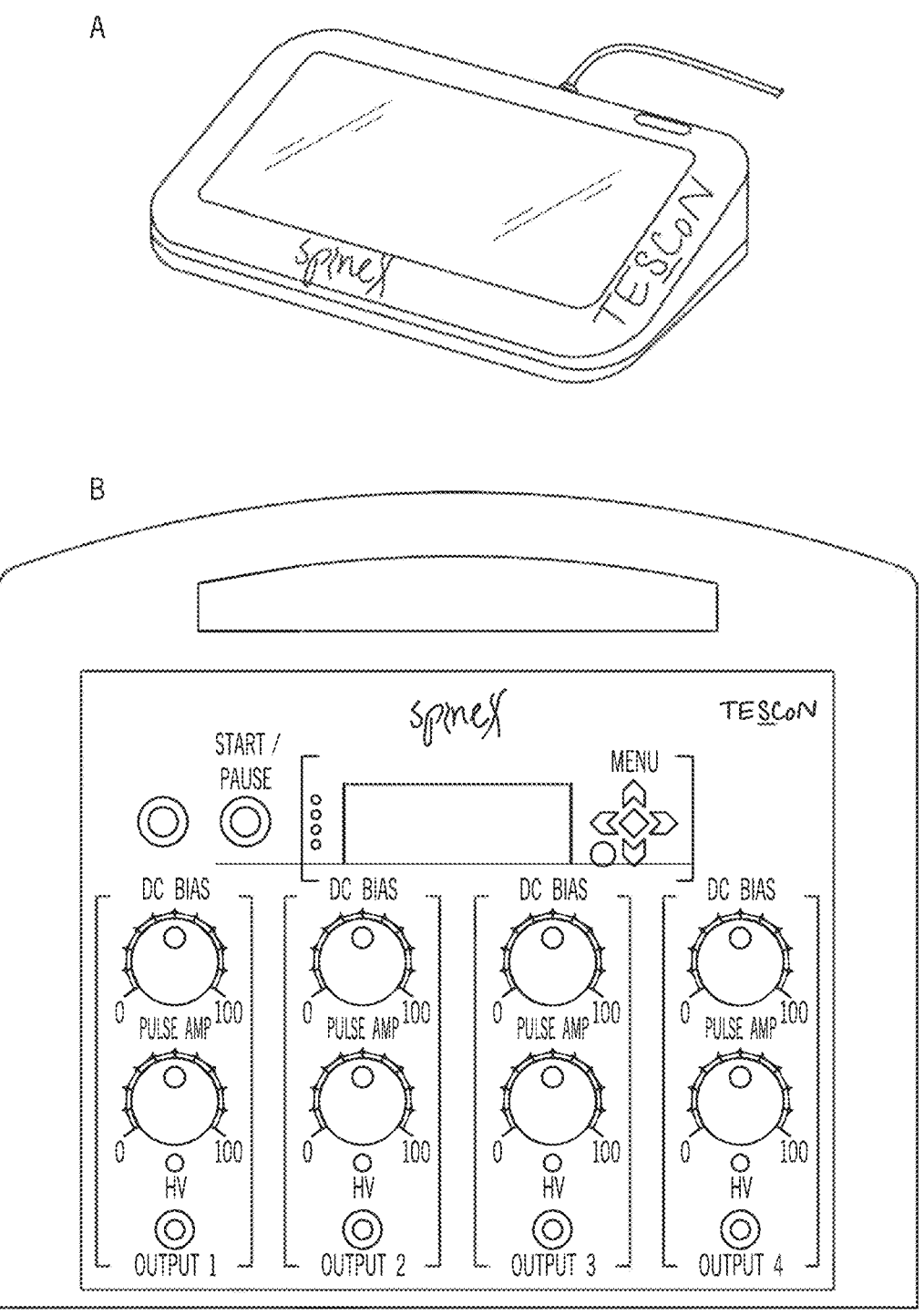

FIG. 5, panels A-B, respectively each illustrate an embodiments of a Transcutaneous Electrical Spinal Cord Neuromodulator (TESCoN™) device.

Figure 6:
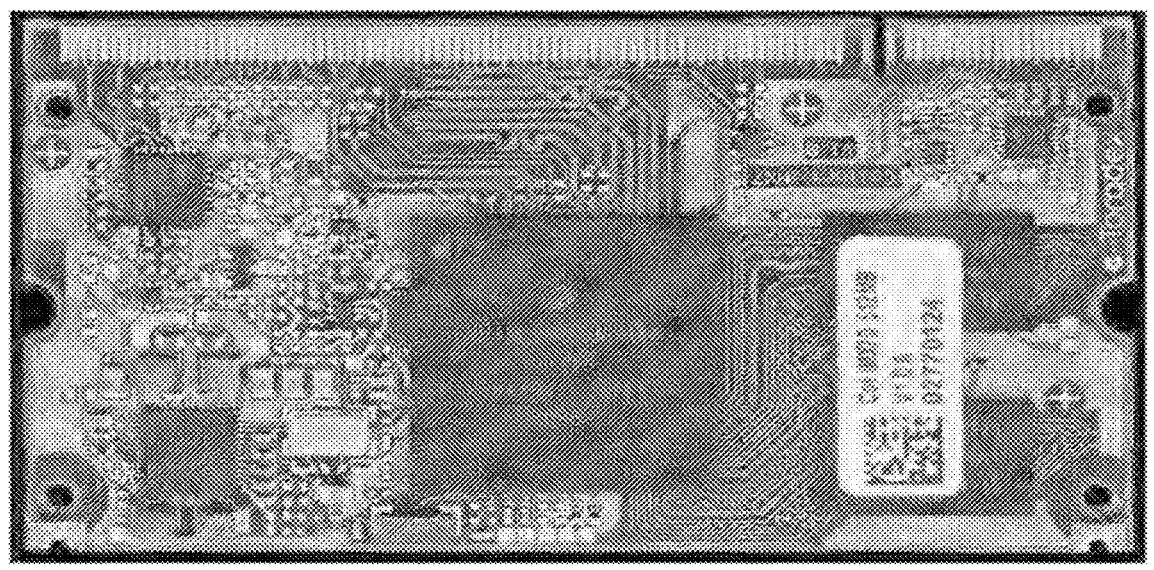

FIG. 6 illustrates one embodiment of an SODIMM.

Figure 7:
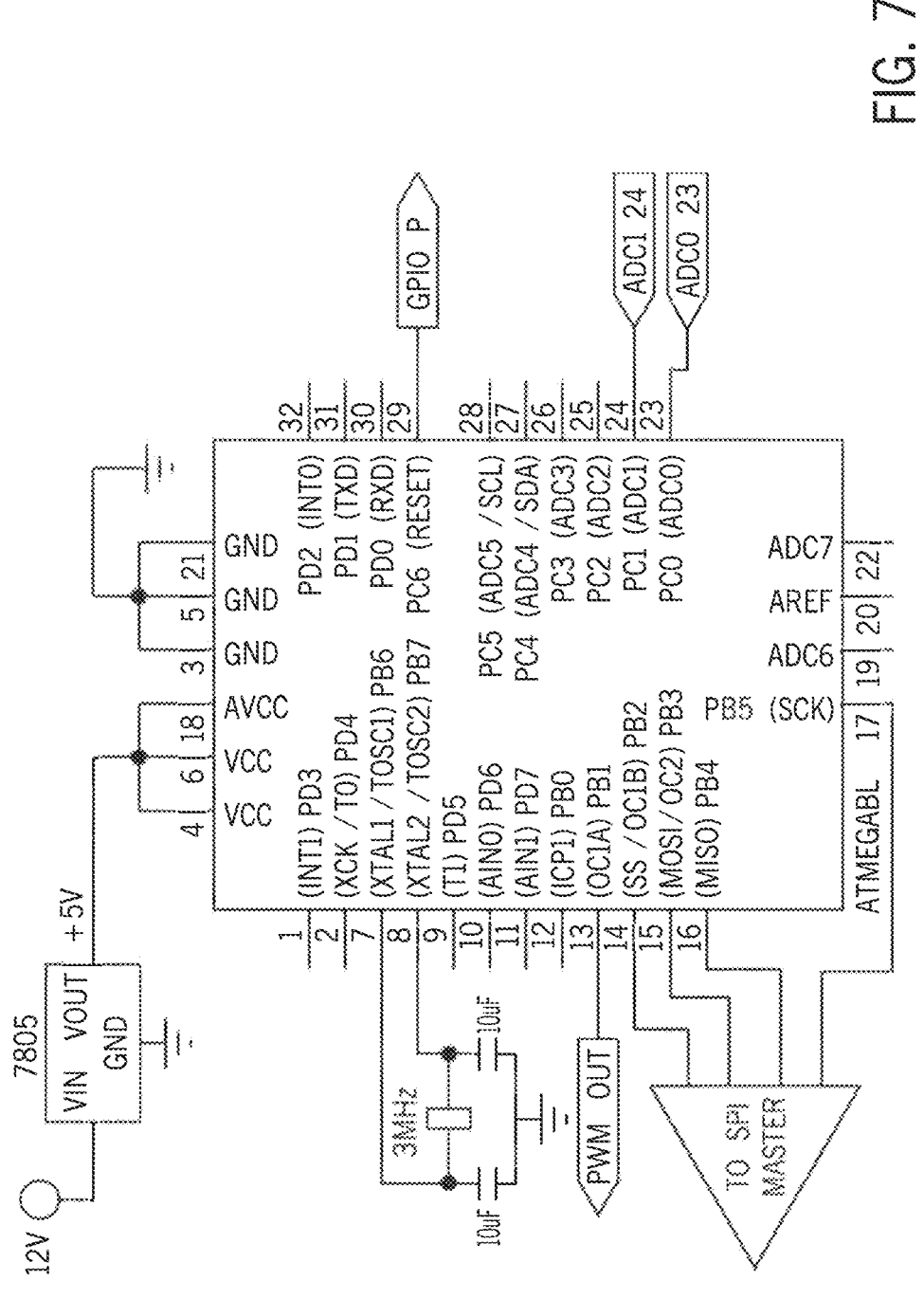

FIG. 7 illustrates a circuit diagram for one power supply of a channel. In certain embodiments each channel shall has one such unit.

Figure 8:
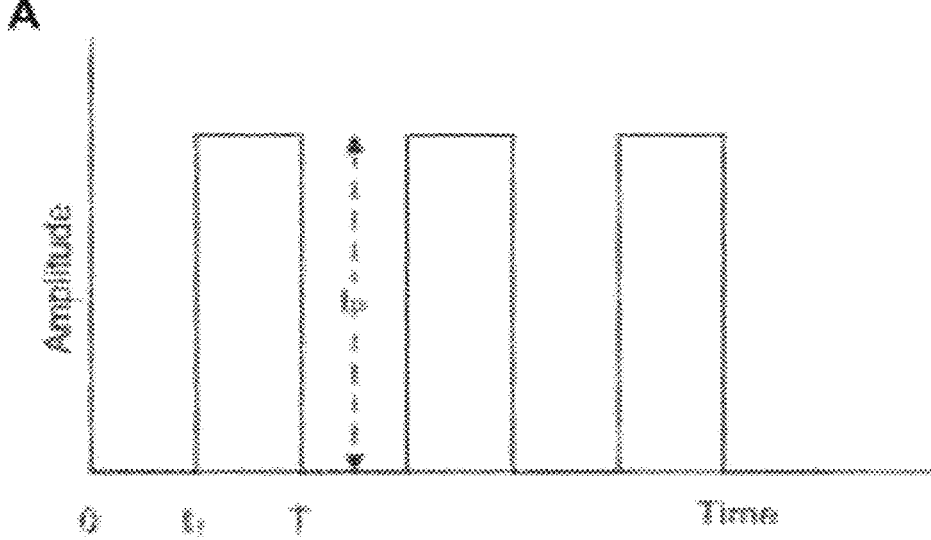

FIG. 8, panels A and B, illustrate waveform parameters for used in analysis. Panel A) monophasic pulses. Panel B) Delayed biphasic pulses.

Figure 9:
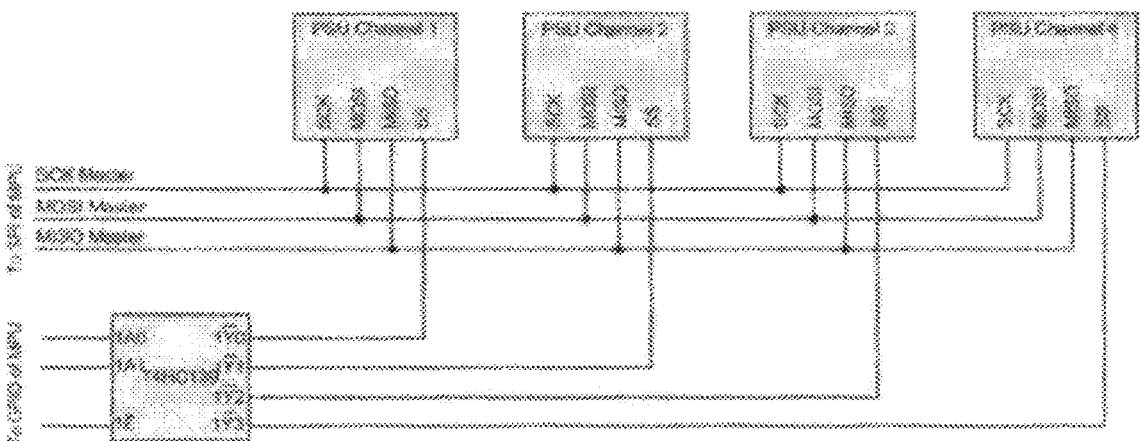

FIG. 9 illustrates one embodiment for controlling the PSU.

Figure 10:
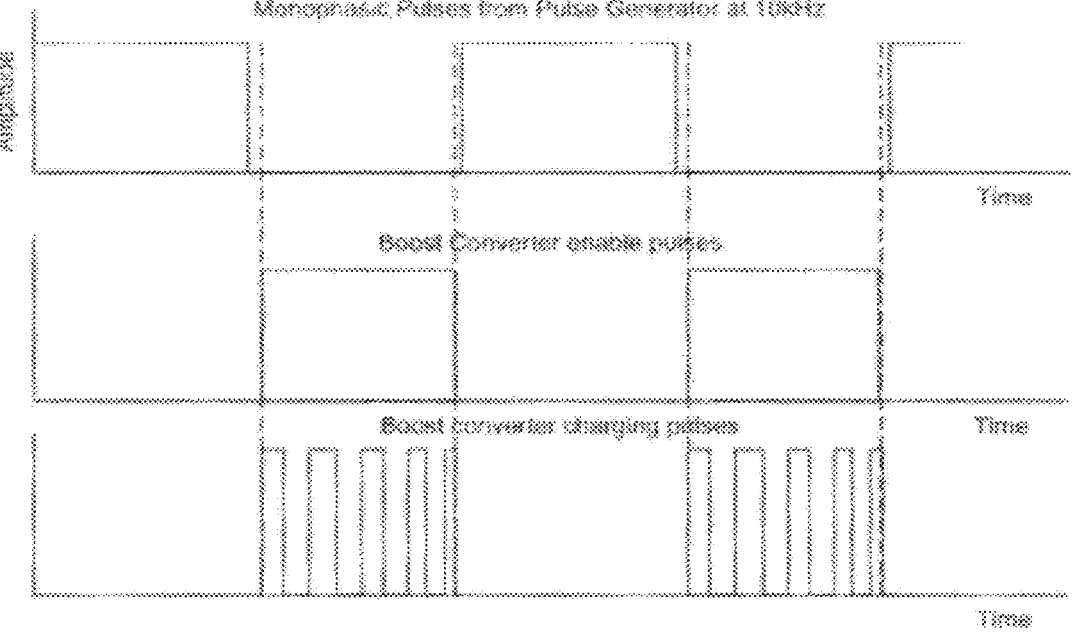

FIG. 10 illustrates one embodiment of a timing sequence.

Figure 11:
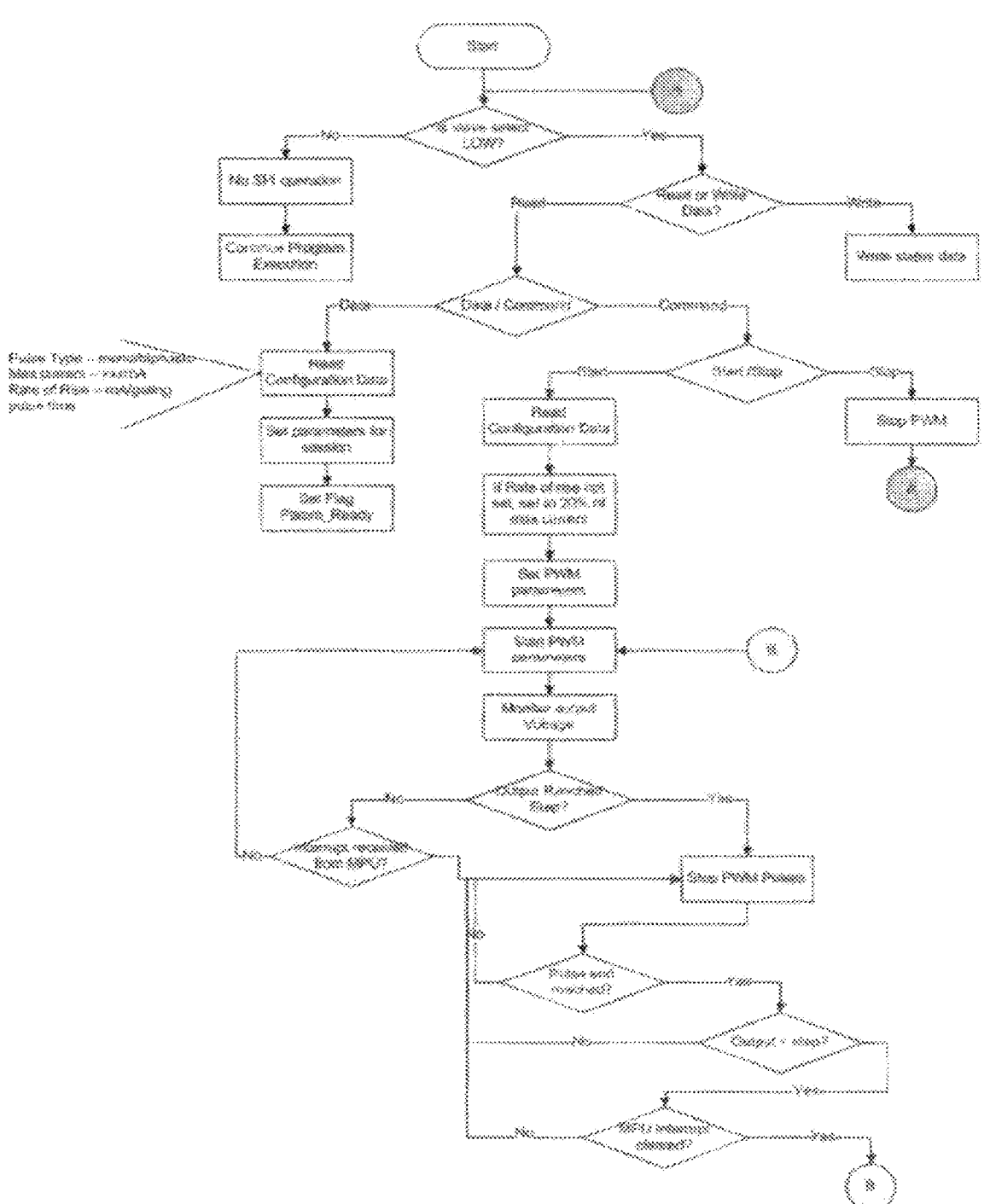

FIG. 11 illustrates a flow chart for power supply software.

Figure 12:
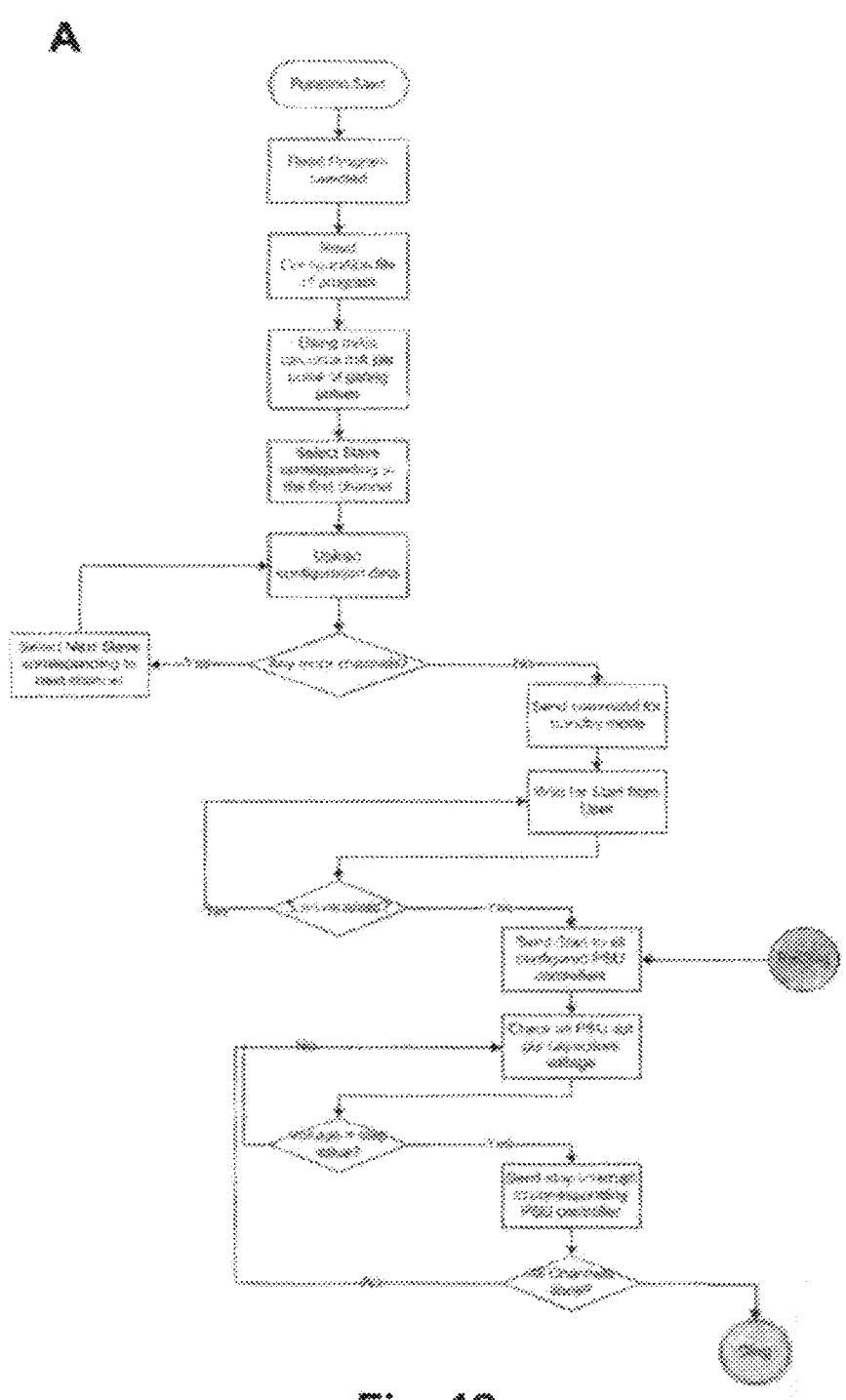

FIG. 12, panels A-B, shows a flowchart illustrating the functionality of the function on MPU for PSUs.

Figure 13:
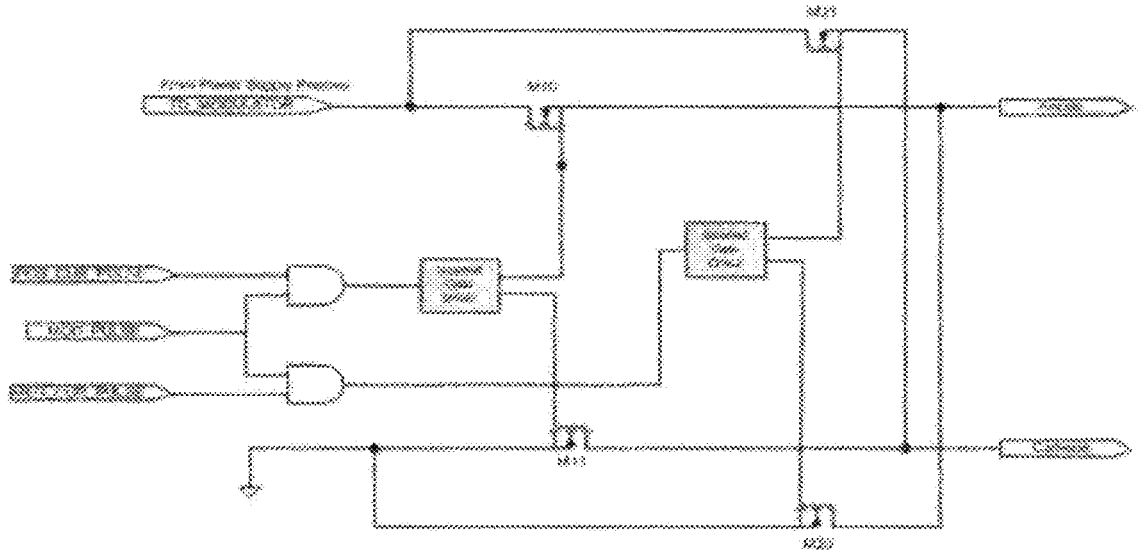

FIG. 13 illustrates AND gate used to gate monophasic or biphasic pulses.

Figure 14:
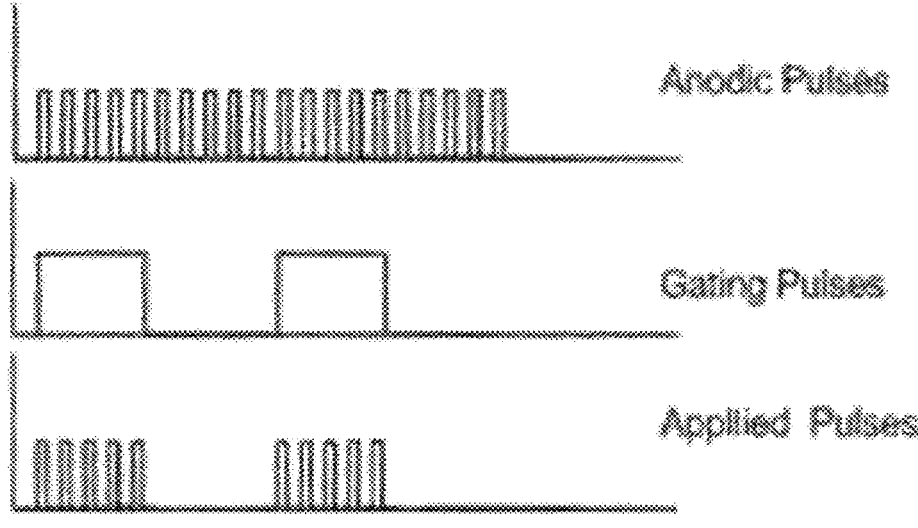

FIG. 14 illustrates working of AND gate combination for monophasic pulses.

Figure 15:
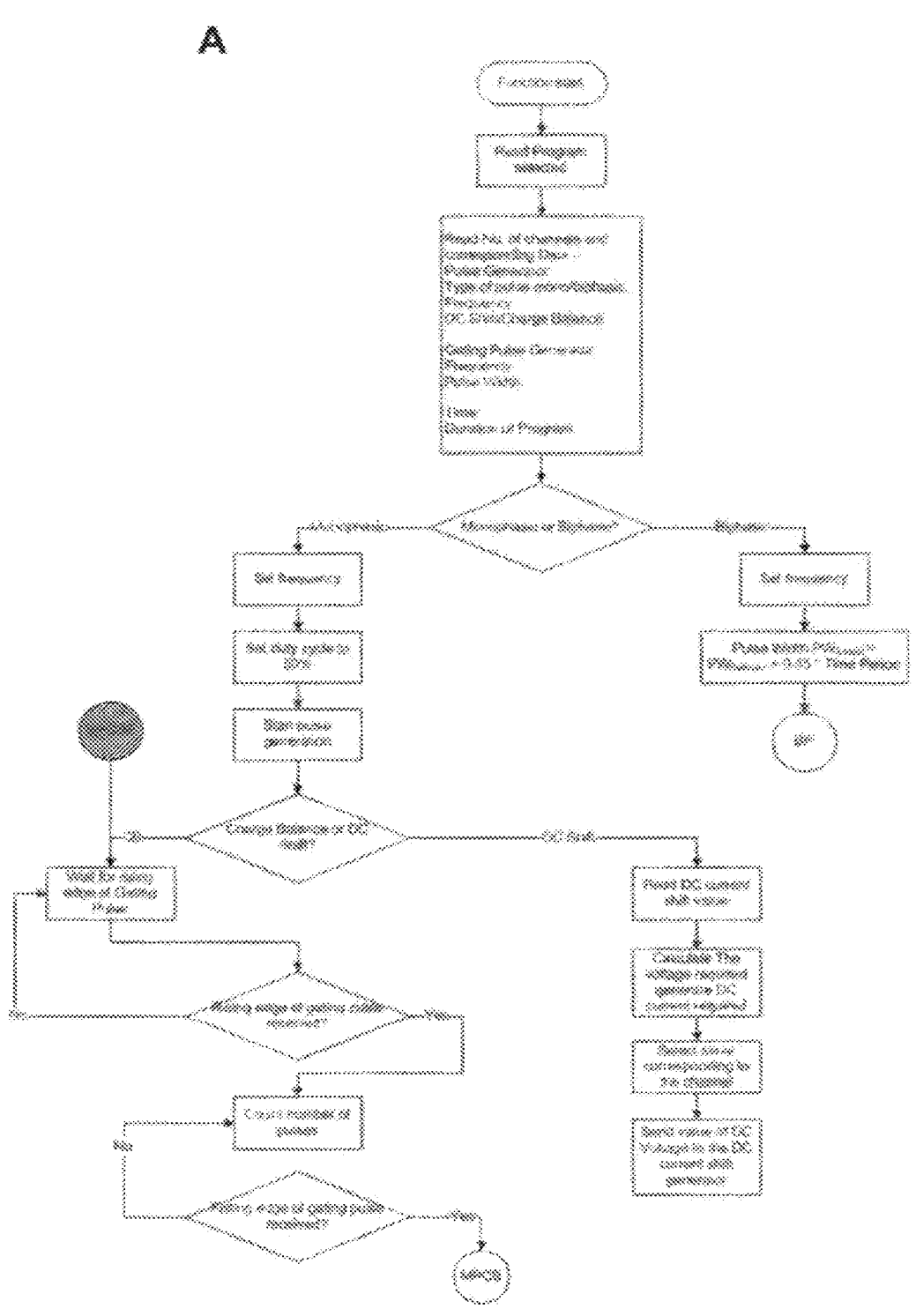

FIG. 15, panels A-C, illustrates flow chart for software that drives pulse generator.

Figure 16:
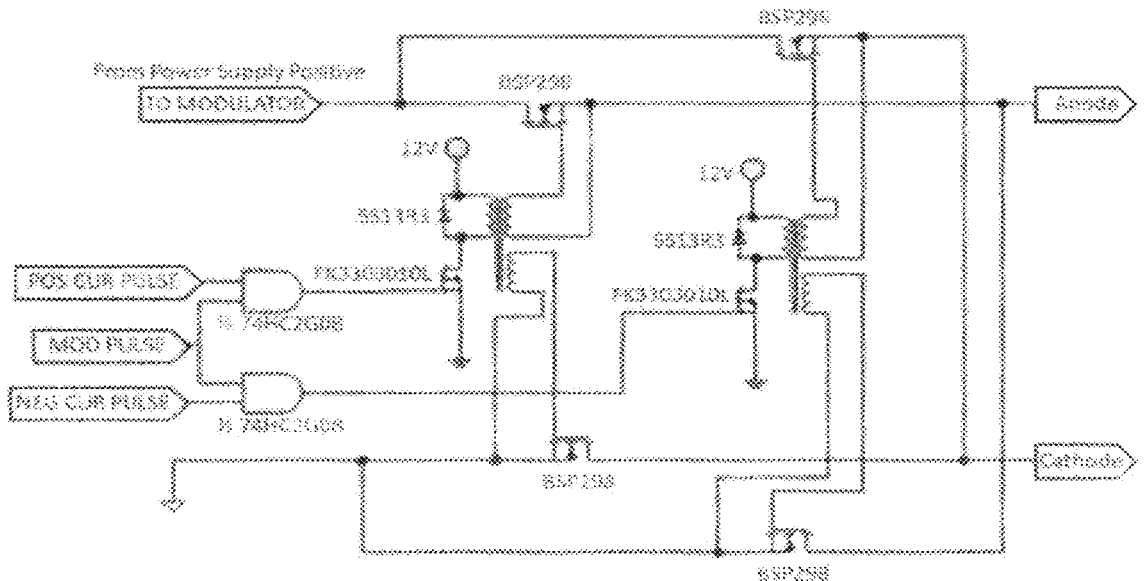

FIG. 16 illustrates a circuit diagram for the pulse generator and modulator unit. In certain embodiments each channel has one such unit.

Figure 17:
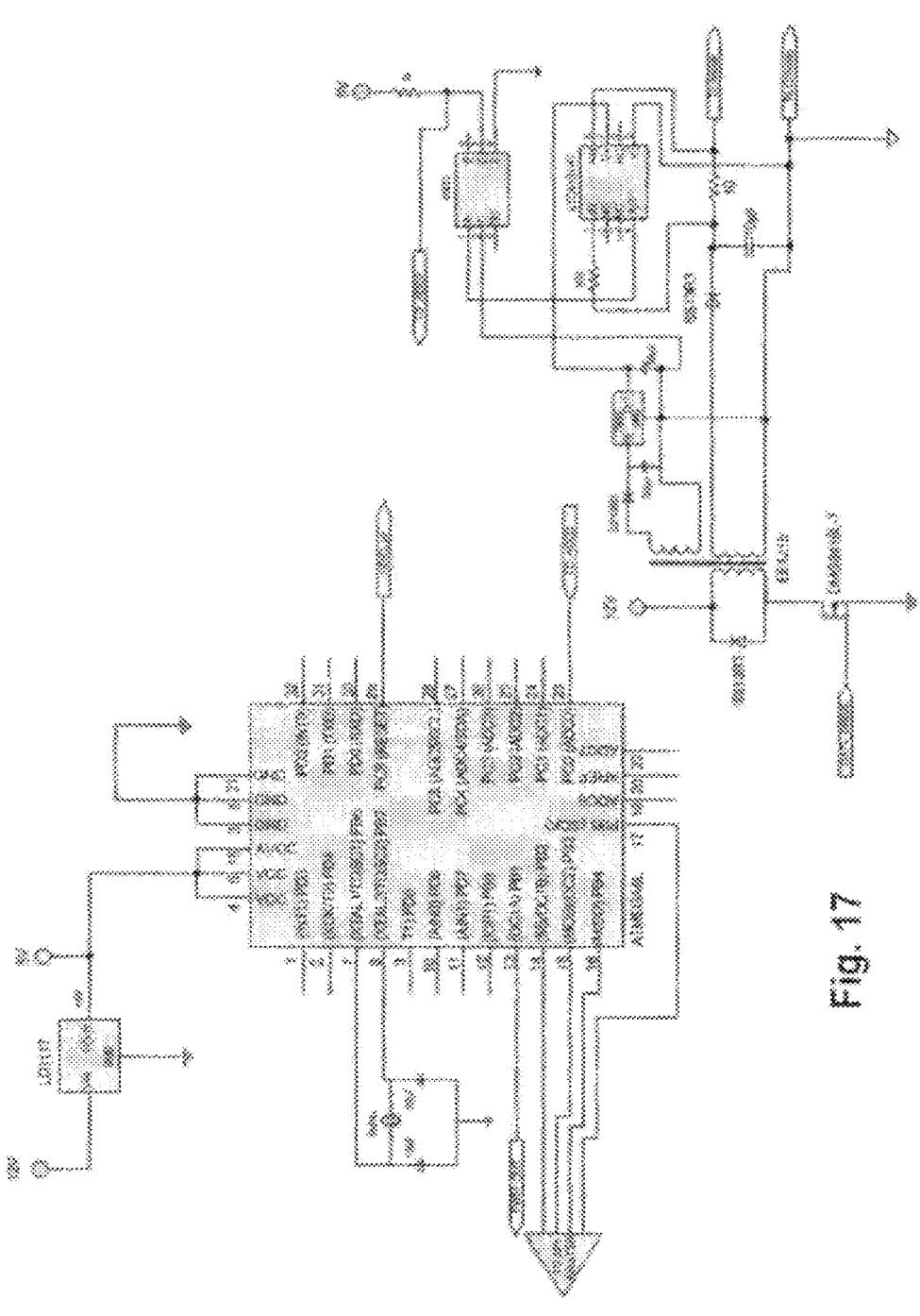

FIG. 17 illustrates a circuit diagram for a DC shift generator. In certain embodiments this is used to introduce DC shift in the monophasic pulses without charge balance. In certain embodiments this is for the anodic pulses only.

Figure 18:
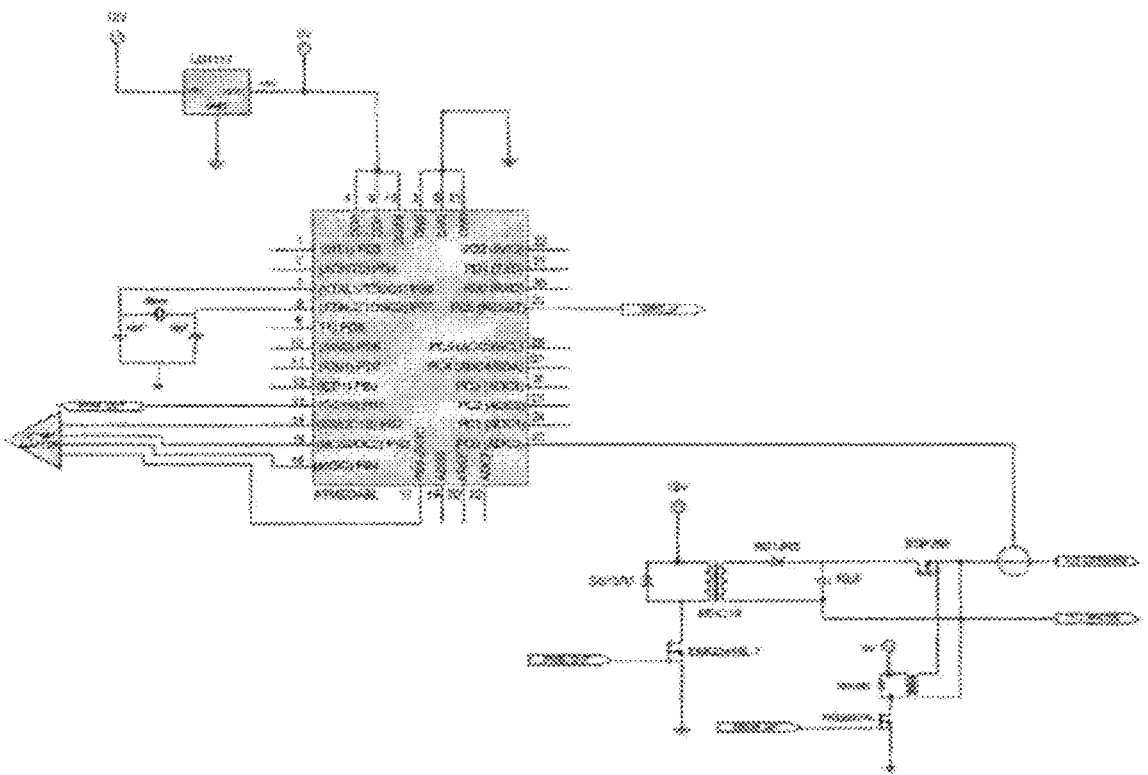

FIG. 18 illustrates a circuit diagram for a charge balance unit.

Figure 19:
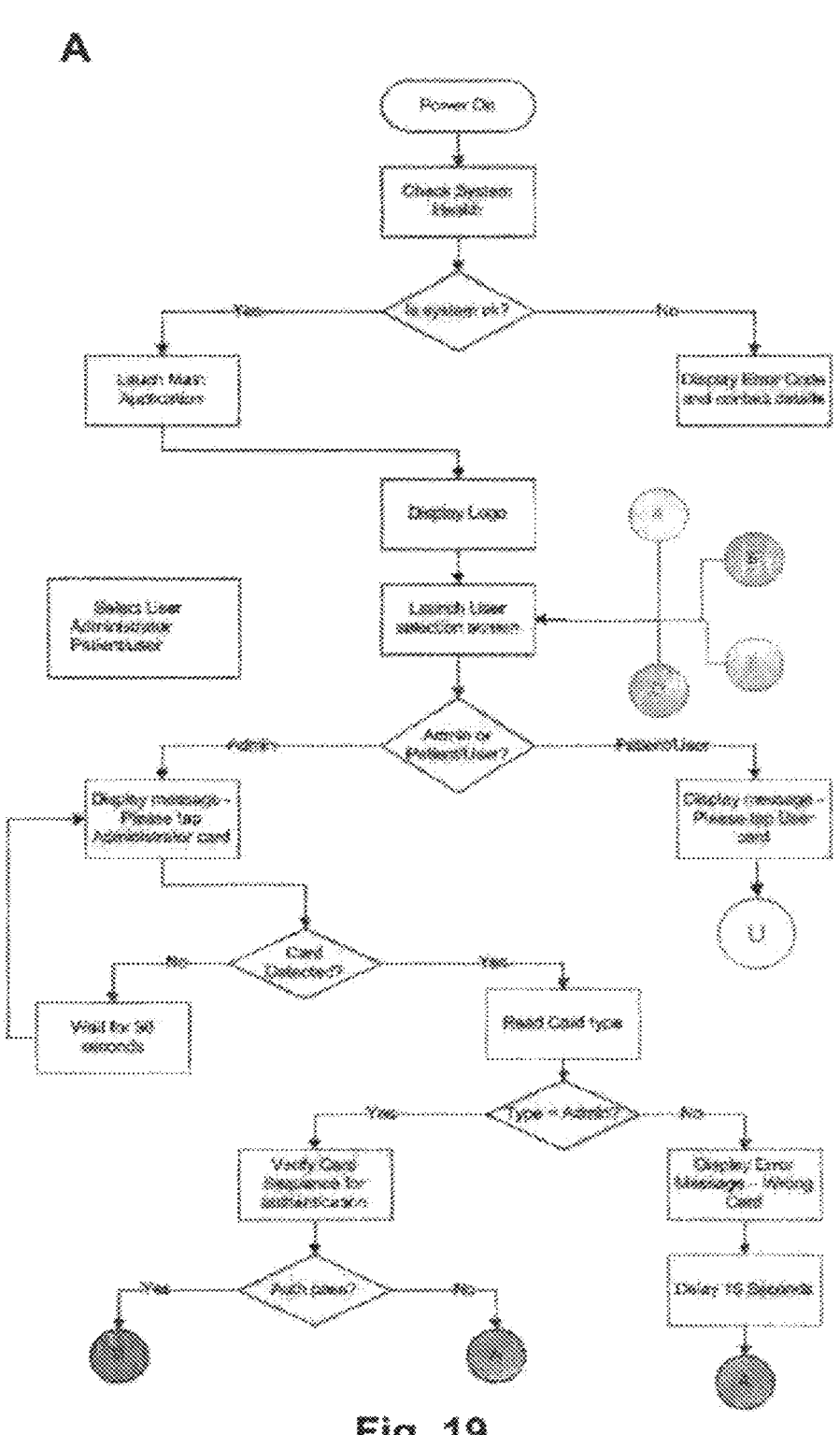

FIG. 19, panels A-O, illustrates a flow chart depicting stimulator operation.

Figure 20:
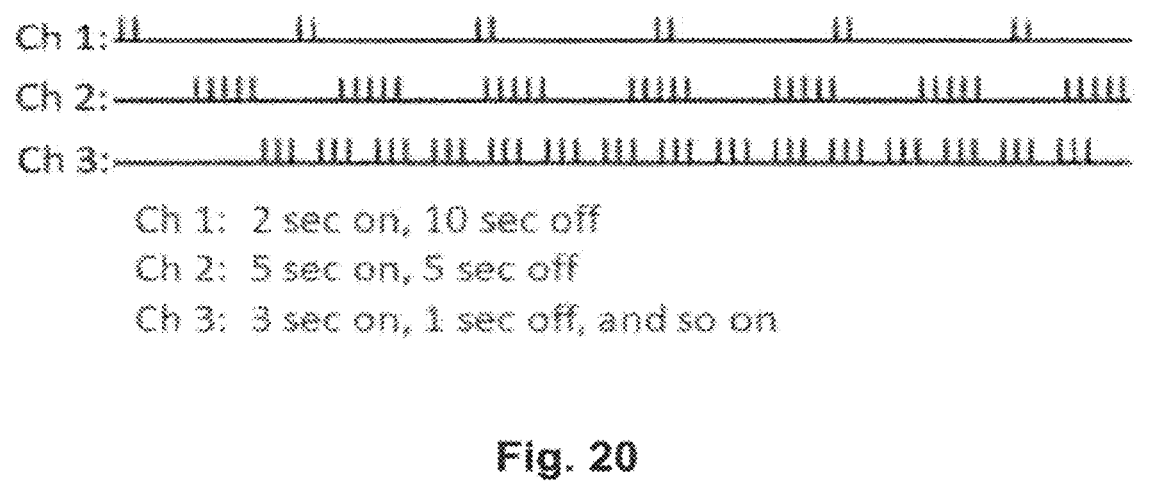

FIG. 20 shows one illustrative, but non-limiting example of intermittent stimulation, e.g., where stimulation patterns are different and staggered between channels.

Figure 21:
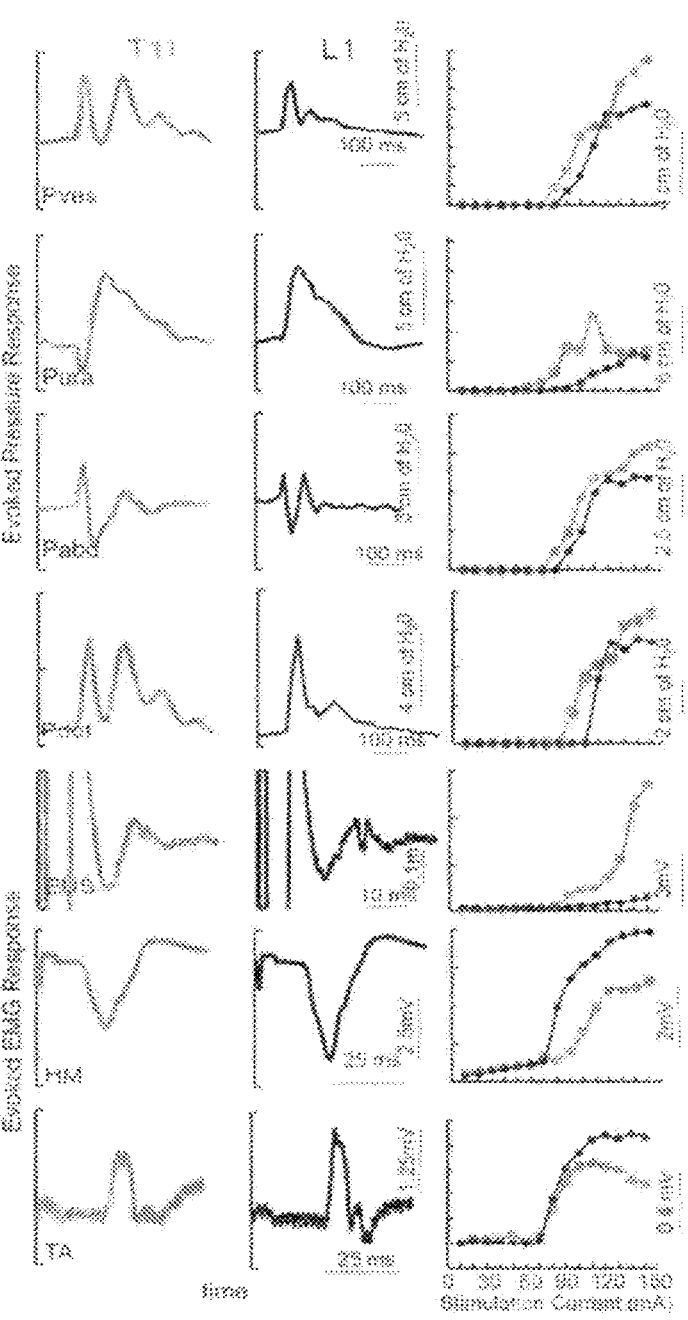

FIG. 21 illustrates an example of TSCS evoked pressure changes and EMG responses (average of 5 responses) from the vesicular (Pves), urethral (Pura), abdominal (Pabd) and detrusor (Pdet) pressures and Urethral sphincter (EUS) EUS, Hamstring (HM) and Tibialis Anterior (TA) EMGs at 150 mA TSCS between T11-T12 and L1-L2 vertebral processes from a subject (566729, AIS A, T4). Recruitment curves for the example showed on the left.

Figure 22:
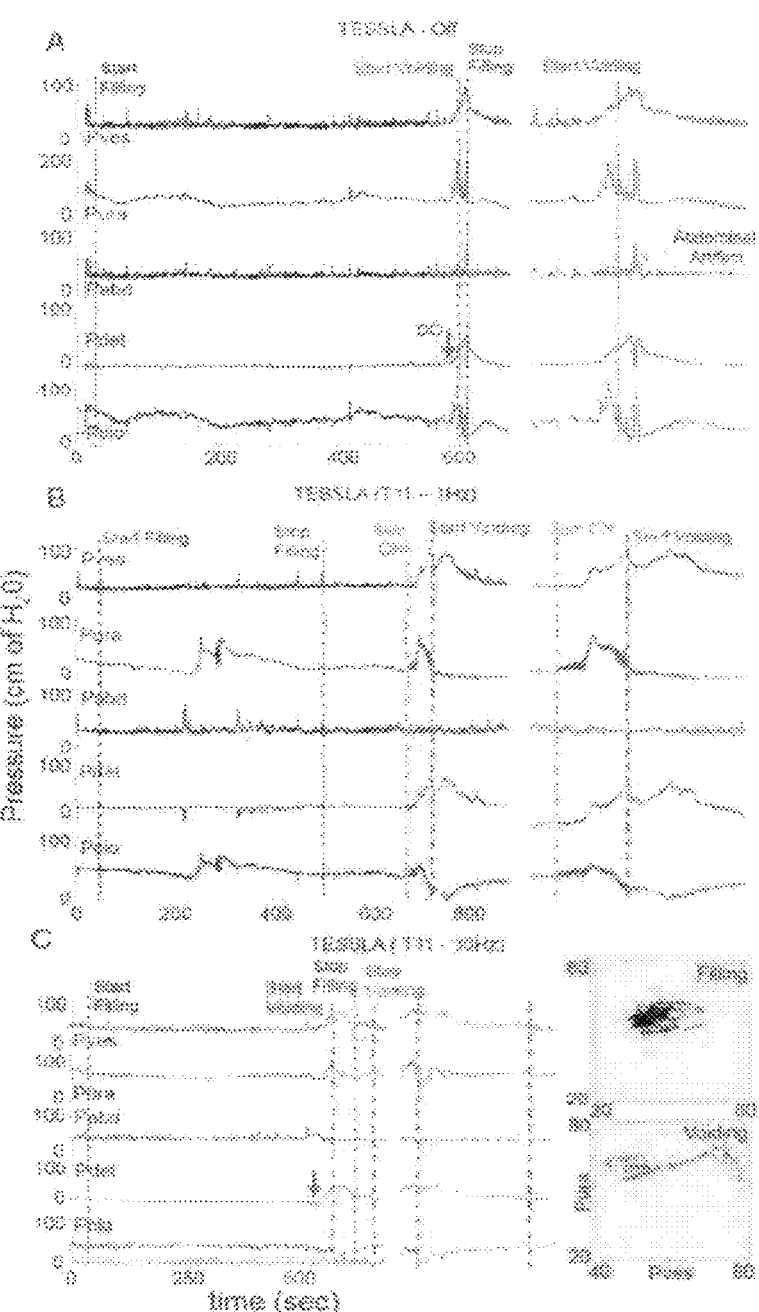

FIG. 22, panels A-C, shows Examples of urodynamic recording from a representative subject (566729). Panel A) without TESSLA, panel B) with TESSLA at 1 Hz (T11), and panel C) with TESSLA at 30 Hz (T11). Note the presence of detrusor over activity (DO) with 205 ml infused (see Table 6) and high level of detrusor sphincter dyssynergia (DSD) in the absence of TESSLA but a greater level of reciprocal activation between the Pura and Pdet in the presence of TESSLA and during voiding. Note the increased bladder capacity (281 ml, see Table 6) in the presence of TESSLA at 30 Hz compared to baseline as well as the reduced DSD during voiding. Pdet is defined as Pves-Pabd and Pclo is defined as Pves-Pura.

Figure 23:
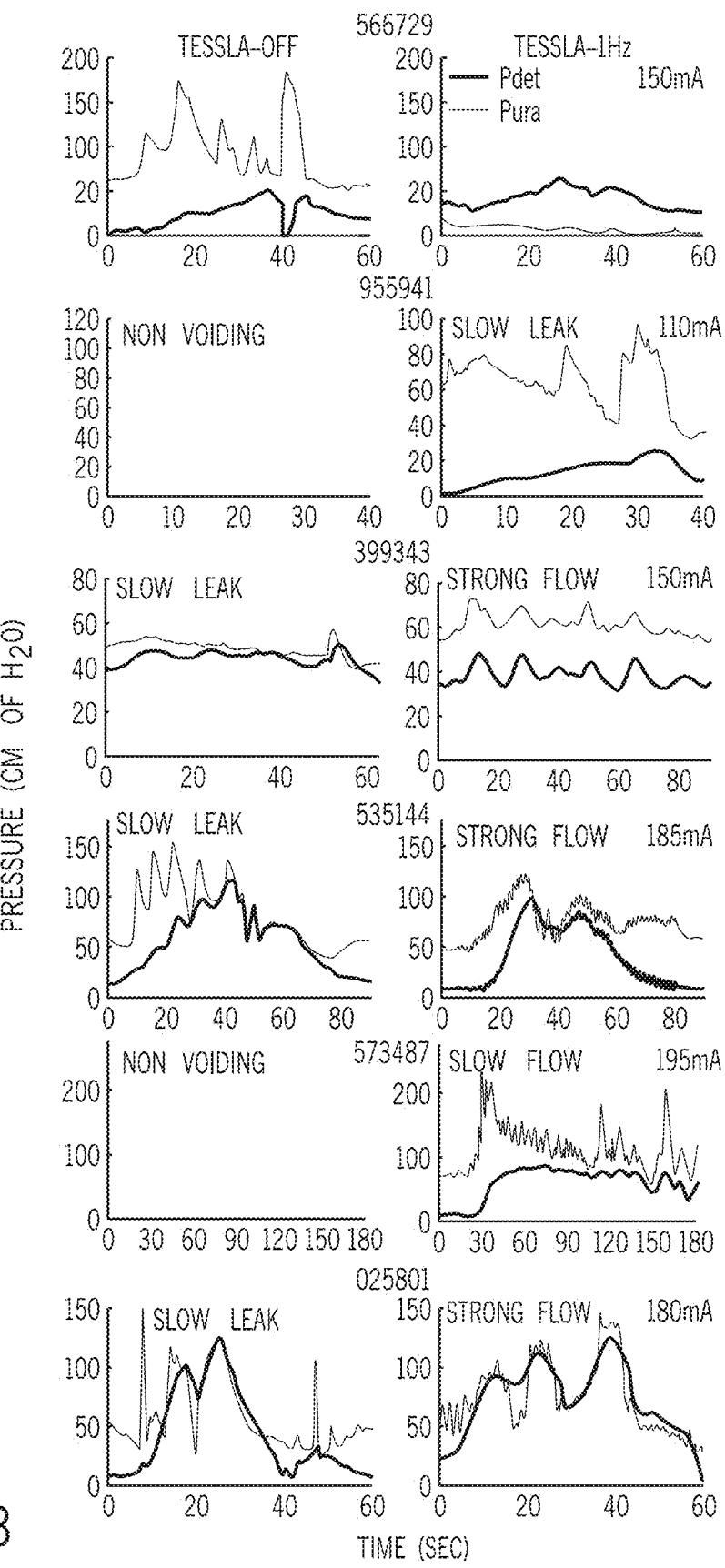

FIG. 23 shows Pdet and Pura during voiding without and with TESSLA (1 Hz) for the 6 individual subjects. Yellow highlight identifies the region of voiding. Note: 2 subjects (955941, 573487) demonstrated a non-voiding responses during TESSLA Off, thus the pressure traces are not included.

Figure 24:
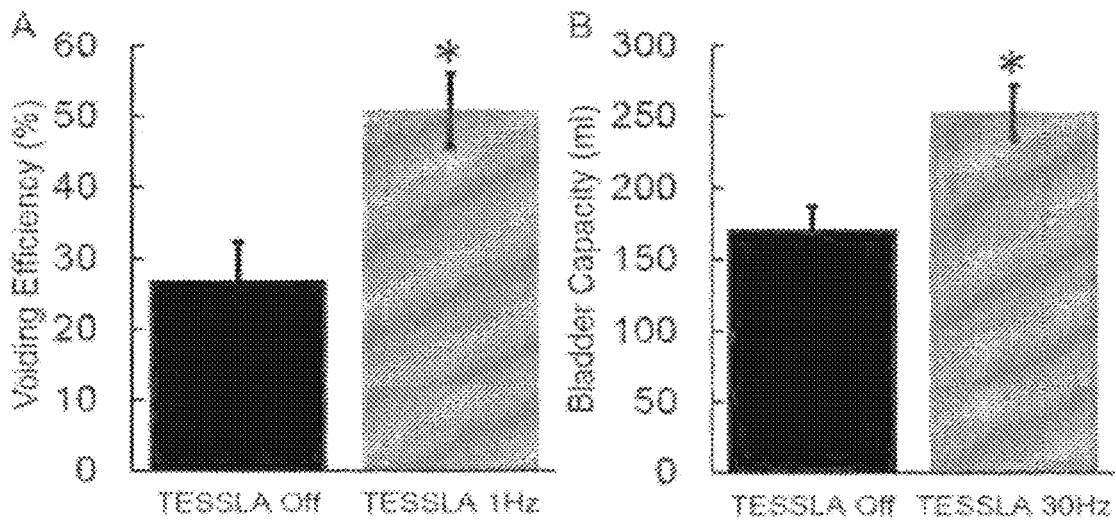

FIG. 24. Panel A shows voiding efficiency for the 7 individuals tested in the absence of TESSLA and TESSLA at 1 Hz. Panel B shows bladder capacity in the absence of TESSLA and TESSLA at 30 Hz. * significantly different from TESSLA Off at P<0.05 (Statistical difference identified via paired t test).

Figure 25:
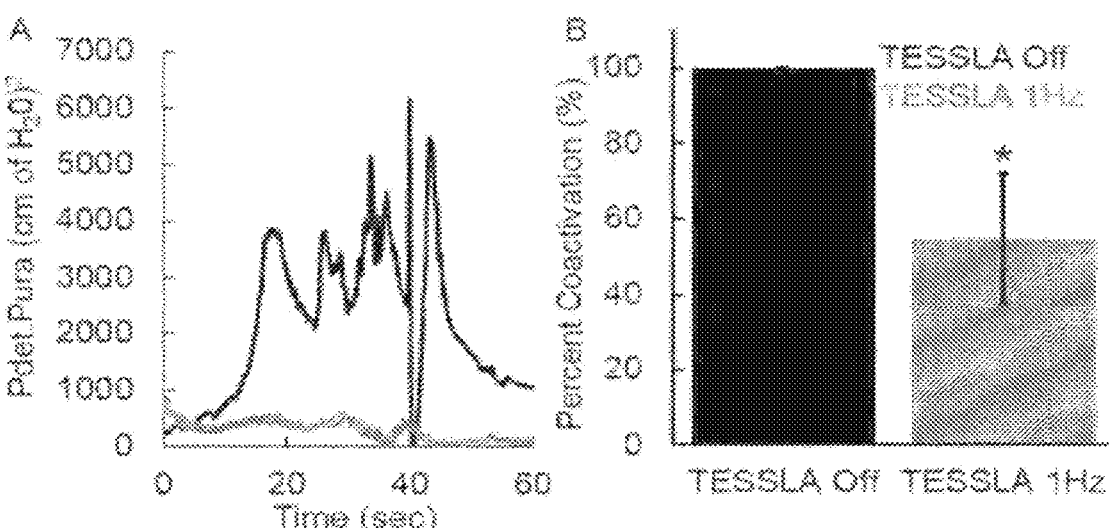

FIG. 25. Panel A) Co-activation between Pdet and Pura during voiding with TESSLA off (black) and TESSLA at 1 Hz (red) in a single subject (566729). Panel B) Normalized (to TESSLA Off) co-activation between Pdet and Pura per second during voiding for the subjects (n=5) that demonstrated voiding with TESSLA off. * significantly different from TESSLA Off, demonstrating lowered level of DSD with TESSLA 1 Hz compared to TESSLA Off (Statistical difference identified via paired t test).

Figure 26:
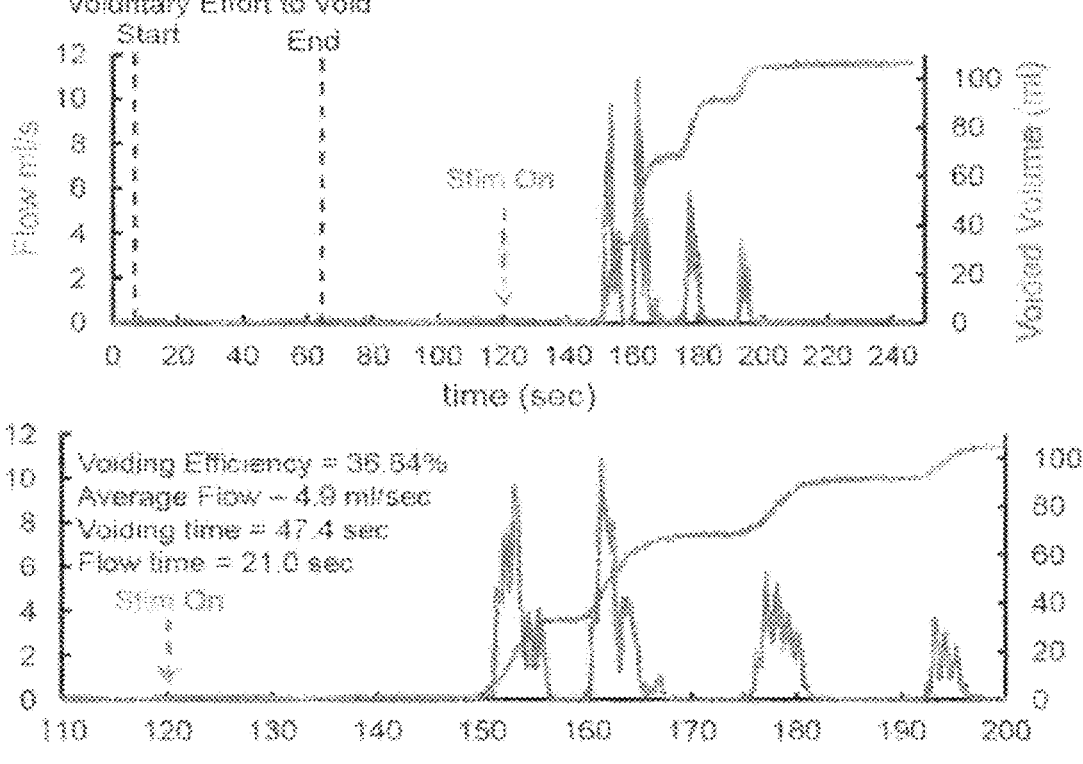

FIG. 26. Representative Uroflow conducted on one subject in the absence and presence of TESSLA (150 mA, 1 Hz at T11). Note the start of voiding and flow only after TESSLA is turned on.

Figure 27:
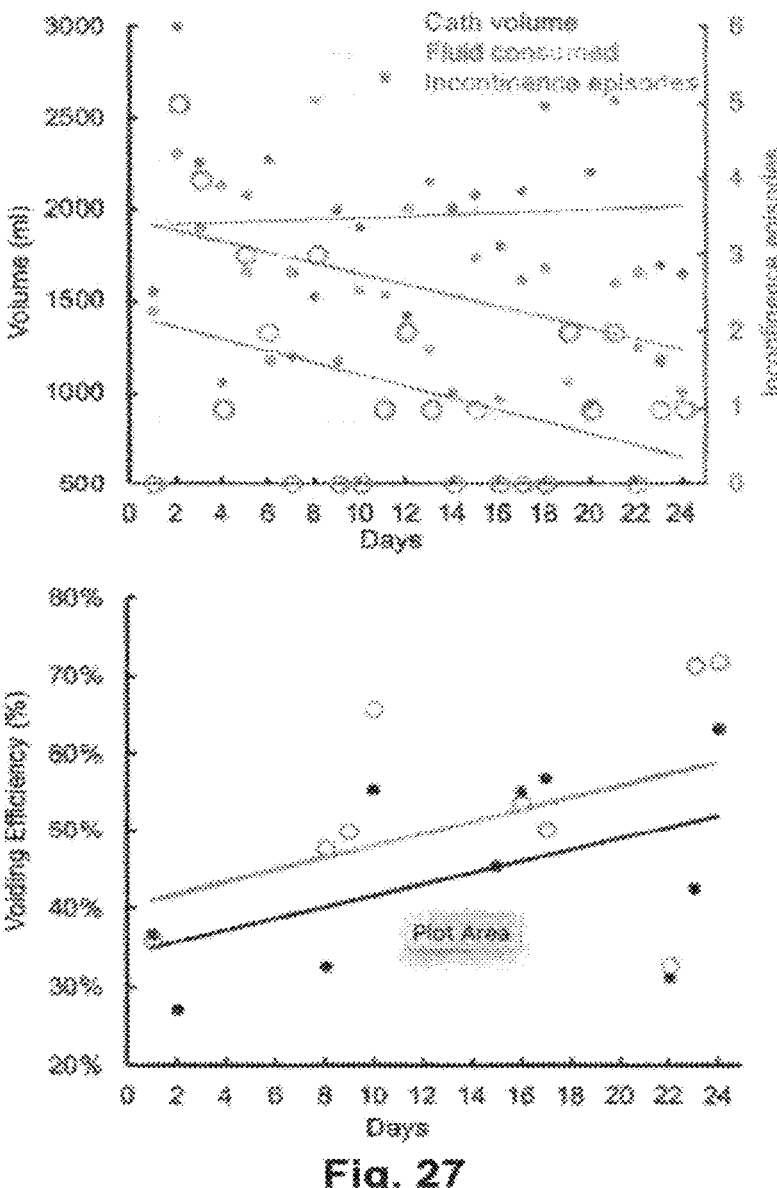

FIG. 27 shows that chronic transcutaneous spinal neuro-modulation improves bladder function in humans.

Figure 28:
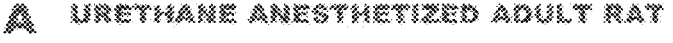
Figure 28:
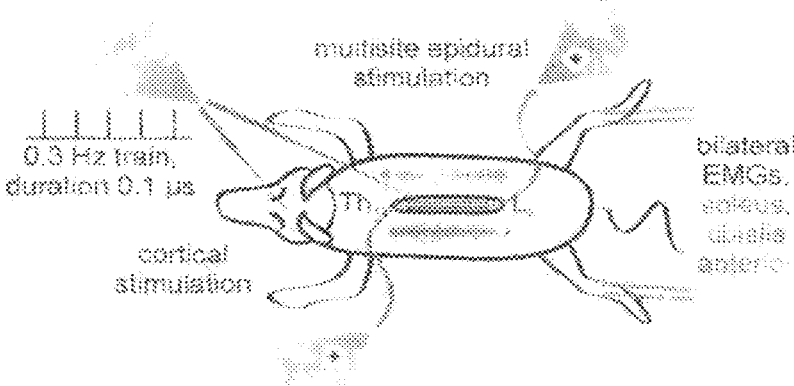
Figure 28:
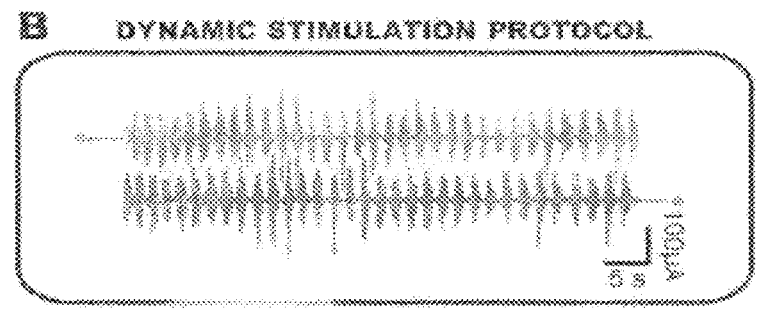
Figure 28:
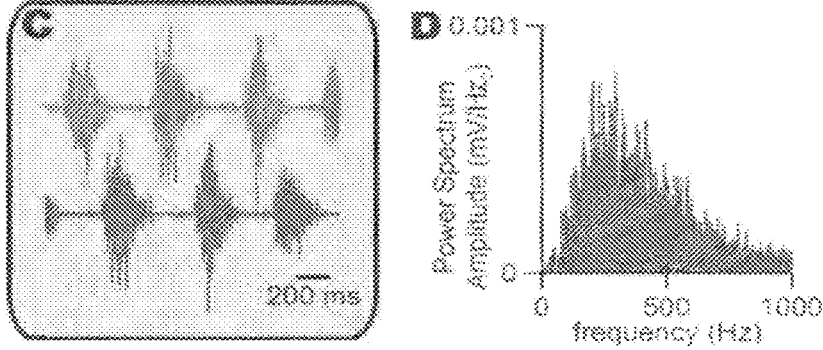

FIG. 28, panels A-D, shows that the experimental setup allows for multiple sites of simultaneous stimulation and recording from an adult rat under urethane anesthesia. In panel A, three types of stimulation are applied (zigzag arrows). First, a train of stimuli (0.3 Hz) at weak intensity is continuously applied either through an epidural array, or trans-cranially over the cortical motor area. During tonic stimulation at 0.3 Hz, a protocol of stimulation named Dynamic Stimulation (DS) is delivered over 4 spinal segments, from vertebrae Th12 to L2 Responses to stimulation were recorded from extensor (tibialis anterior, TA) and flexor (soleus, Sol) muscles through wire EMG electrodes bilaterally implanted in the muscle belly. Two stimuli with opposite cathode location are simultaneously delivered through the electrodes located at the extremities of the array. DS lasts 30 s and is composed of a waveform sampled from the Sol EMG activity (29.5 s) during treadmill stepping (13.5 cm/s) in an intact rat. Through off-line analysis, the original EMG trace is duplicated and delivered with a staggered onset of 0.5 s. (panel B). The two stimulating waveforms were supplied at the same time, but out of phase, rostrally and caudally (blue waveform, cathode at L2, red waveform with cathode to Th 12, respectively). In the box in panel C, a magnification of two actual stimulating waveforms indicates that they are composed of rhythmic bursts characterized by higher frequency discharges (100-500 Hz), as confirmed by the Power Spectrum shown in panel D.

Figure 29:
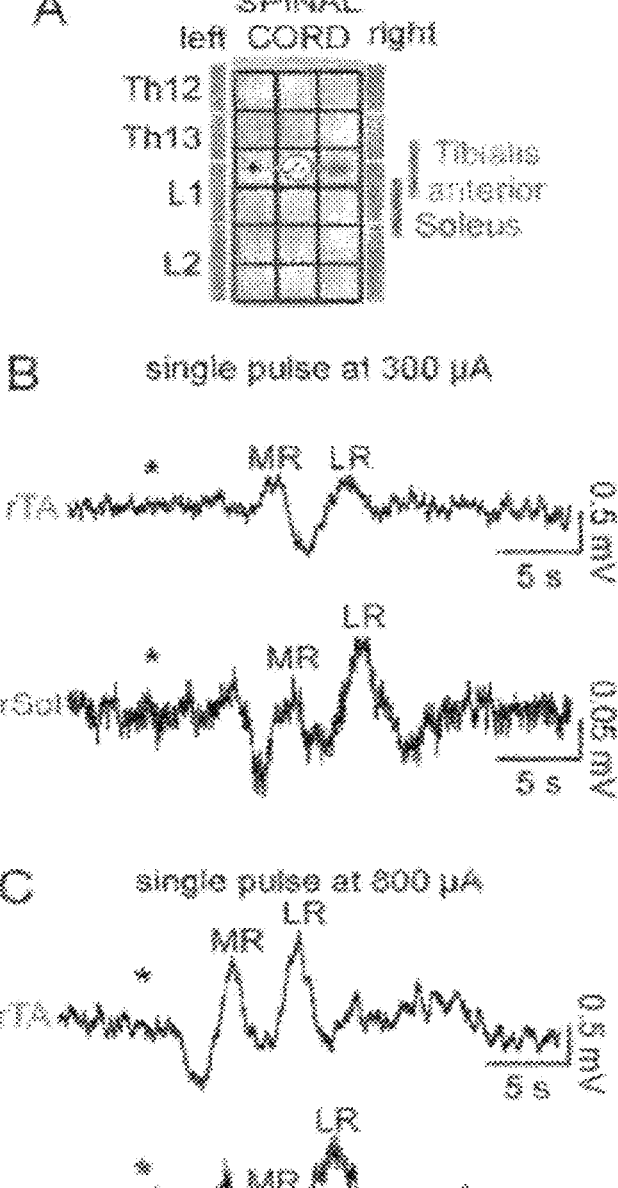

FIG. 29, panels A-G, shows that weak electrical stimuli delivered through the epidural array generate small and variable responses from TA and Sol muscles. In panel A, a train of square monophasic weak impulses (300 stimuli, 0.3 Hz, 300 μA, single pulse duration 0.1 ms) is continuously delivered (15 min) to the central sites of the array, as indicated in the cartoon (L1 vertebral level, cathode on the left). In panel B, recordings from right TA and Sol display small amplitude responses with a middle (MR) and a late response (LR), characteristically lacking an early response (ER) in the first five ms after the artifact of stimulation. In panel C, by increasing the intensity of stimulation (800 μA), EMG responses increase in amplitude and are characterized by the appearance of an ER. In the box in panel D are reported the time to peak values of MRs and LRs for muscles TA (above) and Sol (below). In panel E, the time courses of peak amplitude of MRs (above) and LRs (below) over 300 consecutive pulses are recorded from TA muscle. In panel F, the time courses of peak amplitude of MRs (above) and LRs (below) over 300 consecutive pulses are recorded from Sol muscle. In panel G, the plots indicate a lack of correlation among the amplitude of each stimulus evoked from TA and Sol. MRs (above) and LRs (below) are separately analyzed. The scatter plot in panel G reflects unique relationships between the TA and Sol for both MR and LR, with the ratio being higher in the Sol for the MR, but the opposite is true for the LR. Note also the higher probability of a higher amplitude of about 18 micro volts for the Sol.

Figure 30:
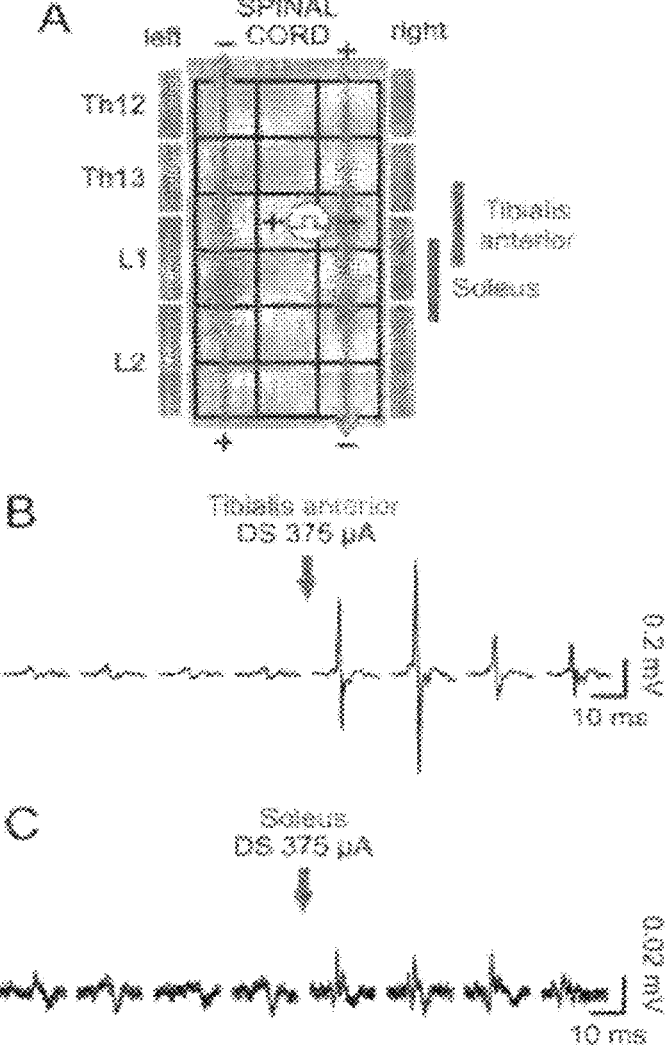

FIG. 30, panels A-K, shows that DS increases the amplitude of MRs of spinally-induced responses even at the end of stimulation. In panel A, the cartoon summarizes the stimulation setting. Two highly varying waveforms are delivered longitudinally between the extremities of the array on the two sides of the cord, while spinally-induced responses are continuously elicited by single pulses delivered from two close electrodes placed at the center of the array (vertebral levels T13/L1, spinal level L3/L6 cathode on the left). Before DS, small responses are induced in control by weak single pulses (400 μA; 0.1 ms) from rTA (panel B) and lSol (panel C) muscles. Right after the delivery of DS for 30 s (grey arrows, 375 μA), the amplitude of EMG responses increased, mainly on TA. Time courses from rTA (panel D) and lSol (panel E) quantify the peak of MR (black dots) and LR (red dots) during the continuous delivery of 300 pulses (15 min). The supply of DS at the intensity of 375 μA for the duration of 30 s (black square on the top) does not affect LRs (red dots), while it augments the amplitude of MRs (black dots), more dramatically on TA. By increasing the strength of stimulation (450 μA) the potentiation of MR peaks is longer on lTA (panel F) with a feeble effect also on LR (red dots). Also MRs from lSol become higher when DS is delivered at 450 μA (panel G). Histograms report the mean peaks of MRs after DS for 20 consecutive sweeps, expressed as the percentage of pre-DS control values pooled from many experiment in which DS was serially increased from 150 μA to 600 μA. Pauses of 5 min are interposed between two consecutive DSs. MR peaks of TA statistically increase since DS delivery at 375 μA (H: *, P<0.001), while, on Sol, DS increases the peak of MRs starting from 450 μA (I: *, P=0.002). Similar analysis is performed for the same experiments as in panels H and I for LRs, showing no effect following DSs, even at higher amplitudes in both TA (panel J) and Sol (panel K) muscles.

Figure 31:
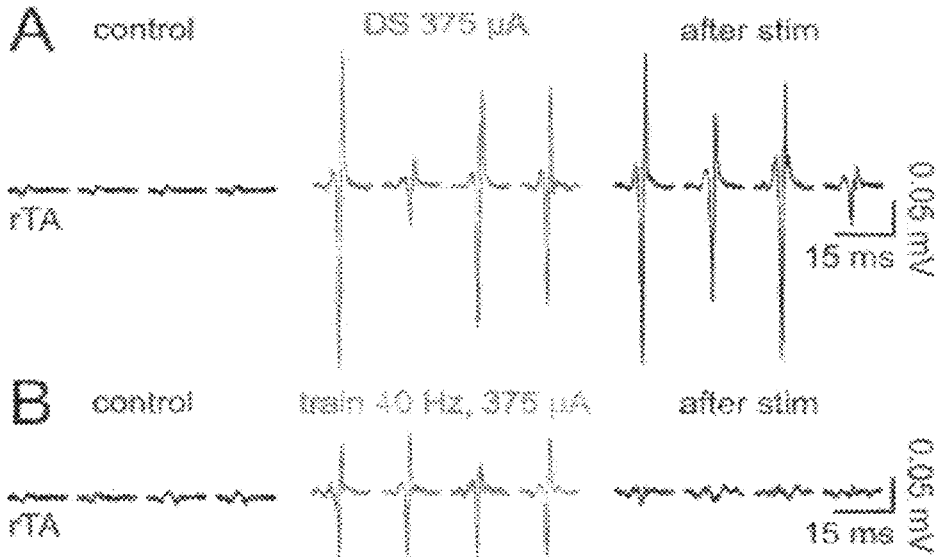

FIG. 31, panels A-D, shows that compared to a stereotyped train of pulses, DS largely increases spinally-induced responses, even after protocol termination. In panel A, weak single pulses (0.1 ms) applied to L1/L2 vertebral level (L5/S2 spinal level, cathode on the left) induce small spinally-induced responses from rTA, in the absence of any continuous stimulation (control). During DS (375 µA), EMG responses are largely increased (middle), an effect that persists even after the end of stimulation (right). In the same preparation, a stereotyped train at 40 Hz augments motor responses only during delivery of the protocol, returning to baseline values as soon as stimulation ends (panel B). Panel C) A complete time course for the experiment in panels A and B reports the peaks of middle responses (MR) for 420 consecutive single pulses (21 min). Single EMG responses are higher after DS than after the following delivery of 40 Hz train. Note that prior to the delivery of 40 Hz train, baseline completely recovered to pre-stimulus values. Below are reported the magnifications of the time course during DS (left) and 40 Hz trains (right), stating that the potentiation of DS persists for 90 s after protocol delivery, while spinally-induced responses return to control baseline values right after the end of the 40 Hz train. Histogram in panel D summarizes mean data from six tibialis anterior muscles. For each bar, mean peaks of MRs from 20 consecutive sweeps were compared before and right after the delivery of protocols. DS significantly potentiates the amplitude of MRs compared to a train of stereotyped pulses at 40 Hz (*, P=0.031).

Figure 32:
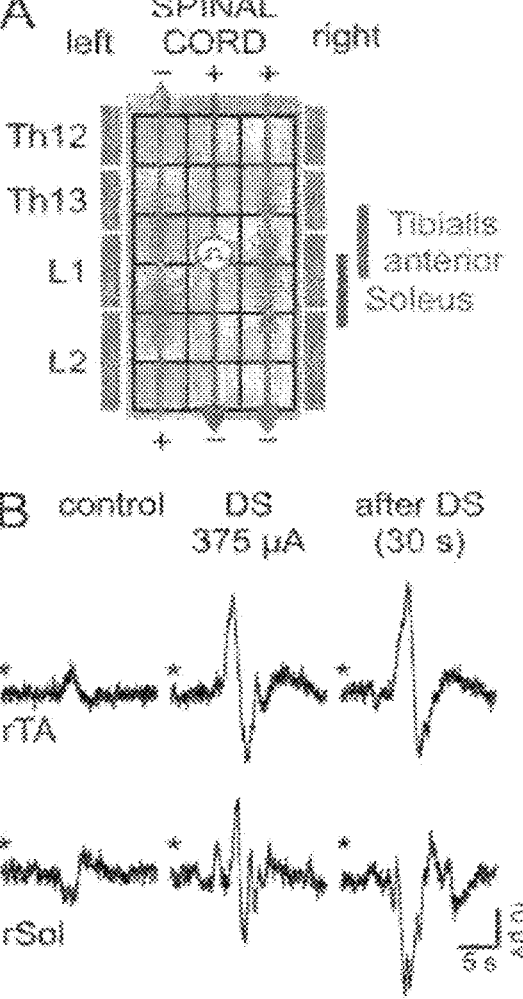

FIG. 32, panels A-F, shows that DS facilitates MRs also in spinally-induced responses elicited by longitudinal stimulation across the array. In panel A, the cartoon summarizes the stimulation setting. Two dynamically varying waveforms are longitudinally delivered between the extremities of the array on the two side of the cord, while spinally-induced responses are continuously elicited by single monophasic pulses longitudinally delivered along the entire length of the array (rostral cathode). In panel B (right), weak single pulses (0.1 ms) induce small EMG responses from tibialis anterior (TA, above) and soleus (Sol, below) muscles of the right hindlimb. During delivery of DS (375 µA), the amplitude of EMG responses increases in both muscles (middle). The potentiation of MRs persists even after 30 s from the end of DS (right). In panels C and D, the entire time course (940 stimuli, 47 min total duration) is reported for the right TA (panel C) and right Sol (panel D) for a sample experiment in which DS intensity was serially increased from 150 µA to 600 µA. MRs of spinally-induced responses are continuously recorded during delivery of DS (30 s, red dots) and during each pause between two consecutive DSs (5 min, black dots). DS augments the amplitude of MRs, starting from the intensity of 225 µA. By increasing the strength of stimulation, the potentiation of MR peaks is higher and longer on both muscles. Histograms in panels E and F report the mean peaks of MRs for right TA (panel E) and right Sol (panel F) as the average out of 20 consecutive sweeps before DS (control) and the average of 20 consecutive sweeps right after DS termination at each different strength of stimulation. MR peaks statistically increase at 375 µA and 600 µA for TA (E: *, P=0.019) and only at 375 µA for Sol (F: *, P=0.032).

Figure 33:
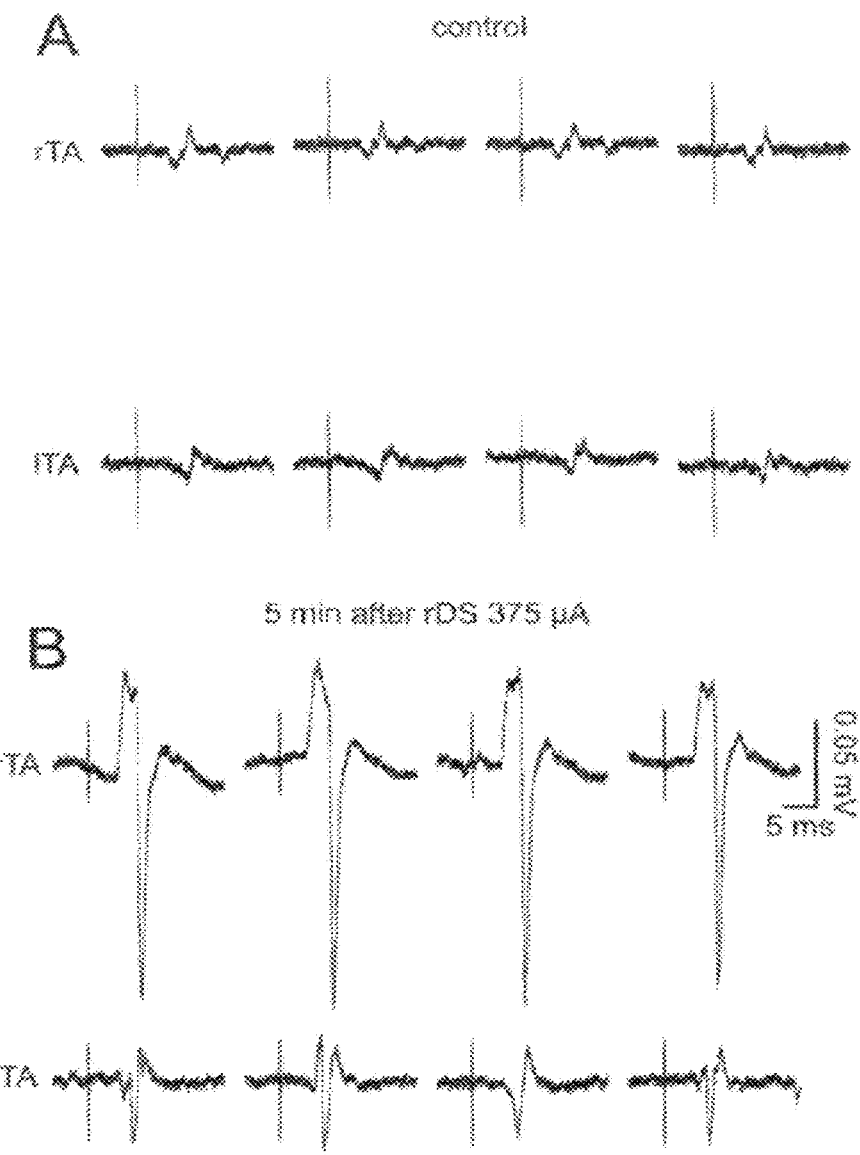

FIG. 33, panels A-D, shows that repetitive delivery of DS potentiates longer spinally-induced responses. In panel A, small spinally-induced responses on right (up) and left (below) TAs were induced by a train of weak square pulses (frequency 0.3 Hz; intensity=500 µA; duration=0.1 ms), horizontally applied between T13 and L1 vertebral levels (L3/L6 spinal level, cathode on the left). Eight slots of DS (30 s) were serially delivered with 1 min pause from one another in a protocol named: repetitive DS (rDS, total duration=11 min). At the end of the last DS delivered, the same single pulses used in control can now evoke larger responses from both TAs (panel B). In panel C is reported the time course of the entire experiment shown in panels A and B, where 640 single pulses are delivered at 0.3 Hz for a total duration of 32 min. rDS is reported as a serial alternation of 8 DS repetitions (red) spaced by resting pauses of 1 min during which no DSs were supplied. MR responses from rTA are quite consistent in control before rDS. Amplitude then increases after each slot of DS, reaching the maximum value at the end of rDS and remaining higher than pre-rDS control for at least the following 8 minutes. In panel D, bars report mean data about MRs, calculated by averaging 100 consecutive responses from TA (total duration=5 min) before and after rDS, which show the significant increase in motor responses as induced by rDS (*, P=0.017).

Figure 34:
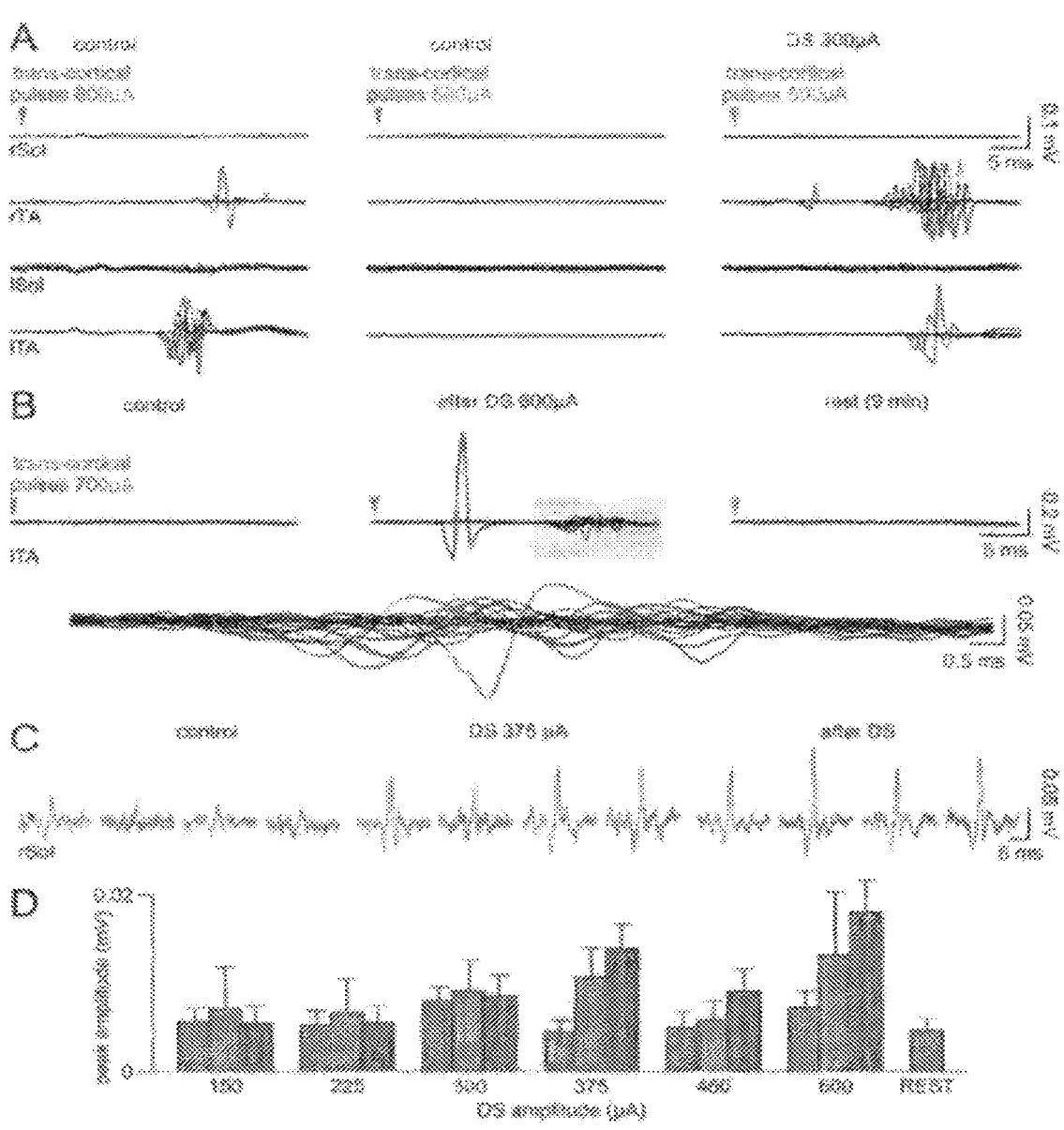

FIG. 34, panels A-D, shows that DS facilitates the reappearance of cortically-evoked EMG responses. In panel A, consecutive traces are superimposed during the delivery of a train of single cortical pulses (arrowheads; duration=1 ms, frequency=0.3 Hz). In the absence of DS (control), single pulses at 800 µA (left, five consecutive traces are superimposed) elicit consistent EMG responses from lTA and some variable responses from rTA. Responses from both muscles disappear when the strength of stimulation is lower (500 µA, middle, 10 consecutive traces are superimposed). During DS delivery at low intensity (300 µA), even weak single pulses (500 µA) are now able to reinstate repetitive responses from rTA and lTA (right, 10 consecutive traces are superimposed). In panel B, from a different animal, 20 consecutive traces are superimposed during the delivery of a train of single cortical pulses (arrowheads; duration=1 ms; intensity=700 µA; frequency=0.3 Hz). In the absence of DS (control), no responses were recorded from lTA. Right after DS delivered at the intensity of 600 µA (middle), a single maximal peak and a consistent bundle of lower and late potentials appear on lTA. These effects persist for about 1 min after the end of DS, as emphasized by the magnification below that corresponds to the shaded gray rectangle above. EMG responses disappear after 9 min from the termination of DS (right). In panel C, in another animal, 4 consecutive small spinally-induced responses evoked by cortical stimulation (duration=0.1 ms; intensity=700 µA; frequency=0.3 Hz) are recorded from rSol in the absence of any DS (control, left, blue traces). During DS at 375 µA (middle, red traces), EMG responses are potentiated for up to 3 min after the termination of DS (right, green traces). In panel D, from the same experiment as in C, peak amplitudes of 20 consecutive sweeps are averaged before DS (blue), during DS supplied at increasing intensities (150-600 µA; red) and after DS delivery (green). Note that the potentiation post-DS (green bar) is higher at the maximal strength (600 µA).

Figure 35:
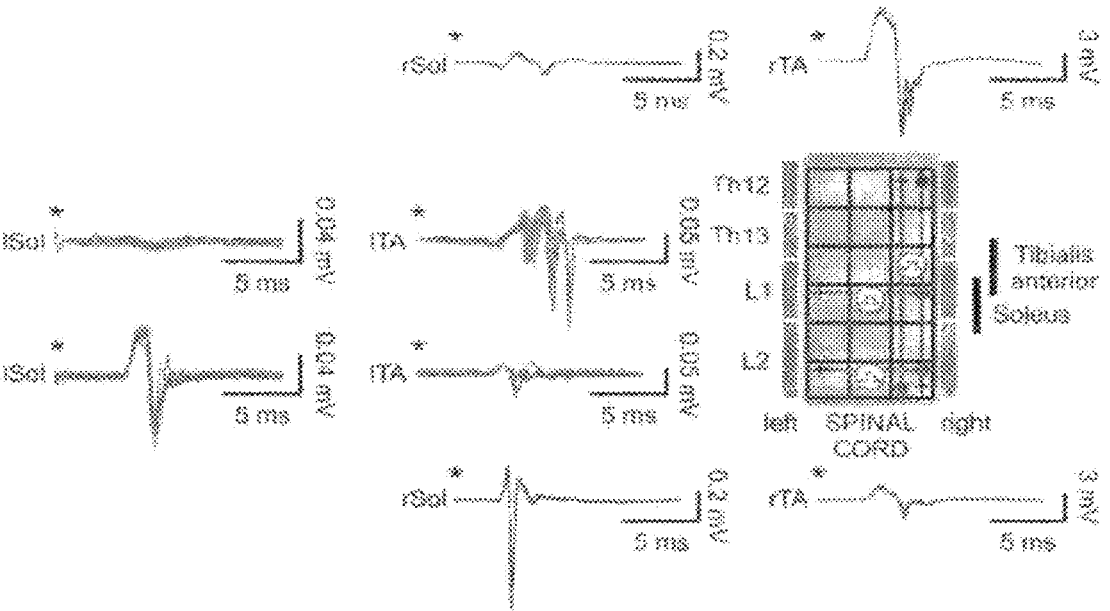

FIG. 35 shows that array for epidural stimulation allows the selective full recruitment of motoneuronal pools. In order to test the reliability of the epidural interface for multisite independent stimulation, EMG responses recorded from the ipsilateral Sol and TA in 5 consecutive stimuli (0.3 Hz) are superimposed for each different configuration of stimulation. Each group of responses is obtained by stimulating different pairs of electrodes in the interface, at the levels indicated by the lines in the cartoon, with the cathode location reported on the arrows (arrowhead anode). Trains of single pulses (duration=0.1 ms; frequency=0.3 Hz, intensity=800 µA) applied along the epidural array selectively evoked full EMG responses from rTA (green traces) or rSol (purple traces) using a rostral cathode or anode, respectively. Thus, the direction of electric field lines passing through the array can be appropriately placed to bias the recruitment of motor pools located at different segmental levels. In addition, when trains of pulses (duration=0.1 ms; frequency=0.3 Hz, intensity=700 μA) were delivered to the cord, corresponding to L1 vertebrae (L5/L6 spinal level), a maximal response was elicited from flexor muscles (red traces, lTA). Conversely, if the stimulation (intensity=200 μA) was applied more caudally, full EMG responses were recorded primarily from extensors (blue traces, lSol). The selective maximal recruitment of Sol or TA on the same limb, obtained either by varying the level of stimulation (vertebral level L1 red, vertebral level L2 blue) or by inverting the cathode location of impulses delivered lengthwise from the extremities of the array (rostral green, caudal purple), demonstrates the unique technical features of the array required for testing the efficacy of spatially defined sites for DS delivery. Note that a different intensity of stimulation is applied to evoke the different couples of responses (800 μA for green and purple traces, 700 μA for red traces, 200 μA for blue traces).

Figure 36:
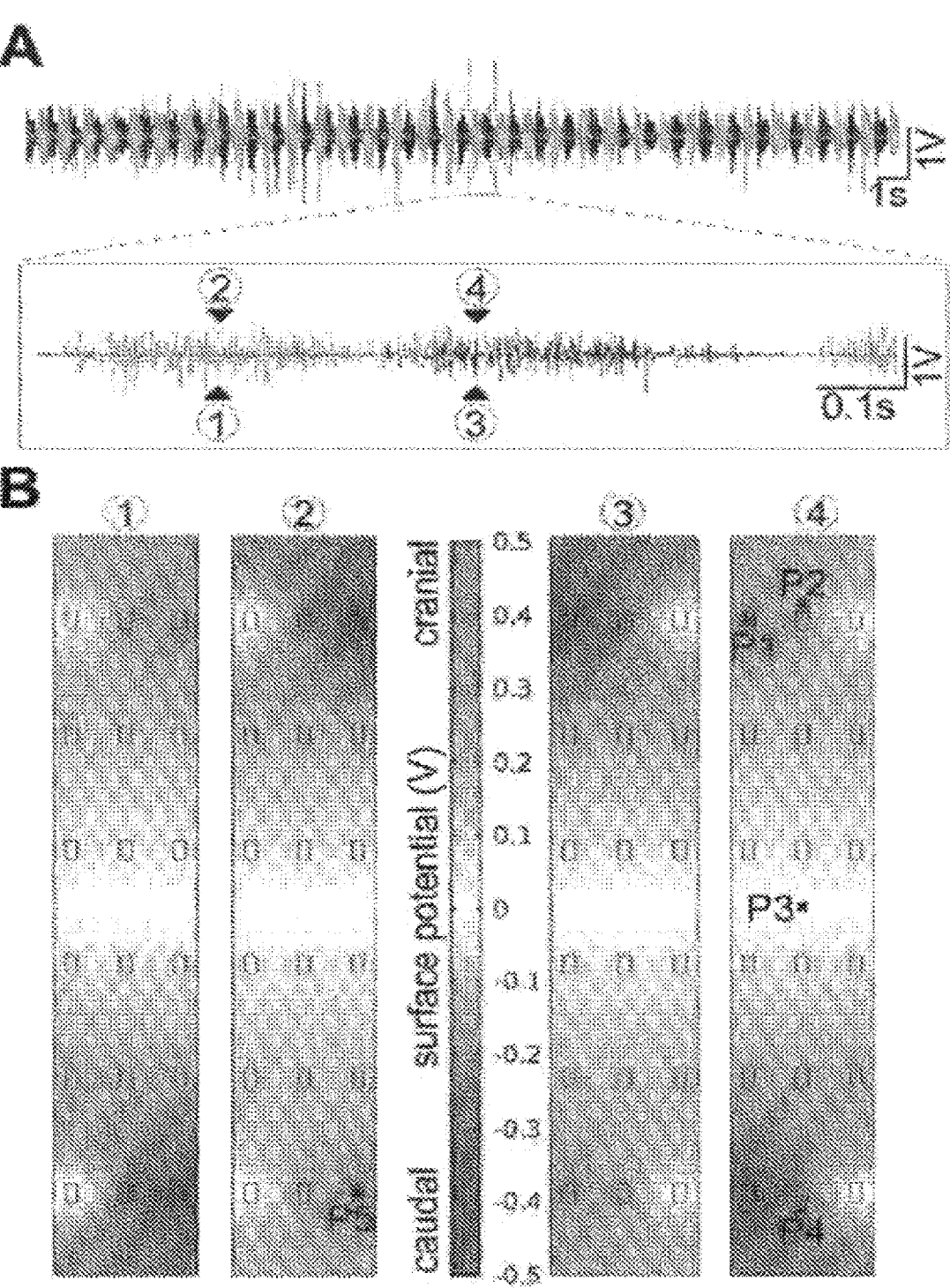

FIG. 36, panels A-C: Finite Element Simulation probes the complex pattern of DS across the surface of the planar array. In order to predict the real pattern of stimulation delivered through the array during DS and visualize the distribution of the effective surface potential under each electrode, a finite element method simulation software was applied. The DS pattern applied to the electrode array is analyzed in COMSOL Multiphysics 5.3 (Comsol Inc., USA), a finite element method simulation software, to visualize effective potential distributing on the surface of the epidural space under the electrode array. This epidural surface was modeled as a resistive medium with electric conductivity of 0.20 S/m (Howell et al. (2014) *Plos One*, 9(12): e114938), and with a bulk ground node. The ground is assumed to be relatively far away from the surface and serves as the general reference for the electrical potential values applied in the simulation. Simulation reported potential distribution under the epidural array in response to the dynamic pattern stimulus (see also supplementary video). Panel A) The two separate stimulation waveforms simultaneously applied to the lateral electrodes of the planar array are superimposed (black and purple traces). A magnification (bottom) shows that the two patterns have non-overlapping bursts, each characterized by high frequency fluctuations within range of 100-300 Hz. Panel B) Heat maps show the distribution of potentials at four consecutive instants, as reported in panel A by the arrows 1 to 4, which are sampled at the most positive and negative peaks of the high frequency activity of two consecutive bursts. The highest (red) and lowest (blue) surface potentials on the heat map correspond to the electrodes where the two dynamically varying waveforms of DS are applied. The whole epidural surface under the array is modulated by both waveforms combined uniquely at each point of the array's surface. B1, B2 refer to the interaction of the stimulus currents from the different stimulation sites (see the pair of top-right and bottom right, as well as the pair of top-left electrodes and bottom left of the array). The area under the surface of the array is fully affected, but with the middle being the least affected. A similar effect occurred when the other waveform was the predominant stimulus applied (B3, B4). Panel C) The resulting stimulation pattern is reported under the selected sites of the array. Waveforms are applied to points P1 and P5 and mainly reflect the two delivered waveforms. The patterns of stimulation at the points P2 and P4 contain a weighted sum of both waveforms. Notably, point P3 shows in the theoretical simulation minimal stimulation, as it is located centrally and equidistant to all terminals where the stimulus is applied. Note that, in the actual experiment, a centric location P3 still undergoes some modulation as its symmetric location may shift due to micro displacements of the electrode array material in the epidural space during the experiment and also a non-uniform structure of the epidural space, which is assumed to be perfectly homogeneous in the simulations.

Figure 37:
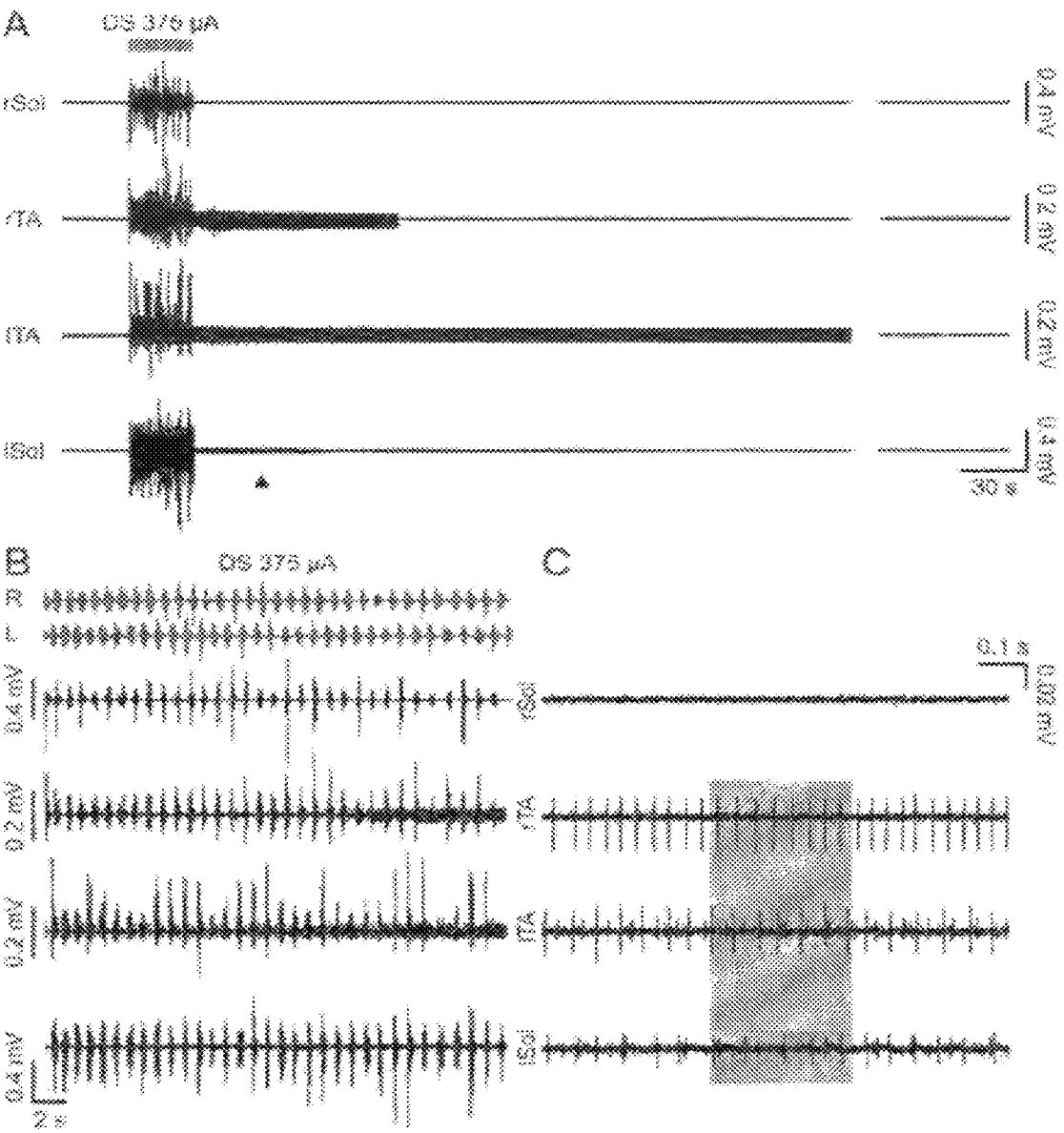

FIG. 37, panels A-D: EMGs show that DS delivery induces bursting contractions, as well as post-DS short-lasting rhythmic discharges uncorrelated among muscles. To ascertain the direct effect of DS on motor pools, in a subset of experiments, continuous EMG recordings were acquired before and after DS delivery. In panel A, four EMG continuous recordings are bilaterally acquired from Sol and TA muscles. Before stimulation, no spontaneous discharges were recorded from the right and left TA and Sol muscles. As soon as DS was delivered (375 μA), bursting EMG activity occurred throughout stimulation with each muscle demonstrating a unique pattern. In panel B, a magnification of EMG traces in A is reported during the entire delivery of DS (30 ms). The two patterns of stimulation applied to the right (R) and left (L) sides of the epidural array are reported in grey at the top of the panel. During DS supply, in each leg, activity from Sol muscles largely reflected the highly varying stimulating waveforms applied to the corresponding side of the spinal cord, while EMGs from TAs showed a tonic activity superimposing the main homologous pattern of stimulation. At the end of DS, high frequency (r and l TA=180 Hz, lSol=167 Hz) rhythmic discharges were recorded from three out of four muscles (panels A, C), with a different persistence within each trace (rTA=92.8 s; lTA=300.5 s; lSol=58.2 s). In panel C, the post-DS tonic activity corresponding to the black arrowhead in panel A is here presented at higher time base scale. The biphasic profile of single rhythmic discharges was largely stereotyped within the same muscle and not apparently correlated among the three muscles, as clearly shown at a faster time base scale in panel D for the traces included in the shaded grey rectangle in panel C and further confirmed by the very low cross correlation functions (CCF$_{rTA/lTA}$=0.008; CCF$_{lTA/lSol}$=0.006; CCF$_{rTA/lSol}$=0.01088). On lTA, after 5.6 min (time breaks correspond to 40 s), EMG baseline recovers to pre-stimulation level.

Figure 38:
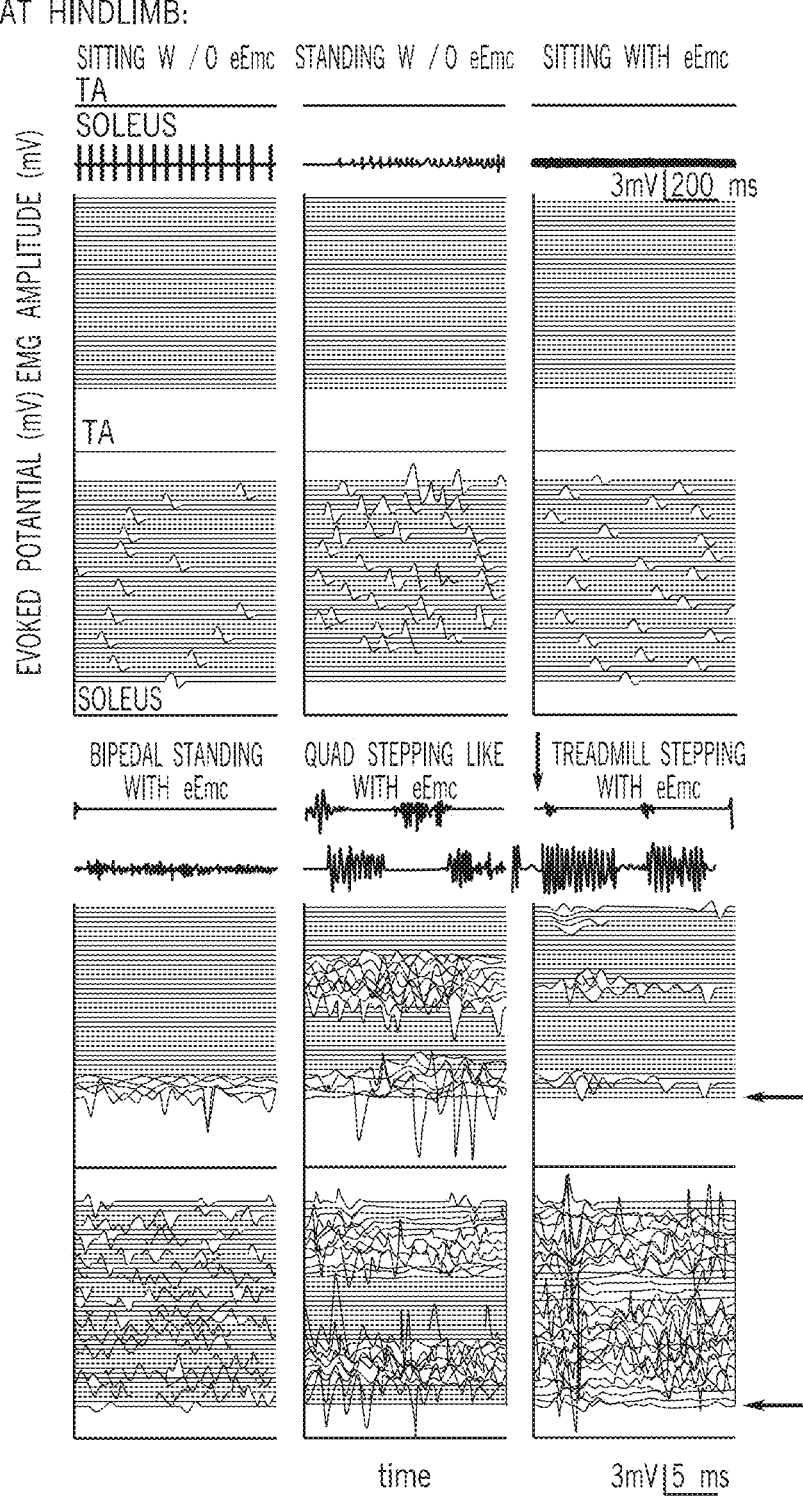

FIG. 38 illustrates other EMG signals used for dynamic stimulation from different animal models and different muscles (e.g., lower extremity, upper extremity, urethral sphincter, pelvic floor)

Figure 39:
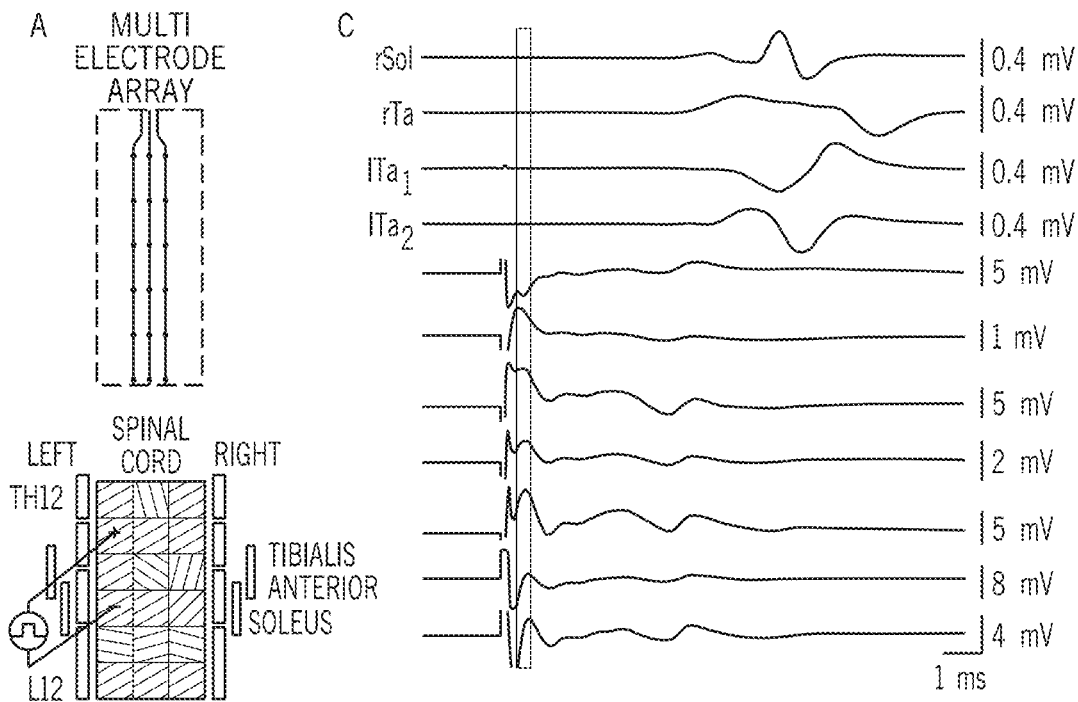

FIG. 39, shows multi-electrode array (panel A), and responses to test impulses (panel C) simultaneously recorded not only from lower limb muscles, but also from multiple sites on the surface of the dorsal cord (panel B).

Figure 40:
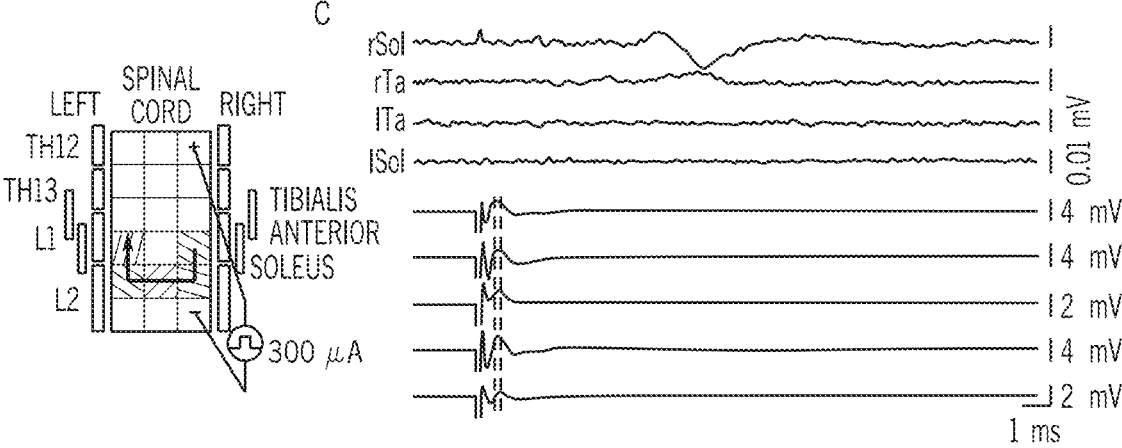

FIG. 40 responses to test impulses simultaneously recorded not only from lower limb muscles, but also from multiple sites on the surface of the dorsal cord.

Figure 41:
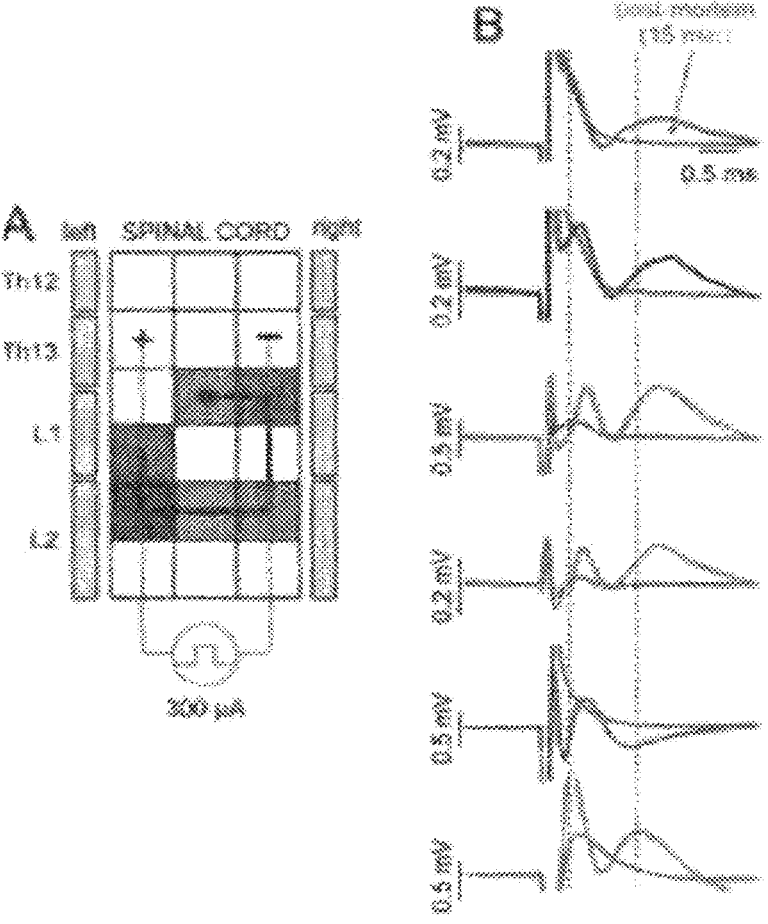

FIG. 41, panels A-B, shows responses to test impulses simultaneously recorded not only from lower limb muscles, but also from multiple sites on the surface of the dorsal cord.

Figure 42:
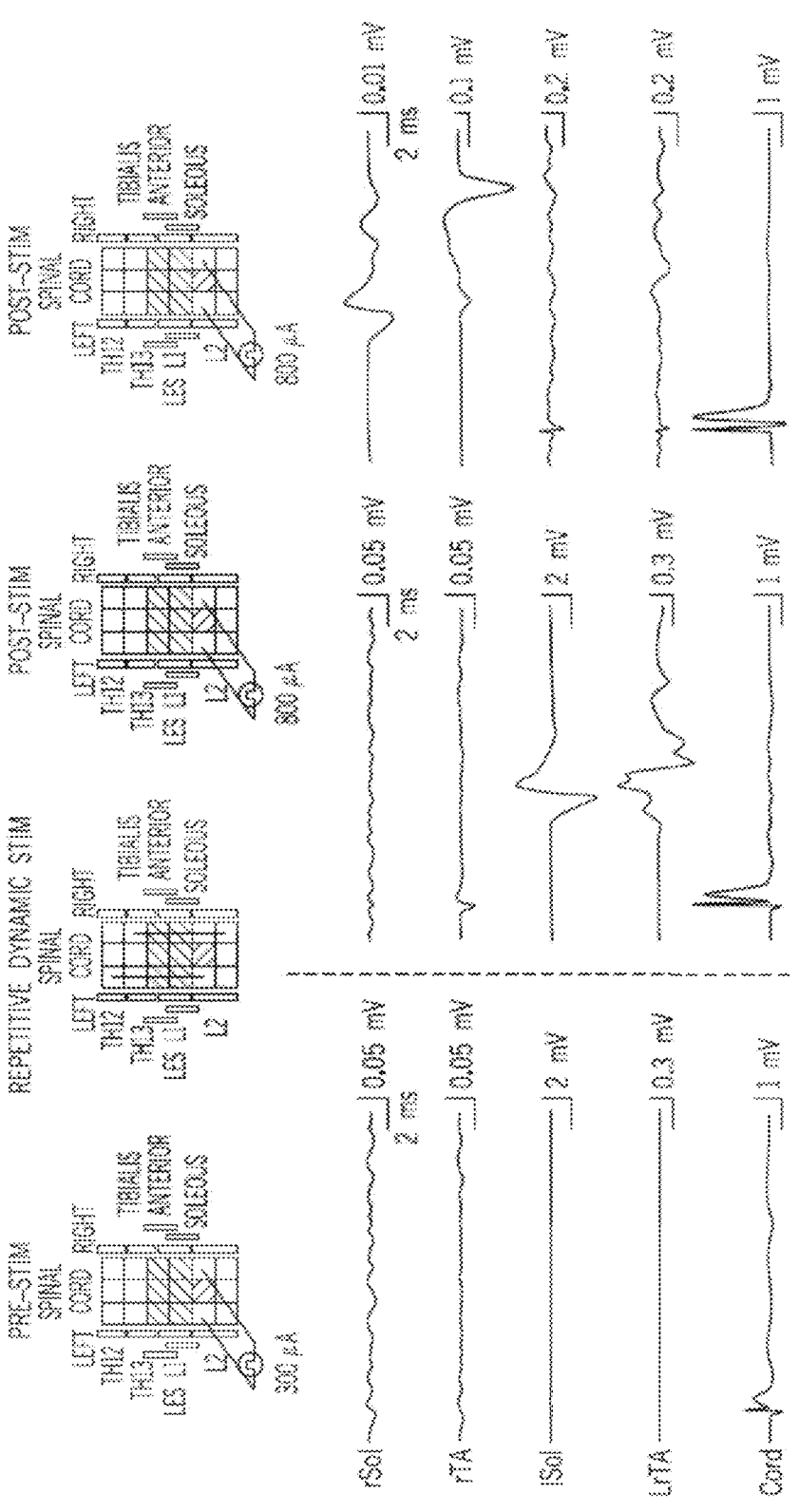

FIG. 42 shows that when the array is acutely placed across a spinal cord contusion at the level of L1, high test pulses delivered below the lesion cannot evoke any spinal reflexes, while only a small response arises from the dorsal cord. Afterwards, a repetitive dynamic stimulation protocol is applied. In turn, the same test pulses are now able to stably evoke muscle contractions from hindlimbs, with greater discharges recorded also from spinal sites.

Figure 43:
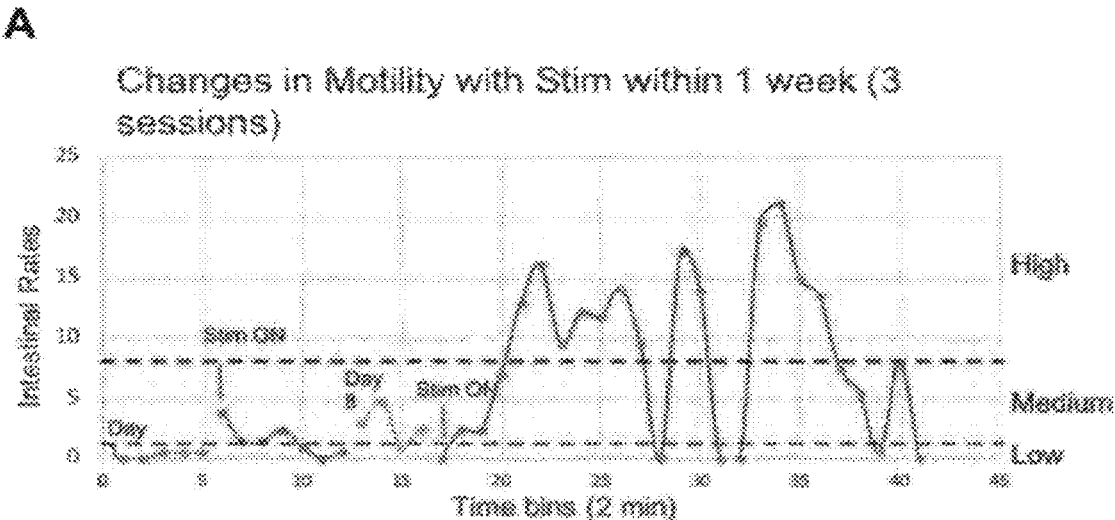
Figure 43:
Figure 43:
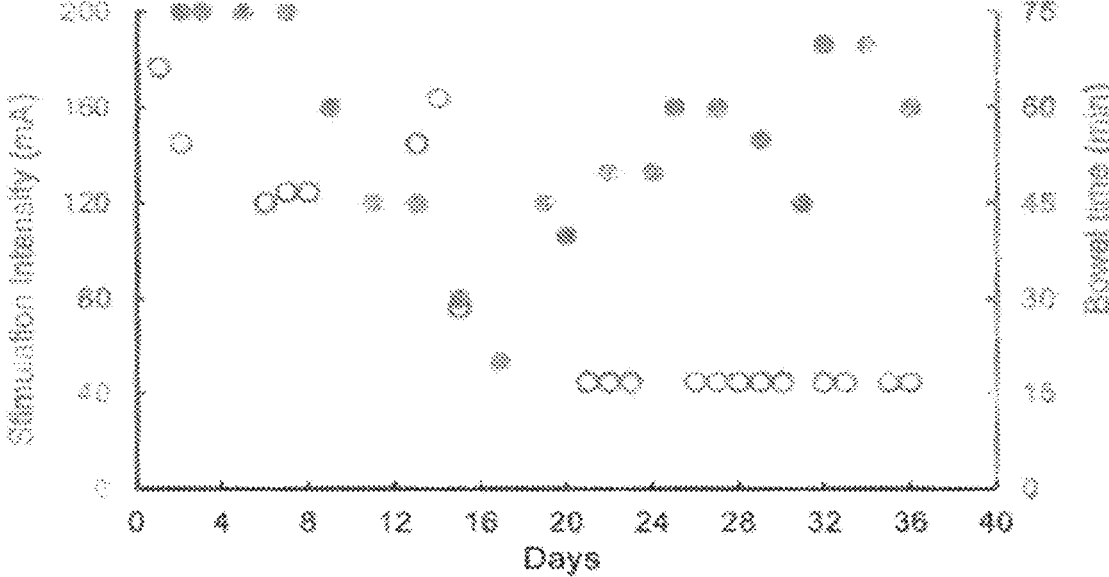

FIG. 43, panels A-B, illustrates changes in bowel function with transcutaneous electrical stimulation. Panel A) Changes in motility with stimulation within 1 week (3 sessions). Panel B) Changes in bowel function.

Figure 44:
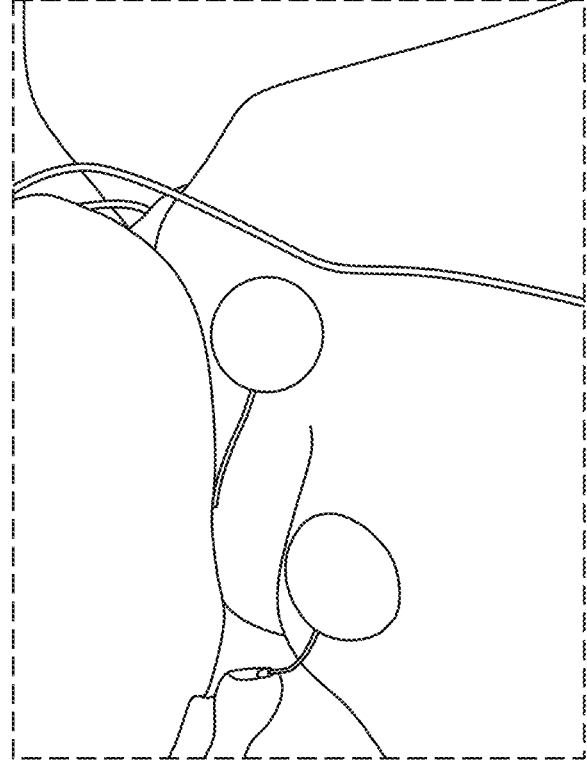

FIG. 44 illustrates placement of transcutaneous electrical stimulation leads on a subject.

Figure 45:
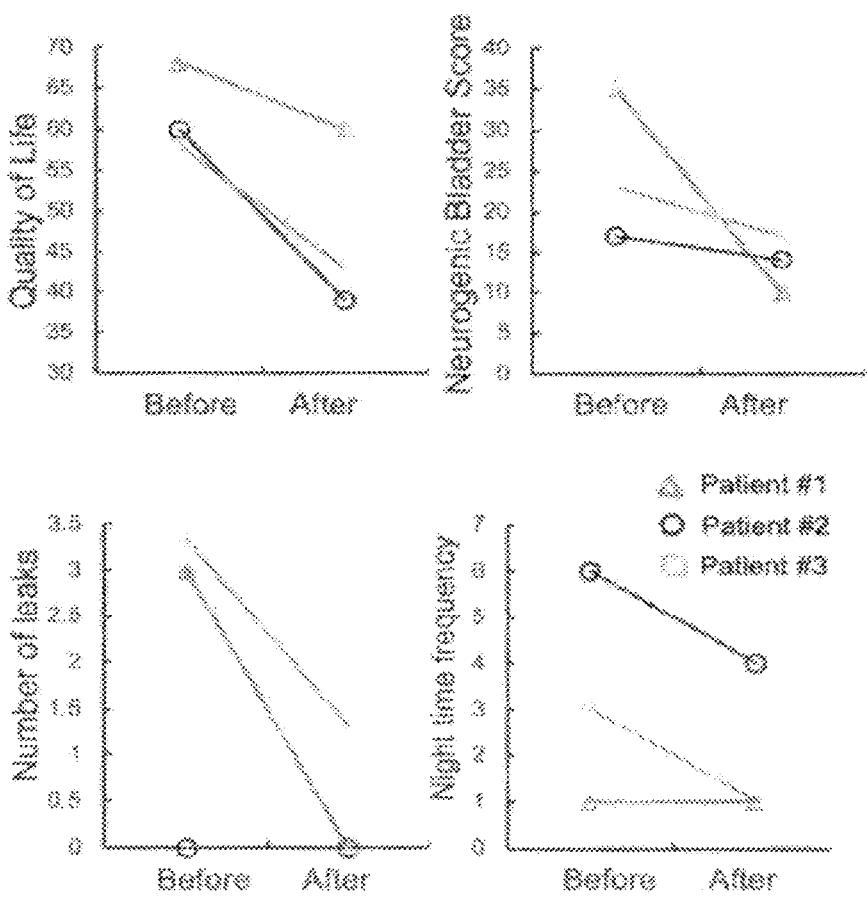

FIG. 45 illustrates the results of pilot studies in humans with stroke after 8 weeks of therapy.

Figure 46:
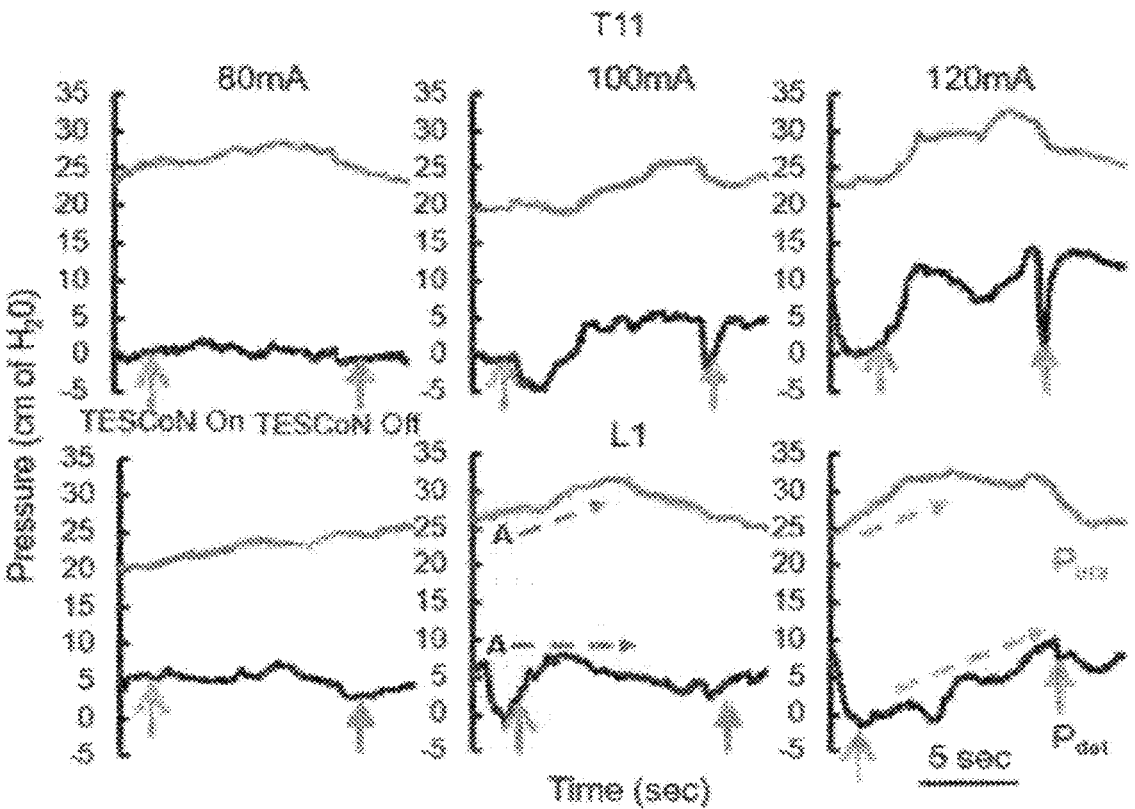

FIG. 46 shows changes in detrusor and urethral pressures with changing parameters of TESCoN. Representative patient demonstrating the protocol to identify parameters of TESCoN that generates minimal change in Pdet along with a change in Pura. In this case stimulation at L1 at 100 mA (yellow box) generated no change in Pdet while Pura increased from ~25 to 32 cm of H20 (A arrows) between TESCoN On and TESCoN off. Note the increase in both the Pura and Pdet at L1 120 mA.

Figure 47:
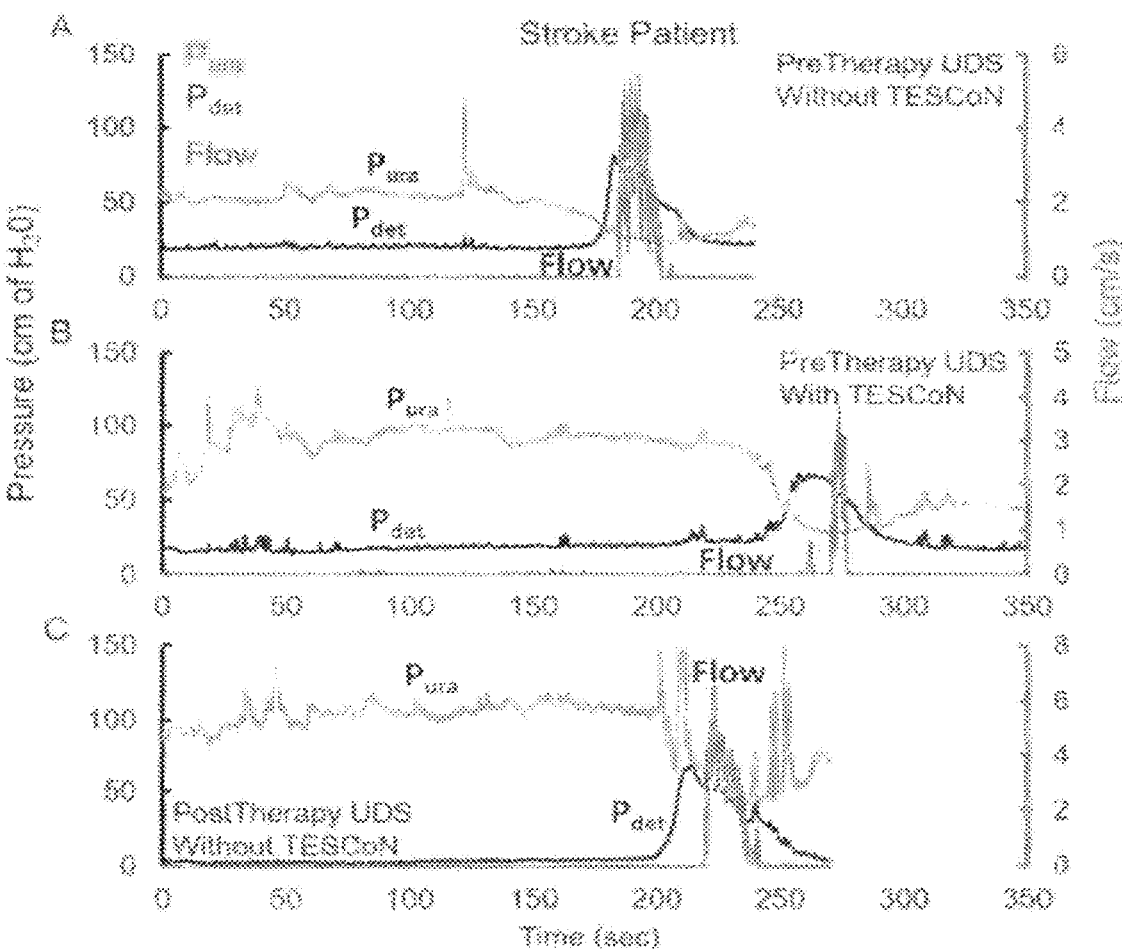

FIG. 47, panels A-F, shows changes in urodynamic studies without and with TESCoN. Representative urodynamic study for a stroke patient, Panel A) before therapy (Pre-Therapy) without and Panel B) with TESCoN and Panel C) after therapy (PostTherapy) and spinal cord injured (SCI), Panel D) before therapy (PreTherapy) without and Panel E) with TESCoN and Panel F) after therapy (PostTherapy). Note the increased bladder capacity (time prior to detrusor contraction), improved flow, improved detrusor and sphincter coordination and increase in urethral pressure during filling both with TESCoN at PreTherapy and PostTherapy (without TESCoN). Black arrow marks the occurrence of detrusor overactivity.

Figure 48:
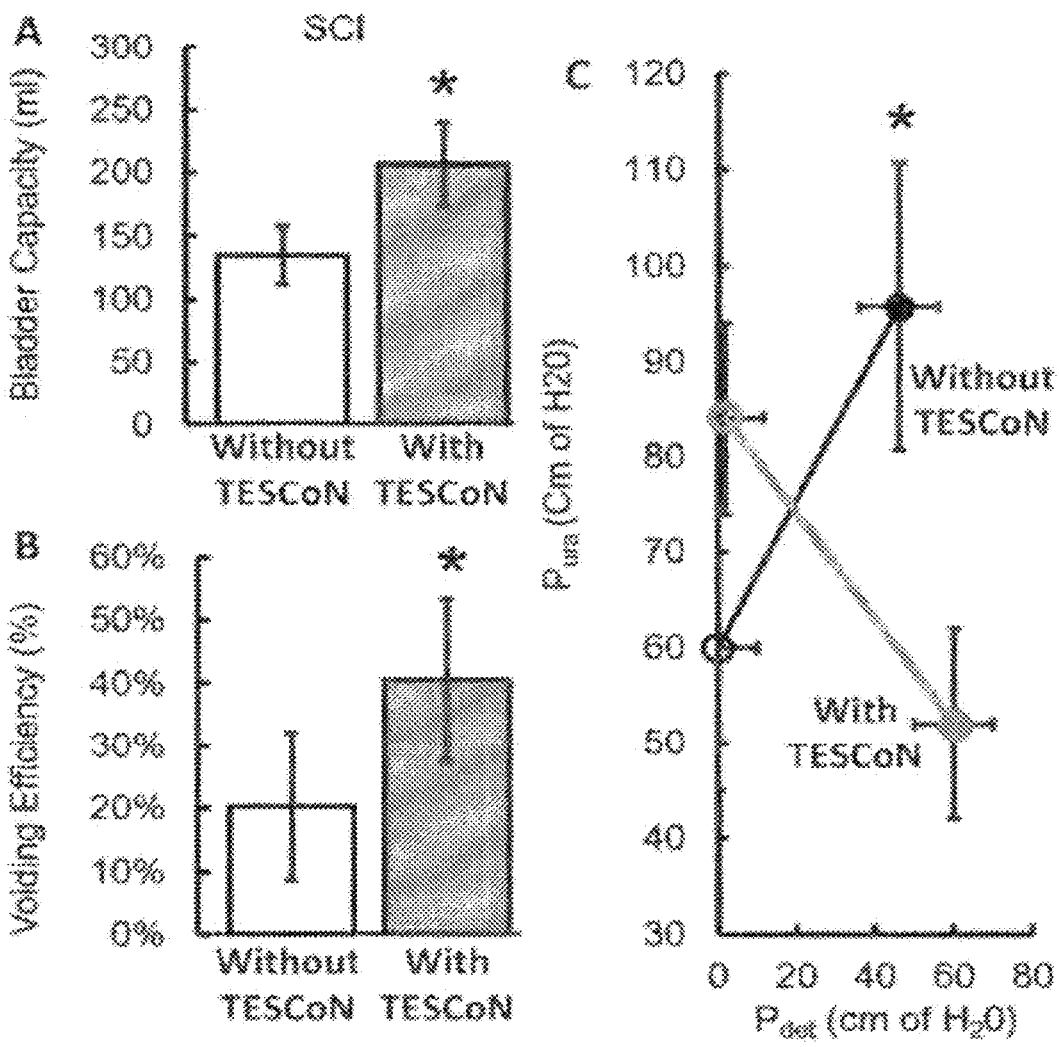

FIG. 48, panels A-C, shows changes in urodynamic parameters during acute stimulation in SCI subjects. Mean±SE (n=5 SCI) without (white bar) and with (red bar) acute delivery of TESCoN. Panel A) bladder capacity, Panel B) Voiding efficiency, Panel C) changes in pressure during filling vs voiding to demonstrate the improvement in Detrusor-Sphincter Dyssynergia (DSD) without (black) and with TESCoN (red).

Figure 49:
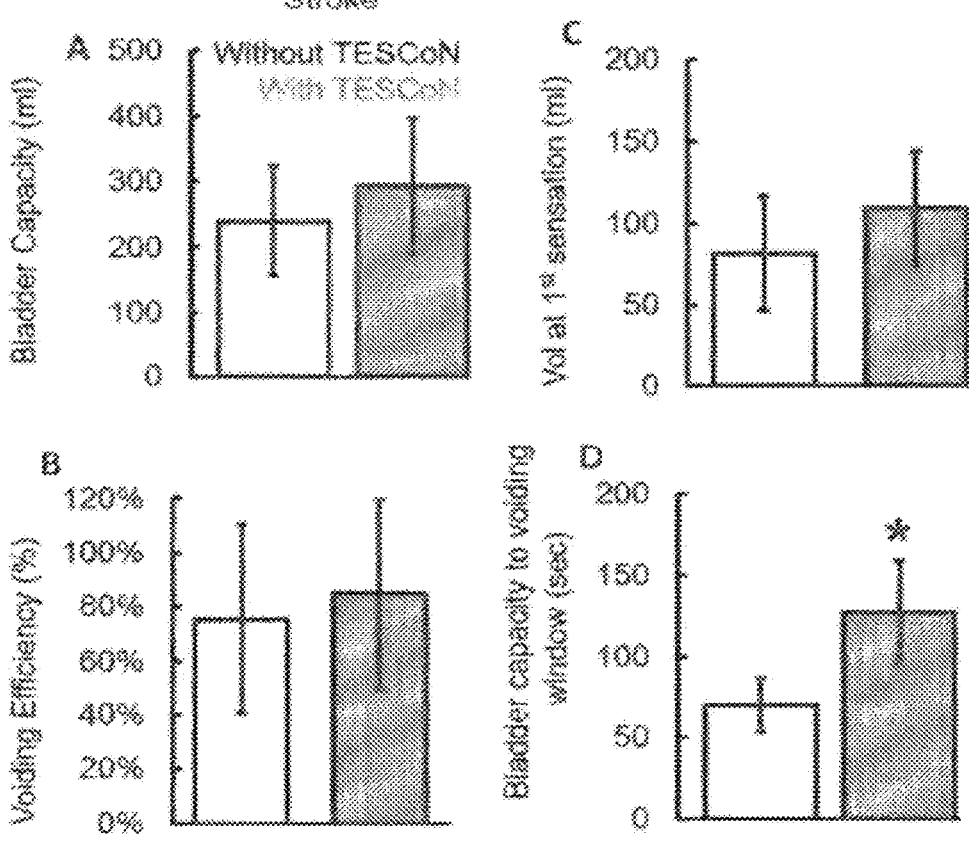

FIG. 49, panels A-D, shows changes in urodynamic parameters during acute stimulation in stroke subjects. Mean±SE (n=5 Stroke) Panel A) bladder capacity, Panel B) Voiding efficiency, Panel C) volume at first sensation during urodynamic study without (white bar) and with (red bar) acute TESCoN and Panel D) time window between bladder capacity and voiding in stroke patients. * statistically significant from without TESCoN at P<0.05.

Figure 50:
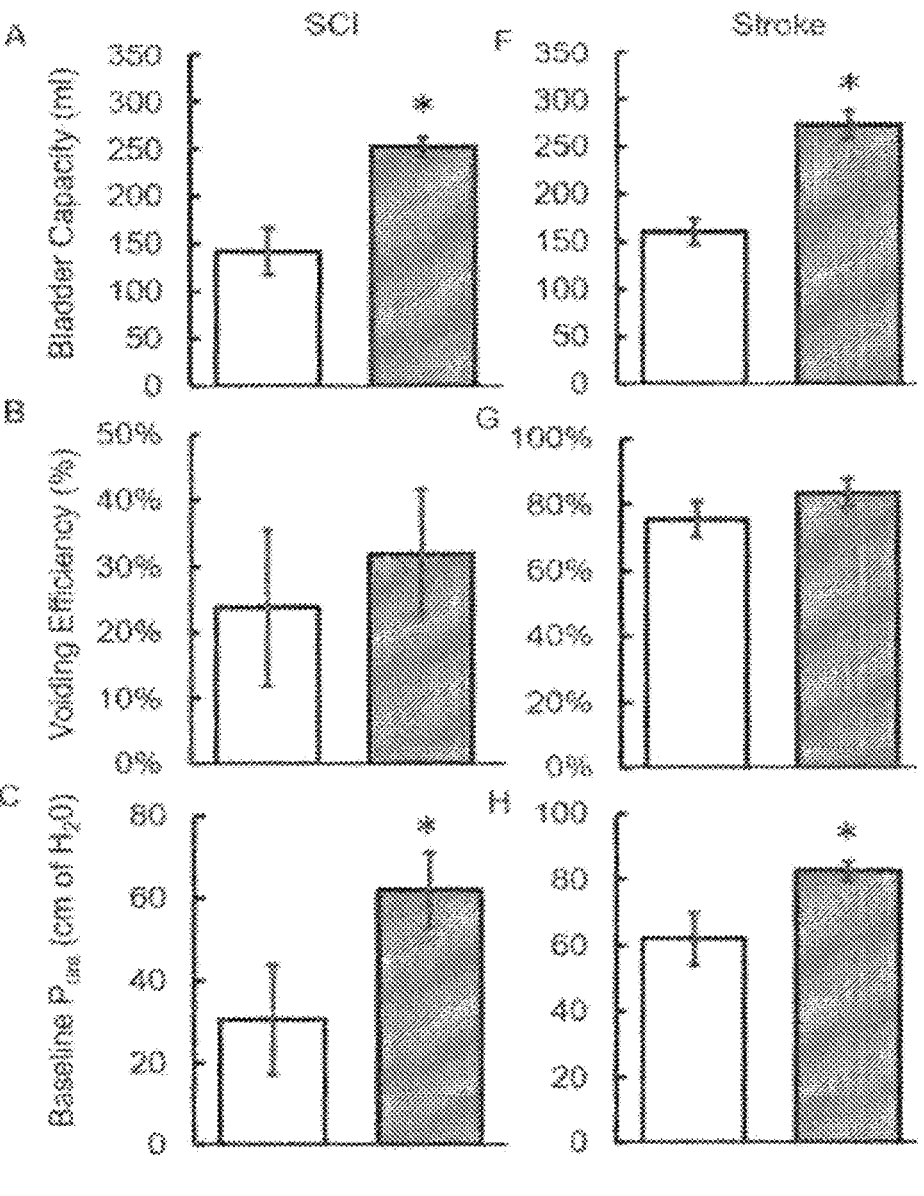

FIG. 50, panels A-E, shows changes in urodynamic parameters after a 8-week course of stimulation. mean±SE (n=5 SCI patients) Panel A) bladder capacity, Panel B) Voiding efficiency Panel C) baseline Pura prior to filling, Panel D) $\Delta P_{ura}$ during bladder filling, Panel E) $\Delta P_{det}$ during voiding as observed during clinical urodynamic studies at Pre-Therapy and Post-Therapy without TESCoN. mean±SE (n=5 stroke patients) F) bladder capacity, G) Voiding efficiency H) baseline $P_{ura}$ prior to filling, I) $\Delta P_{ura}$ during bladder filling, J) $\Delta P_{det}$ during voiding as observed during clinical urodynamic studies at Pre-Therapy and Post-Therapy without TESCoN. *—Significantly different from Pre-Therapy at P<0.05.

Figure 51:
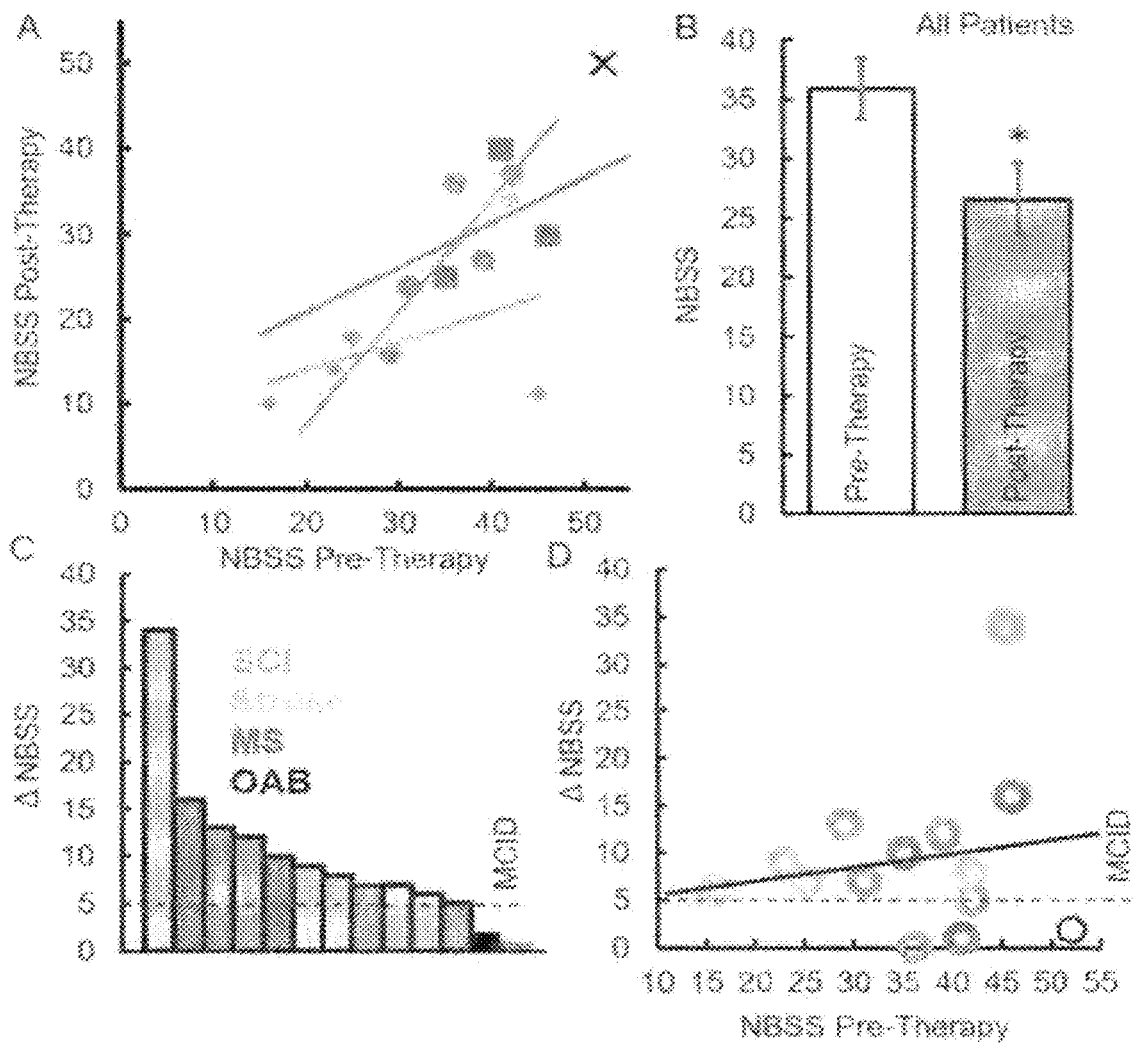

FIG. 51, panels A-E, shows changes in NBSS parameters after TESCoN therapy. Panel A) Neurogenic Bladder Symptom Score (NBSS) at Pre-Therapy and Post-Therapy for the 14 patients tested. Panel B) Mean±SE (n=14 patients) NBSS scores at Pre-Therapy and Post-Therapy. Panel C) Distribution of NBSS score decrease across the 14 patients tested, note only 5 SCI patients are plotted since 5th patient observed a change of 0, Panel D) decrease in NBSS scores relative to the initial NBSS scores, Panel E) mean±SE (n=5 SCI patients, n=5 stroke and n=3MS) NBSS scores at Pre-Therapy and Post-Therapy. MCID: Minimal clinically important difference.

Figure 52:
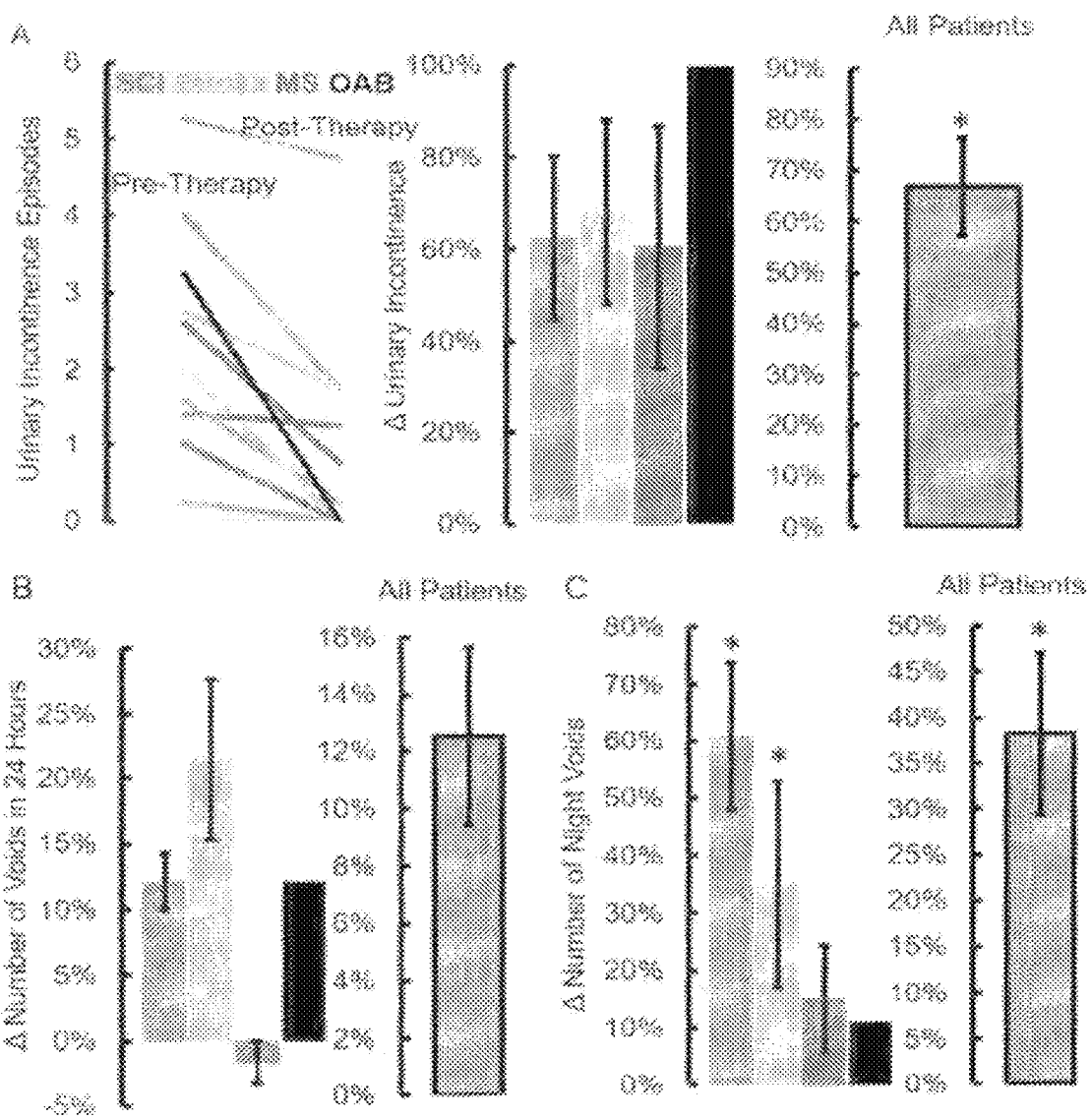

FIG. 52, panels A-C, shows changes in voiding diary parameters after TESCoN therapy. Panel A) Number of urinary incontinence at Pre-Therapy and Post-Therapy for the 14 patients tested, mean±SE percent decrease in incontinence episodes for the 4 patient groups and all patients (n=14 patients) tested, Panel B) mean±SE percent decrease in number of voids for the 4 patient groups and all patients (n=14 patients) tested and Panel C) mean±SE percent decrease in number of night time voiding/CIC episodes during the night (10 pm to 6 am) for the 4 patient groups and all patients (n=14 patients) tested.

Figure 53:
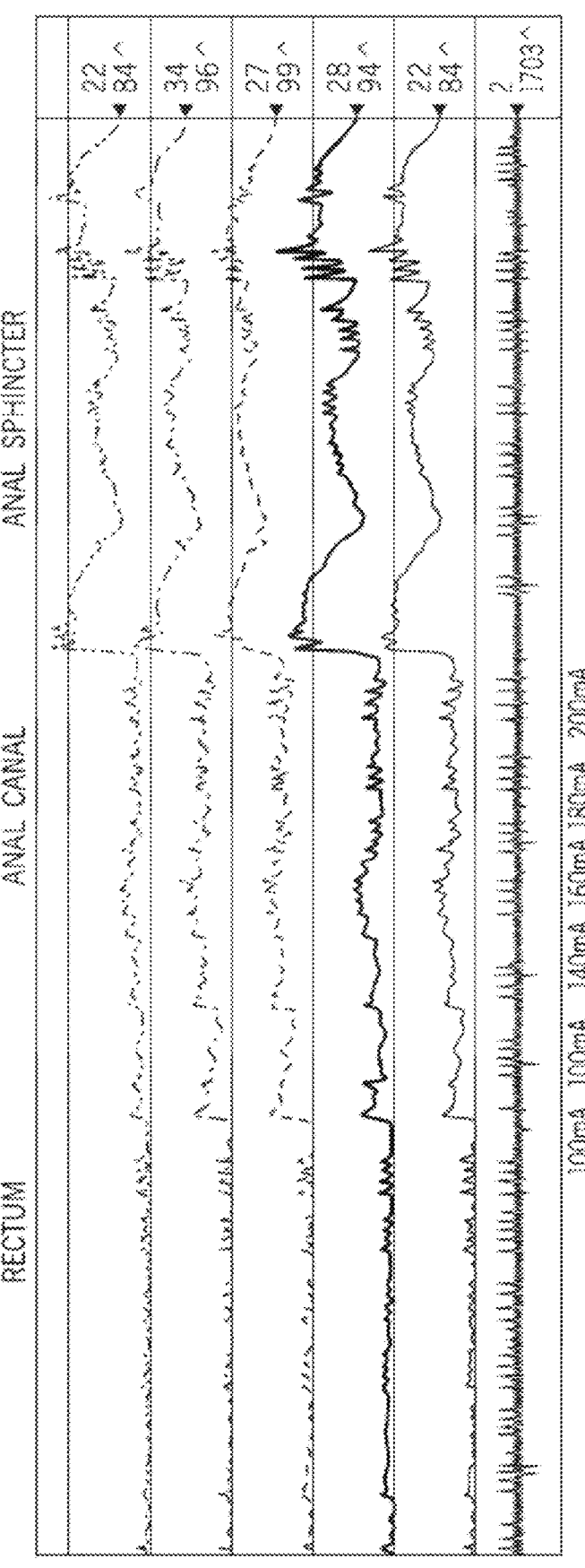

FIG. 53 shows contractions (changes in pressure) in the anorectal regions and anal sphincter regions of the bowel with TESCoN.

Figure 54:
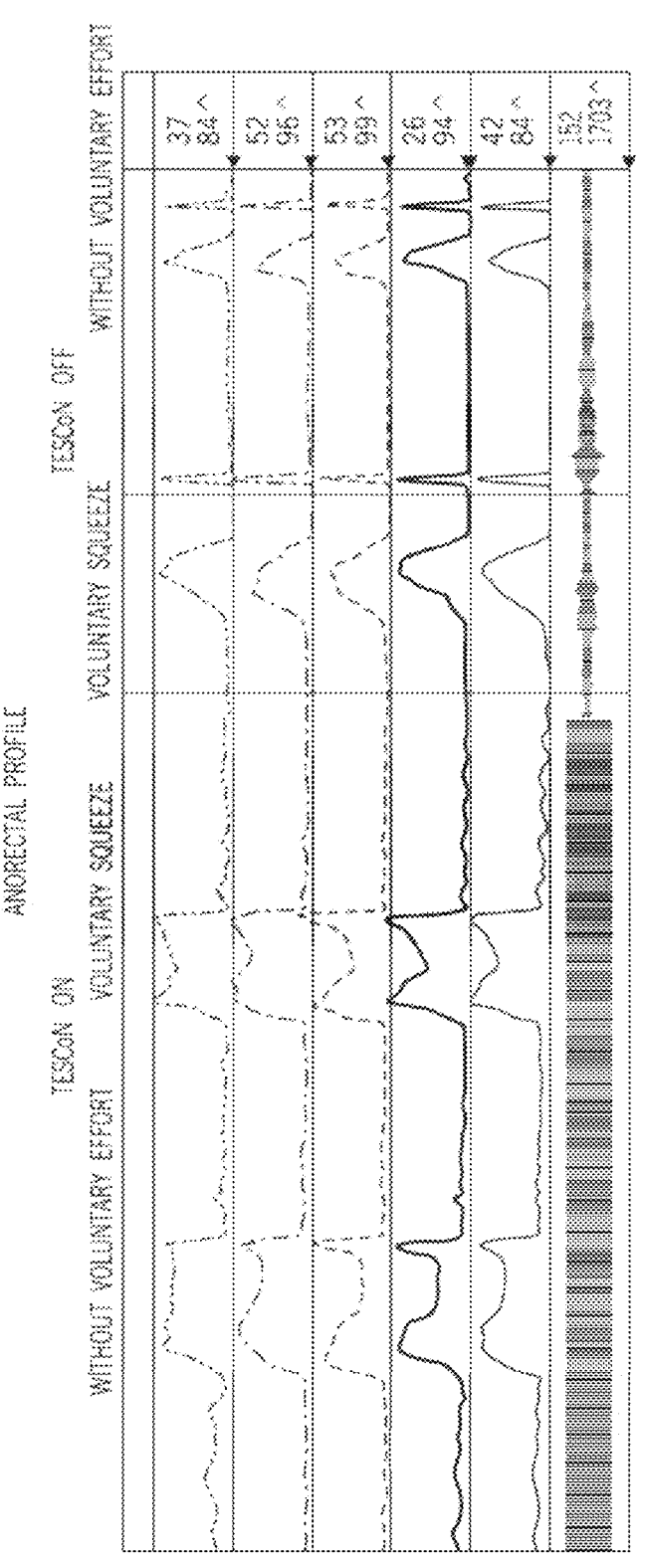

FIG. 54, shows that TESCoN results in increased duration and intensity of pressure change when combining voluntary effort and TESCoN.

Figure 55:
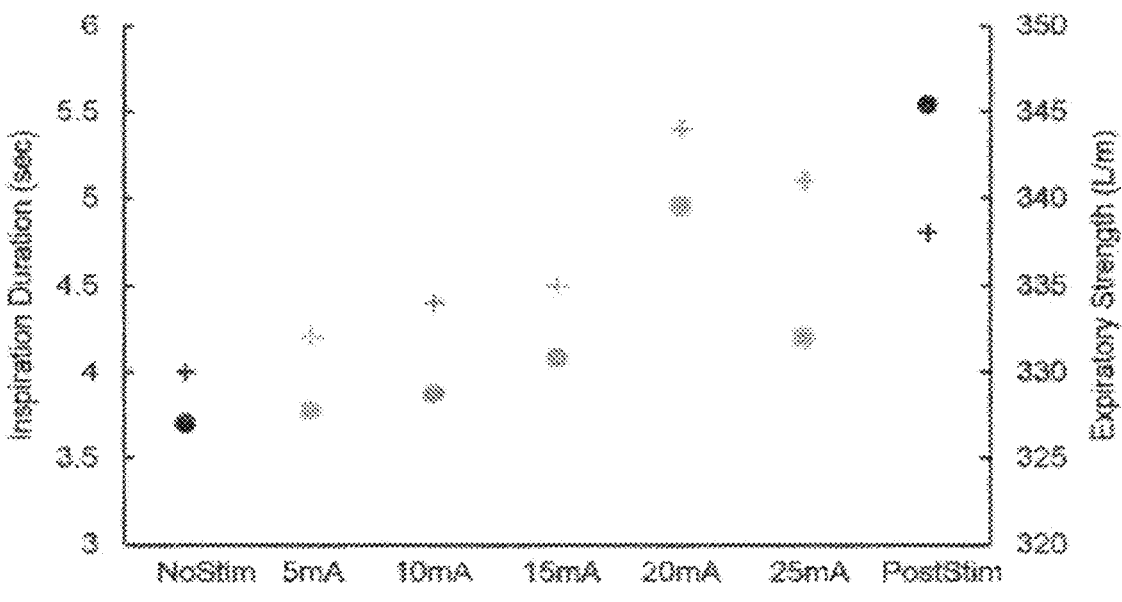

FIG. 55 illustrates measurement of inspiratory (round) and excitatory (plus) capacities while varying the intensity of TESCoN at C5.

Figure 56:
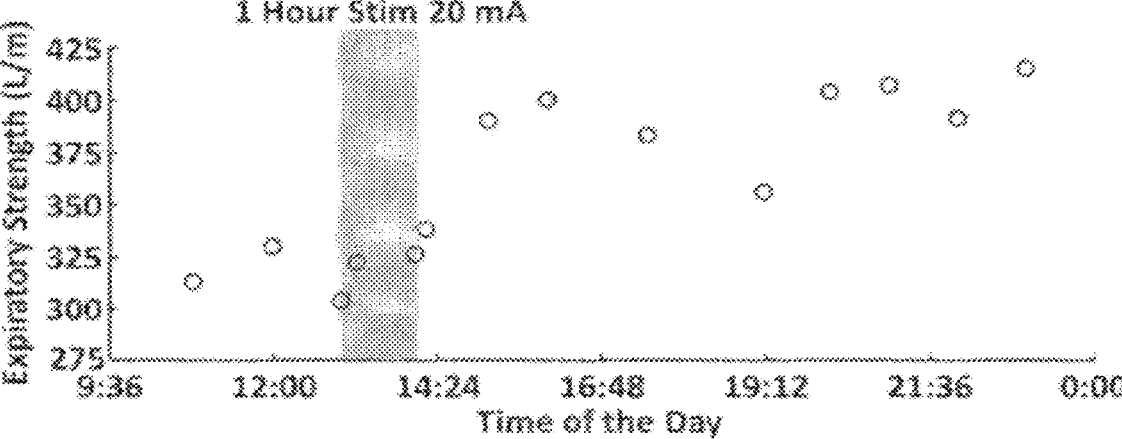

FIG. 56 shows breathing capacities before during and after 1 hour of TESCoN at C5 at 20 mA.

Figure 57:
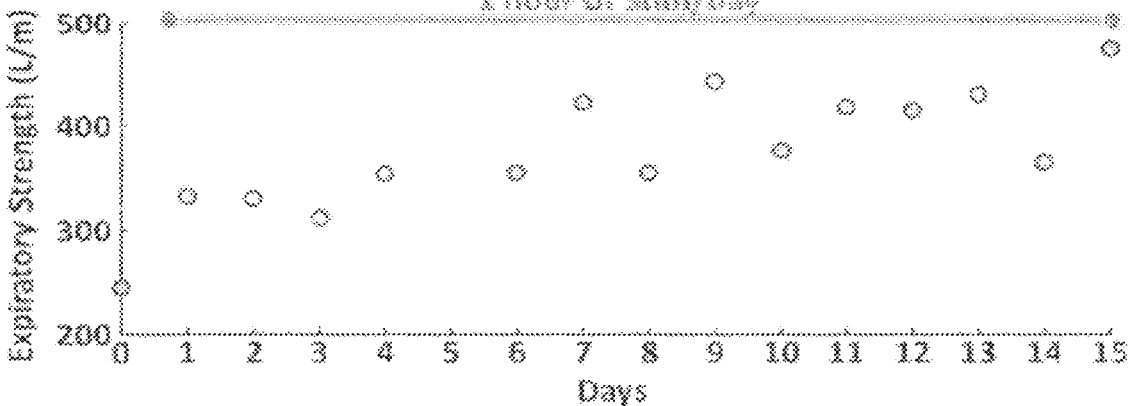

FIG. 57 shows breathing capacities before and during 2 weeks of TESCoN therapy at C5 20 mA.

Figure 58:
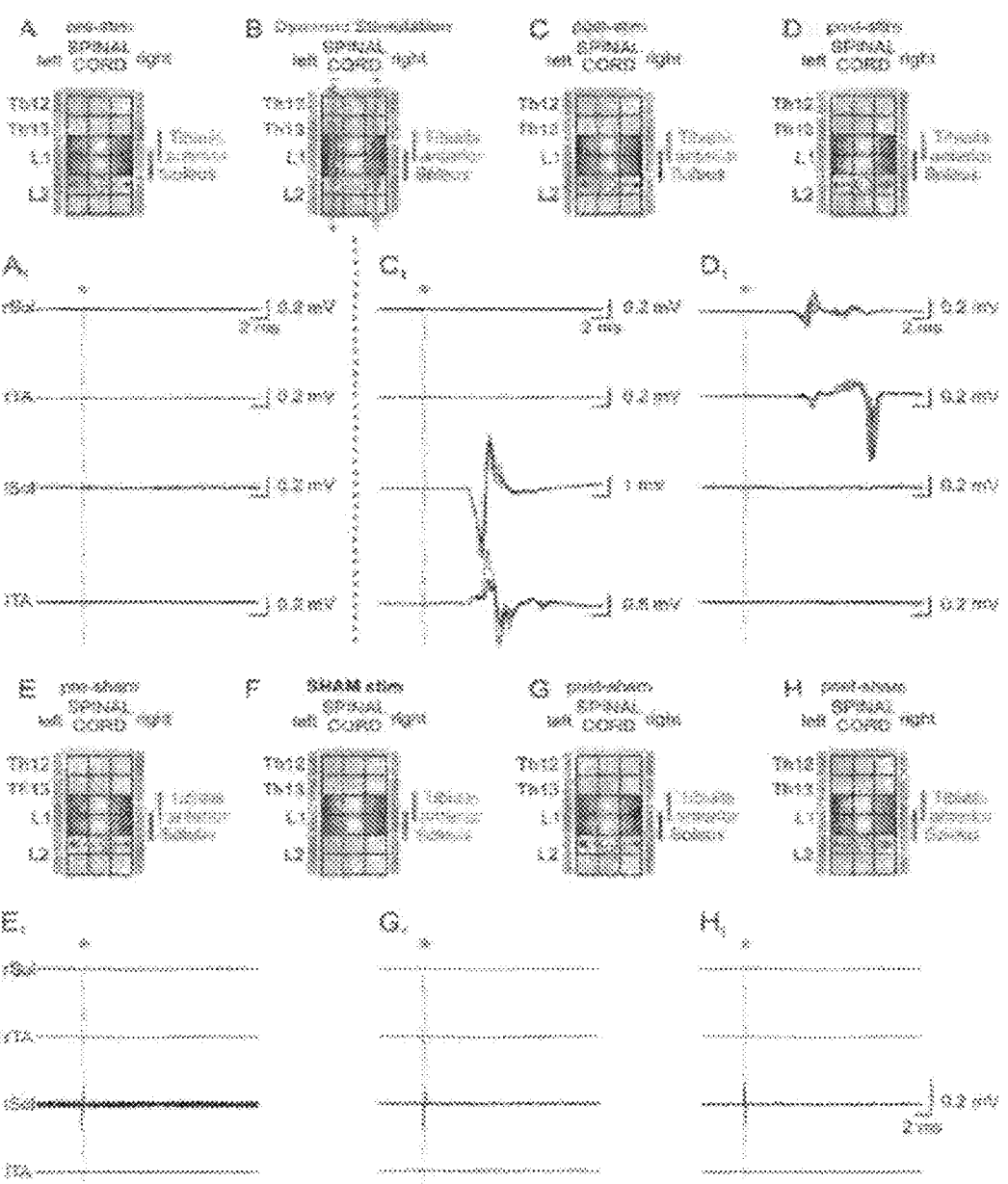

FIG. 58, panels $A-H_1$, shows that. rDS restores spinally-induced responses after acute spinal contusion. In panel A, 90 mins after a calibrate compression to the spinal cord at L5, single pulses (red star and dotted line; intensity=800 µA; duration=0.1 ms) applied to L6 (cathode on the right) are unable to elicit any bilateral EMG responses from Sol and TA muscles (panel A1). After additional 90 mins, rDS was supplied through the lesioned spinal cord (panel B) and 50 mins later (panels C, D), the same stimulation delivered in A now evokes spinally-induced responses from both the left leg (panel $C_1$, cathode on the right) and from the right one, as well, by swapping the position of the poles (panel $D_1$, cathode on the left). In panels E-H the same protocol in panels A-D was followed in an animal that did not receive any rDS. In the latter case, no spontaneous recovery was reported for either configuration of stimulation (panels $G_1$, $H_1$). In each panel $A_1$, $C_1$, $D_1$, $E_1$, $G_1$, $H_1$, five consecutive traces are superimposed.

Figure 59:
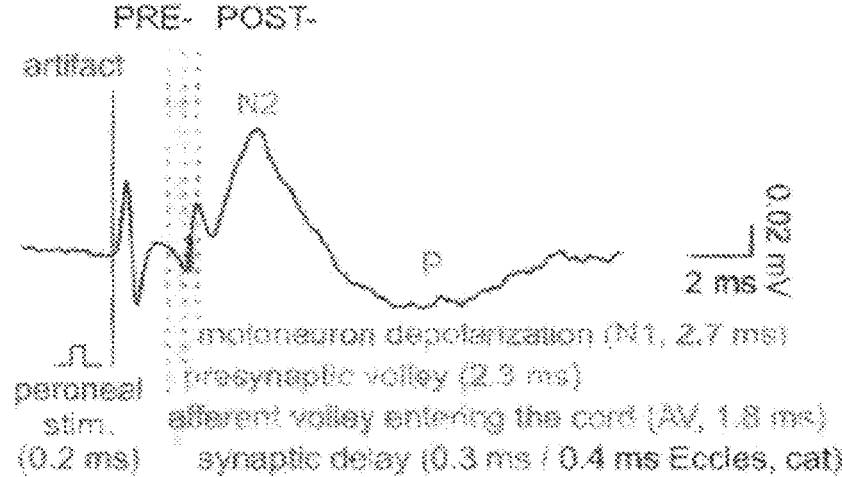

FIG. 59 illustrates cord dorsum potential (CDP) recorded from a single site of an epidural interface.

Figure 60:
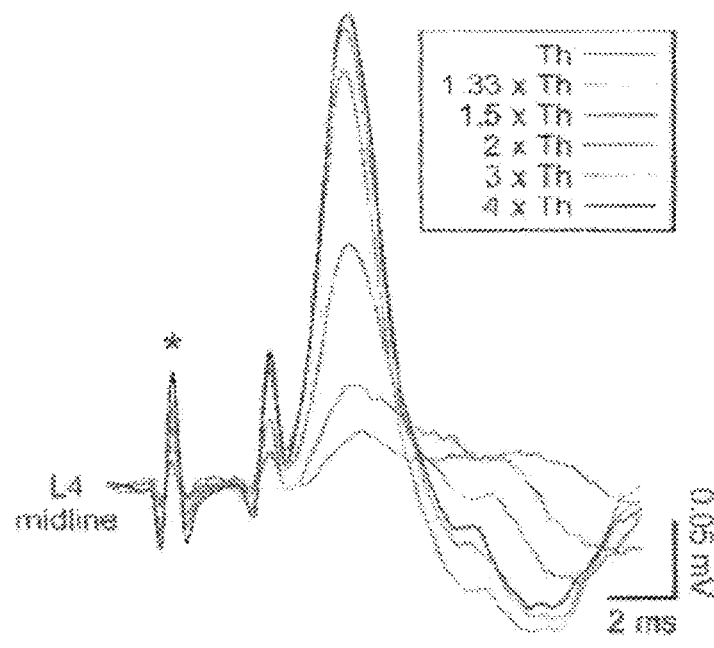

FIG. 60 shows that CDP changes at increasing intensity of stimulation.

Figure 61:
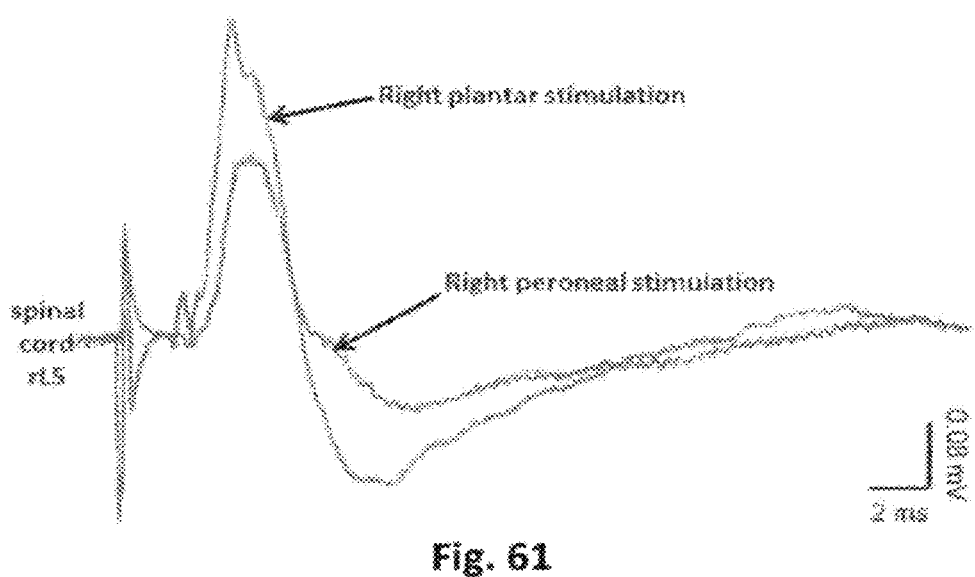

FIG. 61 illustrates responses evoked from the same site of the cord during the serial stimulation of two peripheral nerves.

Figure 62:
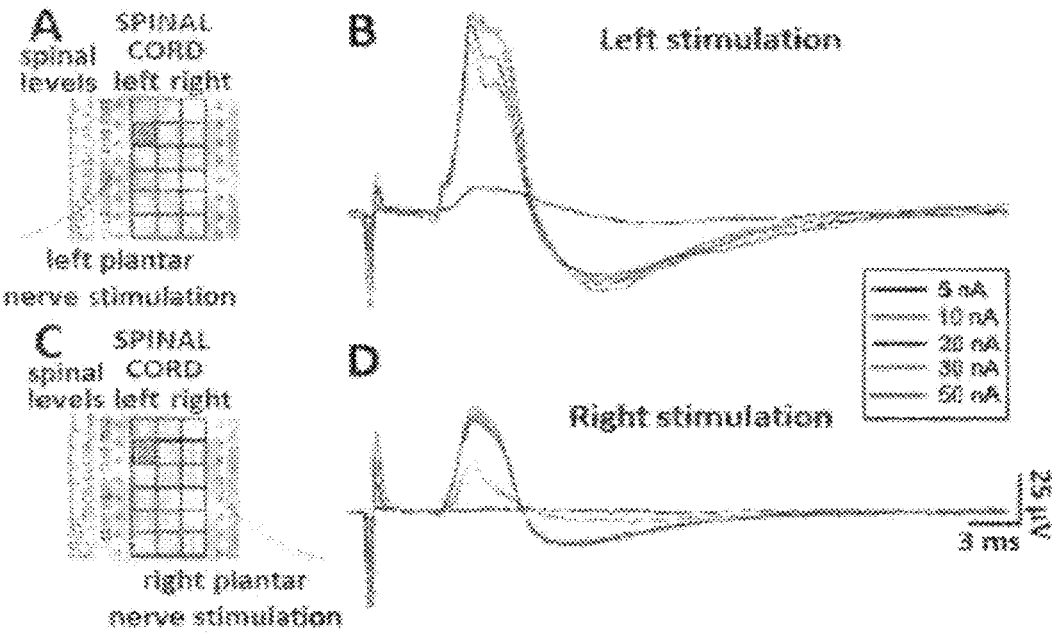

FIG. 62, panels A-D, illustrates responses elicited from the same site of the cord in response to the bilateral stimulation of afferent nerves.

Figure 63:
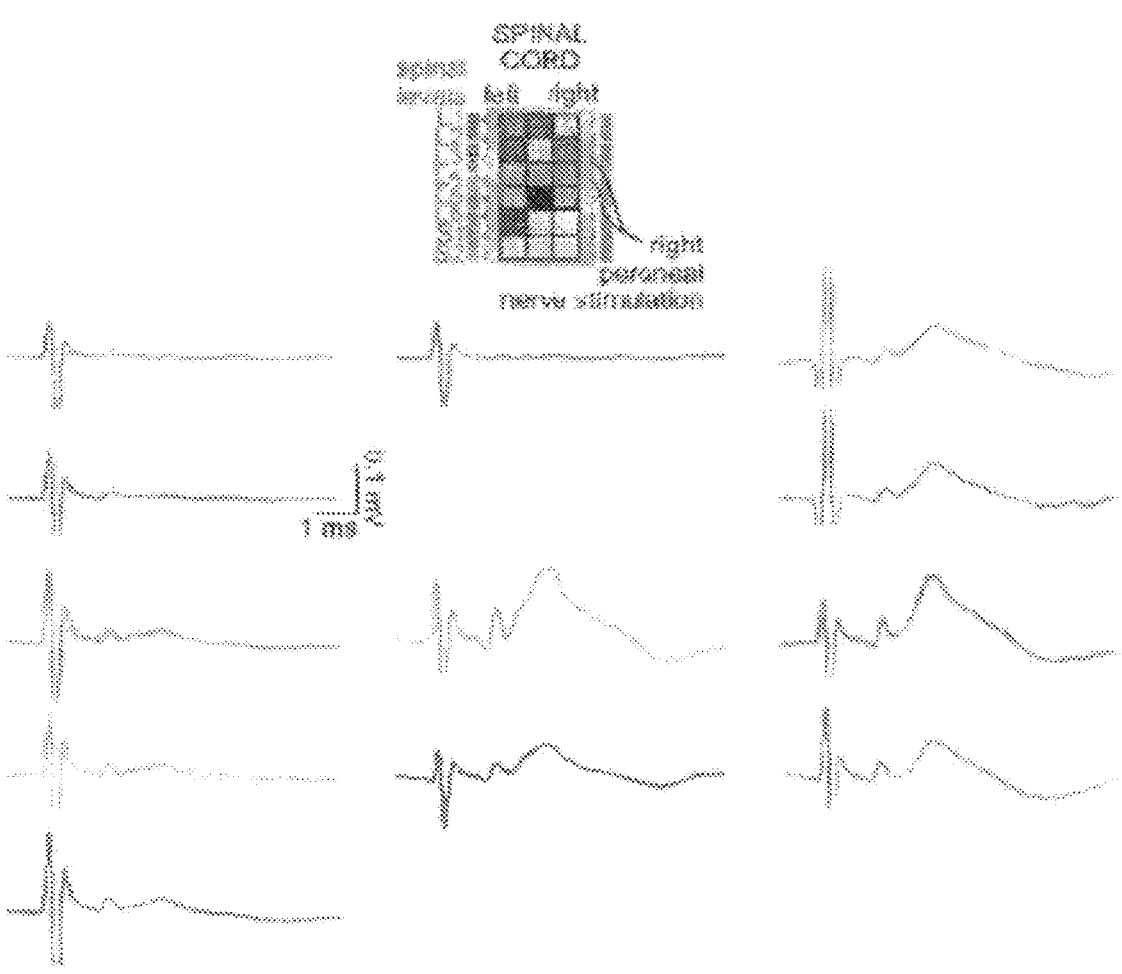

FIG. 63 illustrates multiple CDPs simultaneously derived from different sites of the cord.

Figure 64:
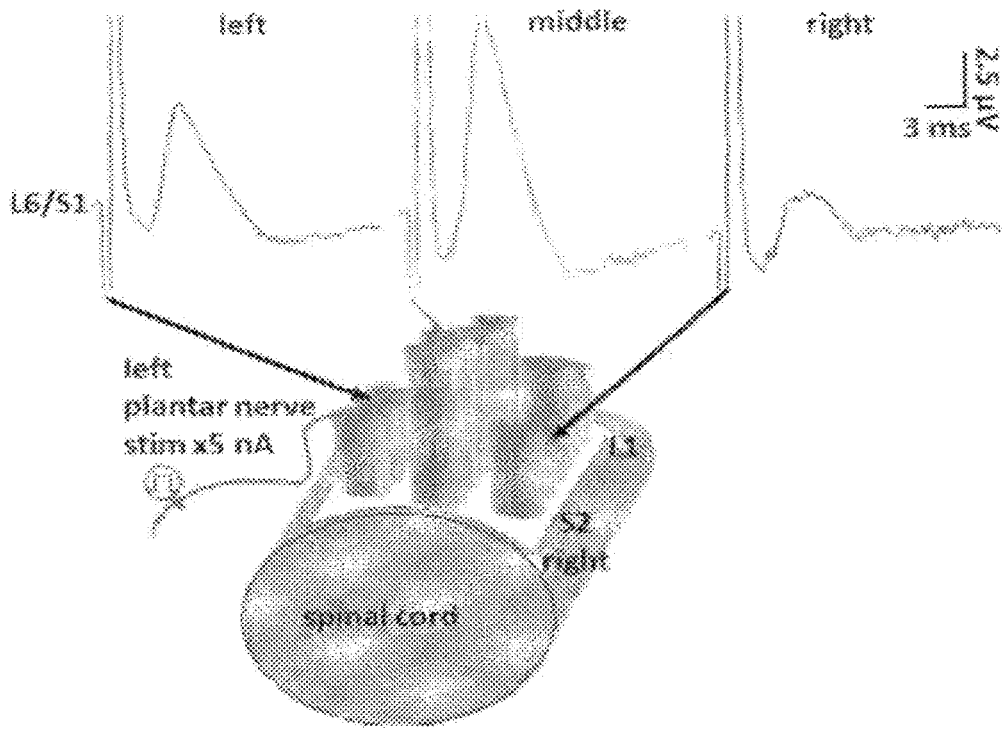

FIG. 64 illustrates responses elicited from different locations on the spinal cord. On occasion, the highest response is elicited from the midline in accordance to what reported elsewhere.

Figure 65:
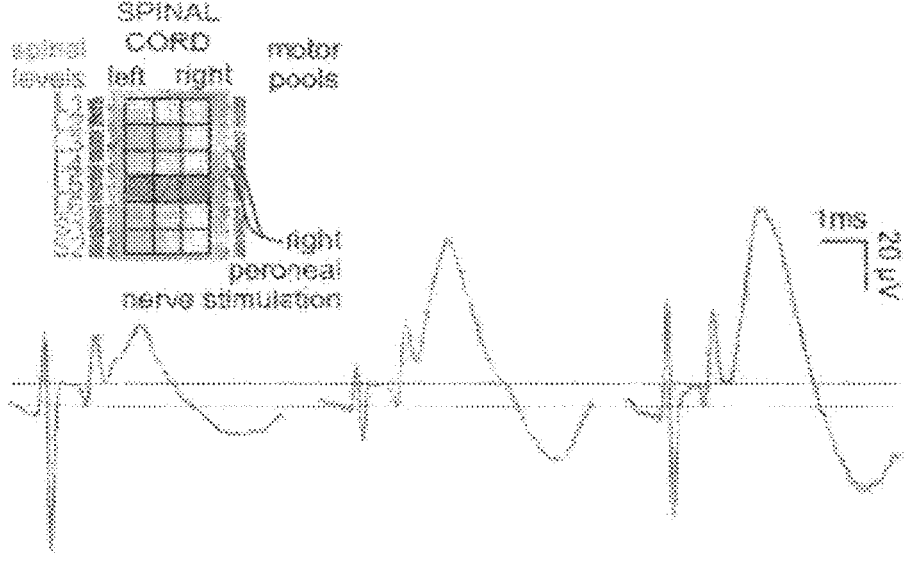

FIG. 65 illustrates calculation of the ratio among N1/AV peaks for each site.

Figure 66:
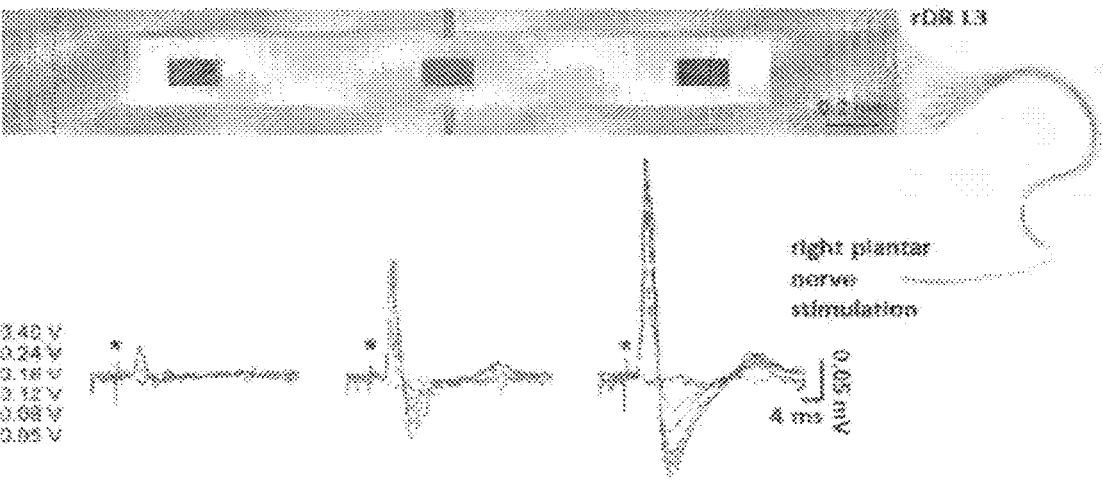

FIG. 66 illustrates the Input output curve for each site, normalized to the highest peak.

Figure 67:
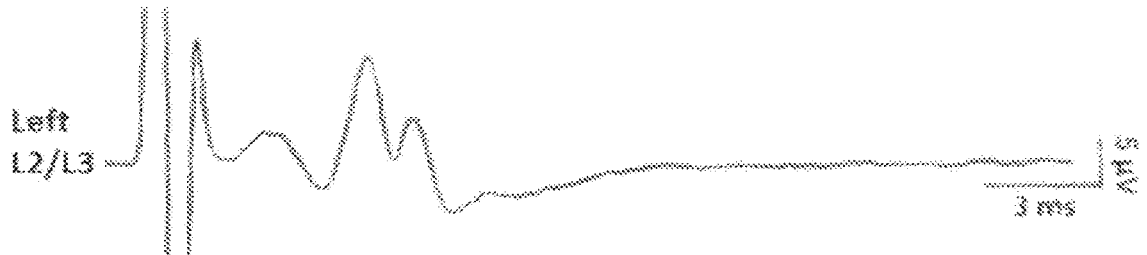

FIG. 67 illustrates CDPs elicited by selective electrical stimulation of the lateral motor cortex.

Figure 68:
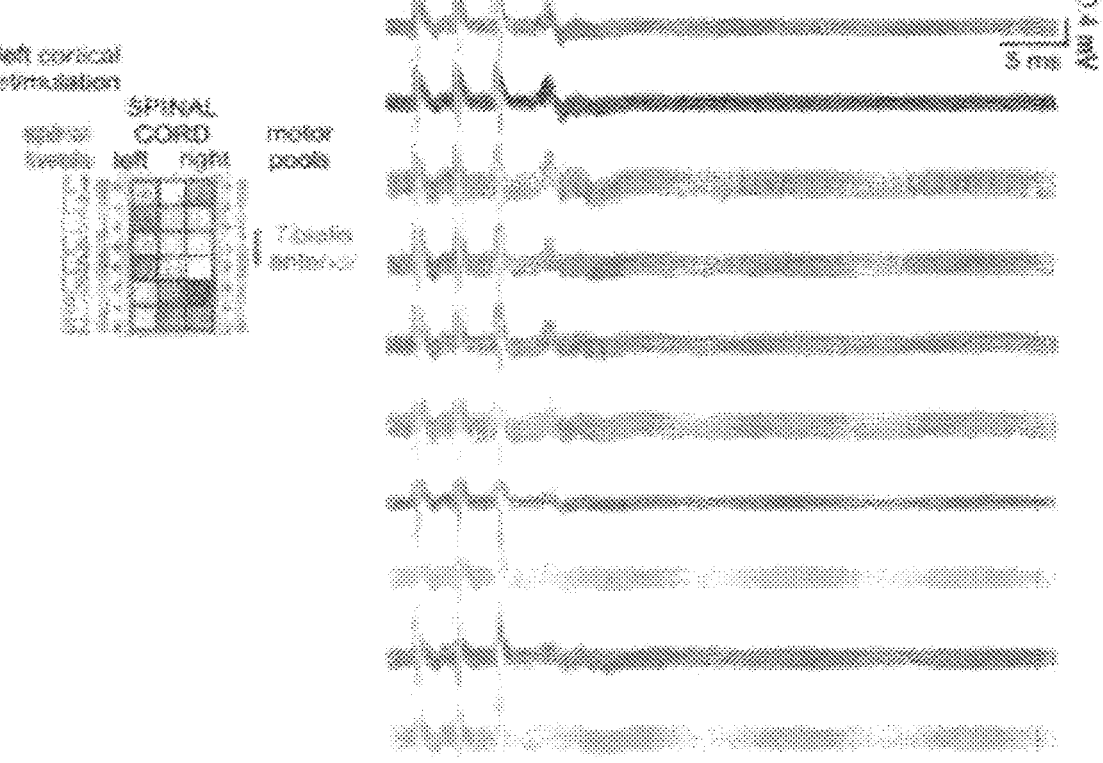

FIG. 68 shows that, using superimposed traces, higher peaks appear to occur contra-laterally to the stimulated cortical area.

Figure 69:
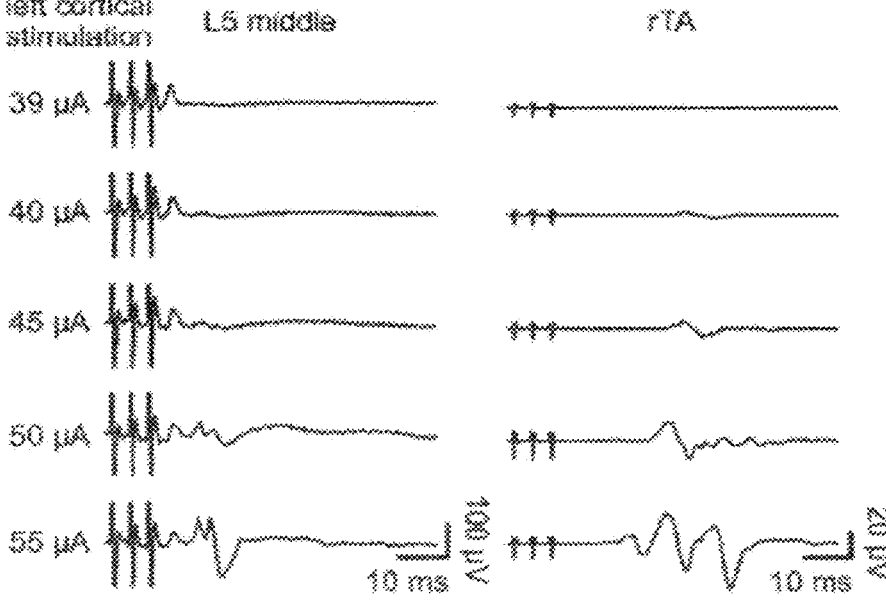

FIG. 69 illustrates effects of increasing the intensity of cortical stimulation.

Figure 70:
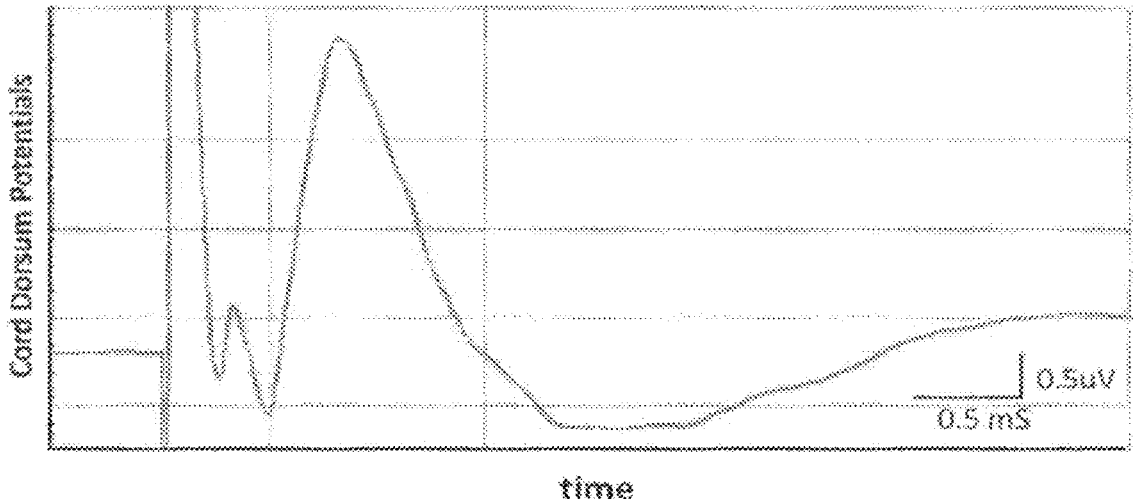

FIG. 70 illustrates that spinally-induced potentials have a shorter latency.

Figure 71:
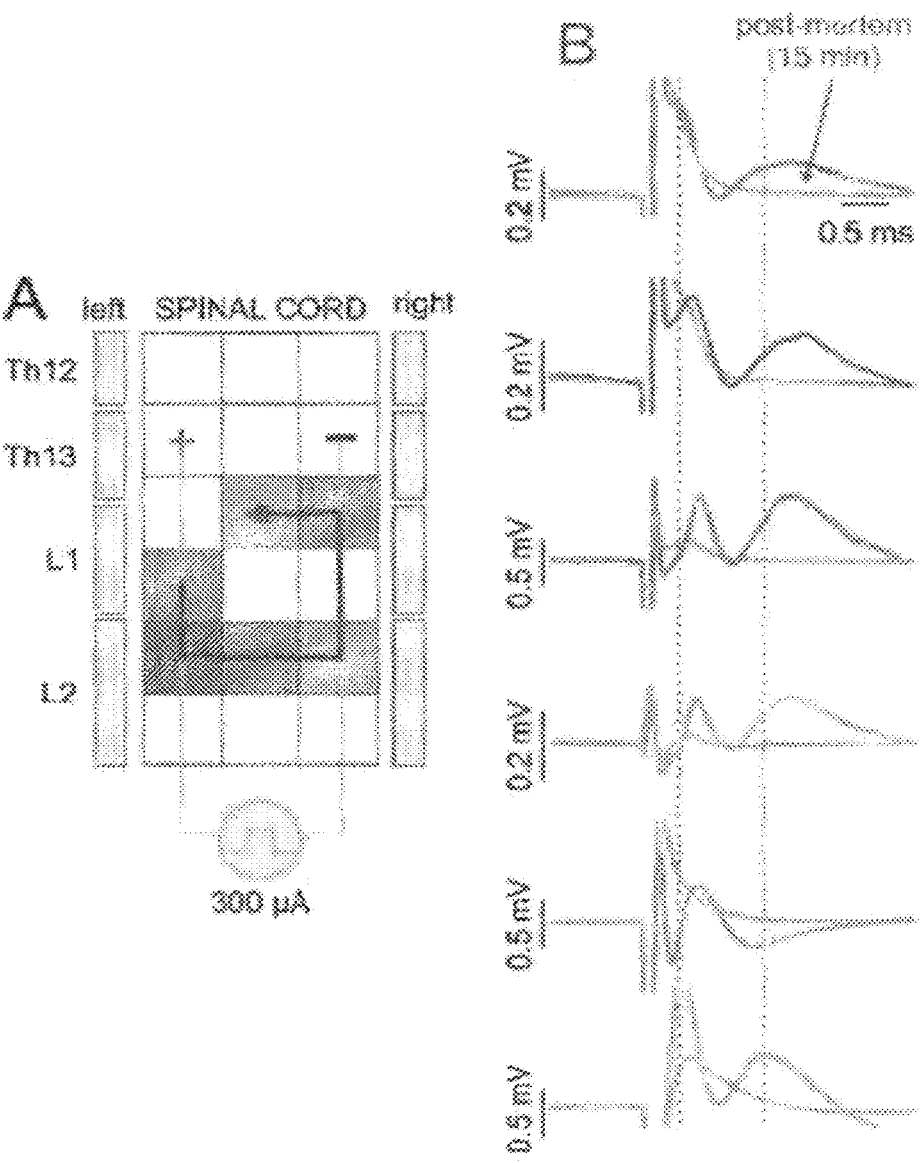
Figure 72:
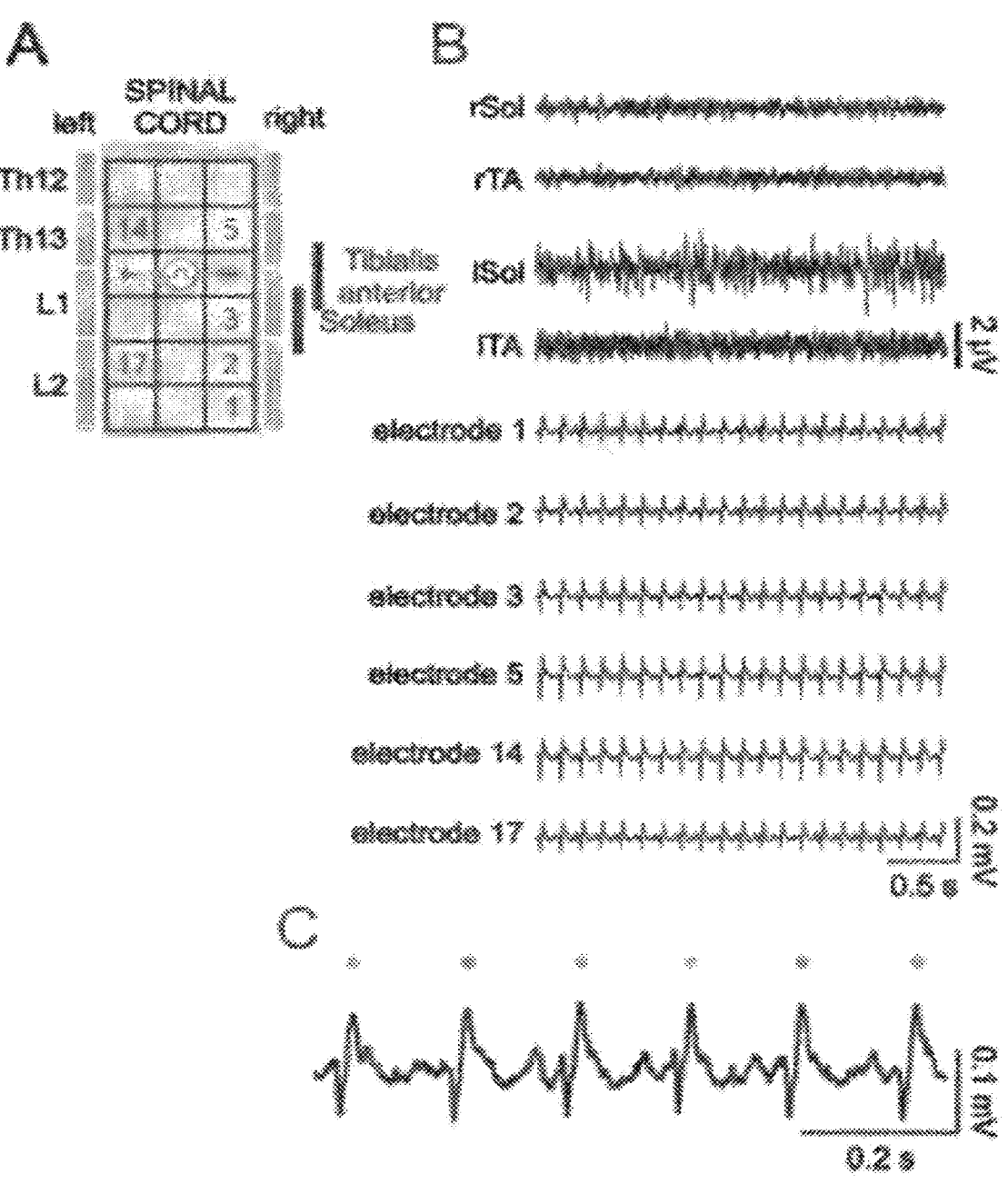

FIG. 71, panels A-B, illustrates multiple recordings during epidural stimulation FIG. 72, panels A-C, illustrates spontaneous discharges were recorded from the array.

Figure 73:
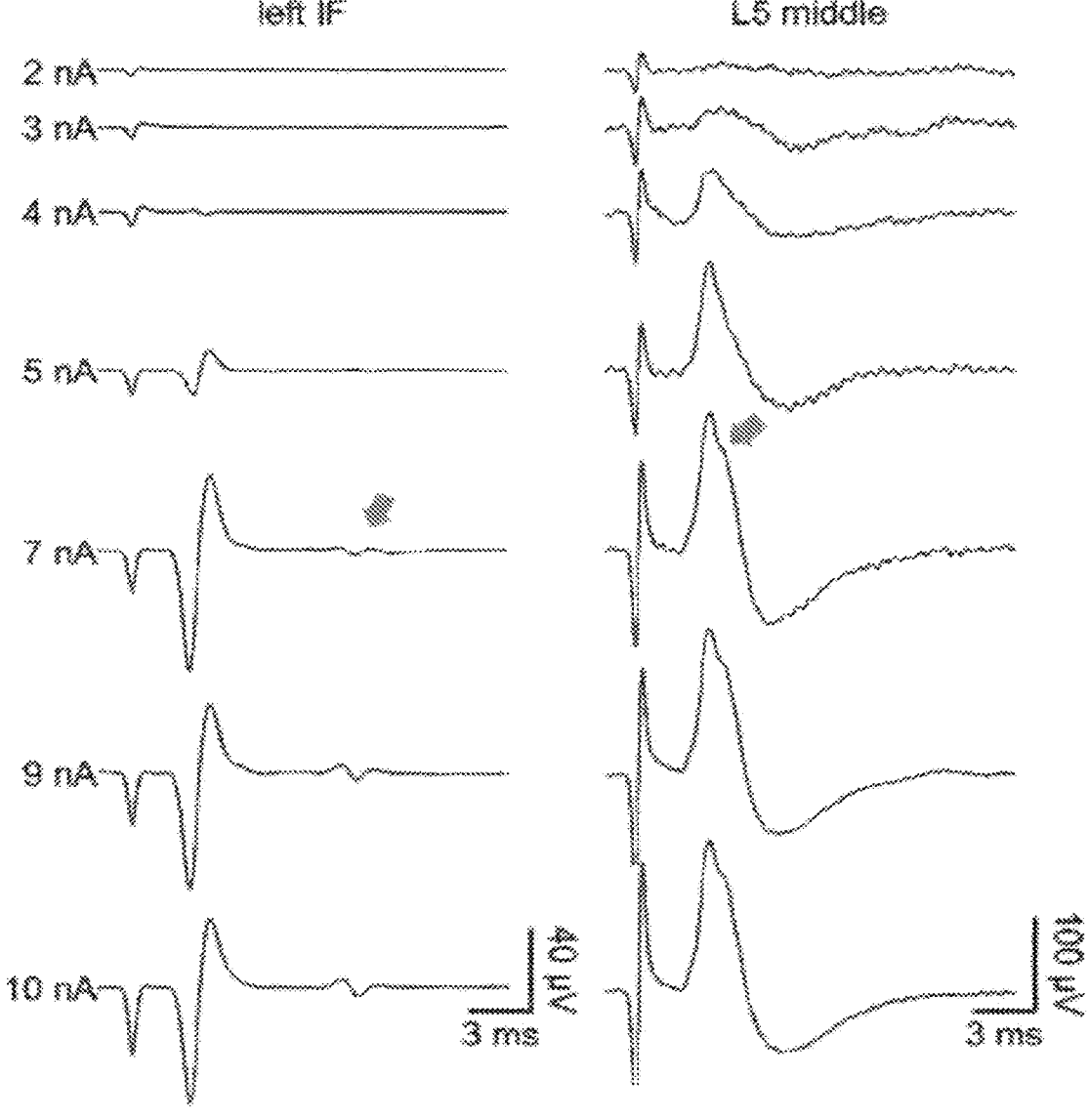

FIG. 73 shows that for increasing intensities of stimulation, CDP composition reflects the appearance of H response.

DETAILED DESCRIPTION

In various embodiments an electrical stimulator is provided that provides effective transcutaneous or epidural stimulation in one or more of a variety of modalities. The electrical stimulator can be used to facilitate, inter alia, bladder and/or bowel function, particularly in subjects where such function is diminished, e.g., due to spinal cord injury, neurodegenerative conditions, and the like. Additionally, methods of using such stimulators to facilitate function (e.g., bladder or bowel function) in various subjects are also provided.

Electrical Stimulators.

Functional Parameters and Electrical Stimulator Configuration.

In various embodiments the electrical stimulators described herein comprise one or more channels where each channel when present can provide a transcutaneous electrical stimulation signal or an epidural stimulation signal. In certain embodiments the electrical stimulator provides one stimulation channel, while in other embodiments the stimulator provides 2 or more independently controllable (programmable) stimulation channels, or 3 or more independently controllable (programmable) stimulation channels, or 4 or more independently controllable (programmable) stimulation channels, or 6 or more independently controllable (programmable) stimulation channels, or 8 or more independently controllable (programmable) stimulation channels, or 12 or more independently controllable (programmable) stimulation channels, or 16 or more independently controllable (programmable) stimulation channels, or 20 or more independently controllable (programmable) stimulation channels, or 24 or more independently controllable (programmable) stimulation channels. In certain embodiments the stimulator provide 2 independently controllable (programmable) stimulation channels, or 3 independently controllable (programmable) stimulation channels, or 4 independently controllable (programmable) stimulation channels, or 5 independently controllable (programmable) stimulation channels, or 6 independently controllable (programmable) stimulation channels, or 7 independently controllable (programmable) stimulation channels, or 8 independently controllable (programmable) stimulation channels. In certain embodiments where there is more than one channel, multiple channels may provide stimulation signals with respect to a common (e.g., neutral or ground) lead. In certain embodiments where there is more than one channel, two or more different channels may provide stimulation signals with respect to a different leads (e.g., a different "reference" lead associated with each channel).

Where there is more than one channel, in certain embodiments, one or more or all of the channels are configured to provide a transcutaneous electrical stimulation or one or more or all of the channels are configured to provide an epidural stimulation signal, or one or more channels are configured to provide a transcutaneous electrical stimulation signal, while one or more other channels are configured to provide an epidural stimulation signal. In various embodiments, such electrical stimulators comprise one or more channels configured to provide one or more of the following stimulation patterns:

i) monophasic electrical stimulation with a DC offset;
    ii) monophasic electrical stimulation with charge balance;
    iii) delayed biphasic electrical stimulation with a DC offset;
    iv) delayed biphasic electrical stimulation with charge balance;
    v) amplitude modulated dynamic stimulation; and/or
    vi) frequency modulated dynamic stimulation.

Figure 1:
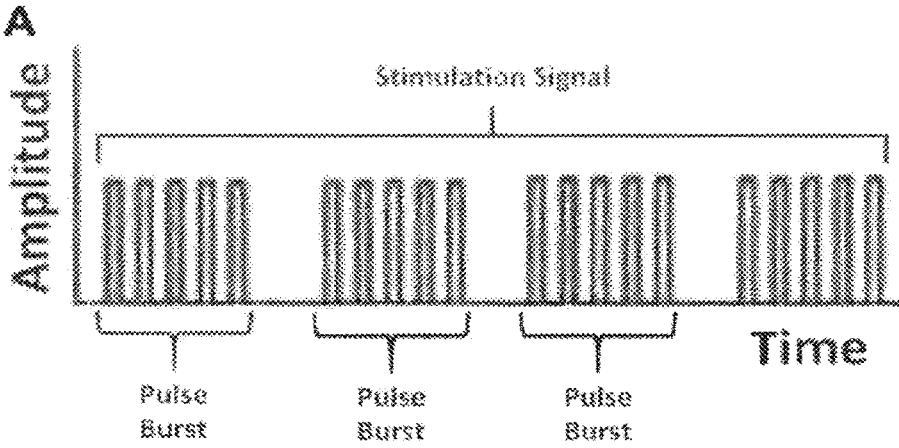
FIG. 1, panels A-C, illustrates various monophasic stimulation patterns. Panel A) Monophasic pulse without DC shift or charge balance. Panel B) Monophasic pulse modulated signal with charge blanc e and no DC shift (offset). Panel C)
Figure 1:
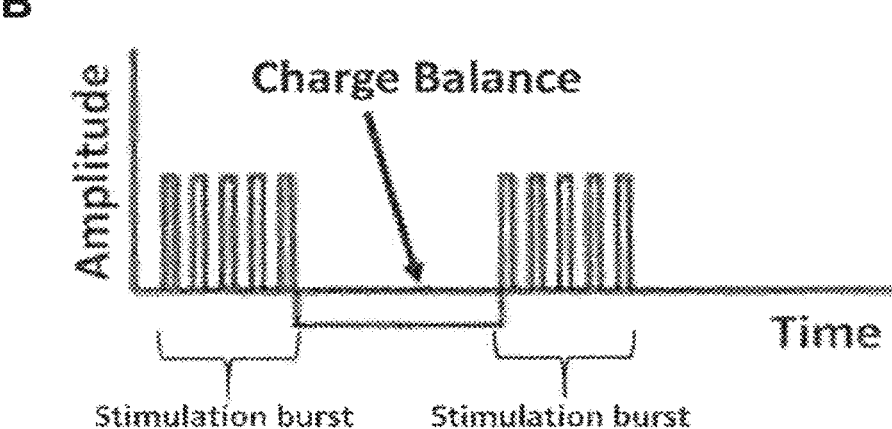
Figure 1:
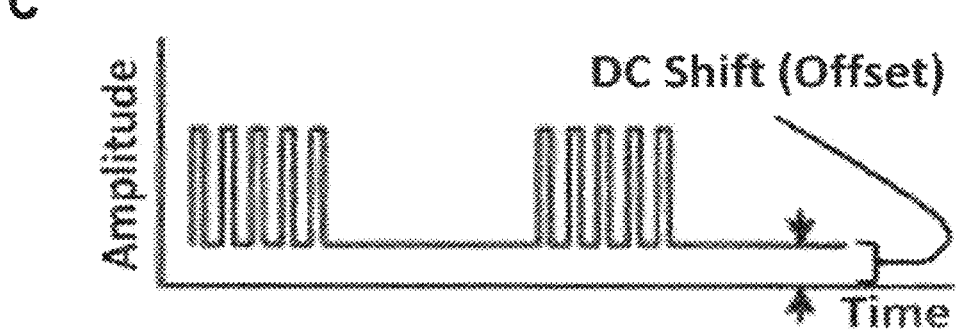

These various stimulation patterns are illustrated in FIGS. 1-3. In particular, FIG. 1, panel A, illustrates a basic monopolar stimulation signal without DC offset or charge balance. As illustrated in this figure the monophasic stimulation signal comprises a series of pulse bursts. The pulses comprising the pulse bursts provide a high (higher) frequency carrier that can be effective to reduce or eliminate stimulation discomfort, particular in transcutaneous electrical stimulation. The frequency and amplitude of the pulse bursts determines the stimulation frequency and amplitude.

FIG. 1, panel B, illustrates a monophasic stimulation pattern (signal) with charge balance. As shown therein, the charge accumulation produced by the stimulation signal can be countered by application of a long pulse having the opposite charge. FIG. 1, panel C, illustrates a monophasic stimulation pattern (signal) with DC shift (offset). IN this case, the signal pulses never reach zero, but are offset by a desired amount.

Without being bound to a particular theory, it is believed the monophasic charge balanced signal, and/or the monophasic signal with DC offset can be more effective in recruiting neural circuits in the stimulated subject. It will be recognized that in certain embodiments the stimulator can be configured to produce a basic monophasic stimulation signal, e.g., as illustrated by FIG. 1, panel A.

FIG. 2, panels A-C, illustrates various biphasic pulse modulated stimulation patterns. Panel A shows a comparison of a biphasic stimulation signal (top) with a delayed biphasic stimulation signal (bottom) where the delay is given by time "d". It will be recognized that a delayed biphasic signal is characterized by a delay (d) between a positive-going and a negative-going pulse, while the basic biphasic signal has no such delay. FIG. 2, panel B illustrates a delayed biphasic pulse modulated signal with charge balance. Charge balance is obtained by maintaining equal areas of anodic and cathodic pulses. FIG. 2, panel C illustrates a delayed biphasic pulse modulated signal with DC shift (offset). In certain embodiments the delay in the delayed biphasic electrical stimulation ranges from about 0.1 μsec up to about 2 μsec, or from about 0.1 μsec up to about 1 μsec.

FIG. 3, panels A and B, illustrate frequency modulated (panel A) and amplitude modulated (panel B) dynamic stimulation patters. In dynamic stimulation patterns (DS) the frequency and/or amplitude of the pulses comprising pulse bursts will vary. As illustrated in panel A, in various embodiments the frequency modulated stimulation pattern will typically vary the pulse frequency within bursts. Conversely, in certain embodiments, e.g., as illustrated in panel B, amplitude modulated stimulation patter, the pulses have same the same frequency within a burst, but the pulse amplitude is adjusted (e.g., varies) within a burst. It is noted that recorded biosignals are typically frequency modulated. As shown herein in Example 2, it is believed that dynamic stimulation patterns can provide more effective recruitment of spinal cord circuitry.

As noted above, in various embodiments, the electrical stimulator provides biphasic electrical stimulation comprises bursts of carrier high frequency pulses that are bursts of carrier high frequency pulses (see, e.g., FIG. 1). In certain embodiments the frequency and amplitude of the bursts provides a stimulation signal frequency and amplitude, and the frequency of the high frequency carrier pulses comprising the bursts is a carrier frequency, e.g., in certain embodiments a pain suppression carrier frequency. Thus, in certain embodiments, the high frequency carrier comprises a pulse frequency sufficient to reduce or block pain or discomfort produced by the stimulation signal. In certain embodiments the high frequency pulses range in frequency from about 5 kHZ up to about 100 kHz, or from about 10 kHz up to about 50 khz, or from about 10 khZ up to about 30 kHz, or from about 10 kHz up to about 20 kHz. In certain embodiments the electrical stimulator provides control of the frequency of the high frequency carrier in steps of 1 kHz at a frequency ranging from 5 to 10 kHz, and in steps of 10 kHz at a frequency ranging from 10 kHz up to 100 kHz.

In certain embodiments at least one channel of the electrical stimulator is configured to provide monophasic electrical stimulation with a DC offset and/or at least one channel of the electrical stimulator is configured to provide delayed biphasic electrical stimulation with a DC offset. In certain embodiments the DC offset on channels providing such is independently controllable and ranges from about 1 mA, or from about 5 mA up to about 40 mA, or up to about 30 mA, or up to about 20 mA.

In certain embodiments at least one channel of the electrical stimulator is configured to provide monophasic electrical stimulation with a charge balance and/or at least one channel of the electrical stimulator is configured to provide delayed biphasic electrical stimulation with a charge balance.

In certain embodiments at least one channel of the electrical stimulator is configured to provide amplitude modulated dynamic stimulation and/or at least one channel of the electrical stimulator is configured to provide frequency modulated dynamic stimulation. In certain embodiments the frequency modulated dynamic stimulation ranges in frequency from about 1 Hz to about 1000 Hz.

In certain embodiments the dynamic stimulation is sourced from a biosignal. Illustrative biosignals include, but are not limited to a signal derived from an EMG, and EEG, or an EKG. In certain embodiments the biosignal is recorded from a vertebrate. In certain embodiments the biosignal is recorded from a mammal. In certain embodiments the biosignal is recorded from a human. In certain embodiments the biosignal is recorded from a non-human mammal (e.g., a non-human primate, a canine, a feline, a bovine, an equine, a porcine, a lagomorph, and the like). In certain embodiments the biosignal comprises a biosignal recorded from a mammal when the mammal is standing, stepping, moving the arms, storing/emptying the bladder, storing/emptying the bowel, breathing. In certain embodiments the electrical stimulator is configured to receive and store a biosignal and to deliver a signal corresponding to that biosignal scaled to a desired maximum stimulation intensity.

In certain embodiments the electrical stimulator is configured to provide a stimulation amplitude ranging from about 1 mA, or from about 3 mA, or from about 5 mA up to about 500 mA, or up to about 400 mA, or up to about 300 mA, or up to about 250 mA, or up to about 200 mA for each of said one or more channels. In certain embodiments the electrical stimulator is configured to provide a stimulation amplitude ranging from about 5 mA up to about 200 mA for each of said one or more channels. In certain embodiments the electrical stimulator is configured to provide pulses that pass a current of 300 mA peak through an impedance of about 300 ohms to about 2000 ohms, or from about 300 ohms to about 900 ohms for each of said one or more channels. In certain embodiments the electrical stimulator is configured to provide a stimulation having a DC offset ranging from about 1 mA to about 30 mA, or from about 1 mA to about 20 mA. In certain embodiments the electrical stimulator is configured to provide a stimulation frequency (burst frequency) for one or more of said channels ranging in frequency from 0.2 Hz up to 10 kHz. In certain embodiments the electrical stimulator provides stimulation frequency control in steps of 1 Hz at a frequency ranging from 0.2 Hz to 100 Hz and/or stimulation frequency control, in steps of 100 Hz at a frequency ranging from 100 Hz to 1 kHz, and/or stimulation frequency control in steps of 1 kHz at a frequency ranging from 1 kHz to 10 kHz.

In certain embodiments the electrical stimulator is configured to provide a stimulation pulse (burst) width ranging from about 0.1 ms up to about 20 ms, or up to about 10 ms, or up to about 5 ms, or up to about 4 ms, or from about 0.2 ms up to about 3 ms. In certain embodiments the electrical stimulator is configured to provide a stimulation pulse (burst) width controllable in steps of 0.1 ms. In certain embodiments the electrical stimulator is configured to provide a pulse width fixed at 1 ms at stimulation frequencies over 10 kHz.

Electrical Stimulator Components.

Various illustrative, but non-limiting embodiments of electrical stimulators are schematically illustrated in FIGS. 4A, 4B, and 4C. The electrical stimulators shown in these figures are illustrated with 4 channels, however it will be recognized that in various embodiments, the stimulator can have more or fewer channels as described above. A photograph of one embodiment of a Transcutaneous Electrical Spinal Cord Neuromodulator (TESCoN™) device is shown in FIG. 5

In various embodiments, e.g., as illustrated in FIGS. 4A, 4B, and 4C, the electrical stimulator 00, comprises a microprocessor unit 02 for receiving and/or programming and/or storing a stimulation pattern for one or more channels comprising said stimulator, a pulse generating unit (PGU) 04 unit control of the microprocessor 02, a pulse modulator (gating) unit 06 (also known as a gating pulse generating unit) under control of the microprocessor 02, and an input/output unit 08 providing user control over the electrical stimulator. In certain embodiments the electrical stimulator further comprises a DC shift (offset) generating unit (OGU) 28 under control of the microprocessor. In certain embodiments the offset generating unit 28 is a component of the pulse generator 04, however in other embodiments, the offset generating unit 28 can be as unit separate from the pulse generating unit. In certain embodiments the electrical stimulator comprises a charge balancing unit 30. In certain embodiments the electrical stimulator comprises a current control unit (CCU) 14. In certain embodiments the electrical stimulator further comprises a monitoring unit 24 operably coupled to the anode 16 and/or cathode 18 leads. In certain embodiments the monitoring unit 24 monitors lead impedance and/or output current. In various embodiments the electrical stimulator comprises a power conditioning unit 10 that comprises a battery or other power source and a power conditioning circuit. In certain embodiments the electrical stimulator comprises a card reader (e.g., a smartcard reader) and/or a biometric input reader 22.

Microprocessor/Microcontroller

The a microprocessor/microcontroller unit 02 is the brain of the system. In various embodiments this unit is responsible for:

a. System health check at startup;
   b. Taking user input through, e.g., an LCD touch panel;
   c. Setting up system parameters with user input.
   d. Generation of pulses as per setting through pulse generator.
   e. Modulation of pulses through pulse modulator circuit.
   f. Battery/power supply power management.
   g. Input control (e.g., LCD touch panel display).

In certain embodiments the microprocessor/microcontroller unit 02 comprises embedded software 12 that controls the overall operation of the system. In other embodiments, the software that controls the overall operation of the system is stored remotely, e.g., on a remote controller device).

In one illustrative, but non-limiting embodiment, the microprocessor/microcontroller unit 02 stores setup (e.g., treatment) parameters received from and administrative user (e.g., physician or other healthcare provider) and executes the program (treatment) for an identified user. In one illustrative, but non-limiting embodiment, the microprocessor/microcontroller unit 02 saves all the administrator-defined parameters to onboard storage (e.g., onboard flash storage, hard drive, solid state drive, etc.). The operating system and the file system for storage of data can also be loaded on the on board storage. In certain embodiments, the microprocessor/microcontroller unit 02 connects to:

1) An input/output device 08 (e.g., a 7 inch touch panel (Display)). This input/output device can be used to display user interface data and receive configuration data as set by the administrative user. It can also display all messages during operation.
   2) A smart card reader (e.g., MiFare card reader (MFCR)) and/or biometric reader. In certain embodiments the card reader reads data from a card near the reader antenna and passes the data on to microprocessor for user verification. Depending on this user verification the microprocessor launches an administrative-user program or a normal user program.
   3) A Pulse generator unit 04 (one unit for each channel). The MPU 02 sends the clock pulse train to the pulse generator units and also controls these through control and feedback interface to get the desired pulse output.
   4. 4 units of Gating pulse generating Unit (GPGU). The MPU sends clock pulses to 4 units of gating pulse generator and also controls these through the control and feedback interface to obtain the desired gating pulse train.
   5. DC current control Unit(s) 14 (DCCCU), typically one for each channel. The MPU 02 controls one DCCCU unit for each channel for generation of the pulse current required through the control and feedback interfaces.
   6. DC Current Amplifier Unit(s) (DCCAU). In certain embodiments, the MPU 02 can control DCCAUs for each channel to fine control the final pulse current.

Thus, in various embodiments, the microcontroller unit 02 can provide storage for the main software (e.g., EEPROM or other storage), storage for configuration parameters set by, e.g., an administrative user; an interface for communication with an external computer for software update(s) and/or data upload(s) and/or data download(s). In certain embodiments the interface is a USB interface, while in other embodiments the interface comprises a wireless interface (e.g., Bluetooth, wifi, etc.).

As noted above, in certain embodiments, the microprocessor 02 comprises embedded software 12. In certain embodiments the embedded software is configured to perform, inter alia, one or more of the following tasks: 1) Generate the user interface on the I/O device 08 (e.g., LCD touch panel); 2) Take the user input from user interface and save the operating parameters in local storage (e.g., EEPROM); 3) Read the operating parameters from local storage (e.g., EEPROM) and program the pulse generator 04 and pulse modulator 06 to function as per user selection; 4) Collect feedback from all the sub-units comprising the electrical stimulator and control the subunits accordingly; 5) Collect all the subsystem level errors and report these on the I/O device 08 (e.g., LCD display); and 6) Provide an emergency stop for the system.

In one illustrative, but non-limiting embodiment, the microprocessor 02 comprises a System on Module from Toradex or equivalent. The Colibri iMX7 from Toradex, is a computer module based on the NXP®/Freescale i.MX 7 embedded System on Chip (SoC). The SoC features a single core ARM® Cortex® A7 processor with an additional ARM Cortex M4 processor. This heterogeneous dual-core system allows for running a second real-time operating system on the M4 core for time and security critical tasks. This is a SODIMM package. This SoM is selected so that the future development can be done without changing the main processor board. The SODIMM is shown in FIG. 6.

In certain embodiments, an illustrative iMX module that can be used is Colibri iMX7S 256 MB. Table 1 shows the brief specifications for this module.

TABLE 1

| Illustrative specifications for IMX module: | |
| --- | --- |
| CPU: | |
| NXP SoC | MCIMX7S5EVM08S |
| SoC Family | i.MX 7 Solo |
| ARM Cortex-A7 CPU Cores | 1 |
| ARM Cortex-M4 CPU Cores | 1 |
| L1 Instruction Cache (each core) | 32 KByte (A7) |
| | 16 KByte (M4) |
| L1 Data Cache (each core) | 32 KByte (A7) |
| | 16 KByte (M4) |
| L2 Cache (shared by A7 cores) | 512 KByte (A7) |
| Tightly-Coupled Memory for M4 Core | 64 KByte (M4) |
| NEON MPE | Yes |
| Maximum CPU frequency | 800 MHz (A7) |
| | 200 MHz (M4) |
| ARM TrustZone | Yes |
| Advanced High Assurance Boot | Yes |
| Cryptographic Acceleration and Assurance Module | Yes |
| Secure Real-Time Clock | Yes |
| Secure JTAG Controller | Yes |
| Memory: | |
| DDR3L RAM Size | 256 MByte |
| DDR3L RAM Speed | 1066 MT/S |
| DDR3L RAM Memory Width | 32 bit |
| SLC NAND Flash (8 bit) | 512 MByte |

TABLE 1-continued

| Illustrative specifications for IMX module: | | |
| --- | --- | --- |
| Interfaces: | | |
| LCD RGB (24 bit, 150 MHz) | 1 | |
| Resistive Touch Screen | 4 | Wire |
| Analogue Audio Headphone out | 1 | (Stereo) |
| Analogue Audio Line in | 1 | (Stereo) |
| Analogue Audio Mic in | 1 | (Mono) |
| SAI (AC97/I2S) | 2* | (Stereo) |
| Medium Quality Sound (MQS) | 1* | |
| Parallel Camera Interface | 1 | |
| I2C | 1 + 2* | |
| SPI | 1 + 3* | |
| UART | 3 + 4* | |
| SD/SDIO/MMC | 1 + 1* | |
| GPIO | Up to 124 | |
| USB 2.0 OTG (host/device) | 1 | |
| 10/100 MBit/s Ethernet | 1 | |
| PWM | 4 + 16* | |
| Analogue Inputs (maximum 1.8 V) | 4 | |
| CAN | 2* | |
| External Memory Bus | 16 bit Multiplexed* | |
| QSPI | 2* | |
| SIM | 4* | |

*These additional interfaces are available on pins that are not defined as standard interfaces in the Colibri architecture. They are alternate functions for pins which provide primary interfaces.

In certain illustrative, but non-limiting embodiments, the software running on the microprocessor unit 02 a linux or android operating system, in certain embodiments a linux operating software and the application software is written for example in C or C++.

Power Conditioning (Power Supply) Unit (PSU).

In various embodiments the power section of the electrical stimulator comprises: 1) A power supply unit 10; 2) A current pulse generator (PGU) 04; 3) A DC shift (offset) generator 28; and/or 4) A charge balance unit 30.

In various embodiments each channel of the electrical stimulator has one main power supply unit 10. This can be used for generating and storing the energy for generation of the required current pulses. In certain illustrative, but non-limiting embodiments the PSUs can be designed around an Atmega 8L micro controller or other similar controller. The microcontroller has been used to generate the PWM control pulses to control the charging of the output capacitor for generating current pulses and to provide remote control from the pain microprocessor unit using SPI master-slave communication. In one illustrative, but non-limiting embodiment, the microcontroller PWM output can be set to work, e.g., at 100 kHz. This allows the output capacitor to be charged to the required level before the next pulse. At a maximum PRF of 10 kHz (PRT=0.1 ms) the PWM of PSU will have 10 pulses to charge the output capacitor as it works at 100 kHz. One illustrative, but non-limiting circuit diagram shown in FIG. 7.

This block generates the required voltage from, e.g., an internal Li Ion battery of 12 Volts to obtain the set current level through the load impedance. One illustrative specification provides for:

Peak Current: 0 mA-300 mA; and/or

Load impedance: 300Ω-2000Ω or 300Ω-900Ω.

Thus, for example, the IEC 60601-2-10 standard states— With a load resistance of 500Ω the output current shall not exceed the limits in Table 2 below.

TABLE 2

| Allowable output current. | |
| --- | --- |
| Pulse Frequency | Current limit |
| d.c | 80 mA |
| ≤400 Hz | 50 mA |
| >400 Hz to ≤1 500 Hz | 80 mA |
| >1 500 Hz | 100 mA |

The above specification also specifies the following: For pulse durations of less than 0.1 s the pulse energy with a load resistance of 500Ω shall not exceed 300 mJ per pulse. For longer pulse durations, the above-mentioned current limit for d.c. applies.

Additionally, in various embodiments the output voltage shall not exceed a peak value of 500 V, when measured under open-circuit condition.

In this case the pulse frequency range is 5 kHz to 10 kHz. So for all pulse frequencies the current across 500Ω resistance should not exceed 100 mA RMS. This will mean:

For a monophasic pulse as illustrated in FIG. 8, panel A:

$$i_{RMS} = \sqrt{\frac{1}{T}\int_0^T i^2(t)\cdot dt} \qquad (1)$$

The pulse function is a variable of time. The current amplitude is "0" between time 0 and $t_1$ and is constant $I_P$ between time $t_1$ and T. This gives $$i_1(t)=0 \quad 0{\le}t{\le}t_1$$

$$i_2(t)=I_P \quad t_1{\le}t{\le}T \qquad (2)$$

So from (1)

$$i_{RMS}^2 = \frac{1}{T}\left[\int_0^{t_1} i_1^2(t)\cdot dt + \int_{t_1}^T i_2^2(t)\cdot dt\right]$$

Using values from (2)

$$i_{RMS}^2 = \frac{1}{T}\left[0^2 * t\big|_0^{t_1} + I_P^2 * t\big|_{t_1}^T\right] = I_P^2/T(T-t_1)$$

In case of monophasic pulses $t_1$=T/2 (50% duty cycle). So, $$i_{RMS}^2 = I_P^2/2$$

$$i_{RMS}=I_P/\sqrt{2} \rightarrow I_P=\sqrt{2}*i_{RMS}=1.414*i_{RMS} \qquad (3)$$

For a biphasic pulse the pulse waveform as depicted in FIG. 8, panel B, again:

$$i_{RMS} = \sqrt{\frac{1}{T}\int_0^T i^2(t)\cdot dt}$$

Here the current amplitude varies as shown below:

$$i_1(t)=0 \quad 0{\le}t{\le}t_1$$

$$i_2(t)=I_P \quad t_1{\le}t{\le}t_2$$

$i_3(t)=0 \quad t_2 \leq t \leq t_3$ $i_4(t)=I_P \quad t_3 \leq t \leq T.$

So, $$i_{RMS}^2 = \frac{1}{T}\left[\int_0^{t_1} i_1^2(t)\cdot dt + \int_{t_1}^{t_2} i_2^2(t)\cdot dt + \int_{t_2}^{t_3} i_3^2(t)\cdot dt + \int_{t_3}^{T} i_4^2(t)\cdot dt\right]$$

$$i_{RMS}^2 = \frac{1}{T}\left[0^2 * t\big|_0^{t_1} + I_p^2 * t\big|_{t_1}^{t_2} + 0^2 * t\big|_{t_2}^{t_3} + I_P^2 * t\big|_{t_3}^{T}\right]$$

$$= \frac{1}{T}I_P^2[t_2 - t_1 + T - t_3]$$

From FIG. 8, panel B:

$t_2-t_1=T-t_3=PW$, the pulse width

Therefore $$i_{RMS}^2 = \frac{1}{T}I_P^2 * 2 * PW$$

In case of bipolar pulses, the pulse width is 45% of the time period, i.e., $$PW=0.45*T$$

This gives:

$$i_{RMS}^2 = 0.9 * I_P^2$$

$$i_{RMS} = \sqrt{0.9} * I_P \rightarrow I_P = \frac{i_{RMS}}{\sqrt{0.9}}$$

From (3) and (4)

For monophasic pulses with 500Ω as output resistance the RMS current should not exceed 100 mA. So the peak current will be $$I_P=1.414*i_{RMS}=1.414*100 \text{ mA}=141 \text{ mA}$$

For biphasic pulses with 500Ω as output resistance the RMS current should not exceed 100 mA. So the peak current will be $$I_P = \frac{i_{RMS}}{\sqrt{0.9}} = \frac{100 \text{ mA}}{\sqrt{0.9}} = 105 \text{ mA}$$

Since the measured value is always $I_{RMS}$, this document only references about $I_{RMS}$ value.

This enforces a requirement that the system shall:

1. Start from the lowest value of current that is "0";
2. Increase the current in steps of 1 mA/s and measure the load impedance by measuring the current through the load and voltage across the load at the same time (load impedance=instantaneous voltage*instantaneous current). Adjust current to reach 100 mA at 500Ω load impedance.
3. Measure the load current for the applied voltage. If the load current is much lower than the current for minimum load impedance, it shall display "Open Load" error and stop the DC to DC converter so that output voltage does not increase.

4. Measure the load current and voltage across load. if the load voltage is "0" for applied load current, system shall display "Output Short" error and stop the DC to DC converter to prevent any damage to the equipment.

The programmable current source is responsible for generation of the required monophasic and biphasic current pulses. This hardware block should also adhere to IEC standard "IEC 60601-2-10, Edition 2.0, 2012-06". In various embodiments, a single supply can be used for generation of both monophasic and biphasic pulses. In the case of biphasic pulses the polarity is changed at the pulse generator unit as will be discussed in pulse generator subsection.

In certain embodiments each Atmega 8L uses one PWM channel for controlling the PSU. In certain embodiments (e.g., a 4 channel embodiment) there are 4 Atmega 8L controllers connected to a single SPI port of the MPU where MPU will be the master of SPI bus and the Atmega 8L controls the slaves as shown in FIG. 9. The Slave select inputs of the Slaves can be connected to 2 GPIO pins of the MPU through a 2 to 4 decoder as shown in the FIG. 9.

There is typically one power supply for each channel. Thus, for example, where the electrical stimulator provides four channels, there are four power supplies units shown as PSU 10 in the block diagram in FIG. 4C, one for each of the channels. In certain embodiments, there are two levels of control in the power supplies. The local control of the power supplies are with the microcontroller Atmega 8L which in turn is controlled by the main MPU 02. In certain embodiments the buck Boost converter will work at 100 kHz.

In certain embodiments, maximum pulse frequency is specified as 10 kHz with a duty cycle of 50%. This means that there is 0.05 ms between two pulses. At 100 kHz the power supply can charge its output capacitor with 5 pulses before the next pulse is applied. The converter shall stop charging its output capacitor before the pulse is applied to stop any ripple appearing in the pulse current. The timing sequence is shown in FIG. 10.

Power required from this power supply is calculated as given below:

The maximum power is drawn from the power supply when the pulse frequency is set at 10 kHz and the peak current is set at 300 mA. Taking the above figures, for monophasic pulses, from equation (3):

$$i_{RMS} = \frac{I_P}{1.414} = \frac{300 \text{ mA}}{1.414} = 212 \text{ mA}$$

For biphasic pulses, from equation (4):

$$i_{RMS}=\sqrt{0.9}*I_P=0.9*300 \text{ mA}=284 \text{ mA} \tag{6}$$

The above calculated RMS currents are drawn from the power supply at the duty cycle of the pulse gating circuit. The pulse gating specification has three scenarios as per functional specification:

1. Pulse Gate frequency varies from 0.2 Hz to 100 Hz in steps of 1 Hz. The pulse width for the modulator shall vary from 0.2 ms to 3 ms in steps of 0.1 ms;
2. Pulse Gate frequency varies from 100 Hz to 1 kHz insteps of 100 Hz. pulse width for the modulator shall be fixed at 1 ms and pulse frequency shall remain fixed t 10 kHz;
3. Pulse Gate frequency is fixed at 10 kHz. and the pulse frequency shall remain fixed at 10 kHz.

From the above specifications the 3rd one will take maximum current from the power supply and it will be the same as calculated in (5) and (6) above.

The output power for a biphasic 10 kHz pulse train for a 900Ω load impedance will be the maximum power output and is $$P_{Out(max)} = i^2_{RMS(max)} * 900 = (284 \text{ mA})^2 * 900 = 72.6 \text{ Watts}$$

This power+losses will have to be supplied by the input power to the converter. Considering worst case efficiency of 80% for the converter, the input power to the boost converter shall be $$P_{in}=1.2*72.6=87 \text{ Watts}$$

Again considering 80% efficiency for the input buck boost converter, the battery power requirement is:

$$P_{Bat}=1.2*87=104 \text{ Watts}$$

If a normal 3.7V Li Ion battery is considered then the current drawn will be:

$$1 = \frac{104}{3.7} = 28 \text{ A}$$

It is always better to go for a higher voltage battery and reduce the demand on current.

In certain embodiments, software for the power supply 10 is in two parts. The first part (module) comprises the Atmega 8L software or equivalent. This software is loaded on the Atmega 8L controller. This software directly controls the power supply output capacitor charging. The MPU 02 shuts down the PWM when it has to send the pulse out to the load. The main function of this software is to make sure the output capacitor is charged to the required value between two successive pulses of the pulse generator. During pulse from pulse generator the charging of power supply output capacitor is halted so that the ripples from charging pulses do not appear on the pulse generator pulses. The flowchart in FIG. 11 illustrates one embodiment of the flow of this software.

The second part comprises software that functions on the microprocessor unit 02. In certain embodiments, this software performs the following tasks:

a. Upload configuration data to Atmega 8L controller.
b. Obtain power supply status from Atmega 8L controller.
c. Stop and Start power supply pulses depending on pulse generator pulse timing and power supply output.
d. This module can also receive the calculated value of load impedance ($V_{RMS}/I_{RMS}$) for the selected frequency of pulse from the Pulse Generator function. This will help in calculating the voltage to which the output capacitor is to be charged for the required rate of rise for pulse current.

The flowchart shown in FIG. 12 shows the functionality of the function on MPU for PSUs.

Pulse Generating Unit.

The pulse generating unit 04 act in combination with a pulse gating unit (pulse modulating unit) 06 to generate a waveform pattern that is delivered to the subject (see, e.g., FIG. 14). In various embodiments the pulse generator unit 04, is responsible for:

a. Generating a pulse train as per user setting;
b. Generating mono-phasic pulses with or without a DC shift; and/or
c. Generating bi-phasic pulses with or without a DC shift.

and thereby provides pulses comprising the bursts of pulses. The pulse gating unit 06 gates these pulses to determine the timing and/or frequency of the pulse bursts (stimulation signal).

In certain embodiments the pulse generator comprises or is operably coupled to a DC current control unit 14. In certain embodiments the current control unit limits current pulses to a peak of about 500 mA, or about 400 mA, and most preferably to about 300 mA.

In various embodiments the PGU(s) 04 time the pulses with a clock pulse received from the MPU 02. The MPU 02 can set the pulse parameters from the configuration files created through, e.g., an admin program. In certain embodiments illustrative, but non-limiting embodiments, the pulse generator unit 04 can generate one or more of the following types of signals:

1) Monophasic waveforms with charge balance and no DC shift;
2) Monophasic waveforms with a DC shift, but no charge balance;
3) Delayed biphasic waveforms with charge balance (e.g., by maintaining same area of anodic and cathodic pulses); and/or
4) Delayed biphasic waveforms with a DC shift on the anodic pulse. In various embodiments the DC shift shall appear between two groups of pulses. The DC shift shall not be charge balanced.

In certain embodiments the pulse generator unit(s) 04 can generate a monophasic waveform with no charge balance or DC shift and/or a delayed biphasic pulses with no DC shift or charge balance, and/or biphasic pulses with no delay, no DC shift, and no charge balance.

In certain embodiments the pulse generator or the pulse generator 04 in combination with the DC current control unit 14 can generate or pass through a dynamic frequency modulated or amplitude modulated waveform. Table 3 illustrates functional parameters for one illustrative embodiment of a pulse generator unit 04

TABLE 3

| Illustrative functional parameters for a pulse generator unit. | |
| --- | --- |
| Functional Requirements | Comment |
| Pulse Repetition Frequency (PRF) shall be variable between 5 kHz to 10 kHz in steps of 1 kHz | |
| Pulses shall be of monophasic or biphasic nature selectable through user interface. | E.g., As shown in FIG. 4C. |
| The pulse train should be of 50% duty cycle. | |
| The pulses shall be able to pass a current of 300 mA peak through an impedance of 300-2000 ohms (or 300-900 ohms). | Composition of this impedance (Capacitance + Resistance) should be made available for design. |

TABLE 3-continued

Illustrative functional parameters for a pulse generator unit.

| Functional Requirements | Comment |
|---|---|
| The current level in the pulses shall vary between 0 mA-300 mA in steps of 1 mA | |
| Monophasic pulses shall have an adjustable DC shift from the 0 level of current. | As shown in FIG. 6. |
| Both monophasic and biphasic pulses shall employ charge balancing so that there are no residual charges left at the electrode-skin contact. | As shown in FIG. 8, panel A. |
| Following monophasic waveforms shall be generated - Monophasic waveform with charge balance but no DC shift | As shown in FIG. 8, panel A. |
| Monophasic waveform shall be generated with DC shift and no charge balance | As shown in FIG. 6. |
| Following biphasic waveforms shall be generated - Biphasic waveform shall be generated with charge balance by maintaining same area of anodic and cathodic pulses. | As shown in FIG. 8, panel A. |
| Biphasic waveform shall be generated with a DC shift on the anodic pulse. The DC shift shall appear between two groups of pulses. DC shift shall not be charge balanced. | As shown in FIG. 8, panel B. |
| User shall be able to program a DC current only through the anode. It shall vary from 1 mA to 20 mA in steps of 1 mA. | |
| There shall be 4 numbers of pulse generators in a single system that shall be controllable independently through user interface. | |
| There shall be an adjustable delay between all 4 pulse generators mentioned in 1.6. This delay shall be adjustable from user interface on LCD touch panel. | |
| The pulse current should have a programmable slow start. Admin shall be able to program the slow start as follows - | Example is shown in FIG. 9. |
| i. 0 mA/s - This shall mean that the current pulses do not have a slow start and will rise to the set value instantaneously. | |
| ii. 1 mA/s - This shall mean that the pulse current shall rise to its set value at 1 mA/s. This shall mean that the pulse current shall rise to its set value at 1 mA/s. This means that at PRF of 5 kHZ, the current shall take 300 seconds to rise to the set value or the 300 mA. | |
| iii. 10 mA/s - This shall mean that the pulse current shall rise to its set value at 10 mA/s. This means that at PRF of 5 kHZ, the current shall take around 30 seconds to rise to the set value or the 300 mA. | |

FIG. 16 shows one illustrative, but non-limiting circuit diagram for a pulse generator and modulator unit. In certain embodiments each channel of the electrical stimulator has one such unit.

Pulse Modulating (Gating) Unit

As noted above, the pulse gating unit (pulse modulating unit) 06 acts in combination with a pulse generating unit 04 to generate a waveform pattern that is delivered to the subject (see, e.g., FIG. 14). In various embodiments the pulse gating unit 06, is responsible for:

a. Gating a number of pulses generated by pulse generator to be available for application to patient; and/or
   b. Generating a preselected delay that can be applied between the group of pulses generated by channels different channels (e.g., by channels 2, 3 and 4 with respect to channel 1 in a 4 channel stimulator).

In various embodiments the pulse gating unit 06 generates gating pulses that decide the excitation time and relaxation time for the stimulator. Pulses from PGU 06 switch on the pulses from PGU 04 to the load and switch off. In certain embodiments PUGs 06 time their pulses with clock pulse from MPU 02. Illustrative PGU operating parameters for one embodiment of an electrical stimulator are shown in Table; This shall work based on the specifications listed in Functional Specification for 4 channel Spinal Cord stimulator, section 4.2, above. The specification parameters are listed below—

TABLE 4

Illustrative parameters for a pulse gating unit 06 in one illustrative, but non-limiting embodiment of an electrical stimulator.

| Parameter | Values |
|---|---|
| This will be used as a gate to allow number of pulses from pulse generator. The pulse modulator shall work at frequencies from - | |
| 1. 0.2 Hz to 100 Hz in steps of 1 Hz in step 1 | pulse width for the modulator shall vary from 0.2 ms to 3 ms in steps of 0.1 ms. |
| 2. 100 Hz to 1 kHz insteps of 100 Hz | pulse width for the modulator shall be fixed at 1 ms and pulse frequency shall remain fixed at 10 kHz. |
| 3. 10 kHz. | This option shall only be available for pulses with DC shift but no charge balance |
| For Step 1 above pulse width for the modulator shall vary from 0.2 ms to 3 ms in steps of 0.1 ms. For Step 2 above pulse width for the modulator shall be fixed at 1 ms and pulse frequency shall remain fixed at 10 kHz. For step 3 above, only DC component of current will be applied. The pulse modulator pulses shall start from the rising edge of the pulse generator pulses. There shall be 4 numbers of pulse modulators for the 4 pulse generators described in requirement 1.6 above. There shall be an adjustable delay between the channels of pulse modulator pulses. | |

FIG. 14 shows the implementation of the pulse generating unit 04 and the pulse gating unit 06. In certain embodiments these two modules are implemented as one. These two modules together generate monophasic and biphasic pulses and also gate these pulses as described herein.

In certain embodiments illustrative, but non-limiting embodiments, as illustrated in FIG. 13, MOSFETs M10 and M11 can be switched together to obtain a positive pulse appearing at anode. MOSFETs M20 and M21 when switch change the polarity of the pulse and a negative pulse appear at the anode. In certain embodiments, MOSFETs M10 and M11 are used in case of monophasic as well as biphasic pulses, whereas MOSFETs M20 and M21 are used only in case of biphasic pulses.

The AND gate combination shown in FIG. 13 can be used to gate the monophasic and biphasic pulses. The working of this is shown in FIG. 14 for monophasic pulses. The anodic pulses from MPU 02 are connected to one of the inputs of the AND gate and the cathodic pulses are connected to one of the inputs of the other AND gate. The second input of both the AND gates are tied together and gating pulses are applied to it. Whenever gating pulse input goes high, anodic and cathodic pulses are applied to the gate drives of M1 and M2 respectively.

For monophasic pulses only anodic pulses are applied and the cathodic pulses input is held at logic level "0". For biphasic pulses both anodic and cathodic pulses are applied.

The voltage and current samples measured from the output are used to calculate the RMS voltage and current. This is done by taking a number of samples of both voltage and current and then taking a sliding window average over the samples. For both monophasic and biphasic pulses $V_{RMS} = V_{Avg}$.

An illustrative, but non-limiting, circuit diagram for one embodiment of the pulse generator unit is shown in in FIG. 16.

FIG. 15 provides illustrative, but non-limiting examples of flowcharts that show the software that drives the pulse generator 04 and the gating pulse generator 06. In certain embodiments this software will operate on the MPU 02 in a Linux (or android) environment.

In certain embodiments, particularly where recorded biosignals (or other variable signals) are to be used for, e.g., dynamic stimulation, the pulse generating unit 04 can be used to read the input (or stored) signal, and the pulse modulating (gating) unit 06 can be used to normalize the dynamic signal to a desired maximum current level.

Shift Generator Unit.

In certain embodiments the DC shift generator unit 28 is another power supply controlled by the mail microprocessor unit 02 over an SPI link. This can be an isolated DC power supply with a low DC current output. This power supply provides DC current between anode and cathode of a channel in the range of, e.g., 1 mA to 20 mA in steps of 1 mA. A shunt can be been used to accurately measure the current. The voltage drop across the shunt is amplified using a differential amplifier and then fed to a high gain optocoupler (gain=500%). The output of the optocoupler is connected to the ADC input of the microcontroller Atmega 8L which is controlling the PSU. The current value set by the user is transferred to the Atmega 8L controller over the SPI bus. Atmega 8L then charges the output capacitor of the PSU using PWM pulses to provide the set current. A circuit diagram for an illustrative embodiment of this DC shift generator is given in FIG. 17. This will be used to introduce DC shift in the monophasic pulses without charge balance, for the anodic pulses only.

Charge Balance Unit.

In certain embodiments the charge balance 30 is on for monophasic pulses with no DC shift. The main microprocessor calculates the area of each pulse (amplitude*pulse width). This gives the total charge content of the pulse. It then calculates the amplitude of current required for the off time of the monophasic pulse that should be applied as cathodic pulse to balance the total charge content of the anodic pulse.

$$\text{Charge balance pulse amplitude} = \frac{\text{Pulse Amplitude} * \text{Pulsewidth}}{\text{Off time of monophasic pulse}}$$

In certain embodiments this unit contains a switching power supply that is controlled by the main microprocessor 02 over an SPI bus. An illustrative circuit diagram for one embodiment of the charge balance unit is given in FIG. 18.

DC Current Control Units

In various embodiments, the electrical stimulator includes a DC current control unit 14. Typically there is one current control unit per channel. This hardware controls the current setup during configuration phase. All DCCUs can be individually programmed by the MPU 02.

Monitoring Unit

In various embodiments, the electrical stimulator includes a monitoring unit 24. In certain embodiments is one monitoring unit for each channel in the stimulator. In certain embodiments these monitoring units will monitor the final current pulses being applied to the patient. These units should be able to shut down the stimulator if it detects an error condition that is beyond recovery.

Input/Output Unit.

In certain embodiments the input/output unit 08 is an integral component of the electrical stimulator and is connected to the microprocessor 02 by one or more electrical connections. In certain embodiments the input/output unit is remotely connected to the electrical stimulator, e.g., through a wifi connection, a Bluetooth connection, an internet connection, and the like. In certain embodiments the input/output unit 08 comprises a touch screen display and/or controller. The display can be a dedicated display or the display of a device (e.g., a cell phone, a tablet, a portable computer, a desktop computer, a centralized healthcare management system, etc.) running appropriate software to control the electrical stimulator. Similarly, in certain embodiments, the microprocessor comprises a dedicated microprocessor unit in the electrical stimulator, while in other embodiments, the microprocessor comprises a microprocessor running in the input/output unit 08 (e.g., a microprocessor operating in a cell phone, a tablet, a portable computer, a desktop computer, a centralized healthcare management system, etc.).

An illustrative, but non-limiting list of functional parameters provided by the user interface include, but are not limited to:

a. UI shall provide two level of user login—Admin logon, and user logon through contactless smart card (e.g., Mifare Card) and/or biometric sensor;

b. Admin level user shall be able to setup all parameters for operations. Admin shall be able to setup more than one program for the user. Number of program shall depend on the storage available on microcontroller.

c. There shall be a Windows PC based application to personalize the Smart Card(s) and/or to train the biometric sensor.

d. User level user shall be allowed to only execute the preset functions only.

e. Admin shall be able to switch ON/OFF any of the channels without changing the state of the other channels.

f. UI shall display any alarm or error condition and also display the contact number for error resolution.

g. The UI design shall meet the usability standard defined in IEC 60601-1-6 and extension IEC 62366.

Card Reader/Biometric Input Unit.

In certain embodiments the electrical stimulator comprises a smart card reader and/or a biometric input reader 22. In certain embodiments, the smart card reader (e.g., MiFare card reader) reads user cards and passes on the data to the user verification software on the MPU 02. If user selects to login as Admin and the card gets verified as Admin card, the MPU 02 launches the Admin program. If the card fails verification, user is not allowed access to the stimulator. Similarly if the user selects the user mode and the card gets verified as user card, the MPU will launch the user program that allows user to select and execute the programs set by Admin. Else, user is not allowed access to stimulator.

Similar functionality can be accomplished by use of a biometric reader. Illustrative biometric sensors include sensors that detect fingerprints, retinal patterns, facial recognition, and the like.

Other Considerations.

Connectors and cabling suitable for the electrical stimulator are well known to those of skill in the art. Thus, for example, the cables for the channels can be flexible cables with, e.g., silicon rubber insulation. In certain embodiments each cable can contain at least one pair of conducting wires for anode and cathode for the channel. Connectors for the cables can include any connector know to be suitable for such applications. In one illustrative, but non-limiting embodiment, one end of the cable comprises a 3.5 mm stereo jack to connect to the stimulator unit. The other end of the cable can comprise two 2 mm pins to connect to commercially available disposable electrodes.

In various embodiments the electrical stimulator meets all requirements for FDA approval. In certain embodiments this can include meeting one or more (or all) of the following standards: 1) IEC 60601-1 for basic safety and essential performance; 2) IEC 60601-1-2, general requirements for basic safety and essential performance—Collateral standard for electromagnetic compatibility; 3) IEC 60601-1-4, general requirements for safety for programmable electrical medical systems; 4) IEC 60601-1-6, collateral standard that specifies usability engineering of medical electrical equipment; 5) IEC 60601-1-8, specifying basic safety and essential performance requirements and tests for alarm systems in medical electrical equipment and medical electrical systems and to provide guidance for their application; and/or 6) IEC 60601-2-10, specifying the requirements for the safety and essential performance of nerve and muscle stimulators, for use in the practice of physical medicine. This includes transcutaneous electrical nerve stimulators (TENS) and electrical muscle stimulators (EMS).

Operation of the System

In certain embodiments the electrical stimulator is configured to provide two modes of operation:

i) an administrator mode for clinicians and researchers; and ii) a patient mode for patients that are being treated using the stimulator.

Typically, the administrator mode provides the ability to input or download and store one or more programs comprising stimulation parameters for one or more of the stimulator channels. In certain embodiments the administrator mode provides the ability to store up to 5 stimulation programs, or up to 10 stimulation programs. In certain embodiments the administrator mode provides the ability to input and store electrode placement locations for presentation in patient mode. In certain embodiments the administrator mode provides the ability to measure impedance across each channel and display it to the administrator.

Typically, the patient mode permits program selection using a patient identifier. Illustrative patient identifiers include, but are not limited to a smart card, a patient biometric (eye, facial recognition, thumb or fingerprint recognition) reader, an alphanumeric patient ID, a medical bracelet, smartphone app/tap, smartwatch app/tap, smart ring tap, and the like.

In certain embodiments the electrical stimulator can be operably coupled to a database either directly or wirelessly, or through an internet connection. In certain embodiments the database can contain standardized treatment protocols that may be downloaded to provide basic system stimulation parameters. In certain embodiments the database can contain stimulation parameters optimized for a specific patient and these stimulation parameters are downloaded upon effective validation of the patient to the system.

In other embodiments, the database is stored in the electrical stimulator and standard protocols can simply be selected by an administration (e.g., healthcare provider) or patient specific protocols can be provided upon validation of the subject patient. In certain embodiments the stimulator is programmed directly with particular stimulation protocols (see, e.g., FIG. 19, panels B-O) which then may be stored locally or in a remote database.

FIG. 19, panels A-O, illustrates a flow chart depicting stimulator operation. As shown in FIG. 19, panel, when the system power on, system health is checked and an error code is present if errors are detected. When no errors are detected the system launches a main a main application. The system then instructs the user to identify themselves as an administrator (e.g., healthcare provider) or a patient. If the administrator login is selected, the user is prompted to validate that they have administrator privileges (e.g., using smart card, biometrics, and the like). Similarly, if the patient logon is selected the patient is promoted to validate their identity (e.g., using smart card, biometrics, and the like).

As shown in FIG. 19, panels B-N, when the login is verified as an administrator, options are provided for the addition or deletion of users, the configuration of stimulator parameters (treatment regimen), running various test runs, and the like. Configuration of stimulator parameters can include, for example, the number of channels to be utilized, the stimulation waveform and parameters (e.g., pulse frequency, pulse amplitude, burst frequency (e.g., gating parameters), DC offset, charge balance, etc.) for each channel, the inter-channel timing, and the like.

If the login is verified as a patient, the system can direct the patient to place electrodes and, in certain embodiments, will display electrode placement. In certain embodiments the system can determine that electrodes are affixed to the subject and/or prompt the patient for confirmation of electrode placement. In certain embodiments the system can prompt the patient to initiate the treatment. In certain embodiments the system will allow the user to select a ramp-up rate for stimulus intensity and may permit the patient to voluntarily ramp down or stop stimulation if discomfort is too great.

In certain embodiments three different modes of operation of the stimulator are contemplated. These include, for example, intermittent stimulation (see, e.g., FIG. 20) which, in various embodiments, can be programmed and can provide different stimulation patterns on different channels and can stagger the channels with respect to teach other, manual, manual stimulation where a subject turns on and off each channel as needed, and continuous stimulation where a master on/off switch on the stimulator turns on all of the channels that are programmed.

The foregoing operational flow is illustrative and not limiting. Using the teaching provided herein, numerous operational flows will be available to one of skill in the art. Uses of Electrical Stimulators.

The electrical stimulators described herein are useful for providing transcutaneous electrical stimulation or epidural stimulation, particularly of the spinal cord, for a wide variety of conditions. Without being bound by a particular theory, it is believed that such spinal cord stimulation facilitates activation of various endogenous spinal cord neural circuits that restore a level of functionality. In particular it is believed that such stimulation can facilitate or restore locomotor function (e.g., arm and hand function, walking sitting, standing, holding position, etc.), bladder and/or bowel control where such control is dysfunctional, and various autonomic functions including, but not limited to breathing, cardiovascular function, speech, eating and sexual function.

In certain embodiments, typical subjects include, but are not limited to subjects with a spinal cord injury, an ischemic brain injury, and/or a neurodegenerative condition. In certain embodiments the subject is a subject with a spinal cord injury that is clinically classified as motor incomplete. In certain embodiments the subject is a subject with a spinal cord injury that is clinically classified as motor complete. In certain embodiments the subject has an ischemic brain injury (e.g., a brain injury from stroke or acute trauma). In certain embodiments the subject has a neurodegenerative pathology (e.g., a pathology associated with a condition selected from the group consisting of Parkinson's disease, Huntington's disease, Alzheimer's disease, amyotrophic lateral sclerosis (ALS), primary lateral sclerosis (PLS), dystonia, hemispherictomy, transverse myelitis, conus medularis injury (lower motor neuron injury). and cerebral palsy). In certain embodiments the subject has an idiopathic condition of overactive bladder, and/or constipation. In certain embodiments the subject has muscle loss due to inactive lifestyle and/or aging, and/or obesity.

In certain embodiments the methods contemplated herein comprise applying transcutaneous electrical stimulation to a subject (e.g., a subject as described above), where the method involves providing an electrical stimulator as described herein where the stimulator stores (transiently or non-transiently) one or more stimulation programs and one or more channels of the stimulator are electrically coupled to one or more transcutaneous stimulation electrodes disposed on the surface of a subject's body; and operating the stimulator according to one or more of the programs to provide transcutaneous electrical stimulation to said subject.

In certain embodiments the methods contemplated herein comprise applying epidural electrical stimulation to a subject (e.g., a subject as described above), where the method involves providing an electrical stimulator as described herein where the stimulator stores (transiently or non-transiently) one or more stimulation programs and one or more channels of the stimulator are electrically coupled to one or more epidural stimulation electrodes implanted in the subject; and operating the stimulator according to one or more of the programs to provide epidural electrical stimulation to said subject.

In certain embodiments the stimulator is configured to provide transcutaneous stimulation at one location, or at two or more locations, or at three or more locations, or at four or more locations on the subject and/or the stimulator is configured to provide epidural stimulation at one location, or at two or more locations, or at three or more locations, or at four or more locations on the subject. In certain embodiments all of the active channels of the stimulator provide transcutaneous electrical stimulation. In certain embodiments all of the active channels of the stimulator provide epidural stimulation. In certain embodiments one or stimulator channels are configured to provide transcutaneous electrical stimulation, while other channels are configured to provide epidural electrical stimulation.

In certain embodiments the transcutaneous and/or epidural stimulation is provided by one or more of the following stimulation patterns on one or more independently controlled channels: i) monophasic electrical stimulation with a DC offset; ii) monophasic electrical stimulation with charge balance; iii) delayed biphasic electrical stimulation with a DC offset; iv) delayed biphasic electrical stimulation with charge balance; v) amplitude modulated dynamic stimulation; and/or vi) frequency modulated dynamic stimulation. In certain embodiments the stimulator provides the same stimulation modality and stimulation parameters on 2 or more different channels or on 3 or more different channels, or on 4 or more different channels. In certain embodiments the stimulator provides a different stimulation modality and/or different stimulation parameters on 2 or more different channels or on 3 or more different channels, or on 4 or more different channels.

In certain embodiments the monophasic or biphasic electrical stimulation comprises bursts of carrier high frequency pulses where the frequency end amplitude of said bursts provides a stimulation signal frequency and amplitude, and the frequency of said high frequency carrier pulses comprising said bursts is a pain suppression carrier frequency. In certain embodiments the high frequency carrier comprises a pulse frequency sufficient to reduce or block pain or discomfort produced by the stimulation signal. In certain embodiments the high frequency pulses range in frequency from about 5 kHZ up to about 100 KHz, or from about 10 kHz up to about 50 Khz, or from about 10 khZ up to about 30 kHz, or from about 10 kHz up to about 20 kHz.

In certain embodiments one or more channels of said electrical stimulator provide monophasic electrical stimulation with a DC offset. In certain embodiments the DC offset ranges from about 1 mA, or from about 5 mA up to about 40 mA, or up to about 30 mA, or up to about 20 mA.

In certain embodiments one or more of channels of the electrical stimulator provide monophasic electrical stimulation with charge balance. In certain embodiments one or more channels of said electrical stimulator provide biphasic electrical stimulation with a DC offset. In certain embodiments the DC offset ranges from about 1 mA, or from about 5 mA up to about 40 mA, or up to about 30 mA, or up to about 20 mA. In certain embodiments one or more channels of the electrical stimulator provide biphasic electrical stimulation with charge balance.

In certain embodiments one or more channels of the electrical stimulator provide amplitude modulated dynamic stimulation. In certain embodiments one or more channels of the electrical stimulator provide provides frequency modulated dynamic stimulation. In certain embodiments the frequency modulated dynamic stimulation ranges in frequency from about 1 Hz to about 1000 Hz. In certain embodiments the dynamic stimulation is sourced from a biosignal (e.g., a signal derived from an EMG, and EEG, or an EKG). In certain embodiments the biosignal is recorded from a mammal (e.g., from a human or from a non-human primate). In certain embodiments the biosignal comprises a biosignal recorded from a mammal when the mammal is standing, stepping, moving the arms, storing/emptying the bladder, storing/emptying the bowel.

In various embodiments one or more channels of the electrical stimulator provides a stimulation amplitude ranging from about 1 mA, or from about 3 mA, or from about 5 mA up to about 500 mA, or up to about 400 mA, or up to about 300 mA, or up to about 250 mA, or up to about 200 mA for each of said one or more channels. In certain embodiments one or more channels of said electrical stimulator provide a stimulation amplitude ranging from about 5 mA up to about 200 mA for each of said one or more channels. In certain embodiments one or more channels of said electrical stimulator provide provides pulses that pass a current of 300 mA peak through an impedance of 300-900 ohms for each of said one or more channels. In certain embodiments the stimulator provides a stimulation frequency (burst frequency) for one or more of said channels ranging in frequency from 0.2 Hz up to 10 kHz. In certain embodiments the stimulator provides a stimulation pulse (burst) width on said one or more channels ranging from about 0.1 ms up to about 20 ms, or up to about 10 ms, or up to about 5 ms, or up to about 4 ms, or from about 0.2 ms up to about 3 ms. In certain embodiments the stimulator provides a pulse width fixed at 1 ms at stimulation frequencies over 10 kHz.

In certain embodiments the transcutaneous and/or epidural stimulation is applied to the spinal cord. In certain embodiments the transcutaneous and/or epidural stimulation enhances/facilitates endogenous neural circuitry activity. In certain embodiments the transcutaneous and/or epidural stimulation does not substantially provide peripheral nerve stimulation.

In various embodiments methods of applying dynamic transcutaneous and/or dynamic epidural electrical stimulation to a subject are provided. In certain embodiments the methods involve providing an electrical stimulator as described herein wherein the stimulator stores one or more stimulation programs, and where one or more channels of said stimulator are electrically coupled to one or more transcutaneous stimulation electrodes disposed on the surface of a subjects body, and/or wherein one or more channels of said stimulator are electrically coupled to one or more epidural electrodes disposed on a region of the spinal cord; and operating the stimulator according to one or more of the programs to provide dynamic transcutaneous electrical stimulation to the subject and/or to provide dynamic epidural stimulation to the subject. In certain embodiments one or more channels provides amplitude modulated dynamic stimulation; and/or one or more channels provides frequency modulated dynamic stimulation.

In certain embodiments one or more channels of the electrical stimulator provide amplitude modulated dynamic stimulation. In certain embodiments one or more channels of the electrical stimulator provide provides frequency modulated dynamic stimulation. In certain embodiments the frequency modulated dynamic stimulation ranges in frequency from about 1 Hz to about 1000 Hz. In certain embodiments the dynamic stimulation is sourced from a biosignal (e.g., a signal derived from an EMG, and EEG, or an EKG). In certain embodiments the biosignal is recorded from a mammal (e.g., from a human or from a non-human primate). In certain embodiments the biosignal comprises a biosignal recorded from a mammal when the mammal is standing, stepping, moving the arms, storing/emptying the bladder, storing/emptying the bowel.

In certain embodiments in any of the foregoing methods at least one channel of the transcutaneous and/or epidural stimulation is applied over or more regions straddling or spanning a region selected from the group consisting of the brainstem, C0-C1, C0-C2, C0-C3, C0-C4, C0-C5, C0-C6, C0-C7, C0-T1, C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1. In certain embodiments at least one channel of the transcutaneous and/or epidural stimulation is applied over a region comprising or consisting of C2-C3 or a region therein. In certain embodiments at least one channel of the transcutaneous and/or epidural stimulation is applied at C3.

In certain embodiments in any of the foregoing methods at least one channel of the transcutaneous and/or epidural stimulation is applied over the thoracic spinal cord or a region thereof. In certain embodiments at least one channel of the transcutaneous and/or epidural stimulation is applied over or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3- T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, and T12-T12.

In certain embodiments in any of the foregoing methods at least one channel of the transcutaneous and/or epidural stimulation is applied over the lumbar spinal cord or a region thereof. In certain embodiments at least one channel of the transcutaneous and/or epidural stimulation is applied over or more regions straddling or spanning a region selected from the group consisting of L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6. In certain embodiments at least one channel of the transcutaneous and/or epidural stimulation is applied over the coccyx.

In certain embodiments in any of the foregoing methods at least one channel of the transcutaneous and/or epidural stimulation is applied over a region between T11 and L4. In certain embodiments at least one channel of the transcutaneous and/or epidural stimulation is applied over or more regions selected from the group consisting of T11-T12, L1-L2, and L2-L3. In certain embodiments at least one channel of the transcutaneous and/or epidural stimulation is applied L1-L2 and/or over T11-T12.

In certain embodiments in any of the foregoing methods the transcutaneous and/or epidural stimulation facilities locomotor function (standing and/or stepping). In certain embodiments the transcutaneous and/or epidural stimulation facilitates arm and/or hand control. In certain embodiments the transcutaneous and/or epidural stimulation facilitates speech function. In certain embodiments the transcutaneous and/or epidural stimulation facilitates breathing function. In certain embodiments the transcutaneous and/or epidural stimulation eating and chewing function. In certain embodiments the transcutaneous and/or epidural stimulation facilitates cardiovascular function. In certain embodiments the transcutaneous and/or epidural stimulation facilitates coughing function. In certain embodiments the transcutaneous and/or epidural stimulation vision and focus. In certain embodiments the transcutaneous and/or epidural stimulation facilitates bladder and/or bowel function.

In certain embodiments the transcutaneous and/or epidural stimulation facilitates bladder function. In such instances, illustrative metrics for improvement in bladder function include, but are not limited to one or more of the following:

1) Improved urodynamic bladder capacity;
2) Improved urodynamic voiding efficiency;
3) Improved quality of life score(s) (e.g., as assessed via Neurogenic Bladder Symptom Score);
4) A reduction in incontinence episodes assessed via 3-day voiding diary; and/or
5) Reduced frequency of urinary tract infections.

In certain embodiments criteria for success are defined based on clinically relevant endpoints including at least one of the following:

1) At least 50% reduction in incontinence episodes;
2) A reduction in incontinence (which leads to increased quality of life and decreased healthcare costs);
3) At least a 50% increase in bladder capacity (or increase to 300 ml, whichever is higher);
4) Higher bladder capacity (allows patients to catheterize less frequently and experience less incontinence); and/or
5) 5-point or greater reduction in Neurogenic Bladder Symptom Score (reduced score demonstrates an improvement in quality of life and overall bladder-related health).

In certain embodiments the transcutaneous and/or epidural stimulation facilitates bowel function. In such instances, illustrative metrics for improvement in bladder function include, but are not limited to one or more of the following:

1) Improved time to complete bowel program;
2) A change in the number of complete spontaneous bowel movements per week;
3) Improved motility Index, pressure amplitude and number of contractions (via colonic manometry);
4) Improved constipation and fecal incontinence scores (Cleveland Clinic Constipation Scoring System, Neurogenic Bowel Dysfunction Score);
5) A change (improvement) in anal sphincter resting, squeeze pressure, length of the high-pressure zone and pressure profile of the anal canal (e.g., via high-resolution anorectal manometry);
6) Improved quality of life (PAC-QOL score).

In various embodiments, criteria for success are defined based on clinically relevant endpoints including at least one of the following:

1) 50% or greater reduction in time to complete bowel program (reduction in time to complete bowel program leads to increased quality of life and increased time to complete other activities of daily living);
2) At least a 50% reduction in digital stimulation/suppository use (reduction in need for digital stimulation/suppository leads to increased quality of life and decreased healthcare costs);
3) A 3-point or better reduction in Neurogenic Bowel Dysfunction Score (reduced score demonstrates an improvement in bowel health).

In certain embodiments, particular where bladder and/or bowel dysfunction is to be treated, at least one channel of the transcutaneous and/or epidural stimulation is applied over or more sites selected from T10-T11, T11-T12, T12-L1, L1-L2, L2-L3, and L3-L4. In certain embodiments the transcutaneous electrical stimulation and/or epidural stimulation is applied at a frequency ranging from about 0.5 Hz up to about 100 Hz, or from about 1 Hz up to about 50 Hz, or from about 10 Hz up to about 30 Hz, or from about 0.5 Hz to about 1 Hz, or from about 1 Hz to about 2 Hz, or from about 2 Hz to about 5 Hz, or from about 5 Hz to about 10 Hz, or from about 10 Hz to about 30 Hz, or from about 30 Hz to about 100 Hz to induce bladder or bowel voiding. In certain embodiments the transcutaneous and/or epidural electrical stimulation is applied at a frequency of 10 Hz to 30 Hz, 30 Hz to 50 Hz, 50 Hz to 100 Hz, 100 Hz to 1 Khz, 1 Khz to 10 Khz to induce bladder or bowel retention.

Transcutaneous Stimulation Electrodes.

In certain embodiments of the foregoing methods, the transcutaneous stimulation is applied using any of a number different types of electrodes. Such electrodes include, but are not limited to metal plate electrodes, carbon electrodes, textile electrodes, hydrogel electrodes, needle electrodes, and the like (see, e.g., Keller & Kuhn (2008) *J. Automatic Control.,* 18(2): 34-45). In various embodiments, the electrodes can be adhered using, e.g., tape or other adherent, or in other embodiments, the electrodes are self-adhering.

Metal plate electrodes include, but are not limited to metal plate electrodes covered by fabric tissue. Typically the metal plate is fabricated from a biocompatible material. Often stainless steel or silver/silver chloride electrodes are used. The fabric tissue can be cotton but is often a polymer textile material that has a certain degree of elasticity and doesn't wear out fast. Spongy materials have also been used and recommended (see, e.g., Falk et al. (1983) *N. Engl. J. Med.* 309: 1166-1168). In certain embodiments, the fabric can be made conductive with water or electrode gel. It equally distributes the current over the skin in order to prevent skin burns. Care has to be taken that the electrode does not dry out. In the best case (if completely dry) such a dried out electrode isolates the metal plate from the skin. But while drying out, unequally distributed electrical fields under the electrodes may cause skin burns. The electrodes are typically fixed to the skin with elastic straps (see, e.g., Ijezerman et al. (1996) J. Rehab. Sci. 9: 86-89).

Self-adhesive electrodes for transcutaneous stimulation use a gel to contact a conductive member with the subject's skin (see, e.g., Keller & Kuhn (2008) *J. Automatic Control.,* 18(2): 34-45). The electrode is typically built in a multi-layer configuration, consisting of multiple layers of hydrogel. The skin interface layer often includes an electrically conductive gel with relatively low peel strength for removably contacting the subject's skin. It has a wet feeling and can be removed relatively easily from the skin. In various illustrative, but non-limiting embodiments, the conductive gel is made from co-polymers derived from polymerization, e.g., of acrylic acid and N-vinylpyrrolidone. In various illustrative embodiments, a second hydrogel layer connects the substrate (a low resistive material like carbon rubber or a wire mesh) with the skin hydrogel layer. This second conductive gel layer has a relatively high peel strength that provides good adhesion to the substrate.

In certain embodiments, carbon loaded silicon electrodes can be used (see, e.g., Baker, D. R. McNeal, L. A. Benton, B. R. Bowman, and R. L. Waters, Neuromuscular electrical stimulation: a practical guide, 3 ed. USA: Rehabilitation Engineering Program, Los Amigos Research and Education Institute, Rancho Los Amigos Medical Center, 1993; Nathan (1989) *J. Automatic Control,* 18(2): 35-45; Patterson &

Lockwood (1993) *IEEE Trans. on Neural Systems and Rehabilitation,* 1: 59-62; and the like).

In certain embodiments, the transcutaneous electrical stimulation can be applied via textile electrodes. In one illustrative, but non-limiting embodiment, the textile electrodes can consist of multiple fabric layers (see, e.g., Keller, et al. (2006) *Conf Proc. IEEE Eng. Med. Biol. Soc.* 1: 194-197). In certain embodiments, the fabric layer facing the skin holds embroidered electrode pads made of plasma coated metallized yarn. Because of the thin metal coating (e.g., <25 nm coating particles obtained using a plasma process) the yarn keeps its textile properties and can be embroidered. Silver coatings proved to be most stable and survived 30 washings. A second layer contains the embroidered electrode wiring made from the same materials and was designed such that no short circuits are produced between the pads when stitched together (Id.).

In certain embodiments, the transcutaneous electrical stimulation can be applied via one or more needle electrodes, e.g., as described in PCT Patent Pub No: WO 2017/024276 (PCT/US2016/045898).

It was also discovered that transcutaneous stimulation electrodes applied to a subjects buttocks and/or lower back can be used to facilitate bladder and/or bowel control (e.g., retention and/or voiding). Accordingly, in certain embodiments a toilet seat to facilitate regulation of bladder and/or bowel function is contemplated. In certain embodiments the toilet seat comprises one or more transcutaneous stimulation electrodes where said transcutaneous electrodes are configured to contact a subject siting on said toilet seat at one or more locations where transcutaneous stimulation facilitates bladder and/or bowel voiding.

It will also be recognized that, in certain embodiments such electrodes can be provided in a chair, a couch, an office chair, or even a bed, particularly where bladder and/or bowel retention is to be facilitated.

In certain embodiments a garment comprising one or more transcutaneous stimulation electrodes where the transcutaneous electrodes are configured to contact a subject wearing said garment at one or more locations where said transcutaneous stimulation facilitates bladder and/or bowel retention. In certain embodiments the transcutaneous stimulation electrodes are located to contact a subject at one or more locations selected from the group consisting of C3-C4 through L3-L4. In certain embodiments the transcutaneous stimulation electrodes are located to contact a subject at one or more locations selected from the group consisting of C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2- T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

The foregoing electrodes for transcutaneous electrical stimulation are illustrative and non-limiting. Using the teaching provided herein, numerous other electrodes and/or electrode configurations will be available to one of skill in the art.

Epidural Stimulation and Electrodes

In certain embodiments the epidural stimulation is at a lower amplitude than the transcutaneous stimulation. Accordingly, in certain embodiments, the epidural stimulation is at an amplitude ranging from 0.5 mA, or from about 1 mA, or from about 2 mA, or from about 3 mA, or from about 4 mA, or from about 5 mA up to about 50 mA, or up to about 30 mA, or up to about 20 mA, or up to about 15 mA, or from about 5 mA to about 20 mA, or from about 5 mA up to about 15 mA.

In certain embodiments, the epidural stimulation is applied via a permanently implanted electrode array (e.g., a typical density electrode array, a high density electrode array, etc.).

In certain embodiments, the epidural electrical stimulation is administered via a high-density epidural stimulating array (e.g., as described in PCT Publication No: WO/2012/ 094346 (PCT/US2012/020112). In certain embodiments, the high-density electrode arrays are prepared using microfabrication technology to place numerous electrodes in an array configuration on a flexible substrate. In some embodiments, epidural array fabrication methods for retinal stimulating arrays can be used in the methods described herein (see, e.g., Maynard (2001) *Annu. Rev. Biomed. Eng.*, 3: 145-168; Weiland and Humayun (2005) *IEEE Eng. Med. Biol. Mag.*, 24(5): 14-21, and U.S. Patent Publications 2006/0003090 and 2007/0142878). In various embodiments, the stimulating arrays comprise one or more biocompatible metals (e.g., gold, platinum, chromium, titanium, iridium, tungsten, and/ or oxides and/or alloys thereof) disposed on a flexible material. Flexible materials can be selected from parylene A, parylene C, parylene AM, parylene F, parylene N, parylene D, silicon, other flexible substrate materials, or combinations thereof. Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22(8): 42-49 (2000)), and has flexibility characteristics (Young's modulus~4 GPa (Rodger and Tai (2005) *IEEE Eng. Med. Biology*, 24(5): 52-57)), lying in between those of PDMS (often considered too flexible) and most polyimides (often considered too stiff). Finally, the tear resistance and elongation at break of parylene are both large, minimizing damage to electrode arrays under surgical manipulation. The preparation and parylene microelectrode arrays suitable for use in the epidural stimulation methods described herein is described in PCT Publication No: WO/2012/100260 (PCT/US2012/022257). Another suitable microelectrode array is the NEUROPORT® microelectrode array (Cyberkinetics Neurotechnology Systems Inc., Boston, MA) which consists of 96 platinum microelectrodes, arranged in a 10×10 array without electrodes at the corners, affixed to a 4 mm² silicon base.

In certain illustrative, but non-limiting, embodiments an electrode array is utilized that has a configuration that provides a 32 channel dorsal electrode type A, e.g., substantially as illustrated in FIG. 4A of PCT Application No:

PCT/US2018/015098. In certain illustrative, but non-limiting, embodiments an electrode array is utilized that has a configuration that provides a configuration that is a 48 channel dorsal electrode type B, e.g., substantially as illustrated in FIG. 4B in PCT Application No: PCT/US2018/ 015098. In certain illustrative, but non-limiting, embodiments an electrode array is utilized that has a configuration that provides an 8 channel ventral dual electrode type C, e.g., substantially as illustrated in FIG. 4C of PCT Application No: PCT/US2018/015098. In certain embodiments the electrode array has an inferolateral exiting electrode tail).

The electrode array may be implanted using any of a number of methods (e.g., a laminectomy procedure) well known to those of skill in the art. For example, in some embodiments, electrical energy is delivered through electrodes positioned external to the dura layer surrounding the spinal cord. Stimulation on the surface of the cord (subdurally) is also contemplated, for example, stimulation may be applied to the dorsal columns as well as to the dorsal root entry zone. In certain embodiments the electrodes are carried by two primary vehicles: a percutaneous lead and a laminotomy lead. Percutaneous leads can typically comprise two or more, spaced electrodes (e.g., equally spaced electrodes), that are placed above the dura layer, e.g., through the use of a Touhy-like needle. For insertion, the Touhy-like needle can be passed through the skin, between desired vertebrae, to open above the dura layer. An example of an eight-electrode percutaneous lead is an OCTRODE® lead manufactured by Advanced Neuromodulation Systems, Inc.

Laminotomy leads typically have a paddle configuration and typically possess a plurality of electrodes (for example, two, four, eight, sixteen. 24, or 32) arranged in one or more columns. An example of an eight-electrode, two column laminotomy lead is a LAMITRODE® 44 lead manufactured by Advanced Neuromodulation Systems, Inc. In certain embodiments the implanted laminotomy leads are transversely centered over the physiological midline of a subject. In such position, multiple columns of electrodes are well suited to administer electrical energy on either side of the midline to create an electric field that traverses the midline. A multi-column laminotomy lead enables reliable positioning of a plurality of electrodes, and in particular, a plurality of electrode rows that do not readily deviate from an initial implantation position.

Laminotomy leads are typically implanted in a surgical procedure. The surgical procedure, or partial laminectomy, typically involves the resection and removal of certain vertebral tissue to allow both access to the dura and proper positioning of a laminotomy lead. The laminotomy lead offers a stable platform that is further capable of being sutured in place.

In the context of conventional spinal cord stimulation, the surgical procedure, or partial laminectomy, can involve the resection and removal of certain vertebral tissue to allow both access to the dura and proper positioning of a laminotomy lead. Depending on the position of insertion, however, access to the dura may only require a partial removal of the ligamentum flavum at the insertion site. In certain embodiments, two or more laminotomy leads are positioned within the epidural space of C1-C7 as identified above. The leads may assume any relative position to one another.

In certain embodiments the electrode array is disposed on the nerve roots and/or the ventral surface. Electrode arrays can be inserted into the ventral and/or nerve root area via a laminotomy procedure.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation. In certain embodiments time-varying current and/or time-varying voltage may be utilized.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

The epidural electrode stimulation systems described herein are intended to be illustrative and non-limiting. Using the teachings provided herein, alternative epidural stimulation systems and methods will be available to one of skill in the art.

Use of Neuromodulatory Agents.

In certain embodiments, the transcutaneous and/or epidural stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic, and/or GABAergic, and/or glycinergic, and/or anxiolytic, and/or anti-psychotic drugs is contemplated. These agents can be used in conjunction with epidural stimulation and/or transcutaneous stimulation and/or magnetic stimulation as described above. This combined approach can help to put the spinal cord in an optimal physiological state for neuromodulation utilizing the methods described herein.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg.

Drugs or agents can be delivery by injection (e.g., subcutaneously, intravenously, intramuscularly), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 5).

TABLE 5

| Illustrative pharmacological agents. | | | | | |
| --- | --- | --- | --- | --- | --- |
| Name | Target | Action | Route | Typical Dose (mg/Kg) | Typical Range (mg/kg) |
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| F-15,599 (NLX-101) | 5-HT1A | Agonist | | | |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha 1 | Agonist | I.P. | 2.5 | 1.5-4.5 |
| Prazosin | Alpha 1 | Antagonist | I.P. | 3 | 1.8-3.0 |
| Clonidine | Alpha 2 | Agonist | I.P. | 0.5 | 0.2-1.5 |
| Yohimbine | Alpha 2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

In certain embodiments the neuromodulatory agent comprises one or more drugs selected from the group consisting of 4-(benzodioxan-5-yl)1-(indan-2-yl)piperazine (S15535), 4-amino-(6-chloro-2-pyridyl)-1 piperidine hydrochloride (SR 57227A), 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), 8-hydroxy-2-(di-n-propylamino)tetralin (8-OH-DPAT), alnespirone (s-20,499), befiradol, binospirone (mdl-73,005), buspirone, clonidine, enilospirone (cerm-3,726), eptapirone (F-11,440), eticlopride, F-15,599, gepirone (ariza, variza), ipsapirone (tvx-q-7,821), ketanserin, methoxamine, N-{2-[4-(2-methoxyphenyl)-1-piperazinyl]ethyl}-N-(2-pyridinyl) cyclo-hexanecarboxamide (WAY 100.635), ondanesetron, prazosin, quinpirole, quipazine, revospirone (bay-vq-7,813), tandospirone, tandospirone (sediel), yohimbine, and zalospirone (WY-47,846). In certain embodiments the neuromodulatory agent comprises one or more anxiolytics selected from the group consisting of alnespirone (s-20,499), binospirone (mdl-73,005), buspirone (buspar), enilospirone (cerm-3,726), eptapirone (f-11,440), gepirone (ariza, variza), ipsapirone (tvx-q-7,821), revospirone (bay-vq-7, 813), tandospirone (sediel), and zalospirone (WY-47,846), and/or one or more antipsychotics selected from the group consisting of perospirone (Lullan), tiosprione (BMY-13, 859), and umespirone (KC-9,172).

The foregoing methods are intended to be illustrative and non-limiting. Using the teachings provided herein, other methods involving transcutaneous electrical stimulation and/or epidural electrical stimulation and/or the use of neuromodulatory agents to improve various functions, e.g., in subjects with impaired extremity motor function due to spinal cord or brain injury or pathology will be available to one of skill in the art.

EXAMPLES

The following examples are offered to illustrate, but not to limit the claimed invention.

Example 1

Non-Invasive Neuromodulation of Spinal Cord Restores Lower Urinary Tract Function after Paralysis
Summary of Example 1

It is commonly assumed that restoration of locomotion is the ultimate goal after spinal cord injury (SCI). However, lower urinary tract (LUT) dysfunction is universal among SCI patients and significantly impacts their health and quality of life. Micturition is a neurologically complex behavior that depends on intact sensory and motor innervation. SCI disrupts both motor and sensory function and leads to marked abnormalities in urine storage and emptying. Current therapies for LUT dysfunction after SCI focus on preventing complications and managing symptoms rather than restoring function. In this study, we demonstrate that Transcutaneous Electrical Spinal Stimulation for Lower urinary tract functional Augmentation (TESSLA), a noninvasive neuromodulation technique, can reengage the spinal circuits' active in LUT function and normalize bladder and urethral sphincter function in individuals with SCI. Specifically, TESSLA reduced detrusor overactivity (DO), decreased detrusor-sphincter dyssynergia (DSD), increased bladder capacity and enabled voiding. TESSLA may represent a novel approach to transform the intrinsic spinal networks to a more functionally physiological state. Each of these features has significant clinical implications. Improvement and restoration of lower urinary tract function after SCI stand to significantly benefit patients by improving their quality of life and reducing the risk of incontinence, kidney injury and urinary tract infection, all the while lowering healthcare costs.
New & Noteworthy TESSLA leads to improvement and normalization of the lower urinary tract function after spinal cord injury. TESSLA offers several advantages over current therapies for LUT dysfunction due to SCI. First, it is non-invasive. If the intervention is not tolerated by the subject, it can be immediately discontinued. Second, we demonstrate that TESSLA can modulate the activity of the spinal cord to elicit a specific response in the lower urinary tract. Third, TESSLA can be easily integrated with other rehab programs that a patient may be undergoing.
Introduction It is generally perceived that paralysis caused by spinal cord injury (SCI) only impacts one's ability to ambulate. However, restoration of autonomic functions such as bladder control are of the highest priority to SCI individuals (Anderson (2004) *J. Neurotrauma.* 21(10): 1371-1383; Snoek et al. (2004) *Spinal Cord,* 42(9): 526-532). The function of the lower urinary tract (LUT) includes storage of urine without leakage and timely emptying without urine retention. All of the urinary problems encountered after a SCI are manifestations of impairments in these two functions of the LUT (Burns et al. (2001) *Spine (Phila Pa* 1976), 26(24 Suppl): 5129-136). The LUT is innervated by autonomic and somatic motor nervous system: parasympathetic fibers, originating from the parasympathetic nucleus (S2-S4) promote bladder contraction and voiding; sympathetic fibers originating from the thoracolumbar portion of the sympathetic chain promote bladder relaxation and bladder neck contraction, thus promoting continence; and somatic innervation arising from a distinct region of S2-S4 drives contraction of the external urethral sphincter (EUS), thus also promoting continence (de Groat & Yoshimura (2001) *Annu. Rev. Pharmacol. Toxicol.* 41: 691-721). In a healthy state, bladder and EUS activity are coordinated, with the EUS contracting and the bladder relaxing during urine storage, and the reverse occurring during voiding. Coordination of EUS-bladder activity is mediated by several nuclei in the brainstem. Because SCI disrupts communication between the brainstem and the lumbosacral cord, the bladder and the EUS become uncoordinated, a condition known as detrusor-sphincter dyssynergia (DSD). The sensory innervations to the LUT are as important as motor fibers. The lower urinary tract transmits a variety of sensory information to the central nervous system and that transmission is also interrupted by SCI. As a result, myelinated Aδ fibers that normally ensure normal sensation are replaced by unmyelinated C fibers (de Groat (1997) *Urology,* 50(6A Suppl): 36-52; discussion 53-56; de Groat & Yoshimura (2001) *Annu. Rev. Pharmacol. Toxicol.* 41: 691-721). This leads to the emergence of spinal reflex mechanisms that promote uninhibited detrusor contractions during urine storage (a condition known as detrusor overactivity, DO) and further detrusor-sphincter dyssynergia. DSD can be particularly dangerous: as the bladder contracts against a closed EUS, it generates increased pressures, which can lead to renal injury and loss of bladder compliance (Kaplan et al. (1991) *J. Urol.* 146(1): 113-117).

Current therapy for LUT dysfunction after SCI focuses on managing these complications without addressing the underlying cause or attempting to normalize or restore bladder function. Historically, a variety of electrical stimulation techniques have been proposed to improve urine storage by increasing capacity and reducing DO; and improve urine voiding by stimulating detrusor contraction and sphincter relaxation at patient-determined intervals. These strategies include direct electrical stimulation of the pelvic nerve (Holmquist (1968) *Scand. J. Urol. Nephrol.* Suppl 2: 1-27), the sacral nerve (Granger et al. (2013) *J. Vet. Intern. Med.* 27(1): 99-105; Sievert et al. (2010) *Ann. Neurol.* 67(1): 74-84) or the pelvic plexus and bladder wall (Walter et al. (2005) *J. Rehabil. Res. Dev.* 42(2): 251-560). While promising, these approaches have not been widely implemented due to their invasive nature and need for concurrent sensory denervation (e.g., the sacral nerve stimulator) or lack of long-term effectiveness (e.g., bladder wall plexus stimulator). Additionally, these approaches act locally to reduce DO or induce detrusor contraction by direct nerve stimulation. On the other hand, neuromodulating approaches, such as the one presented here, may promote restoration of LUT function by activating the inherent to the spinal neural networks and re-establish communication between neural centers separated by an injury.

Epidural spinal cord stimulation (ES) has been previously introduced as a novel approach to activate neural networks and enable a variety of functions after SCI (Gerasimenko et al. (2008) *Exp. Neurol.* 209(2): 417-425). This approach has been demonstrated to enable volitional motor function in animal models and humans after SCI (Courtine et al. (2009) *Nat. Neurosci.* 12(10): 1333-1342; Harkema et al. (2011) *Lancet,* 377(9781): 1938-1947). Further, ES of the lumbosacral spinal cord has shown potential utility for activating neural networks associated with LUT function in rodents (Abud et al. (2015) *Am. J. Physiol. Renal Physiol.* 308(9): F1032-1040; Gad et al. (2014) *PLoS One,* 9(9): e108184). However, ES is highly invasive, which limits its application and scope. Recently, transcutaneous spinal cord stimulation (TSCS) has been developed as a non-invasive method to activate neural circuits in the human spinal cord in order to enable function of upper (Gad et al. (2018) *J. Neurotrauma*, 35: 10.1089/neu.2017.5461; Inanici et al. (2018) *IEEE Trans. Neural Syst. Rehab. Engin.* 26(6): 1272-1278), trunk (Rath et al. (2018) *J. Neurotrauma*. 35. 10.1089/neu.2017.5584) and lower extremity (Gad et al. (2017) *Front. Neurosci.* 11: 333; Gerasimenko et al. (2015) *J. Neurotrauma*, 32 (24), 1968-1980). We have demonstrated the feasibility and utility of using TSCS over the thoracolumbar spine to activate the detrusor in neurologically intact rhesus macaques (Gad et al. (2017) *J. Med. Primatol.* 46(6): 359-363; Gad et al. (2018) *J. Neurophysiol.* 119: 1521-1527). In this example, we demonstrate that Transcutaneous Electrical Spinal Stimulation for Lower urinary tract functional Augmentation (TESSLA) can activate and improve LUT function after a severe SCI. We hypothesize that TESSLA activates the spinal neural networks that are active in controlling LUT function. Key features of TESSLA include its non-invasiveness and its subject specific adaptability for the selection of stimulation sites and parameters. In addition, the noninvasive feature of TESSLA may be appealing to a broader population of subjects at a modest cost compared to surgically invasive neuromodulatory devices.

Methods

This study was approved by the Institutional Review Board of Rancho Research Institute, the research arm of Rancho Los Amigos National Rehabilitation Center, Downey, CA. All research participants signed an informed consent form before the start of the study and consented to their data being used in future publications and presentations. Seven individuals (Four male and three females) with SCI at T11 or above who used clean intermittent catheterization to manage the LUT were recruited. Each subject had a stable SCI that occurred at least one year prior to study initiation. Baseline demographic, medical and urodynamic parameters of study participants are shown in Table 6. The experiments were carried out with use of a proprietary non-invasive Transcutaneous Electrical Spinal Cord Stimulator. Six participants were tested for a six-hour period over 2 days (3 hours per day), and one participant underwent additional testing on Day 3. On Day 1, the LUT was mapped to spinally evoked responses. Spinal stimulation was delivered at 0.5 Hz (individually at T11 and L1) with current starting at 10 mA and increasing at increments of 10 mA up to 200 mA (or until tolerable or responses had plateaued). On Day 2, a baseline urodynamic procedure without stimulation was performed with the subjects either in seated (n=4) or supine (n=3) position. Next, TESSLA was delivered at 30 Hz at T11. Urodynamic recording was commenced and the bladder was filled until a detrusor contraction was elicited. The stimulation was turned off and the bladder was fully emptied. Subsequently, the bladder was filled to a 75% capacity. To ensure that reflex bladder contraction did not occur, detrusor pressure was monitored for at least 2 minutes. Next, TESSLA was delivered at 1 Hz at T11 to initiate voiding. When voiding was completed, the bladder was emptied completely. On Day 3, one subject (566729), who was able to sit comfortably on a modified padded toilet seat was asked to undergo a uroflow test in the absence and presence of TESSLA.

TABLE 6

Baseline demographic and medical characteristics and urodynamic parameters of study participants

| Demographic and Medical Characteristics | 566729 | 399343 | 955941 | 5452144 |
|---|---|---|---|---|
| Gender | Male | Female | Female | Female |
| Age (years) | 32 | 49 | 43 | 32 |
| Years since injury | 1.25 | 5.67 | 3.08 | 2.08 |
| Level of injury | T4 | C6 | T11 | T6 |
| ASIA classification | A | B | C | A |
| Bladder management | CIC | CIC | CIC | CIC |
| LUT sensation | No | Yes | Yes | Yes |
| Urinary incontinence | One episode per day | None | Rare | One episode per week |
| LUT medications | None | Fesoterodine 8 mg daily | Oxybutynin ER 14 mg daily | Mirabegron 50 mg daily |
| Bowel regimen | SUP/DS | SUP/DS | Enema/DS | DS |
| Autonomic dysreflexia | No | Yes | No | Yes |

| LUT Characteristics | TESSLA Off | TESSLA Off | TESSLA Off | TESSLA Off |
|---|---|---|---|---|
| Vol at first detrusor contraction (mL) | 205  281 | 164 | 356  500 | 71  212 |
| Voiding efficiency | 12.2%  39.8% | 8.5%  36.2% | 0.0%  10.5% | 64.7%  100% |
| Post void residual (mL) | 180  127 | 150  90 | 440  335 | 25  0 |
| Sensation of fullness |  |  |  |  |
| Sensation of detrusor contraction |  | Yes | Yes |  |
| Detrusor-sphincter dyssenergia | No | No | No | No |
| Maximum change in Pdet during voiding (cm of H2O) | 36  65 | 45  45 | NA  31 | 113  90 |
| Maximum change in Pura during voiding (cm of H2O) | −44 | −2 | NA  −30 | 40  −15 |

TABLE 6-continued

Baseline demographic and medical characteristics and urodynamic parameters of study participants

| Demographic and Medical Characteristics | 25801 | 151947 | 573487 |
|---|---|---|---|
| Gender | Male | Male | Male |
| Age (years) | 48 | 38 | 23 |
| Years since injury | 1.00 | 23 | 3.56 |
| Level of injury | C3 | T6 | T6 |
| ASIA classification | C | A | A |
| Bladder management | CIC | CIC | CIC |
| LUT sensation | No | Yes | Yes |
| Urinary incontinence | Multiple times a day | None | Few episodes per week |
| LUT medications | None | Onabotinum toxin | None |
| Bowel regimen | DS | Sup/DS | DS |
| Autonomic dysreflexia | Yes | No | No |

| | TESSLA | | TESSLA | | TESSLA | |
|---|---|---|---|---|---|---|
| LUT Characteristics | Off | | Off | | Off | |
| Vol at first detrusor contraction (mL) | 87 | 198 | 258 | 323 | 52 | 95 |
| Voiding efficiency | 0.0% | 54.4% | 7.3% | 14.8% | 96.2% | 100% |
| Post void residual (mL) | 160 | 155 | 330 | | 2 | 0 |
| Sensation of fullness | Yes | Yes | Yes | Yes | | Yes |
| Sensation of detrusor contraction | | Yes No | | No No | | No |
| Detrusor-sphincter dyssenergia | | | | | | |
| Maximum change in Pdet during voiding (cm of H2O) | NA | 51 | 34 | 20.7 | 114 | 56 |
| Maximum change in Pura during voiding (cm of H2O) | NA | | | −11 | 77 | −53 |

LUT: Lower Urinary Tract, CIC: Clean intermittent catheterization, Sup: Suppository, DS: Digital Stimulation.

Urodynamic Study

The external genitalia were prepared and draped in sterile fashion. The urethra was lubricated and a 7-Fr triple lumen T-DOC® Air-Charged™ urodynamic catheter (Laborie, Ontario, Canada) was placed per urethra with the distal pressure port positioned within the bladder and the proximal pressure port within the external urethral sphincter. Position within the urethral sphincter was confirmed by the pressure reading from the proximal port. Electromyography (EMG) of the external urethral sphincter was performed with bilateral patch electrodes placed at the anal verge. Abdominal pressure measurement was obtained via a 7-Fr single-lumen T-DOC® Air-Charged™ catheter (Laborie, Ontario, Canada) placed per rectum. Urodynamic studies (UDS) were performed according to International Continence Society urodynamic standards using a Goby™ urodynamic system (Laborie, Ontario, Canada) with a fill rate of 30 ml/min (Rosier et al. (2016), International Continence Society Good Urodynamic Practices and Terms 2016: Urodynamics, uroflowmetry, cystometry, and pressure-flow study, *Neurourol Urodyn*. 36. 10.1002/nau.23124). In addition to EMG, the following urodynamic parameters were recorded: vesical pressure ($P_{ves}$), abdominal pressure ($P_{abd}$), external urethral sphincter pressure ($P_{ura}$) and flow rate. Detrusor pressure ($P_{det}$) was obtained by subtracting $P_{abd}$ from $P_{ves}$. Closure pressure ($P_{clo}$) was obtained by subtracting $P_{ves}$ and $P_{ura}$. Bladder capacity was defined as the bladder volume at which urinary incontinence occurred. Postvoid residual saline was withdrawn by using the indwelling urodynamic catheter to empty the bladder following urination. Voiding efficiency was defined as $$\frac{\text{Voided Volume}}{\text{Voided Volume} + \text{Postvoid Residual}}.$$

Noninvasive Spinal Cord Stimulation

TSCS was delivered between spinous processes using 2.0 cm-diameter round gel adhesive electrodes (Axelgaard, ValuTrode® Cloth) as cathode and two 5.0×10.0 cm² rectangular electrodes (Axelgaard, ValuTrode® Cloth) placed over the iliac crests as anode.

Mapping

Transcutaneous Spinal Cord Stimulation (TSCS) was delivered individually along the midline between spinous processes at T11-T12, and L1-L2 at 0.5 Hz to map the LUT. Stimulation was started at 10 mA and increased in increments of 10 mA up to 200 mA or until it was no longer tolerable. Each intensity of stimulation determined by the pulse width was repeated 5 times to assess reproducibility of responses.

Testing

The stimulation intensity and site chosen were based on the recruitment curves obtained from mapping studies (FIG. 21). Similar methods have been used in our animal studies (Gad et al. (2014) *PLoS One*, 9(9): e108184; Gad et al. (2016) *Exp. Neurol.* 285(Pt B): 182-189). During functional UDS studies with TESSLA, the frequency was set at either 1 Hz or 30 Hz. The intensity used during 1 Hz and 30 Hz TESSLA was determined based on responses observed during the mapping studies.

Urodynamic Studies with TESSLA

30 Hz Stimulation

The bladder was emptied via the indwelling urodynamic catheter. TESSLA at 30 Hz was initiated at T11. The bladder was then infused with saline at a rate of 30 ml/min until a detrusor contraction occurred. At the end of the detrusor contraction, the bladder was manually emptied via the infusion port to calculate the residual volume.

1 Hz Stimulation

The bladder was emptied via the indwelling urodynamic catheter. The bladder was filled with saline to 75% of bladder capacity (determined by baseline UDS) at a rate of 30 ml/min. Filling was then stopped and detrusor pressure was monitored for at least 1 to 2 minutes to ensure that no detrusor contraction occurred. Next, TESSLA was delivered at a frequency of 1 Hz at T11. Within 60 secs of stimulation, a detrusor contraction was induced. After the induced detrusor contraction ended, bladder was manually emptied via the infusion port to calculate the residual volume.

Data Analysis

The studies provided several urodynamic parameters were analyzed including: 1) infused volume; 2) post void residual; 3) voiding efficiency; 4) peak pressure during detrusor and urethral contraction; 5) peak-to-peak pressures and EMG amplitude during mapping studies. These average peak to peak responses for each intensity were used to generate the recruitment curves for each site of stimulation. 6) Co-activation between Pdet and Pura per second during voiding was defined as Pdet*Pura/voiding duration to assess the level of DSD, 7) Bladder capacity was defined as the volume at which first DO with leakage occurred. 8) Infused volume at which first DO occurred was used to quantify severity of DO.

Statistical Analysis

The paired t test was used to compare data between groups with TESSLA Off and TESSLA On using Graphpad software.

Results

Mapping over T11-12 demonstrated detrusor contractions with lower levels of activation of the urethra and abdomen, whereas stimulation of L1-2 minimally activated the detrusor, urethra and abdomen (FIG. 21). Note the unique pattern of responses in the Pves, Pura, Pabd and Pdet. Lower extremity responses were consistent with those reported earlier (Gad et al. (2017) Front. Neurosci. 11: 333; Sayenko et al. (2015) J. Appl. Physiol. 118(11): 1364-1374). The contractions in the detrusor and urethra, identified via pressure changes, were used as indicators to identify appropriate sites for functional studies. The site at which the largest detrusor contraction was observed at the lowest stimulation intensity was used for functional studies in the next phase.

Baseline UDS demonstrated features that are typical of UDS recordings in individuals with SCI (FIG. 22, panel A, Table 6, (Weld & Dmochowski (2000) Urology, 55(4): 490-494)). TESSLA delivered at T11 at 1 Hz resulted in improved voiding efficiency (VE), increased flow rate, decreased residual volume and improved coordination between the detrusor and sphincter (FIG. 22, panel B, and FIG. 23). The voiding efficiency increased from 26.99±15.41 to 50.80±5.25% (P<0.05, n=7). In contrast, TESSLA delivered at 30 Hz at T11 resulted in reduced DO during urine storage, i.e., increased bladder capacity (FIG. 22, panel C, and FIG. 24) and improved detrusor-sphincter coordination during voiding (FIGS. 23 and 25, n=5, P<0.05). The bladder capacity increased from 170.54±15.86 to 252.59±18.91 ml (P<0.05, n=7). Since the SCI subjects were unable to generate a voluntarily induced detrusor contraction, the infused volume at which an involuntary contraction in the detrusor was used as a surrogate biomarker to assess the severity of DO (brown arrow, FIG. 22). As shown in FIG. 24, significantly decreased DO was observed when TESSLA at 30 Hz was applied. When UDS was repeated without stimulation, reversal to baseline was observed. Stimulation at multiple sites (T11+L1+Co1) used during locomotor training in the past (Gerasimenko et al. (2015) J. Neurophysiol. 113(3): 834-842; Gerasimenko et al. (2015) J. Neurotrauma, 32 (24), 1968-1980) did not enable efficient bladder voiding.

At the end of the study, one subject underwent an unintubated uroflow test. The subject was initially asked to void in the absence of TESSLA and subsequently in the presence of TESSLA. A voiding contraction was induced when TESSLA was turned on at T11 at 1 Hz with a VE of 36.84% and average flow rate of 4.9 ml/s (FIG. 26). The procedures were well tolerated by all subjects with no change in blood pressure, heart rate, skin irritation (during and after the procedures) and change in spasticity (after the procedure). None of the subjects reported episodes of increased incontinence during the days following the experimental sessions. Even though urodynamic procedures are known to trigger episodes of autonomic dysreflexia (AD) (Giannantoni et al. (1998) Spinal Cord, 36(11): 756-760) due to overfilling of the bladder, care was taken to ensure that the bladder was not overfilled and did not induce symptoms of AD.

Discussion

Previous studies have shown feasibility of using invasive ES to selectively activate neuronal networks in experimental models. ES over the L3 spinal segments activated the spinal EUS bursting center in rats and promoted the switch between the bladder storage automaticity phase to voiding with improved coordination between detrusor and sphincter in both intact and spinal animals (Abud et al. (2015) Am. J. Physiol. Renal Physiol. 308(9): F1032-1040). Previous studies have also shown that LUT function improves with ES aimed at restoring locomotor function after SCI (Gad et al. (2014) PLoS One, 9(9): e108184; Harkema et al. (2011) Lancet, 377(9781): 1938-1947), including improvement in continence, bowel and sexual function in human subjects (Hubscher et al. (2018) PLoS One, 13(1): e0190998). While locomotor-based therapies resulted in improvements in bladder capacity and voiding efficiency, multiple studies suggest that fine tuning of stimulation parameters play an important role in defining the level of functional recovery after SCI (Gad et al. (2013) J. Neuroeng. Rehabil. 10: 2; Rejc et al. (2017), J. Neurotrauma. 34(9): 1787-802). Each of these above-mentioned studies highlight the automaticity that is intrinsic to the spinal networks controlling LUT function and the ability to activate the appropriate neural networks (spinal micturition centers) based on the site and pattern of stimulation. Continuously delivered TESSLA with a partially filled bladder results in an overall increase in detrusor pressure past a threshold while lowering the urethral pressure to initiate voiding. This is one of the key features of the TESSLA induced voiding, wherein TESSLA activates the neural networks that control LUT function to initiate voiding. Multisite stimulation that has been reported to be most effective in enabling locomotion (T11+L1+Co1, (Gerasimenko et al. (2015) J. Neurophysiol. 113(3): 834-842; Gerasimenko et al. (2015b) J. Neurotrauma, 32 (24), 1968-1980)) were not effective in enabling voiding. Further, it was necessary to fine-tune stimulation parameters for each subject. Though 30 Hz stimulation resulted in increased bladder capacity (reduced DO) and improved coordination between detrusor and sphincter (reduced DSD), the overall voiding efficiency was similar to baseline, suggesting the need to fine tune the spinal circuitry based on the intended application i.e. low frequency to initiate voiding (Gad et al. (2014) *PLoS One*, 9(9): e108184) vs high frequency to increase bladder capacity (present data) and to enable locomotor function (Gad et al. (2016) *Exp. Neurol.* 285(Pt B): 182-189; Lavrov et al. (2006) *J. Neurophysiol.* 96(4): 1699-1710).

Modeling (Danner et al. (2011) *Artif Organs*, 35 (3): 257-262) and experimental (Hofstoetter et al. (2018) *PLoS One*, 13(1): e0192013) studies have shown that transcutaneous stimulation (Sayenko et al. (2015) *J. Appl. Physiol.* 118(11): 1364-1374) can depolarize at least a subset of the same neural structures as recruited by implanted epidural electrodes (Sayenko et al. (2014) *J. Neurophysiol.* 111(5): 1088-1099). Data obtained from experiments with epidural stimulation and transcutaneous stimulation demonstrate that, with increasing intensity, the stimulus response relationship of the early (short latency) and medium components in many muscles shares some characteristics with the H-reflex and M-wave interactions and can recruit dorsal afferents, interneurons and motor neurons. The present study shows that TESSLA can be used to stimulate the neural circuitries in the spinal cord of human subjects with SCI and facilitate LUT function by reducing DO, decreasing DSD, increasing bladder capacity and enabling voiding. Each of these features has significant clinical and functional implications. Controlling DO and increased bladder capacity lead to fewer incontinence episodes, thus benefitting patients' health and self-confidence. Decreasing DSD lowers the risks of high pressure voiding, loss of bladder compliance and kidney injury. Additionally, our finding that TESSLA mediates recovery of bladder-sphincter synergy suggests that coordination between the detrusor and the external urethral sphincter can occur at the spinal level, thus challenging the dogma that bladder-sphincter coordination is facilitated solely by the brainstem. TESSLA may effect these changes by reducing pathological spinal mechanisms that arise after a SCI, e.g., the emergence of spinal reflex mechanisms mediated by unmyelinated vesical afferents (C-fibers) (de Groat & Yoshimura (2001) *Annu. Rev. Pharmacol. Toxicol.* 41: 691-721). Finally, TESSLA directly addresses one of the primary dysfunctions caused by SCI, i.e. the inability to void on command.

Several neuromodulation systems have been previously developed to improve LUT function after SCI (Gaunt & Prochazka (2006) *Prog. Brain Res.* 152: 163-194). Examples of such systems include the dorsal penile/clitoral nerve, tibial nerve and sacral nerve stimulators. Of these, the dorsal penile nerve stimulator has been most extensively studied in the SCI population. This device takes advantage of a urethral guarding reflex: by stimulating a branch of the pudendal nerve (in this case, the dorsal penile nerve), detrusor contractions are inhibited. Dorsal penile nerve stimulation has been assessed in several studies of SCI patients with promising results for decreasing incontinence and promoting a larger bladder capacity (Kirkham et al. (2001) *Spinal Cord*, 39(8): 420-428; Lee et al. (2003) *Arch. Phys. Med. Rehabil.* 84(1): 136-140). Despite these successes, the penile nerve stimulator has several limitations, including the need for continuous stimulation to inhibit contractions, and the practical implications of attaching the device to the genitalia. Furthermore, in contrast to TESSLA, dorsal penile nerve stimulation does not address recovery of bladder sensation or promote bladder emptying. Indeed, we are not aware of any neuromodulation techniques that stimulate the spinal cord directly in a noninvasive manner to facilitate LUT functional recovery after SCI.

Each of the improvements in LUT function observed with TESSLA is consistent with the priorities set by NIBIB/NIH at the workshop entitled "Addressing Paralysis through Spinal Stimulation Technologies" in November, 2014 (Pettigrew et al. (2017) *IEEE Trans. Biomed. Eng.* 64(2): 253-262). The data presented here directly addresses and validates five out of the six objectives proposed for restoring bladder function. In addition, we hypothesize that TSCS could address other pelvic autonomic functions such as bladder, bowel and sexual function, discussed at the consortium. While the discussion at the consortium focused on epidural stimulation, we would like to emphasize that TESSLA offers the additional unique feature of being noninvasive.

In conclusion, TESSLA offers several advantages over current therapies for LUT dysfunction due to SCI. First, TESSLA is non-invasive. If the intervention is not tolerated by the subject, it can be immediately discontinued. Second, we demonstrate that TESSLA can modulate the spinal networks devoted to micturition with a critical level of specificity. Third, TSCS and training used to enable upper (Gad et al. (2018) *J. Neurotrauma*, 35: 10.1089/neu.2017.5461) and lower extremity (Gerasimenko et al. (2015) *J. Neurotrauma*, 32 (24), 1968-1980) function led to plastic changes in the spinal networks in absence of stimulation. Similarly, TESSLA may result in plastic changes to the neural circuitry controlling bladder filing, voiding and sensation. However, further studies are desirable to determine impact of TESSLA and training on LUT function in the long term.

Example 2

Dynamic Electrical Stimulation: A Novel Tool to Neuromodulate Spinal Networks
Summary of Example 2

Potentiation of synaptic efficiency in spinal networks is reflected in the magnitude of modulation of spinally and supraspinally motor-evoked responses. After spinal cord injury, volitional control can be facilitated when elicited by pairing cortical and peripheral nerve stimulations. To facilitate synaptic potentiation of descending input with epidural electrical stimulation of the spinal cord alone, we designed a novel neuromodulation method called dynamic stimulation (DS), using patterns derived from a hindlimb EMG signal during stepping. DS was applied dorsally to four lumbosacral segments through a high-density epidural array composed of 18 independent platinum-based micro-electrodes. At the interface array/spinal cord, the temporal and spatial features of DS neuromodulation affect the entire lumbosacral network, particularly the most rostral and caudal segments. In fully anesthetized adult female rats, DS induced a short-lasting increase in spinal cord excitability and generated a more robust potentiation of spinally-induced motor output compared to tonic stimulation. Further, DS facilitated weak cortical input to recruit muscle contractions. Thus, DS has unique features necessary for amplifying both peripheral and supraspinal input to spinal locomotor networks compared to traditional tonic waveforms, which in turn elevate the potential to regain significant levels of functional recovery after a spinal lesion.
Introduction Based on the Hebbian principle of associative plasticity, synaptic potentiation can be induced in the central nervous system by applying two converging inputs with a precise temporal order (Zhang et al. (1998) *Nature*, 395: 37-44; Song et al. (2000) *Nat. Neurosci.*, 3: 919-926; Dan & Poo (2006) *Physiol. Rev.*, 86: 1033-1048; Caporale & Dan (2008) *Annu. Rev. Neurosci.*, 31: 25-46). Indeed, in the spinal cord, motor evoked EMG responses were facilitated by trains of electrical pulses applied simultaneously to the cortex and to a peripheral nerve in healthy (Poon et al. (2008) *Exp. Brain Res.*, 188: 13-21; Cortes et al. (2011) *Clin. Neurophysiol.*, 122: 2254-2259) and spinal cord injured persons (Bunday & Perez (2012) *Curr. Biol.*, 22: 2355-2361; Tolmacheva et al., (2017) *J. Neurotrauma*, 34: 2668-2674; Urbin et al., (2017) *J. Neurophysiol.*, 118: 2171-2180). Potentiation of synaptic activity in spinal networks might account for the recovery of volitional motor control of paralyzed lower limbs reported so far in ten individuals with a chronic, "complete" spinal cord injury (Harkema et al. (2011) *Lancet*, 377: 1938-1947; Angeli et al., (2014) *Brain*, 137: 1394-1409; Gerasimenko et al. (2015) *J. Neurotrauma.*, 32: 1968-1980; Grahn et al. (2018) *Mayo. Clin. Proc.*, 92: 544-554; Taccola et al. (2018) *Prog. Neurobiol.*, 160: 64-81).

The first aim of this study is to explore whether synaptic potentiation may be elicited in the spinal cord by a non-uniform, epidural stimulation pattern that also exploits pairing of pulses converging onto spinal circuits from different segments. Secondly, we investigated whether any potentiation of synaptic transmission in the spinal cord can facilitate weak descending input to agonist and antagonist muscles in hindlimbs.

As previously demonstrated, one effective measure of synaptic efficiency in the spinal cord is represented by spinal evoked motor responses shown as the EMG signals generated by muscle contractions elicited by single, supra-threshold electrical pulses epidurally delivered to the dorsum of the cord (Lavrov et al., (2006) *J. Neurophysiol.*, 96: 1699-1710). Based on the intensity of stimulation, a single epidural stimulus between L2 and S1 spinal levels produced three types of evoked responses, i.e., early (ER; latency 1-4 ms), middle (MR; latency 5-10 ms), and late (LRs; latency 11 ms) in the hindlimb muscles of rats, both intact (Gerasimenko et al. (2006) *J. Neurosci. Methods*, 157: 253-263) and spinalized (Lavrov et al., (2006) *J. Neurophysiol.*, 96: 1699-1710). While ERs likely correspond to the direct recruitment of motoneurons or ventral roots at higher stimulation intensities, an MR has some component consistent with a monosynaptic reflex and an LR with the recruitment of a polysynaptic interneuronal spinal network.

More complex responses are distinctively elicited by stereotyped trains of epidural pulses of different frequencies (Lavrov I et al. (2008) *J. Neurosci.*, 28: 6022-6029). A unique multifrequency stimulating paradigm, including highly varying waveforms sampled from multiple sources, was developed in vitro to optimally recruit neonatal spinal neuronal networks (Taccola (2011) *J. Neurophysiol.*, 106, pp. 872-884; Dose et al. (2013) *Physiol. Rep.*, July; 1(2): e00025; Dose & Taccola, (2016) *Neuromodulation*, 19: 563-575). Based on these results, we hypothesized that a more complex input such as a 'dynamic and noisy' spinal stimulation delivered through a novel epidural interface might further increase the excitability of spinal networks in an in vivo preparation, when compared to a traditional monotonic input. The dynamic stimulation protocol consisted of parameters of stimulation that were temporally and spatially modulated across the entire lumbosacral network. The increased excitability of spinal networks might correspond to the modulation of both spinally-induced responses generated by a segmental and site-specific epidural stimulation and descending weak input elicited by sub-threshold cortical pulses.

Methods

Experimental Design

Data were collected from 32 adult female Sprague Dawley rats (250-300 g body weight). All procedures were approved by the Animal Research Committee at UCLA and are in accordance with the guidelines of the National Institutes of Health (NIH) Guide for the Care and Use of Laboratory Animals and with the European Union directive on animal experimentation (2010/63/EU).

Epidural electrical stimulation of the spinal cord was used to generate motor evoked potentials recorded from selected hindlimb muscles of animals under anesthesia. Animals were initially sedated with isoflurane gas at a constant flow of 1.5%-2.5% to immobilize them, followed by administration of urethane (1.2 mg/Kg, i.p). During surgery, toe pinch was performed periodically to assess the anesthetic level to be maintained with isoflurane gas, as needed. All animals were under the influence of only urethane throughout experiments. At the end of experiments (9-10 hours), animals were sacrificed with isoflurane and sodium pentobarbital (ip, 80-100 mg/Kg).

Intramuscular EMG Electrode Implantation

Animals were kept under anesthesia over a heating pad during the bilateral implantation of intramuscular electromyography (EMG) recording electrodes (Fournier et al. (1983) *Exp. Neurol.*, 80, pp. 147-156; Roy et al. (1985) *Brain Res.*, 337: 175-178) in the tibialis anterior (TA) and soleus (Sol) muscles. Skin and fascial incisions were performed to expose the belly of each muscle. Multistranded, teflon-coated stainless steel wires (AS 632, Cooner Wire Co, Chatsworth, CA, USA) connected to gold plated amphenol connector were passed subcutaneously. Pairs of wires were inserted into the muscle belly using a 23-gauge needle and anchored at their entry and exit from the muscle with knots made with 5.0 Nylon suture. A small notch (0.5-1.0 mm) in each wire was deprived from the insulation to expose the conductor and form the electrodes. Proper placement of electrodes was verified during surgery, by stimulating through the head connector. Bare wire tips were covered by gently pulling the Teflon coating over the tips. All EMG wires were coiled in the back region to relieve stress. A common ground (~1 cm of the Teflon removed distally) was inserted subcutaneously in the mid-back region for EMGs.

EMG recordings from bilateral TA and soleus muscles were band-pass filtered (gain 1000, range 10 Hz to 5 KHz and notched at 60 Hz), amplified using an A-M Systems Model 1700 differential AC amplifier (A-M Systems, Sequim, WA, USA), and finally digitalized at 10 kHz (Digidata® 1440, Molecular Devices, LLC, CA, USA). All surgical sites were closed in layers using 5.0 Vicryl® (Ethicon, New Brunswick, NJ, USA) for all muscle, connective tissue layers and skin incisions in the hindlimbs, while 5.0 Ethilon® (Ethicon, New Brunswick, NJ, USA) was used to close skin incisions in the back.

Epidural Multi Electrode Array Implantation

To simultaneously deliver patterns of intrinsically varying signals to multiple segments of the spinal cord it was necessary to develop a high-density platinum based multi-electrode array consisting of three longitudinal columns and six horizontal rows of independent low-impedance electrodes (total of 18 independent electrodes) (Gad et al. (2013) *J. Neuroeng. Rehabil.*, 10: 2; Chang et al. (2014) *Conf Proc. IEEE Eng. Med. Biol. Soc.* 2014: 6834-6837). The high-definition and flexibility of the epidural interface was proved by the selective activation of extensor or flexor motor pools while varying bipolar stimulation parameters (35).

To implant the multi-electrode array in the epidural dorsal space, a T12 to L2 laminectomy was performed to dorsally expose the spinal cord. After epidural implantation, the array was covered with small cotton balls rinsed in saline. Back muscles and skin were sutured using 5.0 Vicryl® (Ethicon, New Brunswick, NJ, USA), with leads to the array exiting through the skin. A common ground for all array electrodes, independent from EMG ground, was inserted subcutaneously in the left forearm.

Electrical Stimulation Protocols

The experimental set up and the pattern of electrical stimulation used in this study are summarized in the cartoon in FIG. 28. The motor threshold intensity for each preparation, was determined with a train of 40 rectangular pulses at 0.3 Hz. A set of five sweeps was delivered for each amplitude of stimulation and increased by increments of 100 µA ranging from 100 to 800 µA. The threshold for each animal was defined as the minimum intensity required to elicit a detectable EMG response from any one muscle. The input/output protocol was regularly repeated during the experiment to confirm threshold stability. The threshold changed rarely and only slightly. After determining the threshold, a continuous train of 300-700 pulses (0.1 ms pulse duration, 0.3 Hz frequency, at threshold intensity) was delivered to record baseline responses.

We delivered a protocol of electrical stimulation named Dynamic stimulation (DS) consisting of a 29.5 s segment of EMGs collected from the Sol muscle of a neurologically intact adult rat walking on a treadmill at the speed of 13.5 cm/s. The trace was acquired in AC mode (gain 1000, filter range 10 Hz to 5 KHz notched at 60 Hz) with an A-M Systems Model 1700 differential AC amplifier (A-M Systems, Sequim, WA, USA), then digitalized at 10 kHz (DIGI-DATA® 1440, Molecular Devices, LLC, CA, USA) and reduced off-line at a sampling rate of 2000 Hz, through CLAMPFIt® 10.3 software (Molecular Devices, LLC, CA, USA).

The sampled EMG trace was exported as an ASCII text file consisting of two columns of values. The first column values corresponded to the EMG amplitude. The second column consisted of the first column along with a series of zero values for the first 0.5 s. The resulting ASCII text file was exported to a programmable stimulation device (STG® 4008; Multi Channel Systems, Reutlingen, Germany). The two staggered stimulating protocols were simultaneously delivered through two independent output to the left and right external columns of array electrodes with opposite cathode location. DS protocol was applied at different intensities (150, 225, 300, 375, 450, 600 µA), i.e. the difference between the maximum positive and the maximum negative amplitudes of waveforms (peak to peak). At least five min rest was allowed between consecutive deliveries of DS. To test variations on the excitability of neuronal motor networks before and after DS, EMG responses were elicited through a train of rectangular monophasic pulses (100-400 pulses, pulse duration=0.1 ms, frequency=0.3 Hz) at threshold intensity, continuously delivered through a pair of electrodes (usually at T13/L1 vertebral level, L3/L6 spinal level). Repetitive DS (rDS) consisted of eight consecutive 30 s periods of DS intermingled by 1 min rest. After rDS, a long protocol of continuous stimulation (300-900 pulses, duration=0.1 ms, frequency=0.3 Hz, amplitude=Th) was used to follow the baseline recovery for up to 45 min. Interestingly, only electrodes connected to the stimulator for pulse delivery (DS or test pulses) were the active electrodes in use. The other electrodes in contact with the spinal cord were open circuited and disconnected, and thus did not directly impact on the spread of the electric field induced by the active electrodes. This has been validated by the finite element model displayed in this paper, as well as by previous modeling studies from our collaborators (see also independent stimulations in Supplementary FIG. 29).

In a subgroup of animals, trains of single electrical pulses (0.1-1 ms duration, 0.3 Hz frequency, at threshold) were delivered to the left sensorimotor cortex region representing the right lower limbs. Two small metal screws were implanted through the skull, one at 2 mm posterior to lambda and the other one 8 mm anterior to bregma. Wires were connected at the top of each screw for bipolar electrical stimulation (STG 4002®; Multi Channel Systems, Reutlingen, Germany) with cathode rostral to anode.

Data Analyses

The spinally evoked EMG responses were divided into early (ER, latency 1-4 ms), middle (MR, latency 5-10 ms) and late responses (LR, latency 11-15 ms) relative to the stimulation pulse (Lavrov et al., (2006) *J. Neurophysiol.*, 96: 1699-1710). The amplitude and time to peak of each EMG response was determined using Clampfit® 10.3 software (Molecular Devices, LLC, CA, USA) to trace time courses. Responses were statistically compared by individually calculating the peak of 20 or 100 consecutive sweeps immediately before and after the application of DS. Then, single peaks were averaged for statistical comparison. The ratio between the standard deviation and the mean of the amplitude provided the amplitude coefficient of variation (CV), which is an index of consistency of spinally-evoked EMG responses (the lower the CV, the less variable responses are). The power spectrum of the patterns composing DS was obtained through Clampfit® 10.3 software (Molecular Devices, LLC, CA, USA). The strength of coupling among pairs of EMG signals was defined by the cross-correlation function (CCF) analysis performed by Clampfit® 10.3 software (Molecular Devices, LLC, CA, USA).

Experimental Design and Statistical Analysis

Data are indicated as mean±SD values, with n referring to the number of experiments. After determining the normality of the distribution of data based on a Kolmogorov-Smirnov normality test, statistical analysis was performed using SigmaStat® 3.5 software (Systat Software, CA, USA) to compare the mean±SD of different experimental conditions. All parametric values were analyzed using Student's t-test (paired or unpaired) to compare two groups of data, or ANOVA for more than two groups. Among non-parametric values, Wilcoxon Signed-Rank test was adopted for two groups, and Kruskal-Wallis ANOVA on Ranks for more than two groups. For multiple comparisons, we applied either Tukey's methods or Dunn's methods, depending on data being parametric or non-parametric. Within each sample of non-parametric data, repeated measures were performed using Friedman test. Results reached significance when $P < 0.05$.

Results

The central question explored is the functional modulation of supraspinal-spinal connectivity using novel patterns of current derived from locomotion EMGs (named Dynamic Stimulation, DS) delivered to spinal networks via an epidural electrode array. Therefore, we initially collected the baseline trend of endogenous spinal modulation of the motor output during continuous weak stimulation and compared them to the modulatory effects induced by DS and the delivery of traditional stereotyped protocols. Finally, we wondered whether any increase in spinal network excitability induced by DS can facilitate weak descending corticospinal input.

Weak Pulses Locally Applied to the Spinal Cord Evoked Small Stochastically Modulated EMG Responses The synaptic efficiency of spinal networks was represented by small EMG responses to low intensity stimuli applied to spinal networks projecting to specific motor pools. Indeed, submaximal modulation strengths produce an excitability state that enables spinal networks to be more responsive to proprioceptive input (Gad et al. (2013) *J. Neuroeng. Rehabil.,* 10: 108).

To continuously explore the functionality of spinal networks, trains of epidural pulses (0.1 ms, 0.3 Hz) were segmentally delivered to the spinal cord (T13 vertebral level, L3/L4 spinal level, cathode on the left), as schematized in the cartoon of FIG. 29, panel A. Initially, stimulation was delivered at a weak intensity (300 µA), i.e. the lowest to induce appreciable deflections of the baseline from right TA and Sol (FIG. 29, panel B). The latencies of these responses matched the characteristics of middle (MR) and late responses (LR), as described previously (Lavrov et al., (2006) *J. Neurophysiol.,* 96: 1699-1710; Gerasimenko et al. (2006) *J. Neurosci. Methods,* 157: 253-263) i.e., time to peaks: $MR_{TA}$=7.6 ms; $LR_{TA}$=12 ms; $MR_{Sol}$=8.5 ms; $LR_{Sol}$=12.8 ms), while no early responses (ER) were observed. By increasing the intensity of stimulation to 800 µA (FIG. 29, panel C), peak amplitude was potentiated and ERs became evident shortly after pulse delivery (time to peaks: 1.5 ms for rTA, 1.7 ms for rSol; FIG. 29, panel C) and the time to peak of both MR and LR was considerably reduced (time to peaks: $MR_{TA}$=5.4 ms; $LR_{TA}$=9.4 ms; $MR_{Sol}$=4.9 ms; $LR_{Sol}$=11.6 ms).

At weaker intensities of stimulation (300 µA), spinally-induced responses were highly varying for both onset and peak amplitude. The time to peak calculated for consecutive sweeps is reported in the whisker plots, showing the variability for 300 repetitions (FIG. 29, panel D). The time courses of amplitude for 300 consecutive sweeps (total duration=15 min) were plotted for both MRs and LRs recorded from TA (FIG. 29, panel E) and Sol (FIG. 29, panel F). All responses were characterized by a large variability in amplitude, as indicated by the high CVs ($MR_{TA}$=0.22; $LR_{TA}$=0.17; $MR_{Sol}$=0.20; $LR_{Sol}$=0.35). Nevertheless, this great variability does not parallel any patterned modulation of the motor output between extensor and flexor muscles, as confirmed by the lack of a clear correlation among peaks of responses expressed in pairs of MRs and LRs reported for TA and Sol (FIG. 29, panel G). No activity-dependent plasticity occurs during continuous sub-threshold low frequency stimulation. Thus, this protocol can be considered as a suitable tool for tracing baseline excitability levels of neuronal motor networks. Therefore, spontaneous intrinsic fluctuations of small spinally evoked responses induced by weak pulses represent the spontaneous change of excitability of the motor pool specific spinal networks being tested.

DS Potentiated MRs Induced by Segmental Single Pulses, Mostly on TA

To investigate whether DS modulates spinally evoked motor output even after ending the DS protocol, a train (0.3 Hz) of weak electrical pulses (400 µA; 0.1 ms) was continuously delivered to vertebral levels T13/L1 (spinal level L3/L6, cathode on the left) before, during and at the end of the protocol. Weak responses recorded in pre-DS control from right TA (FIG. 30, panel B) and left Sol (FIG. 30, panel C) were potentiated immediately after 30 s of DS delivered at the intensity of 375 µA. This effect was more prominent in TA, where responses occasionally achieved maximal recruitment. From the same experiment in FIG. 30, panel B, C, 300 consecutive EMG responses (over 15 mins), each separately analyzed for the MRs and LRs, were used to draw a time course for peak amplitude respectively for TA and Sol. Despite the variability in control, DS delivery strongly increased MR peaks from rTA, starting from the beginning of DS and lasting for up to four min after the end of DS (FIG. 30, panel D). A milder and shorter effect was observed in the lSol (FIG. 30, panel E).

In the same preparation, when intensity of DS was increased to 450 µA, MR potentiation was prolonged on lTA (FIG. 30, panel F), and lSol (FIG. 30, panel G). To better characterize the optimal intensity of DS to potentiate spinally-induced responses, DS was serially applied to the same animal by increasing the amplitude from 150 to 600 µA. The effect on peak amplitude of MRs and LRs for TA and Sol for 20 consecutive sweeps (1 min) immediately before and after DS delivery showed that DS statistically modulated the peaks of MRs starting from 375 µA for TA (FIG. 30, panel H; P<0.001, Kruskal-Wallis One Way ANOVA on Ranks followed by multiple comparisons versus control group with Dunn's Method, n=6-8) and 450 µA for Sol (FIG. 3 I; P=0.002, Kruskal-Wallis One Way ANOVA on Ranks followed by multiple comparisons versus control group with Dunn's Method, n=4-6), while LR components were not statistically modulated by DS even when it was delivered at the highest intensities (FIG. 30, panels J, K). Interestingly, in a subset of three experiments, continuous EMG recordings were acquired before and after DS delivery. Short-lasting (at least 1 min) rhythmic discharges were acquired right after DS supply (FIG. 37).

DS is More Effective than Standard Stimulation in Potentiating Weak EMG Responses To determine whether the DS was more effective than standard stimulation for modulating spinal networks, the two protocols were compared in the same animals and at the same intensity (375 µA), while sub-threshold test pulses were segmentally delivered to the spinal cord at L1/L2 vertebral level (L5/S2 spinal level, cathode on the left). The amplitude of small responses evoked from rTA by weak segmental stimulation were highly augmented during the delivery of DS, as well as immediately after stimulation (FIG. 31, panel A). In addition, the standard protocol at 40 Hz increased EMG responses, but the effect was lower than with DS and limited to the time of train delivery, quickly returning to pre-stimulation control values as soon as stimulation stopped (FIG. 31, panel B). The time course for 420 consecutive pulses (21 min) was traced to cover the entire experimental protocol (FIG. 31, panel C). DS largely potentiated the amplitude of MRs, which recovered their baseline in 1.5 min. After a 10 min rest, a train at 40 Hz facilitated MRs, but to a lesser extent than DS and only during the delivery of the 40 Hz stimulation (FIG. 31, panel C). As visualized below with a higher time scale, this effect was also shorter than the one induced by DS, which in fact increased the MR peak even after stimulation ended. Similar results were collected when the order of the two protocols was inverted with respect to the experiment shown in FIG. 31, panel A, namely 40 Hz train before DS. In six experiments mean peaks of MRs from 20 consecutive sweeps were compared before and right after the delivery of protocols (FIG. 31, panel D). DS significantly potentiates the amplitude of MRs compared to a train of stereotyped pulses at 40 Hz (*, P=0.031, Wilcoxon Signed Rank Test, n=6).

DS Potentiated MRs Induced by Single Pulses Delivered Lengthwise Through the Array DS increased the amplitude of MRs when EMG responses were induced by segmental stimulation of the spinal cord. We wondered if a similar modulating pattern arises from spinal reflexes elicited by single pulses delivered along the cord To explore whether DS can modulate the ascending and descending connectivity along the cord, small responses from TA and Sol were induced by single and weak pulses (500 μA) applied through the entire length of the array (FIG. 32, panel A). At an intensity of 500 μA, small baseline responses in the rTA and rSol had similar amplitude (FIG. 32, panel B, left). Analogously, DS at 375 μA comparably augmented the peak of both responses (FIG. 32, panel B, middle), an effect that persisted for both TA and Sol muscles even after protocol termination (FIG. 32, panel B, right). In one preparation, the strength of DS was serially increased (150-600 μA), potentiating the peak of MRs only during stimulation at 225 μA on both TA and Sol. However, starting from the intensity of 375 μA, facilitation of MRs persisted even after the end of stimulation, an effect further potentiated by higher strengths of DS (FIG. 32, panels C, D). Among four experiments, in which 20 consecutive test pulses (375 μA, 1 min) were considered before and after DS, MR peak amplitude were significantly potentiated for both TA (FIG. 32, panel E, P=0.019, paired t-test, n=4) and Sol (FIG. 32, panel F, P=0.032, paired t-test, n=4) with the TA responses higher than the Sol. In summary, single pulses applied along multiple spinal segments induced EMG responses from TA and Sol with a similar sensitivity to DS. On the other hand, when DS was delivered at maximal strength (600 μA), the amplitude of responses from TA became greater than from Sol.

Repetitive Delivery of a Longer DS Affects Spinally-Induced Responses

As reported above, the effects of DS were observed during protocol application and for a short post stimulation window (~2 mins). This suggests that, apart from a mere summation of concurrent electrical pulses applied to different sources (Dose et al. (2016) *Spinal Cord,* 54: 93-101), DS could induce synergistic responses lasting longer after the stimulation was stopped. Indeed, with multiple and serial deliveries of DS, longer resting pauses were necessary to stably recover pre-stimulation baseline values, suggesting the additive effect of repetitive DS applications supplied at short distance. Thus, a protocol named 'repetitive Dynamic Stimulation (rDS)' was designed by delivering eight slots of DS, regularly interposed by one-minute pauses, to reach the total length of eleven minutes.

Small spinally-induced responses were evoked by the continuous delivery of weak segmental pulses (500 μA) to the left side of the cord between T13 and L1 vertebral levels (L3/L6 spinal level, cathode on the left; FIG. 33, panel B). The rDS protocol largely increased the peak of MRs at the end of its delivery (FIG. 33, panel A) and the amplitude of the MR component continued to increase after delivery of multiple DSs (FIG. 33, panel C). This effect persisted after stimulation for up to eight minutes. Comparison of the mean values obtained by averaging single peak amplitudes of 100 consecutive EMG responses (5 min) was made among values recorded from pre-rDS control and at the end of repetitive stimulation showing the significant increase in motor responses as induced by rDS (FIG. 33, panel D, P=0.017, paired t-test, n=7) showed that the rDS protocol increased the peak of MRs within five minutes after ceasing stimulation, showing a more persistent effect than single applications.

Increasing the Excitability of Spinal Networks Facilitates Descending Input

DS modulates EMG responses induced by pulses applied segmentally or longitudinally to the spinal cord. We asked if this effect could be associated with a potentiation of pulse conduction along descending fibers. To better explore this possibility, motor responses from hindlimbs were bilaterally evoked by cortical stimulation (0.1-1 ms duration). At the strength of 800 μA, these motor potentials were characteristically composed of a first response at −10 ms and a late, and more varying, response at ~25-35 ms (FIG. 34, panel A right). In the same experiment, sub-threshold pulses (500 μA) did not induce any motor-evoked potentials (FIG. 34, panel A middle). Nevertheless, when single pulses at the same weak intensity were delivered in conjunction with DS, even at an intensity as low as 300 μA, TA motor potentials appeared (FIG. 34, panel A left) and then rapidly vanished once DS terminated. In another animal, by doubling the strength of DS (600 μA), the appearance of motor evoked responses induced by sub-threshold single pulses persisted even for a couple of minutes after the end of spinal stimulation, eventually disappearing in the later post-stimulation resting phase (FIG. 34, panel B). In another animal, small motor responses were evoked by single pulses at 700 μA and were potentiated by DS (375 μA), an effect that persisted at the end of DS (FIG. 34, panel C). As observed by serially increasing the intensity of DS starting from 150 μA to 600 μA, 375 μA was the lowest strength of DS at which cortically-evoked motor potentials persisted to be higher than pre-stimulation controls, for even two minutes after the end of the protocol (FIG. 34, panel D).

In summary, DS potentiated motor-evoked potentials induced by direct electrical stimulation of motor areas. Even more importantly, when paired with cortical pulses at sub-threshold intensity, unable to generate any responses in control, DS facilitated the expression of motor responses. This makes the innovative protocol potentially noteworthy for exploiting the spared electrically-incompetent motor fibers after spinal lesion to reestablish some longitudinal connectivity along the injured cord and enhance or even recover volitional motor control.

Discussion

Dynamic Vs. Tonic Stimulation Patterns

In the current study, we adopted a stochastic pattern of modulation dynamically delivered to multiple sites along the spinal cord. These dynamically varying patterns consisted of continuously changing frequencies, amplitudes and polarities, as opposed to the traditional 'clean' rectangular waves of single frequency and amplitude. We call this method of modulation: dynamic stimulation (DS) in contrast to the more static profile of trains of stereotyped pulses. In fully anesthetized adult rats, this tool elicited stereotyped rhythmic discharges after the end of the protocol likely reflecting a short-lasting increase in spinal network excitability.

Furthermore, DS increased components of the EMG responses having latencies between 5 and 10 ms (MR) and elicited by segmental epidural weak pulses, an effect that persisted beyond the end of protocol. The efficacy of DS depended upon its strength, with its effects already visible at low levels (about 225 μA) of stimulation. Moreover, compared to a standard tonic 40 Hz stimulation, DS was more effective in augmenting the amplitude of spinally-induced responses, for even a longer period after protocol termination. Facilitation of responses appeared also when elicited by weak pulses applied with an epidural array over as many as four spinal segments or trans-cranially over the cortical motor area. Repetitive delivery of DS induced an even longer facilitation of EMG response amplitudes. Thus, stimulation with asynchronous DS patterns increased synaptic efficiency of spinal networks and facilitated corticospinal connectivity in the adult rat under in vivo conditions.

Variability of Motor Responses Elicited During Sub-Threshold Stimulation

In the present study, single pulses at weak intensities elicited small motor responses that characteristically spanned multiple segments of the spinal cord (Gerasimenko et al. (2015) *J. Neurotrauma.,* 32: 1968-1980; Minassian et al. (2007) *Muscle Nerve,* 35: 327-336). Once the dorsal surface is stimulated with single pulses, compound EMG responses with different latencies are obtained. Then, by increasing the strength of stimulation, responses appeared first with an intermediate latency, followed by a later one and finally, at the highest intensity, a short latency response (Lavrov et al., (2006) *J. Neurophysiol.,* 96: 1699-1710; Gerasimenko et al. (2006) *J. Neurosci. Methods,* 157: 253-263) that corresponds to the direct activation of ventral motoneurons. It has been reported previously that the amplitude of each evoked response was modulated by increasing stimulation intensity up to a maximal muscle recruitment (Id.).

The low intensity stimuli predominantly used in this study approximated the threshold for muscular activation, without inducing overt limb movement. The low intensity stimuli responses that have intermediate and late EMG latencies reflect the recruitment of multiple combinations of synapses within and perhaps among other spinal networks. On the other hand, when weak impulses were delivered at low frequency over a long period, motor-evoked responses were spontaneously modulated. Indeed, amplitude and latency of baseline motor responses varied randomly, without any correlation between the activation of motor pools from flexors and/or extensors, revealing that random, spontaneous synaptic events appear to be an intrinsic feature of the neuromotor system that can be exploited by an asynchronous pattern of stimulation to induce resonance (Martinez et al. (2007) *J. Neurophysiol.,* 97: 4007-4016). This effect was observed in adult rats under anesthesia and presumably would be even more dramatic in an awake rat, where the spinal network's state of excitability changes continuously as it processes vast multi-modal input (Gerasimenko et al. (2006) *J. Neurosci. Methods,* 157: 253-263). The spontaneous modulation that is intrinsic to spinal networks presumably plays a role in defining the effect of direct electrical stimulation of the spinal cord, especially at low intensities. Further, if frequency of stimulation is a crucial factor for reaching a certain level of selectivity to tune distinct motor outputs (Minassian et al. (2007) *Hum. Mov. Sci.,* 26: 275-295), the real impact of stimulation relies on the physiological state of the spinal networks when a given ensemble of multimodal input arrives at a given combination of motor pools. Indeed, the intrinsic frequency of modulation of the network's excitability is crucial, especially at low intensities of stimulation, in summating or filtering external pulses and then defining the effective frequency of stimulation received by the network. Although DS increased the amplitude of EMG responses, they remained variable, suggesting that DS exploits the same endogenous mechanisms of modulation of the motor output even in the anesthetized state.

Stimulation with Dynamically Varying Waveforms

The mechanisms of traditional epidural stimulation using trains of stereotyped impulses and the adoption of selected frequencies that can selectively activate stepping or standing after lesion are still poorly understood. Likewise, the mechanisms by which DS waveforms increase spinally-evoked responses remains unclear. Indeed, in neonatal in vitro preparations, "noisy" waves were addressed to the lumbar CPG to trigger an epoch of locomotor-like discharges (Nistri et al. (2010) Ann. N.Y. Acad. Sci. 1198: 242-251). Contrariwise, here, asynchronous stimulation was primarily addressed to the lumbosacral propriospinal networks to affect the excitability of circuits responsible for the modulation of spinally-induced motor output. However, by applying DS to anesthetized adult animals in vivo, more questions arise regarding the level of complexity required to elicit an optimal response. In addition, the more intact preparation makes it difficult to distinguish slight effects on the motor output, i.e., the role played by each singular feature of DS, namely the use of two lateral waveforms instead of only one, while staggering the onset and cathode location of the two patterns. Nonetheless, configuration of DS was chosen which provides high level of variability in amplitude, frequency and direction of the electric field.

At the same time, the rhythmic spontaneous activity appearing among multiple motor pools a few minutes after DS delivery, suggests a short-lasting modulation of interneuronal networks that orchestrate the selection of different motor pools to activate within the lumbosacral segments. A similar increase in spontaneous activity of motor pools did not occur in reduced preparations, even when undergoing longer periods of stimulation (Dingu et al. (2016) *Neuromodulation,* 19: 38-46). On the other hand, in vivo experiments involving weight bearing stepping are almost certain to reveal a much higher level of variable, but also patterned, multi-modal input and how this input is altered when the spinal networks are neuromodulated into different physiological states.

In summary, after DS, a single weak electrical stimulus applied to the dorsum of the cord can facilitate recruitment of a more excitable, or possibly larger, interneuronal networks. Perhaps this will result in the activation of more motoneurons and more motor pools that can generate a more robust motor response.

In addition, in our protocol, two dynamically varying waveforms were continuously delivered with a staggered onset. The large number of spikes and the range of frequencies and its variability within the two waves of DS may converge with optimal latency onto the spinal network to exploit phenomena of spike timing-dependent plasticity (Song et al. (2000) *Nat. Neurosci.,* 3: 919-926; Dan & Poo (2006) *Physiol. Rev.,* 86: 1033-1048). In particular, in the lumbar network, DS might optimally pair the antidromic depolarization of post-synaptic terminals with the orthodromic depolarization of pre-synaptic terminals, as reported in previous paired-pulse stimulation protocols that increased amplitude of EMG responses (7).

A Novel Paired Associative Stimulation Confined to the Cord.

Ascending and descending stereotyped trains of pulses delivered to the extremities of the motor pathway (the peripheral nerve and the cortex) and converging onto spinal networks effectively facilitated the motor output even after injury (Poon et al. (2008) *Exp. Brain Res.,* 188: 13-21; Cortes et al. (2011) *Clin. Neurophysiol.,* 122: 2254-2259; Bunday & Perez (2012) *Curr. Biol.,* 22: 2355-2361; Tolmacheva et al., (2017) *J. Neurotrauma,* 34: 2668-2674; Urbin et al., (2017) *J. Neurophysiol.,* 118: 2171-2180). Recently, paired associative stimulation has been confirmed by shortening the distance between the two stimulating sites, i.e. pulses applied to the cortex and to the spinal cord directly (Dixon et al. (2016) *J. Neurophysiol.,* 116: 904-916; Mishra et al. (2017) *J. Physiol.,* 5: 6953-6968). However, so far, a more local associative stimulation of spinal networks has been hindered by the lack of epidural arrays with fully independent electrodes allowing simultaneous stimulation of two segments of the cord with different patterns. Contrariwise, the novel interface used in this study allows pairing of two pulse patterns converging onto spinal networks and delivered rostrally and caudally along four spinal segments. In our protocol, two dynamically varying waveforms were continuously delivered with a staggered onset. The large number of spikes and the range of frequencies and its variability within the two waves of DS may converge with optimal latency onto the spinal network to exploit phenomena of spike timing-dependent plasticity (Song et al. (2000) *Nat. Neurosci.*, 3: 919-926; Caporale & Dan (2008) *Annu. Rev. Neurosci.*, 31: 25-46). In particular, in the lumbar network, DS might optimally pair the antidromic depolarization of post-synaptic terminals with the orthodromic depolarization of pre-synaptic terminals, as reported in previous paired-pulse stimulation protocols that increased amplitude of EMG responses (Bunday & Perez (2012) *Curr. Biol.*, 22: 2355-2361).

In addition, in individuals with a clinically-defined complete spinal cord injury, finding the optimal latency of the two associated stimuli used to facilitate the motor output might be difficult because of the wide variability in real-world spinal injuries. Indeed, each lesion can trigger a unique pattern of polysynaptic tract rerouting, which can potentially request different pairing latencies. Our epidural stimulation protocol consisting of two patterns of different wide spectrum harmonics should provide multiple combinations for the coupling of ascending and descending input, increasing the probability to optimally tune the latency of pairing that could benefit a higher number of individuals.

Conclusion

In the present study, we explored a novel pattern of noisy stimulation delivered through an innovative spinal epidural interface. These two resources provided the means for testing the potential of variable and multisite spinal stimulation, by generating an increase in spinal network excitability and a more robust modulation of lumbosacral networks compared to tonic patterns of stimulation. Further, the DS paradigm of stimulation was linked to patterns associated with the facilitation of the motor output induced by subthreshold cortical input.

Extended Data

FIG. 38 illustrates other suitable EMG signals used for Dynamic Stimulation from different animal models and different muscles (lower extremity, upper extremity, urethral sphincter, pelvic floor). Suitable EMG signals include, but are not limited to primate (e.g., rhesus, human) hand and/or arm muscles, pelvic floor muscles, leg and/or foot muscles, and the like.

As illustrated in FIGS. 39, 40, and 41, in three different animals, responses to test impulses are simultaneously recorded not only from lower limb muscles, but also from multiple sites on the surface of the dorsal cord. The depolarization evoked in the adjacent sites of the spinal cord appears, with a different latency, starting a few hundreds of microseconds after the artifact of local stimulation.

As shown in FIG. 42, when the array is acutely placed across a spinal cord contusion at the level of L1, high test pulses delivered below the lesion cannot evoke any spinal reflexes, while only a small response arises from the dorsal cord. Afterwards, a repetitive dynamic stimulation protocol is applied. In turn, the same test pulses are now able to stably evoke muscle contractions from hindlimbs, with greater discharges recorded also from spinal sites.

Highlights.

Multiple potentials can be simultaneously recorded from different sites of the surface of the dorsal cord, through an innovative technology, which shows that epidural stimulation evokes an activation pattern not following a simple passive conduction of the stimulus along the cord, but highlights preferential directions for input transmission.

Shortly after a contusive lesion, repetitive delivery of dynamic stimulation across the lesion site recovers hindlimb muscle contractions and increases the amplitude of cord dorsum potentials.

Example 3

ReMoTESS: Restore Motility with Transcutaneous Electrical Spinal Stimulation

Introduction:

GI logic INC has developed a disposable, non-invasive, acoustic gastro-intestinal surveillance (AGIS) biosensor. The AGIS sensor (AbStats) allows continuous and automated analysis of bowel sounds across the acoustic spectrum-including hertz ranges below the threshold detected by the human ear. AbStatas has been successfully tested in Postoperative ileus (POI) patients to identify acoustic intestinal rates (IR). Using this approach, we used AbStats to identify the effects of Transcutaneous Electrical Spinal Stimulation (TESS) on the IR. This method uses our TESS device developed for lower urinary tract function (TESSLA) and is termed as ReMoTESS (Restore Motility with Transcutaneous Electrical Spinal Stimulation).

Methods:

AbStat sensors were attached to the patient as recommended. Initial 15 mins of data was recorded as baseline without TESS. Next, TESS was turned on at T1 or L1 vertebral levels with varying frequencies and intensities. A bStats was continuously monitoring the IR.

Results:

During the baseline period, IR ranged between 0 and 0.5 (averaged every 2 min). Introduction of ReMoTESS (high frequency) at L1 increased the IR over a period on an hour. However, ReMoTESS delivered at T11 or L1 (low frequency) significantly increased the IR within minutes of it being delivered. The most effective site to increase IR seemed to range from T8-L1. The increased IR changed the overall motility from low motility to moderate to high motility suggesting the use of ReMoTESS to improve quality of life of patients with constipation and overall low motility (see, e.g., FIG. 43).

Using the same approach, ReMoTESS delivered between T8 and T11 (high frequency) seemed to reduce motility with the more effective sites being the caudal site (~T11), suggesting the use of ReMoTESS to improve quality of life of patients with fecal incontinence.

Conclusion:

Delivering TESS in a unique manner activates the spinal cord to improve quality of life of patients with GI dysfunction by restoring normal motility (ReMoTESS) and can be used on patients with fecal incontinence as well as patients with constipation.

Example 4

ReSUITS: Recovery of Stress & Urge urinary Incontinence using Transcutaneous Stimulation Overactive bladder affects 12 to 30% of the world's population. The accompanying urinary urgency, frequency and incontinence can have a profound effect on an individual's quality of life, leading to depression and loss of self-worth, social isolation, avoidance of sexual activity and loss of productivity at work. Additionally, healthcare costs associated with overactive bladder are estimated to be between $65 and $75 billion per year in the US alone.

We demonstrated using a unique non-invasive spinal cord stimulation approach, TESSLA, we can improve overall bladder function in individuals with complete and incomplete spinal cord injuries.

Similarly we have demonstrated in able bodied individuals with an idiopathic bladder, TESSLA is an effective therapy tool to improve bladder function by reducing urge to stress and urge incontinence The symptoms seen in the patients include:

reduced sensation of bladder fullness inability to hold a filled bladder frequent day-time urination frequent night-time urination stress incontinence due to sneezing, coughing or laughing urge incontinence High effort to void Increased time between start of effort to void and start of actual flow of urine Wet diapers Wet clothing After undergoing therapy using the TESSLA device, the patients report:

Improved sensation of bladder fullness, i.e., they know when their bladders are full Allowing them a longer window to find a restroom Sensation occurs with minimal urge, thereby giving patients better control Reduced urge at the time of voiding Increased period between voiding cycles during the day Increased periods between voiding cycles at night Reduced incidences of incontinence due to stress such as cough or laughter Reduced incidences of urge due to overfilled bladder More natural voiding with minimal effort Decreased time between effort applied and start of void Reduced need for diapers The same is applicable in individuals with a neuropathic bladder with conditions including Stroke Multiple Sclerosis Parkinson's disease Alzheimer's disease Cerebral palsy Non-invasive stimulation of nerve roots.

Electrodes placed over the S2-S3 roots

Electrodes placed over the exit of the foramen

Stimulation delivered in the following configuration:

Spinal Cord Only

Spinal Cord+Nerve Root

Spinal Cord+Foramen

Nerve Root only

Nerve Root+Foramen

Spinal Cord+Nerve Root+Foramen

Applied stimulator is shown in FIG. 44. Results of pilot studies in humans with stroke are shown in FIG. 45.

As illustrated in Tables 7 and 8 there is a high incidence of bladder dysfunction in the population. Accordingly, the methods described herein find wide utility.

TABLE 7

| Incidence of idiopathic bladder dysfunction. | |
| --- | --- |
| Category | Prevalence of bladder dysfunction |
| Pediatric | 4-15% |
| Adult Male | 46% |
| Adult female | 15% |
| Adult female (post pregnancy) | 50% |
| Geriatrics | 10-30% |
| Diabetes | 35% |

TABLE 8

| Incidence of bladder dysfunction associated with neurological impairment. | | |
| --- | --- | --- |
| Category | Incidence/Year | Prevalence of bladder dysfunction |
| Spinal cord injury | 17,000 | >90% |
| Stroke | 800,000 | 40% |
| Multiple sclerosis | 10,000 | 75% |
| Cerebral palsy | 10,000 | 80% |
| Parkinson's disease | 60,000 | >90% |
| Cauda equina | 4,000 | >90% |

Moreover as compared to other modalities, the methods described herein are far less expensive. Additionally, the methods described herein provide numerous primary benefits including, but not limited to a reduced need for diapers and catheters, reduced leaks, reduced urinary tract infections (UTIs), increased productivity and self-confidence including the ability to increase activities associated with daily life, and thereby provide greater independence and reduced medical costs. From a healthcare giver's perspective, the methods provided herein result in increased efficiency, and fewer complications (e.g., infections associated with catheterization).

Example 5

Transcutaneous Electrical Spinal Cord Neuromodulator (TESCoN) Improves Symptoms of Overactive Bladder Summary of Example 5

Neuromodulation is a therapeutic technique that is well-established in the treatment of idiopathic Lower urinary tract (LUT) dysfunction such as overactive bladder (OAB). We have recently developed a novel neuromodulation approach, Transcutaneous Electrical Spinal Cord Neuromodulation (TESCoN) and demonstrated its acute effects on LUT dysfunction after spinal cord injury (SCI) during urodynamic studies. We found that TESCoN can promote urinary storage and induce urinary voiding when delivered during urodynamic studies. The objective of this study was to determine whether TESCoN can retrain the spinal neural networks to induce chronic improvement in the LUT, such that positive changes can persist even in the absence of stimulation. In addition, we wished to examine the effect of TESCoN on LUT dysfunction due to multiple pathologies. To achieve this objective, 14 patients (SCI=5, stroke=5, multiple sclerosis (MS)=3, and idiopathic OAB (iOAB)=1) completed 24 sessions of TESCoN over the course of 8 weeks. Patients completed urodynamic studies before and after undergoing TESCoN therapy. Additionally, each subject completed a voiding diary and the Neurogenic Bladder Symptom Score questionnaire before and after receiving TESCoN therapy. We found that TESCoN led to decreased detrusor overactivity, improved continence, and enhanced LUT sensation across the different pathologies underlying LUT dysfunction. This study serves as a pilot in preparation for a rigorous randomized placebo-controlled trial designed to demonstrate the effect of TESCoN on LUT function in neurogenic and nonneurogenic conditions.

Introduction

The lower urinary tract (LUT, consisting of the bladder and bladder outlet) serves two main roles: to store and empty urine. LUT dysfunction occurs when either storage or voiding are impaired, resulting in urinary incontinence or retention. LUT dysfunction is common in patients with neurological disease and the general population (de Groat (1997) *Urology*, 50: 36-52; discussion 53-36; Jeong et al. (2010) *The Urologic clinics of North America* 37: 537-546). In the case of neurological disease, LUT dysfunction occurs because the normal pathways responsible for communication between the LUT and the neural micturition centers become disrupted. While the mechanism of idiopathic LUT dysfunction is not as obvious, the nervous system is thought to be at least partially implicated in the majority of cases. LUT dysfunction has profound effects which range from endangering patients' health (as the case of poorly managed LUT dysfunction after spinal cord injury (SCI)) to significantly impacting patients' quality of life (as in the case of idiopathic over active bladder (iOAB) and post-stroke LUT dysfunction).

While it is often assumed that paralyzed individuals prioritize recovery of ambulation, multiple studies have demonstrated that restoration of bladder function is ranked among the top 2-3 priorities, above goals such as regaining lower extremity function (Anderson (2004) *J. Neurotrauma*, 21: 1371-1383). Likewise, urinary incontinence after stroke is a well-known risk factor for long-term disability, depression and institutionalization (Panfili et al. (2017) *The Urologic clinics of North America*, 44:403-414). Current therapy for LUT focuses on managing these complications without addressing the underlying cause or attempting to normalize or restore function (Stohrer et al. (2009) *European urology*, 56: 81-88). Urinary incontinence, frequency and urgency present across diseases such as SCI, stroke, multiple sclerosis (MS) and iOAB. While the reasons for this may vary, detrusor overactivity (or uninhibited detrusor contractions) is a common physiologic phenomenon observed in these conditions. Multiple therapies exist for correcting urinary storage function; however, they are not always suitable populations (e.g., anticholinergic medications in patients with cognitive impairment; intravesical botulinum toxin in patients at risk for retention) and they do not attempt to restore normal LUT function. On the other hand, the premise of neuromodulation is to correct the underlying neurological deficit and thus restore function to an end organ. Some neuromodulation techniques are well-established in iOAB including sacral nerve stimulation (Dasgupta et al. (2005) *J. Urology*, 174: 2268-2272) and percutaneous tibial nerve stimulation (Peters et al. (2010) *J. Urology*, 183: 1438-1443). We have recently developed a novel neuromodulation approach, Transcutaneous Electrical Spinal Cord Neuromodulation (TESCoN) a novel noninvasive neuromodulation technique to facilitate functional restoration after neurological injury. This modality engages the automaticity and the feedforward (Gerasimenko et al. (2017) *Neuroscientist* 23: 441-453) features of the spinal neural networks to activate the intrinsic control of the spinal networks that is sufficient to enable recovery of voluntary control. We have previously demonstrated that acute TESCoN facilitates urinary storage and promotes bladder emptying in individuals with SCI during urodynamic studies (Gad et al. (2018) *Front. Neurosci.* 12: 432). Patients experienced decreased detrusor overactivity, exhibited increased bladder capacity and improved detrusor-sphincter dyssynergia when stimulation was delivered at a high frequency; on the other hand, when stimulation was delivered at a low frequency subjects demonstrated improved voiding efficiency. These changes in LUT function were only noted during active stimulation. In this study we wished to determine whether repetitive stimulation over the course of several weeks can retrain the spinal neural networks to relearn timely storage and voiding. In addition, given the similarities in storage LUT symptoms and physiologic phenomena (e.g., detrusor overactivity) across multiple conditions, we wished to expand the application of TESCoN to LUT dysfunction due to stroke, MS and iOAB. Finally, our objective was to provide a clinical assessment of the effect of TESCoN on the LUT by examining changes in voiding diaries and validated clinical questionnaire following a course of the therapy.

Methods

Patient Recruitment

This study was approved by the Institutional Review Board of Rancho Research Institute, the research arm of Rancho Los Amigos National Rehabilitation Center, Downey, CA. All research participants signed an informed consent form before the start of the study and consented to their data being used in future publications and presentations. Five patients (four males and one female) with stable (greater than 1-year post diagnosis) SCI at T8 or above who used clean intermittent catheterization (CIC), five patients (three males and two females) with stable cortical stroke (greater than 1-year post diagnosis), three female patients with progressive MS symptoms for at least 1 year and one female patient with idiopathic OAB were recruited (see, Table 9). All patients experienced symptoms of urinary incontinence and sensate (i.e. non-SCI) patients reported urinary frequency and urgency.

TABLE 9

Table summarizing 14 patients, their pathology (n = 5 SCI, 5 Stroke, n = 3 MS and n = 1iOAB) location of injury, severity of injury, months post injury, current bladder management technique, LUT symptoms and current medications.

| Pt # | Gender | Pathology | Severity | Months Post | Bladder Management | Lower Urinary Tract Symptoms | Lower Urinary Tract Medication |
|------|--------|-----------|----------|-------------|--------------------|------------------------------|--------------------------------|
| P1 | M | SCI | AIS A | 18 | CIC | Incontinence | None |
| P2 | F | SCI | AIS A | 29 | CIC | Incontinence | Mirabegron 50 mg |
| P3 | M | SCI | AIS C | 20 | CIC | Urge Incontinence | None |
| P4 | M | SCI | AIS A | 135 | CIC | Urge Incontinence | Tolterodine LA 4 mg |

TABLE 9-continued

Table summarizing 14 patients, their pathology (n = 5 SCI, 5 Stroke, n = 3 MS
and n = 1iOAB) location of injury, severity of injury, months post injury,
current bladder management technique, LUT symptoms and current medications.

| Pt # | Gender | Pathology | Severity | Months Post | Bladder Management | Lower Urinary Tract Symptoms | Lower Urinary Tract Medication |
|------|--------|-----------|----------|-------------|--------------------|-----------------------------|-------------------------------|
| P5 | M | SCI | AIS C | 48 | CIC | Urgency/ Incontinence | Solifenacin 10 mg |
| P6 | M | CVA | | 50 | Volitional | Urgency/ Nocturia | Tolterodine LA 4 mg |
| P7 | M | CVA | | 36 | Volitional | Urgency/urge Incontinence | Tolterodine LA 4 mg |
| P8 | F | CVA | | 78 | Volitional | Urgency/ Incontinence | Tolterodine LA 4 mg |
| P9 | F | CVA | | 75 | Volitional | Urgency/ Incontinence | Oxybutynin 5 mg TID |
| P10 | M | CVA | | 75 | Volitional | Urgency/ Frequency | None |
| P11 | F | MS | | 48 | Volitional | Urge Incontinence | None |
| P12 | F | MS | | 240 | Volitional | Incontinence | None |
| P13 | F | MS | | 24 | Volitional | Urge Incontinence | Tolterodine LA 4 mg Tamsulosin 0.8 mg |
| P14 | F | iOAB | | 48 | Volitional | Urge Incontinence/ Frequency | None |

SCI: Spinal cord injury, CVA: Cerebral vascular accident, MS: Multiple sclerosis, CIC: Clean Intermittent Catheterization.

Initial Assessment

Each patient underwent a detailed medical history and physical examination and completed an assessment of LUT symptoms using the Neurogenic Bladder Symptom Score (NBSS). A baseline urodynamic study was performed in SCI and stroke subjects according to International Continence Society (ICS) guidelines using a Goby Urodynamics System from Laborie (Ontario, Canada). In order to mimic a clinical setting where patients may not be evaluated with urodynamics prior to therapy, MS and idiopathic OAB subjects were assessed only with a detailed history and physical, a voiding diary, and the NBSS. Following the initial visit, each subject completed a 4-day voiding diary.

Delivery of Spinal Stimulation

Stimulation was delivered using a proprietary TESCoN device (spineX, Inc). The stimulation waveform consisted of two alternating pulses of opposite polarities separated by a 1 uS delay to form a delayed biphasic waveform. The pulses consisted of a high frequency biphasic carrier pulse (10 KHz) combined with a low frequency (30 Hz) burst pulse each with a pulse width of 1 ms. Stimulation was applied using an adhesive electrode over the interspinous ligaments of T11 and L1 serving as the cathode and two adhesive electrodes over the iliac crests as the anodes. The frequencies were selected based on our previous findings demonstrating greatest reduction in incontinence and increase in bladder capacity (Gad et al. (2018) *Front. Neurosci.* 12: 432).

Identification of Stimulation Parameters

Patients with SCI and stroke underwent formal evaluation for selection of stimulation parameters as previously published. In brief, a urodynamic two-port urethral catheter and a urodynamic rectal catheter were placed to measure intravesical ($P_{ves}$), external urethral sphincter ($P_{ura}$) and abdominal ($P_{abd}$) pressures respectively. Stimulation was delivered as described above. Dose response curves were constructed for each parameter with incremental increase in stimulation intensity. The stimulation intensity that generated a noticeable change in $P_{ura}$ with little to no change in $P_{det}$ was selected (FIG. 46). This stimulation intensity did not cause any discomfort to the patients. Urodynamic studies were then performed according to ICS guidelines with concurrent TESCoN stimulation. Again, to mimic a clinical setting which precludes such an assessment, subjects with MS and idiopathic OAB were stimulated at a preselected frequency (30 Hz) and location (T11 and L1). Stimulation intensity was set as the highest current that did not cause cutaneous discomfort or cause any muscle activation in pelvic floor muscles or lower extremity muscles.

TESCoN Therapy Course

Following the baseline evaluation, the patients were invited to return for an 8-week long course of TESCoN Subjects received stimulation for 90 minutes. Each subject completed three stimulation sessions a week.

Post-Stimulation Assessment

Within one week after the last stimulation session, SCI and stroke patients completed another clinical urodynamic study in the absence of TESCoN. All patients also completed the NBSS at this time and submitted a voiding diary starting 4 days prior to the final assessment.

Data and Statistical Analysis

The following urodynamic variables were collected in SCI and stroke subjects: 1) Bladder capacity, 2) Voiding efficiency, 3) Maximum detrusor pressure during voiding contraction, 4) Change in urethral sphincter pressure during filling and voiding contraction, 5) volume at first sensation and 6) time between bladder capacity and beginning of voiding contraction. '$\Delta P_{ura}$ Filling' was defined as the change in pressure observed in $P_{ura}$ during the filling cycle. '$P_{ura}$ Baseline' was defined as the pressure in the $P_{ura}$ prior to start of filling. '$\Delta P_{det}$ void' and '$\Delta P_{ura}$ void' were defined as the change in pressures observed in $P_{det}$ and $\Delta P_{ura}$ respectively between bladder capacity and voiding. The paired t-test was used to determine the significance of differences in urodynamic parameters, NBSS scores of participants and number of daily voids and incontinence episodes with and without TESCoN and before and after therapy.

Results

Urodynamic Assessment of SCI and Stroke Patients

During baseline urodynamics, SCI patients demonstrated detrusor overactivity at low volumes, low voiding efficiency and detrusor sphincter dyssynergia during voiding. Stroke patients demonstrated low bladder capacity, detrusor overactivity, and appropriate voiding efficiency (FIG. 47) (Weld & Dmochowski (2000) *Urology*, 55: 490-494; Weld et al. (2000) *Urology*, 56: 565-568). Acute delivery of TESCoN in SCI patients reduced detrusor overactivity, increased bladder capacity, improved coordination between detrusor and the external urethral sphincter and increased voiding efficiency (FIG. 48), consistent with our earlier observations (Gad et al. (2018) *Front. Neurosci.* 12: 432). In contrast, stroke patients did not demonstrate a change in bladder capacity or voiding efficiency. However, stroke patients exhibited an increase in the volume at first bladder sensation, and a significant increase in the ability to delay urination, as measured by the time between reaching bladder capacity and initiation of voiding (P<0.05) (FIG. 49). After completing the 8-week therapeutic intervention, both sets of patients (n=5 Stroke and n=5 SCI) demonstrated an increased bladder capacity (P<0.05, FIG. 50, panel A) (without TESCoN); however, no change in voiding efficiency was observed in either group (50, panel B). The average baseline pressure recorded at the urethral port ($P_{ura}$) and the change in $P_{ura}$ during the filling phase of the urodynamic cycle were higher (P<0.05) after compared to before therapy (50, panels C & D). Detrusor pressure ($P_{det}$) during voiding did not change before vs after therapy (FIG. 50, panel E).

Clinical Assessment of Patients

All patients underwent a clinical assessment in the form of a 4-day voiding diary and NBSS. Eleven (n=4 SCI, n=5 Stroke and n=2 MS) out of thirteen neurogenic patients reported at least a five-point decrease (minimal clinically important difference, MCID) in the NBSS (Welk et al. (2018) *Spinal Cord.* 56: 259-264) (FIG. 51, panel A). The mean score in the NBSS decreased from 35.9±2.6 to 26.6±3.1 (P<0.05) with the highest change being 34 points and the lowest being 0 (FIG. 51, panels C & D). Note that significant decrease in NBSS scores were observed in all pathologies (FIG. 51, panel E). The distribution of NBSS decrease among the different underlying pathologies showed no obvious trends. All patients also reported a significant decrease in the number of incontinence episodes/day (~68% reduction in leaks, P<0.05) (FIG. 52, panel A), a reduction (12%) in the number of voiding/CIC episodes per day (FIG. 52, panel B) and a significant reduction (~37%) in night time voiding/CIC episodes as recorded on the voiding diary (FIG. 52, panel C). No Adverse Events (AE) were reported. All patients reported to be satisfied with the therapy and would have continued beyond the 8 weeks if the therapy was offered.

Discussion

Neuromodulation Enables Restoration of Sensation and Motor Control of LUT

Multiple components of the nervous system play a role in LUT control. Thus, when one or more components of the nervous system are affected by a disease, LUT dysfunction can ensue. Although modern management techniques have ensured that LUT dysfunction is rarely dangerous, it almost inevitably has a marked impact on patients' quality of life. Some current therapies for LUT dysfunction in neurogenic and idiopathic situations are effective for preventing incontinence (e.g., anticholinergics, beta-agonists, botulinum toxin injection) but they do not restore normal bladder sensation or voiding function and sometimes achieve continence at their expense. On the other hand, spinal neuromodulation is a technique whose premise is to restore neural control functions by delivering a sub-motor threshold electrical stimulus that can transform the controlling neural networks into more functional physiological states. After 8 weeks of noninvasive spinal cord stimulation, bladder capacity increased. SCI patients also demonstrated improved detrusor-sphincter dyssynergia during detrusor contractions. All patients reported an improved sensation of bladder fullness and an increased latency time between sensation of urgency and the first episode of detrusor overactivity (or volitional voiding contraction). These effects appeared to be durable as they were observed even one week after therapy was concluded.

A commons question in the field of neuromodulation is, how epidural and transcutaneous spinal stimulation compare? Some of the more Important comparisons are 1) the ability to deliver the desired stimulation parameters to the most functionally effective neuronal networks for a given target organ system, 2) patient acceptability and ease and accessibility of delivery of the intervention 3) cost of the intervention and 4) safety of the intervention. To date, there is insufficient knowledge to weigh the advantages, but it seems reasonably safe to conclude that both approaches should continue to be developed and tested. Given the data to date, it seems almost inevitable that the best choice of approach will be based on the net result of pros and cons for a given patient as judged by the patient, the physician and the caregivers.

To briefly expand on some of these points, it is obvious that using the transcutaneous approach, multiple organ systems can be targeted simply by moving the electrode along the length of the spinal cord (Gad (2018) *J. Neurotrauma*, 35: 2145-2158; Gad et al. (2018) *Front. Neurosci.* 12: 432; Gad et al. (2018) *J. Neurophysiol.* 119: 1521-1527; Inanici et al. (2018) *IEEE Trans. Neural Sys. & Rehab. Engin. IEEE Engineering in Medicine and Biology Society* 26: 1272-1278; Phillips et al. (2018) *J. Neurotrauma*, 35: 446-451; Rath et al. (2018) *J. Neurotrama*, 35: 2540-2553; Hofstoetter et al. (2019) *J. Neurotrauma*, 10.1089/neu.2019.6588; Sayenko et al. (2019) *J. Neurotrauma*, 36: 1435-1450). Epidural stimulation has been effective in treating both autonomic (Harkema et al. (2018) *Front. Hum. Neurosci.* 12: 83; Herrity et al. (2018) *Sci. Rep.* 8: 8688; Hubscher et al. (2018) *PloS One*, 13: e0190998) and motor functions (Grahn et al. (2017) *Mayo Clin Proc.* 92: 544-554; Angeli et al. (2018) *New Eng. J. Med.* 379: 1244-1250; Gill et al. (2018) *Nature Med.* 24: 1942; Wagner et al. (2018) *Nature*, 563: 65-71) while maintaining the overall location of the implant even though the scope of the neural networks being neuromodulated may be more limited compared to transcutaneous stimulation. Evidence to date suggest that the transcutaneous approach in general has a greater advantage because of a more encompassing combination of networks that can be modulated to multiple organ systems. The activation of a broader network may enable multiple muscle groups and rely of the automaticity and feedforwardness of the spinal cord (Gerasimenko et al. (2017) *Neuroscientist* 23: 441-453). A disadvantage of the transcutaneous approach is the inconvenience to frequently don and doff the electrodes and the lower spatial resolution compared to the epidural approach. While only a side-by-side comparison in the same patient may provide more definitive answers, the transcutaneous approach definitely can help screen potential responders and provide insights regarding effective sights for stimulation. One could proceed from the transcutaneous approach to the Implantation strategy if this would be viewed as a more long-term solution. The reverse approach however, would be more problematic.

Clinically Significant Levels of LUT Function can be Restored

As important as the physiological changes observed on urodynamic testing were the clinical improvements assessed by the voiding diary and the NBSS. The NBSS is a validated questionnaire (Welk et al. (2018) *Spinal Cord.* 56: 259-264) that addresses common urological complaints in patients with neurological disease (e.g., incontinence, frequency, urgency and their impact on quality of life). The ability of NBSS to detect a meaningful clinical change has been recently shown in a pilot study of SCI and multiple sclerosis patients, receiving botulinum toxin injections for neurogenic urinary incontinence (Fragala et al. (2015) *Int. Neurol. J.* 19: 272-277). Over 85% of the neurogenic bladder patients in our study reported a statistically significant and clinically meaningful improvement in the overall NBSS score after TESCoN therapy was completed. Among the various domains of the questionnaire, there was improvement in the incidence of incontinence, quality of life and voiding/storage domains of the NBSS. As expected, there was no significant change in the consequences domain of the NBSS as the questions in this section of the questionnaire represent chronic problems related to the urinary tract (e.g., bladder and kidney stones), that would not be expected to improve immediately with positive change in LUT function. However, all patients also reported either a significant decrease in the number of urinary incontinence episodes per day or a decrease in the number of night time voiding cycles. Similar to the responses observed in the NBSS scores, no obvious trends were observed across the pathologies.

Mechanistic Factors that Contribute to Restoration of LUT Functions

Although the mechanistic details of how spinal neuromodulation can improve bladder function is not known, multiple but highly linked mechanisms probably contribute to the observed improvements. We postulate that stimulation modulates both afferent and efferent spinal networks into a more functional state. Neuromodulation may alter the responsiveness of spinal networks to bladder filling and emptying and increase the conscious awareness of these states. After chronic TESCoN therapy, subjects reported improved bladder sensation and decreased urinary urgency. Together, these findings suggest that parts of the CNS responsible for conscious sensation in the brain may have been re-engaged along with re-activation and/or retraining of local spinal centers controlling the LUT, reflecting a highly significant level of functional neural plasticity. It is interesting to note that despite the varied pathology, location and severity of injury, the spinal control of detrusor and urethral sphincter muscles were intact and could be transformed using a non-invasive modality. Our finding that voiding efficiency after 8 weeks of treatments did not change when urodynamic test was repeated in absence TESCoN suggests that the parasympathetic system, that drives bladder emptying, may require ongoing stimulation in order to induce a functional change. On the other hand, it appears that TESCoN can induce long standing neuroplasticity in the sympathetic and somatic system, which drives bladder storage, as evidenced by our finding that bladder capacity and $P_{ura}$ showed improvement even in the absence of stimulation.

Despite the potential shortcomings of the limited number of patients and lack of sham stimulation which will be addressed in future randomized controlled clinical trials, these data demonstrate the ability to transform the neural control of bladder function from a dysfunctional to a functional state using non-invasive spinal neuromodulation. Our previous results have demonstrated improvement in multiple functions (locomotion and autonomic function) with spinal neuromodulation during function rehabilitation (Gerasimenko et al. (2015) *J. Neurotrauma,* 32: 1968-1980; Gad et al. (2017) *Front. Neurosci.* 11: 333). In this study, however, since the patients were seated while receiving TESCoN therapy, minimal improvements in locomotor function were observed. TESCoN could prove to be a critical component of in our clinical toolbox while designing rehabilitation therapies for patients that suffer from multiple organ dysfunction (autonomic and motor) due to paralysis. In addition, future studies will also identify potential chronic changes in the cortex during simultaneous functional MRI recordings during urodynamic studies. These data allow us to speculate about multiple neural mechanisms that can account for end-organ dysfunction in neurogenic and non-neurogenic states (e.g., loss of connectivity between centers responsible for end organ control, formation of aberrant neural connections resulting in abnormal function). However, the intrinsic spinal networks controlling the LUT seem to not only persist post injury, but also have the potential to undergo transformation to a more functional state. These observations are consistent with our studies of noninvasive spinal cord stimulation in other applications such as lower extremity (Gerasimenko et al. (2015) *J. Neurotrauma,* 32: 1968-1980; Gad et al. (2017) *Front. Neurosci.* 11: 333), and upper extremity functional rehabilitation (Gad (2018) *J. Neurotrauma,* 35: 2145-2158; Inanici et al. (2018) *IEEE Trans. Neural Sys. & Rehab. Engin. IEEE Engineering in Medicine and Biology Society* 26: 1272-1278), where we have consistently observed some restoration of voluntary control in individuals clinically diagnosed with complete motor and sensory paralysis. We hypothesize that neuromodulation enables activity-dependent mechanisms that transform functionally incompetent spinal and supraspinal networks to higher functional states. The idea that neuromodulation can affect a part of the CNS remote from the site of stimulation is supported by data from other groups. For example, sacral nerve stimulation (a peripheral nerve neuromodulation modality commonly employed for idiopathic overactive bladder) is known to generate changes in brain signaling even during acute delivery of stimulation (Dasgupta et al. (2005) *J. Urology,* 174: 2268-2272). The encouraging findings that TESCoN can improve LUT symptoms in a variety of disease states encourages the exploration of its use in other brain pathologies associated with LUT dysfunction (e.g., Parkinson's disease, cerebral palsy), thus expanding the potential impact of this technology to a wider range of diseases.

Conclusion:

We have successfully demonstrated that TESCoN can 1) reduce detrusor overactivity, increase bladder capacity and reduce episodes of incontinence in patients with spinal cord injury, stroke, multiple sclerosis and idiopathic over active bladder, 2) functional transformation of the sensory component of bladder control to improve sensation of fullness bladder and awareness by delaying the time between reaching bladder capacity and initiation of voiding and 3) significantly reduce the number of incontinence episodes and night time voids that also reflects in the changes in NBSS scores. These observations suggest that the level of functional autonomy that is intrinsic to the neural circuitry that controls bladder function. This is a highly attractive clinical target for regaining greater levels of function in SCI and other etiologies of neurogenic bladder because it is a non-invasive form of neuromodulation that can re-engage and restore, via activity-dependent mechanisms, the automaticity intrinsic to the autonomic control of the LUT.

Example 6

Regulation of Bowel with TESCoN

As shown in FIG. 53, acute delivery of TESCoN (arrow) results in contractions (changes in pressure) in the anorectal regions and anal sphincter regions of the bowel. Increasing intensities of TESCoN results in stronger contractions in the bowel region.

Additionally, as shown in FIG. 54, acute and chronic delivery of tonic TESCoN resulted in increased duration and intensity of pressure change when combining voluntary effort and TESCoN.

Example 7

Regulation of Breathing with TESCoN

As shown in FIG. 55, acute delivery of TESCoN while varying the intensity of stimulation activates the diaphragm and other pelvic floor muscles to increase both inspiration and expiratory capacities. One hour of TESCoN therapy at C5 (highlight) results in long term increase in breathing capabilities even without TESCoN (FIG. 56). Additionally, two weeks of TESCoN therapy resulted in increased breathing capabilities even in the absence of TESCoN (FIG. 57).

Example 8

Acute Neuromodulation Restores Spinally-Induced Motor Responses after Severe Spinal Cord Injury Summary of Example 8

Epidural electrical spinal stimulation can facilitate recovery of volitional motor control in individuals that have been completely paralyzed for more than a year. We recently reported a novel neuromodulation method named Dynamic Stimulation (DS), which short-lastingly increased spinal excitability and generated a robust modulation of locomotor networks in fully-anesthetized intact adult rats. In the present example, we applied repetitive DS patterns to four lumbosacral segments acutely after a contusive injury at L1. Repetitive DS delivery restored the spinally-evoked motor EMG responses that were previously suppressed by a calibrated spinal cord contusion. Sham experiments without DS delivery did not allow any spontaneous recovery. Thus, DS uniquely provides the potential for a greater long-term functional recovery after paralysis.

Introduction

A spinal cord injury significantly reduces the level of resting activity in caudal spinal neural networks (Frigon & Rossignol (2008) *J. Physiol.* 586: 2927-2945) and may reduce or even suppresses evoked potentials that are spinally-induced from lesioned motor networks (Courtine et al. (2009) *Nat. Neurosci.* 12: 1333-1342). Likewise, excitability of networks caudal to the lesion are also largely altered, even in segments not visually affected by the initial trauma (Taccola et al. (2010) *Eur. J. Neurosci.* 31: 60-78).

However, their baseline excitability can be modified by neuromodulation via tonic electrical epidural or transcutaneous spinal cord stimulation and/or pharmacological activation. These protocols can modulate the excitability farther or closer to the motor threshold needed to generate action potentials within and among sensory-motor and autonomic networks in response to other sources of stimulation (Gerasimenko et al. (2015) *J. Neurotrauma,* 32: 1968-1980). Thus, tonic neuromodulation of the physiological states of the spinal networks changes the probability of excitation of the networks exceeding the threshold of excitation. Changes on the basal excitability of spinal networks explain how cutaneous and proprioceptive input, as well as input from descending motor pathways, allow one to recover supra spinal-spinal connectivity after severe paralysis (Gad et al. (2013) *J. Neurophysiol.* 110: 1311-1322). These critical amounts of sensory excitation and/or supraspinal input added to the elevation of baseline excitability levels are the two main conditions to reach motor threshold and therefore generate movement (Taccola et al. (2018) *Prog. Neurobiol.* 160: 64-81). Indeed, spinal cord networks have been converted from a non-responsive state to one that can generate sufficient depolarizing currents to induce coordinated action potentials among interneurons projecting to motoneurons of multiple motor pools.

To elicit locomotor-like patterns from spinal networks, a unique stimulating paradigm characterized by a noisy waveform was developed in vitro to optimally recruit neonatal spinal neuronal networks (Taccola (2011) *J. Neurophysiol.* 106: 872-884). This stochastic pattern of modulation was then delivered dynamically to distinct sites of the spinal cord of fully anesthetized adult in vivo rats (Taccola et al. (2020) *Brain Stim.* 13(1: 20-34). This method was named Dynamic Stimulation (DS), as opposed to the more static profile of trains of stereotyped pulses. DS generated patterns of muscle bursting followed by short-lasting rhythmic discharges (Taccola et al., in press). Moreover, DS augmented distinct components of the EMG responses elicited by segmental epidural weak pulses, during and after the end of DS protocol delivery. Repetitive delivery of DS further increased the amplitude of spinally-induced EMG responses.

However, along with reduced background activity in spinal networks, we have demonstrated reduced amplitudes in spinal evoked motor responses within 1 week after a severe SCI (Lavrov et al. (2008) *J. Neurosci.* 28: 6022-6029). Further, the response intensities and latencies vary based on site of stimulation and duration of the injury (Gad et al. (2013) *J. Neurophysiol.* 110: 1311-1322). In addition, the time course of the reemergence of spinally-induced responses were similar to the recovery of stepping after a severe SCI, indicating that evoked responses from hindlimb muscles can represent a potential biomarker of the functional recovery after SCI (Gad et al. (2015) *J. Neurophysiol.* 113: 3386-3396). However, the mechanism linking the modulation of background activity in the spinal networks with the modulation of motor-evoked responses still remains poorly understood.

The objective of this study is to determine the efficacy of dynamic noisy patterns in restoring motor control after a calibrated spinal cord injury.

Experiments were performed on 8 adult female Sprague Dawley rats (250-300 g body weight). All procedures have been approved by the Animal Research Committee at UCLA and are in accordance with the guidelines provided by the National Institutes of Health (NIH) *Guide for the Care and Use of Laboratory Animals* and with the European Union directive for animal experimentation (2010/63/EU).

Firstly, animals were sedated with isoflurane gas at a constant flow of 1.5%-2.5%, followed by urethane (1.2 mg/Kg, i.p).

Subsequently, recording wire electrodes (AS 632, Cooner Wire Co, Chatsworth, CA, USA) for intramuscular electromyography (EMG) were implanted bilaterally in the tibialis anterior (TA) and soleus (Sol) muscles. EMG signals were band-pass filtered (gain 1000, range 10 Hz to 5 KHz and notched at 60 Hz), amplified (A-M Systems Model 1700 differential AC amplifier, A-M Systems, Sequim, WA, USA), and finally digitalized at 10 kHz (Digidata® 1440, Molecular Devices, LLC, CA, USA).

Delivery of signals was performed using a high-density platinum based multi-electrode array, structured in three longitudinal columns and six horizontal rows of paired electrodes (Chang et al. (2014) *Conf Proc IEEE Eng Med Biol Soc.* 6834-6837; Taccola et al. (2020) *Brain Stim.* 13(1: 20-34). Array implantation in the epidural dorsal space was performed after a T12 to L2 laminectomy, to dorsally expose the spinal cord.

To determine threshold intensity for each preparation, a train of 40 rectangular pulses at 0.3 Hz was adopted. Five sweeps were delivered for each stimulation amplitude, moving up by 100 µA increments, ranging from 100 to 800 µA. Threshold was defined as the minimum intensity for eliciting a detectable EMG response from any muscle. As recently reported (Taccola et al. (2020) supra), DS consists of an EMG segment (29.5 s long) collected from the Sol muscle of a neurologically-intact adult rat during stepping. The trace, once acquired in AC mode (gain 1000, filter range 10 Hz to 5 KHz notched at 60 Hz) through an A-M Systems Model 1700 differential AC amplifier (A-M Systems, Sequim, WA, USA), was digitalized at 10 kHz (Digidata® 1440, Molecular Devices, LLC, CA, USA) and then reduced off-line at a sampling rate of 2000 Hz, using Clampfit® 10.3 software (Molecular Devices, LLC, CA, USA). Afterwards, the original EMG segment was duplicated, applying a staggered offset of 0.5 s and then exported (as an ASCII text file) to a programmable stimulator (STG 4002®; Multi Channel Systems, Reutlingen, Germany) to be applied to different electrode combinations within the array. The protocol was delivered to the two lateral columns of electrodes in the array with opposite rostro-caudal cathode/anode polarity.

Spinal cord functionality was tested under urethane by applying trains of electrical pulses (test pulses) (0.1 ms duration, 0.3 Hz frequency). Pulse amplitude was increased after 5 sweeps in the range of 100-800 µA in order to define threshold intensity and trace a recruitment curve after injury. Severe spinal cord injuries abolishing spinally induced motor responses, were performed using a calibrated customized device, composed of a steel rod of 33.0 g weight dropping on the exposed cord from 5 cm of height. The end of the rod is a cylindrical protrusion of 1 mm radius to directly impact on the dorsal spinal midline at L5/L6. The impounder was left on the original injury site for 10 seconds before being carefully raised from the cord surface. During the impact, the trunk was stabilized by supporting the animal's belly with a rod, 2 cm high, under the chest. After 40-90 min from lesion, spinal cord functionality was tested under urethane by applying trains of electrical pulses (test pulses) (0.1 ms duration, 0.3 Hz frequency). Pulse amplitude was increased after 5 sweeps in the range of 100-800 µA in order to define threshold intensity and trace a recruitment curve after injury. The entire protocol for assessing spinal cord functionality spanned 40 min and was replicated twice before DS delivery. Repetitive DS (rDS) consisted in the delivery of eight consecutive DS patterns of 30 s with 1 min intervals, for a total duration of 11 min.

Ninety minutes after the lesion, spinally-induced responses in TA and Sol muscles were suppressed (FIG. 58, panel A). Single pulses delivered at maximal intensity (800 µA) to the segment just below the injury site elicited no responses (FIG. 58, panel $A_1$). About three hours after injury, the rDS protocol was applied at the intensity of 600 µA (FIG. 58, panel B) followed by a long resting phase. Fifty minutes after the end of the protocol (FIG. 58, panel C), the same test pulses, delivered with the cathode on the right side, produced a consistent response from the muscles of the left leg, without any output from the right side (FIG. 58, panel $C_1$). Conversely, by inverting the cathode/anode polarity of the test stimuli (FIG. 58, panel D, cathode on the left side), TA and Sol on the right leg showed large muscle contractions without any responses from the left leg (FIG. 58, panel $D_1$). Similar observations were made in four animals, when rDS was applied 190±17 min after the impact. Likewise, spinally-evoked responses that were not present before DS, reappeared when tested 228±18 min after the impact.

Further assessments were made to assure that recovery of spinally-induced responses was enabled by DS and not by a spontaneous recovery over longer resting periods. Therefore, four sham experiments were performed, to replicate the same experimental procedures without any delivery of DS (FIG. 58, panels E-G). In a sample experiment, the lack of EMG responses from the injured cord segment was confirmed by continuous testing for up to 250 min after injury (FIG. 58, panel, panels $E_1$, $G_1$, $H_1$). Moreover, suppression of spinally-induced responses extended also to more rostral and caudal segments, eventually demonstrating a worsening of the functional deficit within the first few hours after initial compression (data not shown).

In the present study, we exploited a recently designed protocol of multisite stimulation with noisy patterns, named Dynamic Stimulation (DS), and its delivery through an epidural interface consisting in a multi-electrode array. Recently, we proved that these two resources modulate locomotor networks and facilitate the motor output induced by subthreshold cortical input. Here, in fully anesthetized animals, we demonstrated that the DS paradigm of stimulation was linked to patterns leading to a greater recovery of motor output after a severe spinal cord injury.

Unlike many studies involving neurorehabilitation, our strategy did not target the locomotor interneuronal networks for locomotion, but was centered at the site of lesion to promote reconnection along adjacent segments. Another original point of this research was that the continuous electrostimulation of the lesioned cord was performed in an acute setting (in the first three hours after injury). This finding suggests the possibility to employ novel dynamic stimulation paradigm either epidurally and/or transcutaneously to the lesioned spinal cord as a first surgical intervention to limit the loss of functions following a spinal cord injury. In addition, acute deliver of rDS could facilitate return of function in multiple organ systems including cardiovascular (Phillips et al. (2018). *J. Neurotrauma,* 35(3): 446-451), bladder function (Kreydin et al. (2020) *Front. Systems Neurosci.,* 14: 1), hand and arm function (Gad et al., 2018, Inanici et al., 2018) and lower extremity function (FIG. 58), all of which are impacted by the spinal cord injury.

The manner in which acute multiple depolarizations, as the ones induced by DS, counteract early functional impairments after SCI has not been explored so far and, likewise, the mechanisms of such recovery are far from being elucidated.

On the contrary, though, a spreading depolarization along the cord has been reported so far to contribute to secondary damage after an impact injury (Gorji et al. (2004) *Neurobiol.*

*Dis.* 15: 70-79), since it releases additional glutamate that reaches a toxic level for cells and leads to functional deficits (Hinzman et al. (2015) *Exp. Neurol.* 267: 243-253). In the present study, the continuous delivery of DS, acutely applied across the lesion site, generated additional depolarizations that, paradoxically, not only did it not worsen the functional deficit, but in fact consistently facilitated the recovery of motor output. This effect was robust, also, in spite of the possible spreading depolarization induced by damage had already concluded when we delivered DS (3 hours after lesion). Alternatively, DS might have confined the spreading depolarization triggered by the trauma, by generating multiple after-hyperpolarizations of cell membranes in response to the insurgence of action potentials evoked by DS in the network neurons. Indeed, these asynchronous and diffused hyperpolarizing events throughout the network could act as unexcitable nodes along the path of spreading depression, limiting the massive propagation.

Moreover, the acute delivery of DS might regress acute phenomena of network dysfunction (Taccola et al. (2010) *Eur. J. Neurosci.* 31: 60-78) by promoting activity-based plastic events (Ganguly & Poo (2013) *Neuron.* 80: 729-741). Indeed, DS provides a pattern of phasic stimulation derived from sampling traces from hind limb muscles during real locomotion. This pattern of input varies in amplitude and frequency and is comparable to that of afferent feedback during gait (Prochazka et al. (1976) *J. Neurophysiol.* 39: 1090-1104). According to this view, application of DS a few hours after the trauma might promote activity-like signals mimicking a locomotor training session long before the subject is stabilized and prepared for neurorehabilitation protocols aimed at facilitating recovery of locomotion.

Extensive amounts of data are accumulating that point to activity-dependent mechanisms in play ranging from RNA expression and synaptic proteins to systems level learning phenomena within and among spinal networks as well as the transformation of dormant to competent spinal connectivity in response to epidural and transcutaneous stimulation when combined with sensory-motor training Perhaps these phenomena can become even more robust at periods soon after the injury occurs. These promising acute data, collected from terminal recordings in fully anesthetized animals, suggest the need for further studies to translate this neuromodulating strategy in the acute stage of a spinal injury and in chronic injuries to confirm DS ability to restore functions. DS may form a critical component of the clinical toolbox that may define the standard of care of patients acutely after spinal cord injury.

Example 9

An Epidural Interface to Derive Multisite Cord Dorsum Potentials During Peripheral, Cortical and Spinal Stimulation We have adopted a novel multielectrode array for epidural stimulation on multiple sites of the spinal cord with highly varying waveforms. We hypothesize that the same technology characterized by independent low-impedance electrodes can be exploited for simultaneous recordings of neuronal potentials from several adjacent sites of the dorsal cord.

Cord Dorsum Potentials are neural signals, extracellularly recorded through penetrating electrodes implanted in the dorsal cord. Classically they were evoked in response to electrical stimulation of afferent nerves (Brooks & Eccles (1947) *Nature,* 159(4049): 760-764) or supra-spinal structures.

At present, only few multi electrode epidural interfaces have been presented as able to record CDPs from the surface of the cord albeit with scarce spatial selectivity among adjacent sites of the cord (Parker et al. (2012) *Pain,* 159(3): 593-601).

Introducing recording devices able to discriminate surface potentials from multiple sites of the cord might possess a great physiological and diagnostic value to trace the topography and the functional organization of spinal networks pre and post lesion.

Our goal in this example is to use our stimulating multi-electrode interface to simultaneously derive CDPs from multiple sites of the surface of the cord during:

1. stimulation of two peripheral nerves,
2. selective stimulation of cortico-spinal fibers, and
3. the direct stimulation of adjacent sites of the cord.

To achieve this aim we performed terminal experiments in fully anesthetized male adult rats (n=27) implanted with an epidural multiple electrode array spanning from L1 to S2 segments and during the bilateral electrical stimulation of the plantar and peroneal nerves, the selective stimulation of lateral motor cortex controlling the hind limbs and pulses epidurally applied to a discrete segment of the spinal cord. Results.

From a single site of the interface, classical CDPs (Brooks & Eccles (1947) supra.) were elicited by stimulating a peripheral nerve (FIG. 59). Mean values for latency and amplitude of AV, N1, N2 and P waves are provided.

Input output experiments showed the CDP changes at increasing intensity of stimulation (FIG. 60). Latency and amplitude values are provided by the analysis of AV, N1, N2 and P waves at increasing intensities of stimulation (expressed as times×Th).

As shown in FIG. 61, responses evoked from the same site of the cord during the serial stimulation of two peripheral nerves have distinct latencies in accordance to each nerve length/conduction.

Responses elicited from the same site of the cord in response to the bilateral stimulation of afferent nerves acknowledge the omolateral representation on the cord (FIG. 62).

The stimulation of an afferent nerve elicited simultaneous responses from multiple sites of the interface (FIG. 63). Latency and amplitude mean values were provided by the analysis of AV, N1, N2 and P waves at each site. Albeit the pooled data did not show any statistical significance, exemplar traces in the figure, as well as the data from single experiments, identified the localization of post-synaptic neuronal target. Topographic representation of the motor pools activated by bilateral stimulation of the plantar and peroneal nerves aligns to previously reported anatomical data.

On occasion, the highest response is elicited from the midline in accordance to what reported elsewhere. (see, e.g., FIG. 64).

It was desired to determine the origin of CDPs. In particular whether the multiple CDPs recorded from the interface are real potentials from different motor pools along the cord or are they the same signal passively conducted from one electrode to another. This issue is addressed using four different approaches.

A first approach involves calculating the ratio among N1/AV peaks for each site: AV is passively conducted on the surface of the cord and remains almost identical for each different site, while N1 depends on the number of interneurons activated on each site (see, e.g., FIG. 65).

A second approach involves measuring the latency of responses. If passively conducted, the contralateral electrode should report the latest responses.

A third approach involves drawing the input output curve for each site, normalized to the highest peak. If passively conducted, the profile of each curve is the same, albeit miniaturized for the farthest electrode (see, e.g., FIG. 66).

A fourth approach involves measuring the amplitude of peaks from central and laterals electrodes: if passively conducted, responses from the central electrode should be halfway between homo- and contra-lateral sites.

CDPs are elicited by selective electrical stimulation of the lateral motor cortex. In analogy to what reported by Noga and colleagues, single or double cortical pulses induced triple-peak responses with consistent latency components (see, e.g., FIG. 67).

In one case, using superimposed traces, higher peaks seemed to occur contra-laterally to the stimulated cortical area (FIG. 68). Here responses seem to be higher at caudal sites and maybe a slight difference in latency appears among multiple traces. Still to be analyzed in detail.

By increasing the intensity of cortical stimulation, the two late peaks appeared in correspondence to muscle recruitment in the contralateral leg (FIG. 69).

CDPs can be recorded by stimulating the adjacent sites of the interface. As illustrated in FIG. 70, spinally-induced potentials have a shorter latency.

Multiple recordings during epidural stimulation revealed staggered onset of neuronal responses, that did not depend solely on the distance from the source of stimulation (FIG. 71).

In fully anesthetized animals, spontaneous discharges were recorded from the array and matched the EKGs recorded from the chest (FIG. 72). Parker and colleagues (Parker et al. (2012) *Pain,* 153(3): 593-601) have already reported a similar observation with epidural dorsal recordings. They simply removed the EKGs by subtraction.

For increasing intensities of stimulation, CDP composition reflects the appearance of H response (FIG. 73). The data suggest that a relationship may exist among the components of CDPs and the appearance of the H response. It is noted that the right side in FIG. 73 is not a good example since, at lowest strengths of stimulation, M response appeared before the H one.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A transcutaneous electrical spinal cord stimulator, said stimulator comprising:
    a plurality of array electrodes configured to be placed in contact with an outer skin surface of a patient directly over a spinal cord on a back positioned between vertebral processes;
    a pulse modulator unit connected to the microprocessor;
    one or more channels configured to provide one or more transcutaneous electrical spinal cord stimulation patterns, via the plurality of array electrodes, to a plurality of nerves in the spinal cord to provide therapy for a disorder of a connection between a brain and a spinal cord of a patient, at least one of which includes a plurality of delayed biphasic electrical stimulation pulses;
    a microprocessor unit in communication with the plurality of array electrodes, the pulse modulator unit, and the one or more channels; and
    a memory in communication with the microprocessor unit and having instructions stored thereon that, when executed, cause the microprocessor unit to:
        receive a plurality of treatment parameters corresponding to the one or more electrical spinal cord stimulation patterns, wherein the plurality of treatment parameters comprises a motor threshold;
        execute the plurality of treatment parameters using the plurality of array electrodes and the pulse modulator unit;
        detect an EMG response; and
        store the plurality of treatment parameters,
    wherein the motor threshold comprises an intensity that excites or inhibits certain neurons or interneurons within the spinal cord to treat connectivity impaired by the disorder of the connection between the brain and the spinal cord of the patient, wherein said neurons or interneurons are remote from a site of said stimulation; and
    wherein the plurality of delayed biphasic electrical stimulation pulses includes an anodic phase and a cathodic phase configured to independently provide therapy to the spinal cord.

2. The electrical stimulator of claim 1, wherein said stimulator comprises two or more or four or more independently configurable channels each capable of independently providing one or more of said stimulation patterns.

3. The electrical stimulator of claim 2, wherein:
    said two or more or said four or more channels provide said stimulation patterns with respect to a common neutral line; or
    each of said two or more or each of said four or more channels provide said stimulation patterns with respect to neutral line for that channel.

4. The electrical stimulator of claim 1, wherein the one or more transcutaneous electrical spinal cord stimulation patterns comprises bursts of low frequency therapeutic pulses configured to activate or inhibit certain neurons or interneurons within the spinal cord and impaired by the disorder,
    wherein said low frequency therapeutic pulses comprise a frequency and an amplitude of high frequency pulses configured to reduce or block pain caused by said bursts of low frequency therapeutic pulses,
    wherein said high frequency pulses range in frequency from about 5 kHz up to about 100 kHz, or from about 10 kHz up to about 50 kHz, or from about 10 kHz up to about 30 kHz, or from about 10 kHz up to about 20 kHz; and
    wherein the low frequency therapeutic pulses range in frequency from about 1 Hz up to about 100 Hz, or from about 10 Hz up to about 50 Hz, or from about 30 Hz up to about 50 Hz, or from a bout 20 kHz up to about 30 kHz.

5. The electrical stimulator of claim 1, wherein:
    one or more channels of said electrical stimulator is configured to provide monophasic electrical stimulation with a DC offset; and/or
    one or more of channels of said electrical stimulator is configured to provide monophasic electrical stimulation with charge balance; and/or one or more channels of said electrical stimulator is configured to provide delayed biphasic electrical stimulation with a DC offset; and/or one or more channels of said electrical stimulator is configured to provide delayed biphasic electrical stimulation with charge balance; and/or one or more channels of said electrical stimulator is configured to provide delayed biphasic electrical stimulation with charge balance where the delay in said biphasic electrical stimulation ranges from about 0.1 μsec up to about 2 μsec, or from about 0.1 μsec up to about 1 μsec; and/or one or more channels of said electrical stimulator is configured to provide dynamic stimulation with amplitude modulation; and/or one or more channels of said electrical stimulator is configured to provide dynamic stimulation with frequency modulation; and/or one or more channels of said electrical stimulator is configured to provide frequency modulated dynamic stimulation where the one or more channels of said frequency modulated dynamic stimulation ranges in frequency from about 1 Hz to about 1000 Hz.

6. The electrical stimulator of claim 5, wherein:

said dynamic stimulation is sourced from a biosignal; and/or said dynamic stimulation is sourced from a biosignal that comprises a signal derived from an EMG, and EEG, or an EKG; and/or said dynamic stimulation is sourced from a biosignal wherein said biosignal is recorded from a mammal; and/or said dynamic stimulation is sourced from a biosignal where said biosignal is recorded from a human or from a non-human primate; and/or said dynamic stimulation is sourced from a biosignal where said biosignal comprises a biosignal recorded from a mammal when the mammal is standing, stepping, moving the arms, storing/emptying the bladder, storing/emptying the bowel, breathing.

7. The electrical stimulator of claim 1, wherein:

said electrical stimulator is configured to provide a stimulation amplitude ranging from about 1 mA, or from about 3 mA, or from about 5 mA up to about 500 mA, or up to about 400 mA, or up to about 300 mA, or up to about 250 mA, or up to about 200 mA for each of said one or more channels; and/or said electrical stimulator is configured to provide a stimulation amplitude ranging from about 5 mA up to about 200 mA for each of said one or more channels; and/or said stimulator is configured to provide pulses that pass a current of 300 mA peak through an impedance of about 300 to about 2000 ohms, or from about 300 to about 900 ohms for each of said one or more channels; and/or said electrical stimulator is configured to provide a stimulation having a DC offset ranging from about 1 mA to about 30 mA, or from about 1 mA to about 20 mA; and/or said stimulator is configured to provide a stimulation frequency (burst frequency) for one or more of said channels ranging in frequency from 0.2 Hz up to 10 kHz; and/or said stimulator provides stimulation frequency control in steps of 1 Hz at a frequency ranging from 0.2 Hz to 100 Hz; and/or said stimulator provides stimulation frequency control, in steps of 100 Hz at a frequency ranging from 100 Hz to 1 kHz; and/or said stimulator provides stimulation frequency control in steps of 1 kHz at a frequency ranging from 1 kHz to 10 kHz; and/or said stimulator is configured to provide a stimulation pulse (burst) width ranging from about 0.1 ms up to about 20 ms, or up to about 10 ms, or up to about 5 ms, or up to about 4 ms, or from about 0.2 ms up to about 3 ms; and/or said stimulator is configured to provide a stimulation pulse (burst) width controllable in steps of 0.1 ms; and/or aid stimulator is configured to provide a pulse width fixed at 1 ms at stimulation frequencies over 10 kHz; and/or said stimulator is configured to control the timing between stimulation signals delivered by different channels.

8. The electrical stimulator of claim 1, wherein said electrical stimulator comprises:

a microprocessor unit for receiving and/or programming and/or storing a stimulation pattern for one or more channels comprising said stimulator;

a pulse generating unit under control of said microprocessor;

a pulse modulator (gating) unit under control of said microprocessor; and an input/output unit providing user control over said electrical stimulator.

9. The electrical stimulator of claim 8, wherein:

said electrical stimulator further comprises a DC shift (offset) generating unit under control of said microprocessor; and/or said electrical stimulator further comprises a DC shift (offset) generating unit under control of said microprocessor where said DC shift generating unit comprises a component of said pulse generating unit; and/or said electrical stimulator further comprises a charge balancing unit; and/or said electrical stimulator further comprises a current control unit; and/or said electrical stimulator further comprises a monitoring unit; and/or said electrical stimulator further comprises a monitoring unit where said monitoring unit monitors lead impedance; and/or said electrical stimulator further comprises a monitoring unit where said monitoring unit monitors output current; and/or said input output unit is directly electrically connected to said stimulator; and/or said input output unit is operably coupled to said stimulator through a wireless connection, a network connection, a wifi connection, or a Bluetooth connection; and/or said electrical stimulator comprises a smart card reader and/or a biometric reader; and/or said electrical stimulator comprises a smart card reader configured to input a patient identifier, and optionally, a treatment protocol associated with said patient identifier; and/or said electrical stimulator comprises a biometric reader; and/or said electrical stimulator comprises a biometric reader that recognizes a fingerprint, a face, and/or an iris; and/or said electrical stimulator comprises a biometric reader that identifies a subject to be treated.

10. The electrical stimulator of claim 1, wherein said electrical stimulator is operably coupled to a database.

11. The electrical stimulator of claim 10, wherein:

said database provides treatment protocols; and/or said database provides treatment protocols for a subject identified to said stimulator by said smart card reader and/or by said biometric reader.

12. The electrical stimulator of claim 1, wherein said stimulator is configured to provide two modes of operation:

i) an administrator mode for clinicians and researchers; and ii) a patient mode.

13. The electrical stimulator of claim 12, wherein:

said administrator mode provides the ability to input and store one or more programs comprising stimulation parameters for one or more of said one or more channels; and/or said administration mode provides the ability to store up to 5 stimulation programs, or up to 10 stimulation programs; and/or said administrator mode provides the ability to input and store electrode placement locations for presentation in patient mode; and/or said administrator mode provides the ability to measure impedance across each channel and display it to the administrator; and/or said patient mode permits program selection using a patient identifier; and/or said patient mode permits program selection using a patient identifier selected from the group consisting of a smart card, a patient biometric (eye, facial recognition, thumb or fingerprint recognition) reader, an alphanumeric patient ID, a medical bracelet, smartphone app/tap, smartwatch app/tap, smart ring tap; and/or said patient mode identifies for the patient sites for transcutaneous stimulation electrodes to be placed; and/or said patient mode turns on the therapy; and/or said patient mode turns on therapy after detecting placement of the necessary electrodes; and/or said patient mode permits the user to set ramp rate options; and/or said patient mode permits the user to set up ramp rate options ranging from about 1 mA/sec to about 10 mA/sec.

14. The electrical stimulator of claim 1, wherein:

each active channel of said stimulator is electrically coupled to one or more electrodes for transcutaneous electrical stimulation; and/or each active channel of said stimulator is electrically coupled to one or more electrodes for transcutaneous electrical stimulation wherein said electrodes comprise paddle electrodes; and/or each active channel of said stimulator is electrically coupled to one or more electrodes for transcutaneous electrical stimulation; and/or each active channel of said stimulator is electrically coupled to one or more paddle electrodes for transcutaneous electrical stimulation wherein:

said paddle electrodes are disposed in clothing; or said paddle electrodes are disposed on a toilet seat; or said paddle electrodes are disposed on a chair or couch; or each active channel of said stimulator is electrically coupled to one or more needle electrodes.

\* \* \* \* \*